United States Patent
Song et al.

(10) Patent No.: US 11,351,170 B2
(45) Date of Patent: Jun. 7, 2022

(54) SUBSTITUTED PYRIMIDINES AS CDK4/6 INHIBITORS

(71) Applicant: Beijing Xuanyi PharmaSciences Co., Ltd., Beijing (CN)

(72) Inventors: Yuntao Song, Palo Alto, CA (US); Xiaoqi Chen, Palo Alto, CA (US)

(73) Assignee: Beijing Xuanyi PharmaSciences Co., Ltd., Beijing (CN)

( * ) Notice: Subject to any disclaimer, the term of this patent is extended or adjusted under 35 U.S.C. 154(b) by 0 days.

(21) Appl. No.: 16/639,412

(22) PCT Filed: Aug. 15, 2018

(86) PCT No.: PCT/IB2018/056140
§ 371 (c)(1),
(2) Date: Feb. 14, 2020

(87) PCT Pub. No.: WO2019/035008
PCT Pub. Date: Feb. 21, 2019

(65) Prior Publication Data
US 2021/0128555 A1    May 6, 2021

Related U.S. Application Data

(60) Provisional application No. 62/545,774, filed on Aug. 15, 2017.

(51) Int. Cl.
| | |
|---|---|
| A61K 31/506 | (2006.01) |
| C07D 239/42 | (2006.01) |
| A61K 31/282 | (2006.01) |
| A61K 31/4745 | (2006.01) |
| A61K 31/7048 | (2006.01) |
| C07D 487/04 | (2006.01) |
| C07D 519/00 | (2006.01) |

(52) U.S. Cl.
CPC .......... *A61K 31/506* (2013.01); *A61K 31/282* (2013.01); *A61K 31/4745* (2013.01); *A61K 31/7048* (2013.01); *C07D 487/04* (2013.01); *C07D 519/00* (2013.01)

(58) Field of Classification Search
CPC ............................ A61K 31/506; C07D 239/42
USPC ........................................... 514/275; 544/331
See application file for complete search history.

(56) References Cited

U.S. PATENT DOCUMENTS

2016/0304517 A1   10/2016  Breinlinger et al.
2018/0305363 A1   10/2018  Liu et al.

FOREIGN PATENT DOCUMENTS

| WO | WO 2015/086525 A1 | 6/2015 |
| WO | WO 2016/173505 A1 | 11/2016 |
| WO | WO 2017/071516 A1 | 5/2017 |
| WO | WO 2018/113771 A1 | 6/2018 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Wolff, Manfred E., Ed. Burger's Medicinal Chemistry and Drug Discovery—Fifth Edition, vol. 1: Principles and Practice, New York: John Wiley & Sons, 1994, 975-977.*
International Search Report and Written Opinion issued by the International Searching Authority for Application No. PCT/IB2018/056140, dated Jan. 22, 2019, 9 pages.
Bisi et al., "Preclinical Characterization of G1T28: A Novel CDK4/6 Inhibitor for Reduction of Chemotherapy-Induced Myelosuppression," Mol. Cancer Ther. 15(5), 2016, 783-793.
Nogrady (1985) Medicinal Chemistry A Biochemical Approach, Oxford University Press, New York, pp. 388-394.

(Continued)

*Primary Examiner* — Douglas M Willis
(74) *Attorney, Agent, or Firm* — Cooley LLP

(57) ABSTRACT

The present disclosure relates to a compound of formula (I), or a pharmaceutically acceptable salt, a solvate, a stereoisomer, or tautomer thereof, a pharmaceutical composition comprising a compound of formula (A) or formula (B), and any subgenera thereof, and use of said compounds and compositions thereof, wherein $R^1$, $R^2$, $R^{3a}$, $R^{3b}$, $R^5$, $R^6$, $X^1$, $X^2$, Y and n are described herein.

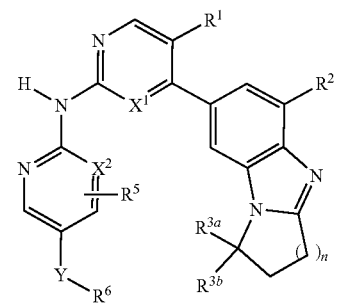

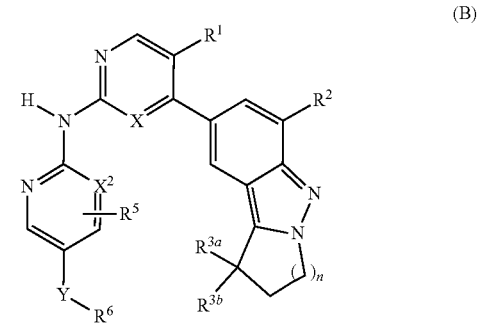

18 Claims, No Drawings

(56) References Cited

OTHER PUBLICATIONS

Roberts et al., "Multiple Roles of Cyclin-Dependent Kinase 4/6 Inhibitors in Cancer Therapy," JNCI, 2012, 104(6), 476-487.
Wang et al., "Design and synthesis of 4-(2,3-dihydro-1H-benzo[d]pyrrolo[1,2-α] imidazol-7-yl)-N-(5-(piperazin-1-ylmethyl)pyridine-2-yl)pyrimidin-2- amine as a highly potent and selective cyclin-dependent kinases 4 and 6 inhibitors and the discovery of structure-activity relationships," Bioorganic & Medicinal Chemistry Letters 28:974-978 (2018).

* cited by examiner

SUBSTITUTED PYRIMIDINES AS CDK4/6 INHIBITORS

CROSS-REFERENCE TO RELATED APPLICATIONS

This application is a U.S. National Stage Application under 35 U.S.C. § 371 of International Application No. PCT/IB2018/056140, filed Aug. 15, 2018, which claims priority to and the benefit of U.S. Provisional Patent Application No. 62/545,774, filed Aug. 15, 2017, the disclosure of each of which are hereby incorporated by reference in its entirety for all purposes.

FIELD OF THE DISCLOSURE

The present disclosure relates to novel compounds having certain biological activities that include, but are not limited to inhibiting cyclin-dependent kinases. The present disclosure relates to aminopyrimidine compounds of formulae (A), (B), (I), or (II), and any subgenera thereof, or a pharmaceutically acceptable salts and derivatives thereof, pharmaceutical compositions thereof, and method of using the same.

BACKGROUND OF THE DISCLOSURE

Sustained proliferative capacity is considered a hallmark of cancer. The cell cycle has been extensively studied and has been at the forefront of biomedical research. The cell cycle has four functional phases: S, G1, G2, and M phase. The underlying regulatory pathways controlling the mammalian cell cycle were extensively investigated. Cyclin-dependent kinases (CDKs) play the central role of regulating the cell proliferation. The human genome encodes 21 CDKs. However, only seven (CDK 1-4, 6, 10, 11) have been shown to have a direct role in the cell cycle progression. Among the cell proliferation points, G1 restriction point is critical, as this point is where cell proliferation becomes independent of mitogens and growth factors. The normal function of the restriction point is essential for maintaining control of cellular proliferation. The restriction point is controlled by the retinoblastoma pathway (CDK4/CDK6-cyclin D1-Rb-p16/ink4a). The retinoblastoma protein (Rb) is a tumor suppressor that inhibits proliferation through binding to and suppressing the activity of the E2F family of transcription factors, and the restriction point is controlled by phosphorylation of Rb by the CDK4 and CDK6 kinases. The central role of the Rb pathway in controlling cellular proliferation is highlighted by its frequent dysregulation in human cancer. The anticancer clinical benefit was demonstrated by palbociclib in breast cancer and palbociclib was approved by FDA in 2015. There are some CDK inhibitor compounds that have gone through or currently undergoing clinical trials.

Chemotherapeutic compounds tend to be non-specific and, particularly at high doses, toxic to normal, rapidly dividing cells. This often leads to a variety of side effects, e.g., bone marrow suppression, adverse effect over healthy cells such as renal epithelial cells.

Both Pfizer compound PD-0332991 and G1 Therapeutics compound G1T28 showed a transient cell cycle arrest in CDK4/6 dependent subsets of healthy cells such as HSPCs (JNCI, 2012, 104(6), 476-487; Mol. Cancer Ther. 15(5), 2016, 783-793).

There has been extensive research in discovering CDK4/6 inhibitors, in view of the number of pathological responses that are mediated by CDK4/6; however, there remains a continuing need for discovering therapeutically effective inhibitors of CDK4/6, for example, for the treatment of hyper-proliferative diseases, or transient protection of normal cells during chemotherapy. Additionally, discovery of novel CDK inhibitors will be useful in combination of other anticancer agents considering the fact that many kinase inhibitors develop resistance.

SUMMARY OF THE DISCLOSURE

In one embodiment of the present disclosure, a pharmaceutical composition is provided comprising a compound of formula (A), (B), (I), or (II), and any subgenera thereof, or a pharmaceutically acceptable salt, solvate, ester, or prodrug thereof.

In one embodiment, the present disclosure relates to compounds of formula (A) or formula (B):

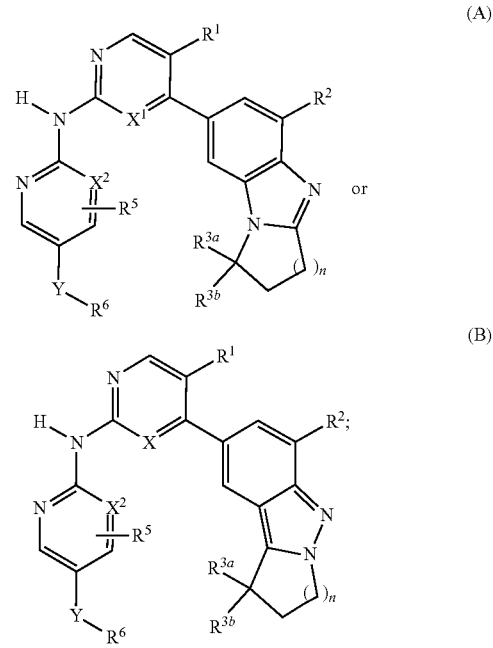

or a pharmaceutically acceptable salt, solvate, ester, or prodrug thereof;
wherein,
$X^1$ and $X^2$ are each independently CH or N;
$R^1$ is selected from hydrogen, fluoro, chloro, bromo, methyl, ethyl, hydroxyl, methoxy, ethoxy, isopropoxy, cyclopropoxy, —OCF$_3$, —OCH$_2$CF$_3$, —OCH$_2$CHF$_2$, —CF$_3$, —CHF$_2$, —CHO, —CH$_2$OH, —CONH$_2$, —CO$_2$Me, —CONHMe, —CONMe$_2$, or cyano;
$R^2$ is selected from hydrogen, fluoro, chloro, methyl, hydroxyl, methoxy, ethoxy, isopropoxy, cyclopropoxy, —OCF$_3$, —CF$_3$, —CHF$_2$, —CH$_2$OH, —CONH$_2$, —CONHMe, —CONMe$_2$, or cyano;
$R^{3a}$ and $R^{3b}$ are each independently H, —C$_{1-6}$ alkyl, or —C$_{1-6}$haloalkyl; or
alternatively, $R^{3a}$ and $R^{3b}$, taken together with the carbon atom to which they are both attached, form a 3-7 membered ring, optionally containing up to two heteroatoms selected from O, S(O)$_x$, or NR$^{11}$, or forms a 7-12 membered heterobicyclic ring which may be fused, bridged or spiro, and includes one to three heteroatoms selected from O, S(O)$_x$, or NR$^{11}$, and wherein the 3-7 membered ring and the 7-12 membered heterobicyclic ring are optionally substituted with up to three substituents selected from hydroxyl, —$C_{1-6}$ alkoxy, —$C_{1-6}$ hydroxyalkyl, $C_{1-6}$ alkoxy-$C_{1-6}$ alkyl-, $C_{1-6}$ alkoxy-$C_{1-6}$ alkoxy-, $C_{2-6}$ hydroxyalkoxy, oxo, thiono, cyano or halo;

Y is -G-, -L-, -G-L-, -L-G-, -L-G-L-, -G-L-G-, -L-G-L-G-, or -G-L-G-L-;

$R^5$ is independently selected from H, $C_{1-6}$ alkyl, halogen, —CN, —$CD_3$, —$CHF_2$, or —$CF_3$;

$R^6$ is H, —$C_{1-6}$ alkyl, —$C_{1-6}$ haloalkyl, —$C_{3-12}$ cycloalkyl, —$NR''R^7$, or a heterocyclyl, wherein —$C_{1-6}$ alkyl, —$C_{1-6}$ haloalkyl, —$C_{3-12}$ cycloalkyl, and heterocyclyl are each optionally substituted with up to three substituents independently selected from $C_{1-6}$ alkyl, —$C_{1-6}$ haloalkyl, F, —OH, oxo, —$CH_2OH$, —$CH_2CH_2OH$, —C(=O)$CH_2OH$, —$CH_2CH_2CH_2OH$, —NR''R'', aziridinyl, azetidinyl, pyrrolidinyl, piperidinyl, or morpholinyl;

G is a divalent linker that can be connected in a chain in either direction, which is selected from absent, —O—, —S(O)$_x$—, —NR''—, —C(=O)—, —C(=NR'')—, —C(=NR$^o$)—, —C(=O)NR''—, —C(=O)O—, —C(=NR'')NR''—, —C(=NR$^o$)NR''—, —S(=O)$_2$NR''—, —NR''C(=O)NR''—, —OC(=O)NR''—, or —NR''S(=O)$_2$NR''—;

L is a divalent linker that can be connected in a chain in either direction, which is selected from absent, —(CR$^a$R$^b$)$_p$—, —(CR$^a$R$^b$)$_p$-cycloalkyl-(CR$^a$R$^b$)$_p$—, or —(CR$^a$R$^b$)$_p$-heterocyclyl-(CR$^a$R$^b$)$_p$—, wherein cycloalkyl and heterocyclyl can be optionally further substituted with up to three substituents selected from F, —OH, oxo, —$C_{1-3}$ alkyl, —$C_{1-3}$ haloalkyl, —$CH_2OH$, —$CH_2CH_2OH$, —$CH_2CH_2CH_2OH$, —NR''R'', aziridinyl, azetidinyl, pyrrolidinyl, piperidinyl, or morpholinyl;

$R^7$ is H, —$C_{1-6}$ alkyl, —$C_{1-6}$ haloalkyl, —$C_{3-12}$ cycloalkyl, heterocyclyl, —$C_6$-$C_{12}$ aryl, $C_6$-$C_{12}$ aryl-$C_1$-$C_6$ alkyl-, 5-12 membered heteroaryl, or 5-12 membered heteroaryl-$C_1$-$C_6$ alkyl-, wherein —$C_{3-12}$ cycloalkyl, heterocyclyl, —$C_6$-$C_{12}$ aryl, $C_6$-$C_{12}$ aryl-$C_1$-$C_6$ alkyl-, 5-12 membered heteroaryl, and 5-12 membered heteroaryl-$C_1$-$C_6$ alkyl- can be optionally further substituted with up to three substituents selected from F, —OH, oxo, —$C_{1-3}$ alkyl, —$C_{1-3}$ haloalkyl, —$CH_2OH$, —$CH_2CH_2OH$, —$CH_2CH_2CH_2OH$, —NR''R'', aziridinyl, azetidinyl, pyrrolidinyl, piperidinyl, or morpholinyl;

$R^{11}$ is H or —$C_{1-6}$ alkyl;

$R^a$, $R^b$ and $R^o$ are each independently H, F, —$C_{1-6}$ alkyl, or —$C_{1-6}$ haloalkyl;

$R''$ is H, —$C_{1-6}$ alkyl, —$C_{1-6}$ haloalkyl, $C_{1-6}$ alkyl-C(=O)—, or $C_{1-6}$ alkyl-S(=O)$_2$—;

n is 1, 2, or 3;

p is independently 0, 1, or 2; and x is 0, 1, or 2;

wherein the compound excludes the compounds exemplified in WO2017/071516 and WO 2016/173505.

In one embodiment of the compounds of formula (A) or formula (B), Y—$R^6$ does not comprise the following sequence in either direction: —O—(CR$^a$R$^b$)—O—, —O—(CR$^a$R$^b$)—NR''—, —O—(CR$^a$R$^b$)—S(O)$_x$—, —NR''—(CR$^a$R$^b$)—N, —NR''—(CR$^a$R$^b$)—S(C)$_x$—, or —S(O)$_x$—(CR$^a$R$^b$)—S(O)$_x$—.

In one embodiment of the compounds of formula (A), Y—$R^6$ is not:

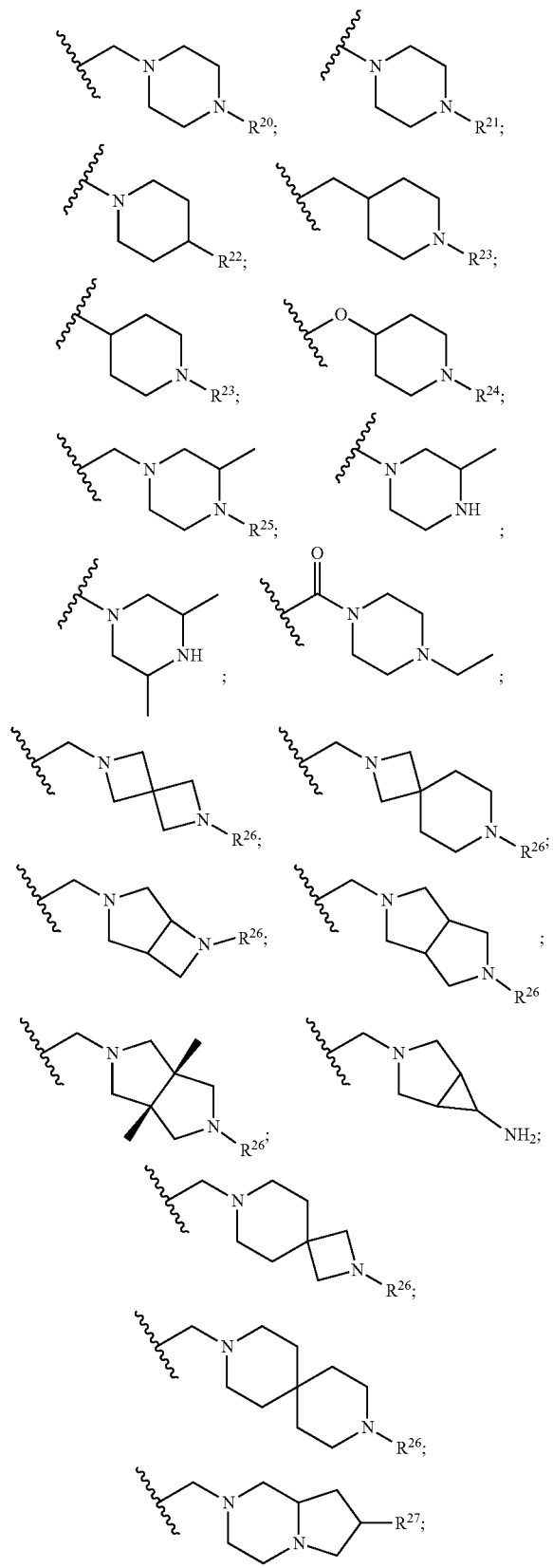

-continued wherein:
$R^{20}$ is H, methyl, ethyl, isopropyl, cyclopropyl, or —CH$_2$CH$_2$F;
$R^{21}$ is H, methyl, ethyl, —CH$_2$CH$_2$OH or —CH$_2$CH$_2$F;
$R^{22}$ is —NH$_2$ or —NMe$_2$;
$R^{23}$ is H, methyl, or ethyl;
$R^{24}$ is H or ethyl;
$R^{25}$ is H or methyl;
$R^{26}$ is H, methyl, or ethyl; and
$R^{27}$ is H or —OH.

In one embodiment of the compounds of formula (A) or formula (B):
$R^1$ is selected from hydrogen, fluoro, chloro, methyl, or cyano;
$R^2$ is selected from hydrogen, fluoro, or cyano;
$R^{3a}$ and $R^{3b}$ are each independently H, —C$_{1-3}$ alkyl, or —C$_{1-3}$ haloalkyl; or
alternatively, $R^{3a}$ and $R^{3b}$, taken together with the carbon atom to which they are both attached, form a 3-7 membered cycloalkyl ring, which is optionally substituted with up to three substituents selected from hydroxyl, —C$_{1-6}$ alkoxy, cyano, oxo, or halo;
$R^5$ is independently selected from H, —C$_{1-3}$ alkyl, F, Cl, —CN, or —CD$_3$;
G is a divalent linker that can be connected in a chain in either direction, which is selected from absent, —O—, —S(O)$_x$—, —NR"—, —C(=O)—, —C(=O)NR"—, —C(=O)O—, or —S(=O)$_2$NR"—;
$R^a$ and $R^b$ are each independently H, F, —C$_{1-3}$ alkyl, or —C$_{1-3}$ haloalkyl;
R" is H, —C$_{1-3}$ alkyl, —C$_{1-3}$ haloalkyl, C$_{1-3}$ alkyl-C(=O)—, or C$_{1-3}$ alkyl-S(=O)$_2$—;
$R^6$ is a H, —C$_{1-3}$ alkyl, —C$_{1-3}$ haloalkyl, —C$_{3-12}$ cycloalkyl, —NR"R$^7$, or a heterocyclyl, wherein —C$_{1-3}$ alkyl, —C$_{1-3}$ haloalkyl, —C$_{3-12}$ cycloalkyl, and heterocyclyl are each optionally substituted with up to three substituents independently selected from F, —OH, oxo, —CH$_2$OH, —CH$_2$CH$_2$OH, —C(=O)CH$_2$OH, —CH$_2$CH$_2$CH$_2$OH, —NR"R", aziridinyl, azetidinyl, pyrrolidinyl, piperidinyl, or morpholinyl; and
$R^7$ is H, —C$_{1-3}$ alkyl, —C$_{1-3}$ haloalkyl, —C$_6$-C$_{12}$ aryl, C$_6$-C$_{12}$ aryl-C$_1$-C$_6$ alkyl-, 5-12 membered heteroaryl, or 5-12 membered heteroaryl-C$_1$-C$_6$ alkyl-, wherein —C$_6$-C$_{12}$ aryl, C$_6$-C$_{12}$ aryl-C$_1$-C$_6$ alkyl-, 5-12 membered heteroaryl, and 5-12 membered heteroaryl-C$_1$—C$_6$ alkyl- can be optionally further substituted with up to three substituents selected from F, —OH, —C$_{1-3}$ alkyl, —C$_{1-3}$ haloalkyl, —CH$_2$OH, —CH$_2$CH$_2$OH, —CH$_2$CH$_2$CH$_2$OH, —NR"R", aziridinyl, azetidinyl, pyrrolidinyl, piperidinyl, or morpholinyl.

In one embodiment of the compounds of formula (A) or formula (B), $R^1$ is hydrogen, fluoro, chloro, methyl, or cyano.

In one embodiment of the compounds of formula (A) or formula (B), $R^2$ is hydrogen, fluoro, or cyano.

In one embodiment of the compounds of formula (A) or formula (B):
Y is -G-, -L-, -G-L-, or -L-G-;
G is a divalent linker that can be connected in a chain in either direction, which is selected from —O—, —S(O)$_x$—, —NR"—, —C(=O)—, —C(=NR")—, —C(=NOR$^o$)—, —C(=O)NR"—, —C(=O)O—, —C(=NR")NR"—, —C(=NOR$^o$)NR"—, —S(=O)$_2$NR"—, —NR"C(=O)NR"—, —OC(=O)NR"—, or —NR"S(=O)$_2$NR"—; and
L is a divalent linker that can be connected in a chain in either direction, which is selected from —(CR$^a$R$^b$)$_p$—, —(CR$^a$R$^b$)$_p$-cycloalkyl-(CR$^a$R$^b$)$_p$—, or —(CR$^a$R$^b$)$_p$-heterocyclyl-(CR$^a$R$^b$)$_p$—, wherein cycloalkyl and heterocyclyl can be optionally further substituted with up to three substituents selected from F, —OH, oxo, —C$_{1-3}$ alkyl, —C$_{1-3}$ haloalkyl, —CH$_2$OH, —CH$_2$CH$_2$OH, —CH$_2$CH$_2$CH$_2$OH, —NR"R", aziridinyl, azetidinyl, pyrrolidinyl, piperidinyl, or morpholinyl.

In one embodiment of the compounds of formula (A) or formula (B):
G is a divalent linker that can be connected in a chain in either direction, which is selected from —O—, —S(O)$_x$—, —NR"—, —C(=O)—, —C(=O)NR"—, —C(=O)O—, or —S(=O)$_2$NR"—; and
L is —(CR$^a$R$^b$)$_p$—.

In one embodiment of the compounds of formula (A) or formula (B), $R^6$ is cycloalkyl selected from cyclopropyl, cyclobutyl, cyclopentyl, cyclohexyl, bicyclo[3.1.0]hexanyl, octahydropentalenyl, bicycle[1.1.1]pentanyl, or cubanyl, each optionally substituted with up to three substituents selected from F, —OH, oxo, —C$_{1-3}$ alkyl, —CH$_2$OH, —CH$_2$CH$_2$OH, —C(=O)CH$_2$OH, —CH$_2$CH$_2$CH$_2$OH, —NR"R", aziridinyl, azetidinyl, pyrrolidinyl, piperidinyl, or morpholinyl. In one embodiment of the compounds of formula (A) or formula (B), $R^6$ is cycloalkyl selected from Table A:
wherein the connectivity of each cycloalkyl can be at any one of CH by replacing a hydrogen for a bond; and
wherein each cycloalkyl is optionally substituted with up to three substituents selected from F, —OH, oxo, —C$_{1-3}$ alkyl, —CH2OH, —CH2CH2OH, —C(=O)CH2OH, —CH2CH2CH2OH, —NR"R", aziridinyl, azetidinyl, pyrrolidinyl, piperidinyl, or morpholinyl.

In one embodiment of the compounds of formula (A) or formula (B): $R^6$ is heterocyclyl selected from Table B:
wherein the connectivity of each heterocyclyl can be at any one of CH or NH by replacing a hydrogen for a bond; and
wherein each optionally substituted with up to three substituents selected from F, —OH, oxo, —C$_{1-3}$ alkyl, —CH$_2$OH, —CH$_2$CH$_2$OH, —C(=O)CH$_2$OH, —CH$_2$CH$_2$CH$_2$OH, —NR"R", aziridinyl, azetidinyl, pyrrolidinyl, piperidinyl, or morpholinyl.

In one embodiment of the compounds of formula (A) or formula (B), $R^6$ is a 5- or 6-membered heterocyclyl, optionally substituted with up to three substituents independently selected from —C$_{1-6}$ alkyl, —C$_{1-6}$ haloalkyl, F, —OH, oxo, —CH$_2$OH, —CH$_2$CH$_2$OH, —C(=O)CH$_2$OH, —CH$_2$CH$_2$CH$_2$OH, or —NR"R".

In one embodiment of the compounds of formula (A) or formula (B), L is a divalent cycloalkyl selected from cyclopropyl, cyclobutyl, cyclopentyl, cyclohexyl, bicyclo[3.1.0]hexanyl, octahydropentalenyl, bicycle[1.1.1]pentanyl, or cubanyl, each optionally substituted with up to three substituents selected from F, —OH, oxo, —$C_{1-3}$ alkyl, —$CH_2OH$, —$CH_2CH_2OH$, —$CH_2CH_2CH_2OH$, —NR″R″, aziridinyl, azetidinyl, pyrrolidinyl, piperidinyl, or morpholinyl. In one embodiment of the compounds of formula (A) or formula (B), L is a divalent cycloalkyl selected from Table A:
wherein the connectivity of each cycloalkyl can be at any two CH on the cycloalkyl by replacing a hydrogen for a bond d; and
wherein each cycloalkyl is optionally substituted with up to three substituents selected from F, —OH, oxo, $C_{1-3}$ alkyl, —$CH_2OH$, —$CH_2CH_2OH$, —$C(=O)CH_2OH$, —$CH_2CH_2CH_2OH$, —NR″R″, aziridinyl, azetidinyl, pyrrolidinyl, piperidinyl, or morpholinyl.

In one embodiment of the compounds of formula (A) or formula (B): L is a divalent heterocyclyl selected from Table B:
wherein the connectivity of each heterocyclyl can be at any two CH and/or NH on the heterocyclyl by replacing a hydrogen for a bond; and
wherein each optionally substituted with up to three substituents selected from F, —OH, oxo, —$C_{1-3}$ alkyl, —$CH_2OH$, —$CH_2CH_2OH$, —$CH_2CH_2CH_2OH$, —NR″R″, aziridinyl, azetidinyl, pyrrolidinyl, piperidinyl, or morpholinyl.

In one embodiment of the compound has the structure of formula (A). In one embodiment, the compound has the structure of formula (A), wherein:
Y is —$(CR^aR^b)_2$—, —$(CR^aR^b)_p$-cycloalkyl-$(CR^aR^b)_p$—, —$(CR^aR^b)_p$-heterocyclyl-$(CR^aR^b)_p$—, -G-L-, -L-G-, -L-G-L-, -G-L-G-, -L-G-L-G-, or -G-L-G-L-;
$R^a$, $R^b$ and $R^o$ are each independently H, F, —$C_{1-6}$ alkyl, or —$C_{1-6}$ haloalkyl;
R″ is H, —$C_{1-6}$ alkyl, —$C_{1-6}$ haloalkyl, $C_{1-6}$ alkyl-C(=O)—, or $C_{1-6}$ alkyl-S(=O)$_2$—;
$R^6$ is H, —$C_{1-6}$ alkyl, —$C_{1-6}$ haloalkyl, —$C_{3-12}$ cycloalkyl, —NR″$R^7$, or a heterocyclyl, wherein-$C_{1-6}$ alkyl, —$C_{1-6}$ haloalkyl, —$C_{3-12}$ cycloalkyl, and heterocyclyl are each optionally substituted with up to three substituents independently selected from F, —OH, oxo, —$CH_2OH$, —$CH_2CH_2OH$, —$C(=O)CH_2OH$, —$CH_2CH_2CH_2OH$, —NR″R″, aziridinyl, azetidinyl, pyrrolidinyl, piperidinyl, or morpholinyl;
G is a divalent linker that can be connected in a chain in either direction, selected from absent, —O—, —S(O)$_x$—, —NR″—, —C(=O)—, —C(=O)NR″—, —C(=O)O—, —S(=O)$_2$NR″—, —NR″C(=O)NR″—, —OC(=O)NR″—, —NR″S(=O)$_2$NR″—;
L is a divalent linker that can be connected in a chain in either direction, selected from absent, —$(CR^aR^b)$—, —$(CR^aR^b)_2$—, —$(CR^aR^b)_p$-cycloalkyl-$(CR^aR^b)_p$—, or —$(CR^aR^b)_p$-heterocyclyl-$(CR^aR^b)_p$—, wherein cycloalkyl and heterocyclyl can be optionally further substituted with up to three substituents selected from F, —OH, oxo, —$C_{1-3}$ alkyl, —$CH_2OH$, —$CH_2CH_2OH$, —$CH_2CH_2CH_2OH$, —NR″R″, aziridinyl, azetidinyl, pyrrolidinyl, piperidinyl, or morpholinyl; and
$R^7$ is H, —$C_{1-6}$ alkyl, —$C_{1-6}$ haloalkyl, —$C_6$-$C_{12}$ aryl, $C_6$-$C_{12}$ aryl-$C_1$-$C_6$ alkyl-, 5-12 membered heteroaryl, or 5-12 membered heteroaryl-$C_1$-$C_6$ alkyl-, wherein —$C_6$-$C_{12}$ aryl, $C_6$-$C_{12}$ aryl-$C_1$-$C_6$ alkyl-, 5-12 membered heteroaryl, and 5-12 membered heteroaryl-$C_1$-$C_6$ alkyl- can be optionally further substituted with up to three substituents selected from F, —OH, —$C_{1-3}$ alkyl, —$C_{1-3}$ haloalkyl, —$CH_2OH$, —$CH_2CH_2OH$, —$CH_2CH_2CH_2OH$, —NR″R″, aziridinyl, azetidinyl, pyrrolidinyl, piperidinyl, or morpholinyl.

In one embodiment, the compound has the structure of formula (A), wherein G is independently selected from —O—, —S(O)$_x$—, —NR″—, —C(=O)—, —C(=O)NR″—, —C(=O)O—, or —S(=O)$_2$NR″—. In another embodiment, G is independently selected from —O—, —S(O)$_x$—, —NR″—, or —C(=O)—.

In one embodiment, the compound has the structure of formula (B).

In one embodiment of the compounds of formula (A) or formula (B), $X^1$ is N; and $X^2$ is CH or N. In another embodiment of the compounds of formula (A) or formula (B): $X^1$ is N; and $X^2$ is CH. In some embodiments of the compounds of formula (A) or formula (B): $X^1$ is CH; and $X^2$ is CH or N. In other embodiments of the compounds of formula (A) or formula (B): $X^1$ is CH; and $X^2$ is CH. In one embodiment of the compounds of formula (A) or formula (B): $X^1$ is CH; and $X^2$ is N. In one embodiment of the compounds of formula (A) or formula (B): $X^1$ is CH or N; and $X^2$ is N.

In one embodiment of the compounds of formula (B):
$X^1$ is N;
$X^2$ is CH;
$R^{3a}$ and $R^{3b}$ are each independently H or —$C_{1-3}$ alkyl;
$R^5$ is H;
Y is selected from —$CH_2$—, —O—$CH_2$—, or —$CH_2$—O—; and
n is 1.

In one embodiment of the compounds of formula (A) has the structure of formula (C)

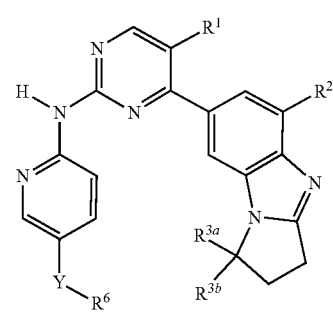

(C)

or a stereoisomer or a pharmaceutically acceptable salt, solvate, ester, or prodrug thereof;
wherein,
$R^1$ is selected from hydrogen, fluoro, chloro, methyl, or cyano;
$R^2$ is selected from hydrogen, fluoro, chloro, or cyano;
$R^{3a}$ and $R^{3b}$ are each independently H, —$C_{1-3}$ alkyl, or —$C_{1-3}$ haloalkyl; or
alternatively, $R^{3a}$ and $R^{3b}$, taken together with the carbon atom to which they are both attached, form a 3-7 membered ring, optionally containing up to two heteroatoms selected from O, S(O)$_x$, or NR$^{11}$, and wherein the 3-7 membered ring is optionally substituted with up to three substituents selected from hydroxyl, $C_{1-3}$ alkoxy, oxo, cyano or F;
Y is —$(CR^aR^b)_2$—, -cycloalkyl-, -heterocyclyl-, —$CR^aR^b$-cycloalkyl-, —$CR^aR^b$-heterocyclyl-, -cycloalkyl-CR$^a$R$^b$—, -heterocyclyl-CR$^a$R$^b$—, -G-CR$^a$R$^b$—, -G-cycloalkyl-, -G-heterocyclyl-, —CR$^a$R$^b$-G-, -cycloalkyl-G-, -heterocyclyl-G-, —CR$^a$R-G-CR$^a$R$^b$—, —CR$^a$R$^b$-cycloalkyl-CR$^a$R$^b$—, —CR$^a$R$^b$-heterocyclyl-CR$^a$R$^b$—, -G-cycloalkyl-G-, -G-heterocyclyl-G-, —CR$^a$R$^b$-G-L-G-, -L-G-CR$^a$R$^b$-G-, -G-CR$^a$R$^b$-G-L-, or -G-L-G-CR$^a$R$^b$—;

R$^a$, R$^b$ and R$^o$ are each independently H, F, —C$_{1-6}$ alkyl, or —C$_{1-6}$ haloalkyl;

R″ is H, —C$_{1-6}$ alkyl, —C$_{1-6}$ haloalkyl, C$_{1-6}$ alkyl-C(=O)—, or C$_{1-6}$ alkyl-S(=O)$_2$—;

R$^6$ is H, —C$_{1-6}$ alkyl, —C$_{1-6}$ haloalkyl, —C$_{3-12}$ cycloalkyl, —NR″R$^7$, or a heterocyclyl, wherein-C$_{1-6}$ alkyl, —C$_{1-6}$ haloalkyl, —C$_{3-12}$ cycloalkyl, and heterocyclyl are each optionally substituted with up to three substituents independently selected from F, —OH, oxo, CH$_2$OH, CH$_2$CH$_2$OH, C(=O)CH$_2$OH, CH$_2$CH$_2$CH$_2$OH, —NR″R″, aziridinyl, azetidinyl, pyrrolidinyl, piperidinyl, or morpholinyl;

G is a divalent linker that can be connected in a chain in either direction, selected from absent, —O—, —S(O)$_x$—, —NR″—, —C(=O)—, —C(=O)NR″—, —C(=O)O—, or —S(=O)$_2$NR″—;

L is a divalent linker that can be connected in a chain in either direction, selected from absent, —(CR$^a$R$^b$)$_p$—, —(CR$^a$R$^b$)$_p$-cycloalkyl-(CR$^a$R$^b$)$_p$—, or —(CR$^a$R$^b$)$_p$-heterocyclyl-(CR$^a$R$^b$)$_p$—, wherein cycloalkyl and heterocyclyl can be optionally further substituted with up to three substituents selected from F, —OH, oxo, C$_{1-3}$ alkyl, CH$_2$OH, CH$_2$CH$_2$OH, CH$_2$CH$_2$CH$_2$OH, NR″R″, aziridinyl, azetidinyl, pyrrolidinyl, piperidinyl, or morpholinyl;

R$^7$ is H, —C$_{1-6}$ alkyl, —C$_{1-6}$ haloalkyl, —C$_6$-C$_{12}$ aryl, C$_6$-C$_{12}$ aryl-C$_1$-C$_6$ alkyl-, 5-12 membered heteroaryl, or 5-12 membered heteroaryl-C$_1$-C$_6$ alkyl-, wherein —C$_6$-C$_{12}$ aryl, C$_6$-C$_{12}$ aryl-C$_1$-C$_6$ alkyl-, 5-12 membered heteroaryl, and 5-12 membered heteroaryl-C$_1$-C$_6$ alkyl- can be optionally further substituted with up to three substituents selected from F, —OH, —C$_{1-3}$ alkyl, —C$_{1-3}$ haloalkyl, —CH$_2$OH, —CH$_2$CH$_2$OH, —CH$_2$CH$_2$CH$_2$OH, —NR″R″, aziridinyl, azetidinyl, pyrrolidinyl, piperidinyl, or morpholinyl;

n is 1, 2, or 3;

p is independently 0, 1, or 2; and x is 0, 1, or 2.

In one embodiment of the compounds of formula (C), R$^{3a}$ and R$^3$ are each independently H or —C$_{1-3}$ alkyl; and Y is —O—CH$_2$— or —CH$_2$—O—.

In one embodiment of the compounds of formula (A) is selected from Compounds 22, 45, 49, 57, 60, 65, 72, 76, 81, or 87, or a stereoisomer or a pharmaceutically acceptable salt, solvate, ester, or prodrug thereof.

In one embodiment of the compounds of formula (B) is selected from Compounds 105 or 106, or a stereoisomer or a pharmaceutically acceptable salt, solvate, ester, or prodrug thereof.

In one embodiment of the compounds of the present disclosure is selected from:

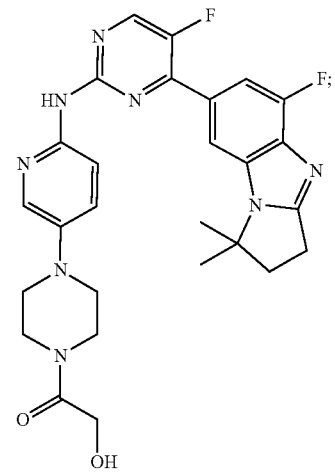

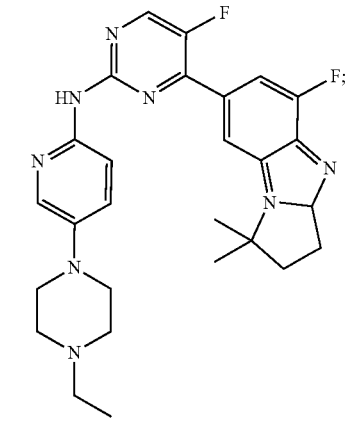

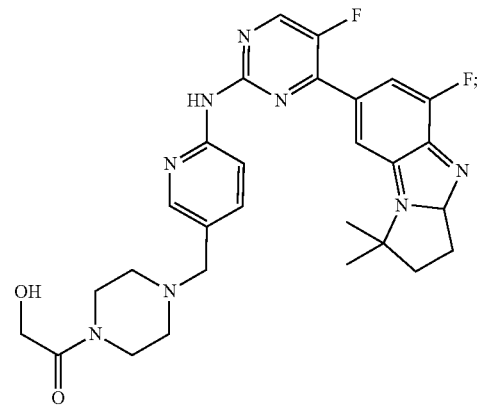

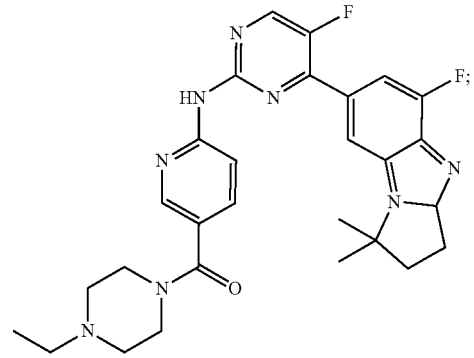

-continued

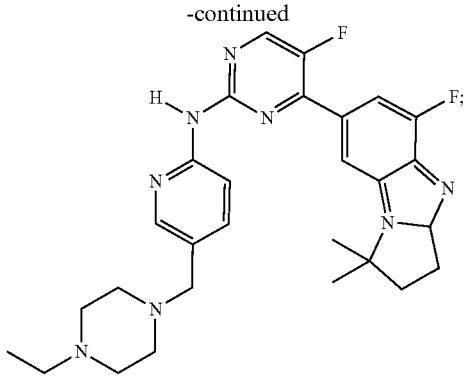

or a stereoisomer or a pharmaceutically acceptable salt, solvate, ester, or prodrug thereof.

In one embodiment, the compound of the present disclosure relates to a compound having the structure of formula (A-I):

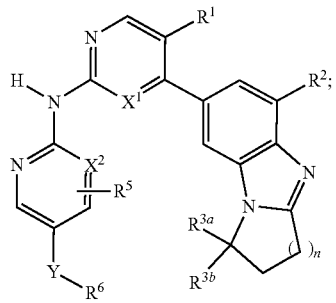

(A-1)

or a pharmaceutically acceptable salt, solvate, ester, or prodrug thereof, wherein, $X^1$ and $X^2$ are each independently CH or N;

$R^1$ is selected from hydrogen, fluoro, chloro, bromo, methyl, ethyl, hydroxyl, methoxy, ethoxy, isopropoxy, cyclopropoxy, —$OCF_3$, —$OCH_2CF_3$, —$OCH_2CHF_2$, —$CF_3$, —$CHF_2$, —CHO, —$CH_2OH$, —$CONH_2$, —$CO_2Me$, —CONHMe, —$CONMe_2$, or cyano;

$R^2$ is selected from hydrogen, fluoro, chloro, methyl, hydroxyl, methoxy, ethoxy, isopropoxy, cyclopropoxy, —$OCF_3$, —$CF_3$, —$CHF_2$, —$CH_2OH$, —$CONH_2$, —CONHMe, —$CONMe_2$, or cyano;

$R^{3a}$ and $R^{3b}$ are each independently H, —$C_{1-6}$ alkyl, or —$C_{1-6}$haloalkyl; or alternatively, $R^{3a}$ and $R^{3b}$, taken together with the carbon atom to which they are both attached, form a 3-7 membered ring, optionally containing up to two heteroatoms selected from O, $S(O)_x$, or $NR^{11}$, or forms a 7-12 membered heterobicyclic ring which may be fused, bridged or spiro, and includes one to three heteroatoms selected from O, $S(O)_x$, or $NR^{11}$, and wherein the 3-7 membered ring and the 7-12 membered heterobicyclic ring are optionally substituted with up to three substituents selected from hydroxyl, —$C_{1-6}$ alkoxy, —$C_{1-6}$ hydroxyalkyl, $C_{1-6}$ alkoxy-$C_{1-6}$ alkyl-, $C_{1-6}$ alkoxy-$C_{1-6}$ alkoxy-, $C_{2-6}$ hydroxyalkoxy, oxo, thiono, cyano or halo;

Y is absent, -G-, -L-, -G-L-, or -L-G-;

$R^5$ is independently selected from H, —$C_{1-6}$ alkyl, halogen, —CN, —$CD_3$, —$CHF_2$, or —$CF_3$;

when Y is absent, $R^6$ is —$C_{1-6}$ alkyl, —$C_{1-6}$ haloalkyl, —$C_{3-12}$ cycloalkyl, —NR"$R^7$, or a 5- or 7-membered heterocyclyl, wherein —$C_{1-6}$ alkyl, —$C_{1-6}$ haloalkyl, —$C_{3-12}$ cycloalkyl, and 5- or 7-membered heterocyclyl are each optionally substituted with up to three substituents independently selected from —$C_{1-6}$ alkyl, —$C_{1-6}$ haloalkyl, F, —OH, oxo, —$CH_2OH$, —$CH_2CH_2OH$, —C(=O)$CH_2OH$, —$CH_2CH_2CH_2OH$, —NR"R", aziridinyl, azetidinyl, pyrrolidinyl, piperidinyl, or morpholinyl;

when Y is -G-, $R^6$ is —$C_{1-6}$ alkyl, —$C_{1-6}$ haloalkyl, —$C_{3-12}$ cycloalkyl, —NR"$R^7$, a 5- or 7-membered heterocyclyl, or

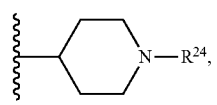

wherein —$C_{1-6}$ alkyl, —$C_{1-6}$ haloalkyl, —$C_{3-12}$ cycloalkyl, and 5- or 7-membered heterocyclyl are each optionally substituted with up to three substituents independently selected from —$C_{1-6}$ alkyl, —$C_{1-6}$ haloalkyl, F, —OH, oxo, —$CH_2OH$, —$CH_2CH_2OH$, —$C(=O)CH_2OH$, —$CH_2CH_2CH_2OH$, —$NR''R''$, aziridinyl, azetidinyl, pyrrolidinyl, piperidinyl, or morpholinyl;

$R^{24}$ is methyl, —$C_{3-6}$ alkyl, —$C_{1-6}$ haloalkyl, —$CH_2OH$, —$CH_2CH_2OH$, —$C(=O)CH_2OH$, or —$CH_2CH_2CH_2OH$;

when Y is -L-, $R^6$ is —$C_{1-6}$ alkyl, —$C_{1-6}$ haloalkyl, —$C_{3-12}$ cycloalkyl, —$NR''R^7$, a 5- or 7-membered monocyclic heterocyclyl, or

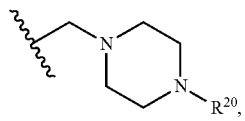

wherein —$C_{1-6}$ alkyl, —$C_{1-6}$ haloalkyl, —$C_{3-12}$ cycloalkyl, and 5- or 7-membered heterocyclyl are each optionally substituted with up to three substituents independently selected from —$C_{1-6}$ alkyl, —$C_{1-6}$ haloalkyl, F, —OH, oxo, —$CH_2OH$, —$CH_2CH_2OH$, —$C(=O)CH_2OH$, —$CH_2CH_2CH_2OH$, —$NR''R''$, aziridinyl, azetidinyl, pyrrolidinyl, piperidinyl, or morpholinyl;

$R^{20}$ is —$C_{4-6}$ alkyl, —$CF_3$, —$CHF_2$, —$C_{3-6}$ haloalkyl, —$CH_2OH$, —$CH_2CH_2OH$, —$C(=O)CH_2OH$, or —$CH_2CH_2CH_2OH$;

when Y is -L-G- or -G-L-, $R^6$ is —$C_{1-6}$ alkyl, —$C_{1-6}$ haloalkyl, —$C_{3-12}$ cycloalkyl, —$NR''R^7$, or heterocyclyl, wherein —$C_{1-6}$ alkyl, —$C_{1-6}$ haloalkyl, —$C_{3-12}$ cycloalkyl, and heterocyclyl are each optionally substituted with up to three substituents independently selected from —$C_{1-6}$ alkyl, —$C_{1-6}$ haloalkyl, F, —OH, oxo, —$CH_2OH$, —$CH_2CH_2OH$, —$C(=O)CH_2OH$, —$CH_2CH_2CH_2OH$, —$NR''R''$, aziridinyl, azetidinyl, pyrrolidinyl, piperidinyl, or morpholinyl;

G is a divalent linker that can be connected in a chain in either direction, which is selected from absent, —O—, —$S(O)_x$—, —$NR''$—, —$C(=O)$—, —$C(=NR'')$—, —$C(=NOR^o)$—, —$C(=O)NR''$—, —$C(=O)O$—, —$C(=NR'')NR''$—, —$C(=NOR^o)NR''$—, —$S(=O)_2NR''$—, —$NR''C(=O)NR''$—, —$OC(=O)NR''$—, or —$NR''S(=O)_2NR''$—;

L is a divalent linker that can be connected in a chain in either direction, which is selected from absent, —$(CR^aR^b)_p$—, —$(CR^aR^b)_p$-cycloalkyl-$(CR^aR^b)_p$—, or —$(CR^aR^b)_p$-heterocyclyl-$(CR^aR^b)_p$—, wherein cycloalkyl and heterocyclyl can be optionally further substituted with up to three substituents selected from F, —OH, oxo, —$C_{1-3}$ alkyl, —$C_{1-3}$ haloalkyl, —$CH_2OH$, —$CH_2CH_2OH$, —$CH_2CH_2CH_2OH$, —$NR''R''$, aziridinyl, azetidinyl, pyrrolidinyl, piperidinyl, or morpholinyl;

$R^7$ is H, —$C_{1-6}$ alkyl, —$C_{1-6}$ haloalkyl, —$C_{3-12}$ cycloalkyl, heterocyclyl, —$C_6$-$C_{12}$ aryl, $C_6$-$C_{12}$ aryl-$C_1$-$C_6$ alkyl-, 5-12 membered heteroaryl, or 5-12 membered heteroaryl-$C_1$-$C_6$ alkyl-, wherein —$C_{3-12}$ cycloalkyl, heterocyclyl, —$C_6$-$C_{12}$ aryl, $C_6$-$C_{12}$ aryl-$C_1$-$C_6$ alkyl-, 5-12 membered heteroaryl, and 5-12 membered heteroaryl-$C_1$-$C_6$ alkyl- can be optionally further substituted with up to three substituents selected from F, —OH, oxo, —$C_{1-3}$ alkyl, —$C_{1-3}$ haloalkyl, —$CH_2OH$, —$CH_2CH_2OH$, —$CH_2CH_2CH_2OH$, —$NR''R''$, aziridinyl, azetidinyl, pyrrolidinyl, piperidinyl, or morpholinyl;

$R^{11}$ is H or —$C_{1-6}$ alkyl;

$R^a$, $R^b$ and $R^o$ are each independently H, F, —$C_{1-6}$ alkyl, or —$C_{1-6}$ haloalkyl;

$R''$ is H, —$C_{1-6}$ alkyl, —$C_{1-6}$ haloalkyl, $C_{1-6}$ alkyl-C(=O)—, or $C_{1-6}$ alkyl-S(=O)$_2$—;

n is 1, 2, or 3;

p is independently 0, 1, or 2; and x is 0, 1, or 2.

In one embodiment of the compounds of formula (A-I), Y is -L-G- or -G-L- and $R^6$ is 5- or 6-membered heterocyclyl which is optionally substituted with up to three substituents selected from F, —OH, oxo, —$C_{1-3}$ alkyl, —$C_{1-3}$ haloalkyl, —$CH_2OH$, —$CH_2CH_2OH$, —$CH_2CH_2CH_2OH$, or —$NR''R''$.

In one embodiment of the compounds of formula (A-I), Y is —O—$CH_2$— or —$CH_2$—O—.

In another embodiment, the pharmaceutical composition comprises a compound of formula (A), (B), (I), or (II), and any subgenera thereof, or a pharmaceutically acceptable salt, solvate, ester, or prodrug thereof, and a pharmaceutically acceptable carrier. In some embodiments, the pharmaceutical composition comprises at least one additional therapeutically active agent. In one embodiment, the additional therapeutically active agent is an anticancer agent.

In one embodiment of the present disclosure, various methods comprising the use of a compound of formula (A), (B), (I), or (II), and any subgenera thereof, or a pharmaceutically acceptable salt, solvate, ester, or prodrug thereof, is disclosed. In one embodiment, a method for modulating cyclin-dependent kinase (CDK) comprises administering to a subject in need thereof, a therapeutically effective amount of a compound of formula (A), (B), (I), or (II), and any subgenera thereof, or a pharmaceutically acceptable salt, solvate, ester, or prodrug thereof. In one embodiment, the modulating CDK is inhibiting CDK. In one embodiment, CDK is CDK4, CDK6, or CDK4/6.

In one embodiment, a method is provided for treating, ameliorating, or preventing a condition which responds to modulation of CDK, comprising administering to a subject in need thereof, a therapeutically effective amount of a compound of formula (A), (B), (I), or (II), and any subgenera thereof, or a pharmaceutically acceptable salt, solvate, ester, or prodrug thereof. In one embodiment, the condition is cancer. In one embodiment, CDK is CDK4, CDK6, or CDK4/6.

In one embodiment, a method is provided for treating a cell proliferative disorder, comprising administering to a subject in need thereof, a therapeutically effective amount of a compound of formula (A), (B), (I), or (II), and any subgenera thereof, or a pharmaceutically acceptable salt, solvate, ester, or prodrug thereof. In one embodiment, the cell proliferative disorder is cancer. In one embodiment, the cancer is breast cancer, colon cancer, ovarian cancer, non-small cell lung cancer, or Rb-positive glioblastoma.

In one embodiment of any one of the methods provided herein, the method further comprises administering at least one additional therapeutically active agent. In one embodiment, the additional therapeutically active agent is an anticancer agent.

In one embodiment, a method for preparing a medicament is provided comprising a therapeutically effective amount of a compound of formula (A), (B), (I), or (II), and any subgenera thereof, or a pharmaceutically acceptable salt, solvate, ester, or prodrug thereof. In one embodiment, the method relates to preparing a medicament for treating a condition which responds to modulation of cyclin-dependent kinase, comprising a therapeutically effective amount of a compound of formula (A), (B), (I), or (II), and any subgenera thereof, or a pharmaceutically acceptable salt, solvate, ester, or prodrug thereof. In one embodiment, CDK is CDK4, CDK6, or CDK4/6.

In one embodiment, a method is provided for protecting a subject from effects of ionizing radiation or chemotherapeutic agents, comprising administering a compound of formula (A), (B), (I), or (II), and any subgenera thereof, or a pharmaceutically acceptable salt, solvate, ester, or prodrug thereof. In one embodiment, the effects of ionizing radiation or chemotherapeutic agents are acute effects or chronic toxic effects in replication-dependent hematopoietic stem cells or progenitor cells (HSPCs).

In one embodiment, a method is provided for protecting hematopoietic cell or progenitor cell populations in subject, comprising administering a compound of formula (A), (B), (I), or (II), and any subgenera thereof, or a pharmaceutically acceptable salt, solvate, ester, or prodrug thereof to a subject in need thereof. In one embodiment, the hematopoietic cell population is a replication-dependent hematopoietic stem cell population. In another embodiment, the subject is exposed to ionizing radiation or chemotherapeutic agents. In other embodiments, the method further comprising administration of a chemotherapeutic agent. In one embodiment, the chemotherapeutic agent is etoposide, carboplatin, topotecan, or a combination thereof. In a certain embodiment, the chemotherapeutic agent is administered within 24 hours or less of the administration of the compound of formula (A), (B), (I), or (II), and any subgenera thereof, or a pharmaceutically acceptable salt, solvate, ester, or prodrug thereof. In one embodiment, a method is provided for protecting a subject from effects of ionizing radiation or chemotherapeutic agents, comprising administering a compound of formula (A), (B), (I), or (II), and any subgenera thereof, or a pharmaceutically acceptable salt, solvate, ester, or prodrug thereof to a subject in need thereof.

DETAILED DESCRIPTION OF THE DISCLOSURE

All publications, patents and patent applications, including any drawings and appendices therein are incorporated by reference in their entirety for all purposes to the same extent as if each individual publication, patent or patent application, drawing, or appendix was specifically and individually indicated to be incorporated by reference in its entirety for all purposes.

While various embodiments of the present disclosure are described herein, it will be obvious to those skilled in the art that such embodiments are provided by way of example only. Numerous modifications and changes to, and variations and substitutions of, the embodiments described herein will be apparent to those skilled in the art without departing from the disclosure. It is understood that various alternatives to the embodiments described herein may be employed in practicing the disclosure. It is also understood that every embodiment of the disclosure may optionally be combined with any one or more of the other embodiments described herein which are consistent with that embodiment.

Where elements are presented in list format (e.g., in a Markush group), it is understood that each possible subgroup of the elements is also disclosed, and any one or more elements can be removed from the list or group.

It is also understood that, unless clearly indicated to the contrary, in any method described or claimed herein that includes more than one act, the order of the acts of the method is not necessarily limited to the order in which the acts of the method are recited, but the disclosure encompasses embodiments in which the order is so limited.

It is further understood that, in general, where an embodiment in the description or the claims is referred to as comprising one or more features, the disclosure also encompasses embodiments that consist of, or consist essentially of, such feature(s).

It is also understood that any embodiment of the disclosure, e.g., any embodiment found within the prior art, can be explicitly excluded from the claims, regardless of whether or not the specific exclusion is recited in the specification.

Headings are included herein for reference and to aid in locating certain sections. Headings are not intended to limit the scope of the embodiments and concepts described in the sections under those headings, and those embodiments and concepts may have applicability in other sections throughout the entire disclosure.

I. Definitions

While the following terms are believed to be well understood by one of ordinary skill in the art, the following definitions are set forth to facilitate explanation of the presently disclosed subject matter.

Throughout the present specification, the terms "about" and/or "approximately" may be used in conjunction with numerical values and/or ranges. The term "about" is understood to mean those values near to a recited value. For example, "about 40 [units]" may mean within ±25% of 40 (e.g., from 30 to 50), within ±20%, ±15%, ±10%, ±9%, ±8%, ±7%, ±6%, ±5%, ±4%, ±3%, ±2%, ±1%, less than ±1%, or any other value or range of values therein or therebelow. Furthermore, the phrases "less than about [a value]" or "greater than about [a value]" should be understood in view of the definition of the term "about" provided herein. The terms "about" and "approximately" may be used interchangeably. Whenever the term "about" or "approximately" precedes the first numerical value in a series of two or more numerical values, the term "about" or "approximately" applies to all numerical values listed in the series. In certain embodiments, the term "about" or "approximately" means within one standard deviation.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

The term "a" or "an" or "the" refers to one or more of that entity; for example, "a kinase inhibitor" refers to one or more kinase inhibitors or at least one kinase inhibitor. As such, the terms "a" (or "an"), "one or more" and "at least one" are used interchangeably herein. In addition, reference to "an inhibitor" by the indefinite article "a" or "an" does not exclude the possibility that more than one of the inhibitors is present, unless the context clearly requires that there is one and only one of the inhibitors.

When the terms "no more than" or "less than" precedes the first numerical value in a series of two or more numerical values, the term "no more than" or "less than" applies to each one of the numerical values in that series of numerical values.

As used herein, the verb "comprise" as is used in this description and in the claims and its conjugations are used in its non-limiting sense to mean that items following the word are included, but items not specifically mentioned are not excluded. The present invention may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The term "exemplary" as used herein means "serving as an example, instance, or illustration". Any embodiment characterized herein as "exemplary" is not necessarily to be construed as preferred or advantageous over other embodiments.

All weight percentages (i.e., "% by weight" and "wt. %" and w/w) referenced herein, unless otherwise indicated, are measured relative to the total weight of the pharmaceutical composition.

As used herein, "substantially" or "substantial" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking, the nearness of completion will be so as to have the same overall result as if absolute and total completion were obtained. The use of "substantially" is equally applicable when used in a negative connotation to refer to the complete or near complete lack of action, characteristic, property, state, structure, item, or result. For example, a composition that is "substantially free of" other active agents would either completely lack other active agents, or so nearly completely lack other active agents that the effect would be the same as if it completely lacked other active agents. In other words, a composition that is "substantially free of" an ingredient or element or another active agent may still contain such an item as long as there is no measurable effect thereof.

The terms below, as used herein, have the following meanings, unless indicated otherwise:

"Acyl" refers to —C(=O)-alkyl radical.

"Amino" refers to the —$NH_2$ radical.

"Cyano" refers to the —CN radical.

"Halo" "halide" or "halogen" refers to bromo, chloro, fluoro or iodo radical.

"Hydroxy" or "hydroxyl" refers to the —OH radical.

"Imino" refers to the =NH substituent.

"Nitro" refers to the —$NO_2$ radical.

"Oxo" refers to the =O substituent.

"Thioxo" refers to the =S substituent.

"Sulfhydryl" and "mercapto" refers to —SH radical.

"Alkyl" or "alkyl group" refers to a fully saturated, straight (linear) or branched hydrocarbon chain radical having from one to twenty carbon atoms, and which is attached to the rest of the molecule by a single bond. Alkyls comprising any number of carbon atoms from 1 to 20 are included. An alkyl comprising up to 20 carbon atoms is a $C_1$-$C_{20}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted. The term "lower alkyl" refers to a $C_1$-$C_6$ alkyl, which can be linear or branched, for example including branched $C_3$-$C_6$ alkyl.

"Alkylene", "-alkyl-" or "alkylene chain" refers to a fully saturated, straight or branched divalent hydrocarbon chain radical, and having from one to twenty carbon atoms. Non-limiting examples of $C_1$-$C_{20}$ alkylene include methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain can be optionally substituted.

"Alkenyl" or "alkenyl group" refers to a straight or branched hydrocarbon chain radical having from two to twenty carbon atoms, and having one or more carbon-carbon double bonds. Each alkenyl group is attached to the rest of the molecule by a single bond. Alkenyl group comprising any number of carbon atoms from 2 to 20 are included. An alkenyl group comprising up to 20 carbon atoms is a $C_2$-$C_{20}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkyl group can be optionally substituted.

"Alkenylene" or "alkenylene chain" refers to a straight or branched divalent hydrocarbon chain radical, having from two to twenty carbon atoms, and having one or more carbon-carbon double bonds. Non-limiting examples of $C_2$-$C_{20}$ alkenylene include ethene, propene, butene, and the like. The alkenylene chain is attached to the rest of the molecule through a single bond and to the radical group through a single bond. The points of attachment of the alkenylene chain to the rest of the molecule and to the radical group can be through one carbon or any two carbons within the chain. Unless stated otherwise specifically in the specification, an alkenylene chain can be optionally substituted.

"Alkynyl" or "alkynyl group" refers to a straight or branched hydrocarbon chain radical having from two to twenty carbon atoms, and having one or more carbon-carbon triple bonds. Each alkynyl group is attached to the rest of the molecule by a single bond. Alkynyl group comprising any number of carbon atoms from 2 to 20 are included. An alkynyl group comprising up to 20 carbon atoms is a $C_2$-$C_{20}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise specifically in the specification, an alkyl group can be optionally substituted.

"Alkynylene" or "alkynylene chain" refers to a straight or branched divalent hydrocarbon chain radical, having from two to twenty carbon atoms, and having one or more carbon-carbon triple bonds. Non-limiting examples of $C_2$-$C_{20}$ alkynylene include ethynylene, propargylene and the like. The alkynylene chain is attached to the rest of the molecule through a single bond and to the radical group through a single bond. The points of attachment of the alkynylene chain to the rest of the molecule and to the radical group can be through one carbon or any two carbons within the chain. Unless stated otherwise specifically in the specification, an alkynylene chain can be optionally substituted.

"Alkoxy" or "—O-alkyl" refers to a radical of the formula —$OR_a$ where $R_a$ is an alkyl, alkenyl or alknyl radical as defined above containing one to twenty carbon atoms. Unless stated otherwise specifically in the specification, an alkoxy group can be optionally substituted.

"Alkylamino" refers to a radical of the formula —$NHR_a$ or —$NR_aR_a$ where each $R_a$ is, independently, an alkyl, alkenyl or alkynyl radical as defined above containing one to twelve carbon atoms. Unless stated otherwise specifically in the specification, an alkylamino group can be optionally substituted.

"Alkylcarbonyl" refers to the —C(=O)$R_a$ moiety, wherein $R_a$ is an alkyl, alkenyl or alkynyl radical as defined above. A non-limiting example of an alkyl carbonyl is the methyl carbonyl ("acetal") moiety. Alkylcarbonyl groups can also be referred to as "Cw-Cz acyl" where w and z depicts the range of the number of carbon in $R_a$, as defined above. For example, "$C_1$-$C_{10}$ acyl" refers to alkylcarbonyl group as defined above, where $R_a$ is $C_1$-$C_{10}$ alkyl, $C_1$-$C_{10}$ alkenyl, or $C_1$-$C_{10}$ alkynyl radical as defined above. Unless stated otherwise specifically in the specification, an alkyl carbonyl group can be optionally substituted.

The term "aminoalkyl" refers to an alkyl group that is substituted with one or more —$NH_2$ groups. In certain embodiments, an aminoalkyl group is substituted with one, two, three, four, five or more —$NH_2$ groups. An aminoalkyl group may optionally be substituted with one or more additional substituents as described herein.

"Aryl" refers to a hydrocarbon ring system radical comprising hydrogen, 6 to 18 carbon atoms and at least one aromatic ring. For purposes of this invention, the aryl radical can be a monocyclic, bicyclic, tricyclic or tetracyclic ring system, which can include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" is meant to include aryl radicals that are optionally substituted.

"Aralkyl", "arylalkyl" or "-alkylaryl" refers to a radical of the formula —$R_b$—$R_c$ where $R_b$ is an alkylene, alkenylene or alkynylene group as defined above and $R_c$ is one or more aryl radicals as defined above, for example, benzyl, diphenylmethyl and the like. Unless stated otherwise specifically in the specification, an aralkyl group can be optionally substituted.

"Carbocyclyl," "carbocyclic ring" or "carbocycle" refers to a rings structure, wherein the atoms which form the ring are each carbon. Carbocyclic rings can comprise from 3 to 20 carbon atoms in the ring. Carbocyclic rings include aryls and cycloalkyl. Cycloalkenyl and cycloalkynyl as defined herein. Unless stated otherwise specifically in the specification, a carbocyclyl group can be optionally substituted.

"Cycloalkyl" refers to a stable non-aromatic monocyclic or polycyclic fully saturated hydrocarbon radical consisting solely of carbon and hydrogen atoms, which can include fused or bridged ring systems, having from three to twenty carbon atoms, preferably having from three to ten carbon atoms, and which is attached to the rest of the molecule by a single bond. Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, 7,7-dimethyl-bicyclo[2.2.1]heptanyl, bicyclo[3.1.0]hexane, octahydropentalene, bicyclo[1.1.1]pentane, cubane, and the like. Unless otherwise stated specifically in the specification, a cycloalkyl group can be optionally substituted.

"Cycloalkenyl" refers to a stable non-aromatic monocyclic or polycyclic hydrocarbon radical consisting solely of carbon and hydrogen atoms, having one or more carbon-carbon double bonds, which can include fused or bridged ring systems, having from three to twenty carbon atoms, preferably having from three to ten carbon atoms, and which is attached to the rest of the molecule by a single bond. Monocyclic cycloalkenyl radicals include, for example, cyclopentenyl, cyclohexenyl, cycloheptenyl, cyclooctenyl, and the like. Polycyclic cycloalkenyl radicals include, for example, bicyclo[2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon radical consisting solely of carbon and hydrogen atoms, having one or more carbon-carbon triple bonds, which can include fused or bridged ring systems, having from three to twenty carbon atoms, preferably having from three to ten carbon atoms, and which is attached to the rest of the molecule by a single bond. Monocyclic cycloalkynyl radicals include, for example, cycloheptynyl, cyclooctynyl, and the like. Unless otherwise stated specifically in the specification, a cycloalkynyl group can be optionally substituted.

"Cycloalkylalkyl" or "-alkylcycloalkyl" refers to a radical of the formula —$R_b$—$R^a$ where $R_b$ is an alkylene, alkenylene, or alkynylene group as defined above and $R_d$ is a cycloalkyl, cycloalkenyl, cycloalkynyl radical as defined above. Unless stated otherwise specifically in the specification, a cycloalkylalkyl group can be optionally substituted.

"Haloalkyl" refers to an alkyl radical, as defined above, that is substituted by one, two, three, four, five, six or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group can be optionally substituted.

"Haloalkenyl" refers to an alkenyl radical, as defined above, that is substituted by one, two, three, four, five, six or more halo radicals, as defined above, e.g., 1-fluoropropenyl, 1,1-difluorobutenyl, and the like. Unless stated otherwise specifically in the specification, a haloalkenyl group can be optionally substituted.

"Haloalkynyl" refers to an alkynyl radical, as defined above, that is substituted by one, two, three, four, five, six or more halo radicals, as defined above, e.g., 1-fluoropropynyl, 1-fluorobutynyl, and the like. Unless stated otherwise specifically in the specification, a haloalkenyl group can be optionally substituted.

"Heterocyclyl," "heterocyclic ring" or "heterocycle" refers to a stable 3- to 20-membered non-aromatic ring radical which consists of two to twelve carbon atoms and from one to six heteroatoms selected from the group consisting of nitrogen, oxygen and sulfur. Heterocyclcyl or heterocyclic rings include heteroaryls as defined below. Unless stated otherwise specifically in the specification, the heterocyclyl radical can be a monocyclic, bicyclic, tricyclic or tetracyclic ring system, which can include fused or bridged ring systems; and the nitrogen, carbon or sulfur atoms in the heterocyclyl radical can be optionally oxidized; the nitrogen atom can be optionally quaternized; and the heterocyclyl radical can be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, a heterocyclyl group can be optionally substituted.

The term "hydroxyalkyl" or "hydroxylalkyl" refers to an alkyl group that is substituted with one or more hydroxyl (—OH) groups. In certain embodiments, a hydroxyalkyl group is substituted with one, two, three, four, five or more —OH groups. A hydroxyalkyl group may optionally be substituted with one or more additional substituents as described herein.

The term "hydrocarbyl" refers to a monovalent hydrocarbon radical, whether aliphatic, partially or fully unsaturated, acyclic, cyclic or aromatic, or any combination of the preceding. In certain embodiments, a hydrocarbyl group has 1 to 40 or more, 1 to 30 or more, 1 to 20 or more, or 1 to 10 or more, carbon atoms. The term "hydrocarbylene" refers to a divalent hydrocarbyl group. A hydrocarbyl or hydrocarbylene group may optionally be substituted with one or more substituents as described herein.

The term "heterohydrocarbyl" refers to a hydrocarbyl group in which one or more of the carbon atoms are independently replaced by a heteroatom selected from oxygen, sulfur, nitrogen and phosphorus. In certain embodiments, a heterohydrocarbyl group has 1 to 40 or more, 1 to 30 or more, 1 to 20 or more, or 1 to 10 or more, carbon atoms, and 1 to 10 or more, or 1 to 5 or more, heteroatoms. The term "heterohydrocarbylene" refers to a divalent hydrocarbyl group. Examples of heterohydrocarbyl and heterohydrocarbylene groups include without limitation ethylene glycol and polyethylene glycol moieties, such as (—$CH_2CH_2O$—)$_n$H (a monovalent heterohydrocarbyl group) and (—$CH_2CH_2O$—)$_n$ (a divalent heterohydrocarbylene group) where n is an integer from 1 to 12 or more, and propylene glycol and polypropylene glycol moieties, such as (—$CH_2CH_2CH_2O$—)$_n$H and (—$CH_2CH(CH_3)O$—)$_n$H (monovalent heterohydrocarbyl groups) and (—$CH_2CH_2CH_2O$—)$_n$ and (—$CH_2CH(CH_3)O$—)$_n$ (divalent heterohydrocarbylene groups) where n is an integer from 1 to 12 or more. A heterohydrocarbyl or heterohydrocarbylene group may optionally be substituted with one or more substituents as described herein.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group can be optionally substituted.

"Heterocyclylalkyl" or "-alkylheterocyclyl" refers to a radical of the formula —$R_b$—$R_e$ where $R_b$ is an alkylene, alkenylene, or alkynylene chain as defined above and $R_e$ is a heterocyclyl radical as defined above, and if the heterocyclyl is a nitrogen-containing heterocyclyl, the heterocyclyl can be attached to the alkyl, alkenyl, alkynyl radical at the nitrogen atom. Unless stated otherwise specifically in the specification, a heterocyclylalkyl group can be optionally substituted.

"Heteroaryl" refers to a 5- to 20-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical can be a monocyclic, bicyclic, tricyclic or tetracyclic ring system, which can include fused or bridged ring systems; and the nitrogen, carbon or sulfur atoms in the heteroaryl radical can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group can be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group can be optionally substituted.

"Heteroarylalkyl" or "-alkylheteroaryl" refers to a radical of the formula —$R_b$—$R_f$ where $R_b$ is an alkylene, alkenylene, or alkynylene chain as defined above and $R_f$ is a heteroaryl radical as defined above. Unless stated otherwise specifically in the specification, a heteroarylalkyl group can be optionally substituted.

"Thioalkyl" refers to a radical of the formula —$SR_a$ where $R_a$ is an alkyl, alkenyl, or alkynyl radical as defined above containing one to twelve carbon atoms. Unless stated otherwise specifically in the specification, a thioalkyl group can be optionally substituted.

The term "substituted" used herein means any of the above groups (i.e., alkyl, alkylene, alkenyl, alkenylene, alkynyl, alkynylene, alkoxy, alkylamino, alkylcarbonyl, thioalkyl, aryl, aralkyl, carbocyclyl, cycloalkyl, cycloalkenyl, cycloalkynyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with halide, cyano, nitro, hydroxyl, sulfhydryl, amino, —$OR_g$, —$SR_g$, —$NR_hR_i$, alkyl, alkenyl, alkynyl, haloalkyl, hydroxyalkyl, aminoalkyl, -alkylcycloalkyl, -alkylheterocyclyl, -alkylaryl, -alkylheteroaryl, cycloalkyl, heterocyclyl, aryl, heteroaryl, —C(=O)$R_g$, —C(=NR$_j$)$R_g$, —S(=O)$R_g$, —S(=O)$_2R_g$, —S(=O)$_2$O$R_k$, —C(=O)O$R_k$, —OC(=O)$R_g$, —C(=O) NR$_h$R$_i$, —NR$_g$C(=O)$R_g$, —S(=O)$_2$NR$_h$R$_i$, —NR$_g$S(=O)$_2$R$_g$, —OC(=O)OR$_g$, —OC(=O)NR$_h$R$_i$, —NR$_g$C(=O)OR$_g$, —NR$_g$C(=O)NR$_h$R$_i$, —NR$_g$C(=NR$_j$)NR$_h$R$_i$, —P(=O)(R$_g$)$_2$, —P(=O)(OR$_k$)R$_g$, —P(=O)(OR$_k$)$_2$, —OP(=O)(R$_g$)$_2$, —OP(=O)(OR$_k$)R$_g$, and —OP(=O)(OR$_k$)$_2$, wherein: each occurrence of $R_g$ is independently selected from hydrogen, alkyl, haloalkyl, hydroxyalkyl, aminoalkyl, -alkylcycloalkyl, -alkylheterocyclyl, -alkylaryl, -alkylheteroaryl, cycloalkyl, heterocyclyl, aryl or heteroaryl; each occurrence of $R_h$ and $R_i$ is independently selected from hydrogen, alkyl, haloalkyl, hydroxyalkyl, aminoalkyl, -alkylcycloalkyl, -alkylheterocyclyl, -alkylaryl, -alkylheteroaryl, cycloalkyl, heterocyclyl, aryl or heteroaryl, or $R_h$ and $R_i$, together with the nitrogen atom to which they are attached, form a heterocyclic or heteroaryl ring; each occurrence of $R_j$ independently is hydrogen, —$OR_g$, alkyl, haloalkyl, hydroxyalkyl, aminoalkyl, -alkylcycloalkyl, -alkylheterocyclyl, -alkylaryl, -alkylheteroaryl, cycloalkyl, heterocyclyl, aryl or heteroaryl; and each occurrence of $R_k$ independently is hydrogen, Z, alkyl, haloalkyl, hydroxyalkyl, aminoalkyl, -alkylcycloalkyl, -alkylheterocyclyl, -alkylaryl, -alkylheteroaryl, cycloalkyl, heterocyclyl, aryl or heteroaryl, wherein each occurrence of Z independently is H$^+$, Li$^+$, Na$^+$, K$^+$, Cs$^+$, Mg$^{+2}$, Ca$^{+2}$, or —$^+$N(R$_g$)$_2$R$_n$R$_i$.

As used herein, the symbol

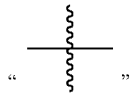

(hereinafter can be referred to as "a point of attachment bond") denotes a bond that is a point of attachment between two chemical entities, one of which is depicted as being attached to the point of attachment bond and the other of which is not depicted as being attached to the point of attachment bond. For example,

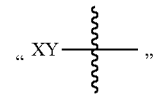

indicates that the chemical entity "XY" is bonded to another chemical entity via the point of attachment bond. Furthermore, the specific point of attachment to the non-depicted chemical entity can be specified by inference. For example, the compound CH$_3$—R$^3$, wherein R$^3$ is H or

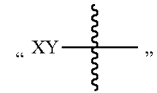

infers that when R$^3$ is "XY", the point of attachment bond is the same bond as the bond by which R$^3$ is depicted as being bonded to CH$_3$.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring can be replaced with a nitrogen atom.

The invention disclosed herein is also meant to encompass the in vivo metabolic products of the disclosed compounds. Such products can result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

As used herein, a "subject" can be a human, non-human primate, mammal, rat, mouse, cow, horse, pig, sheep, goat, dog, cat and the like. The terms "subject" and "patient" are used interchangeably herein in reference, e.g., to a mammalian subject, such as a human subject. The subject can be suspected of having or at risk for having a cancer, such as prostate cancer, breast cancer, ovarian cancer, salivary gland carcinoma, or endometrial cancer, or suspected of having or at risk for having acne, hirsutism, alopecia, benign prostatic hyperplasia, ovarian cysts, polycystic ovary disease, precocious puberty, spinal and bulbar muscular atrophy, or age-related macular degeneration. Diagnostic methods for various cancers, such as prostate cancer, breast cancer, ovarian cancer, bladder cancer, pancreatic cancer, hepatocellular cancer, salivary gland carcinoma, or endometrial cancer, and diagnostic methods for acne, hirsutism, alopecia, benign prostatic hyperplasia, ovarian cysts, polycystic ovary disease, precocious puberty, spinal and bulbar muscular atrophy, or age-related macular degeneration and the clinical delineation of cancer, such as prostate cancer, breast cancer, ovarian cancer, bladder cancer, pancreatic cancer, hepatocellular cancer, salivary gland carcinoma, or endometrial cancer, diagnoses and the clinical delineation of acne, hirsutism, alopecia, benign prostatic hyperplasia, ovarian cysts, polycystic ovary disease, precocious puberty, spinal and bulbar muscular atrophy, or age-related macular degeneration are known to those of ordinary skill in the art.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event of circumstances can or cannot occur, and that the description includes instances where said event or circumstance occurs and instances in which it does not. For example, "optionally substituted aryl" means that the aryl radical can or cannot be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent can be water, in which case the solvate can be a hydrate. Alternatively, the solvent can be an organic solvent. Thus, the compounds of the present invention can exist as a hydrate, including a monohydrate, dihydrate, hemihydrate, sesquihydrate, trihydrate, tetrahydrate and the like, as well as the corresponding solvated forms. The compound of the invention can be true solvates, while in other cases, the compound of the invention can merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

The term "pharmaceutically acceptable" refers to a substance (e.g., an active ingredient or an excipient) that is suitable for use in contact with the tissues and organs of a subject without excessive irritation, allergic response, immunogenecity and toxicity, is commensurate with a reasonable benefit/risk ratio, and is effective for its intended use. A "pharmaceutically acceptable" carrier or excipient of a pharmaceutical composition is also compatible with the other ingredients of the composition.

"An "effective amount" refers to a therapeutically effective amount or a prophylactically effective amount. A "therapeutically effective amount" refers to an amount effective, at dosages and for periods of time necessary, to achieve the desired therapeutic result, such as reduced tumor size, increased life span, increased life expectancy, or sufficient to prevent development of, or to alleviate to some extent, or to abrogate, the disease or disorder being treated. The term "therapeutically effective amount" also refers to an amount of a compound that is sufficient to elicit a biological or medical response of a cell, tissue, organ, system, animal or human which is sought by a researcher, veterinarian, medical doctor or clinician. A therapeutically effective amount of a compound can vary according to factors such as the disease state, age, sex, and weight of the subject, and the ability of the compound to elicit a desired response in the subject. Dosage regimens can be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as smaller tumors, increased life span, increased life expectancy or prevention of the progression of prostate cancer to a castration-resistant form. Typically, a prophylactic dose is used in subjects prior to or at an earlier stage of disease, so that a prophylactically effective amount can be less than a therapeutically effective amount.

"Treating" or "treatment" as used herein covers the treatment of the disease or condition of interest in a mammal, preferably a human, having the disease or condition of interest, and includes:

1. preventing the disease or condition from occurring in a mammal, in particular, when such mammal is predisposed to the condition but has not yet been diagnosed as having it;
2. inhibiting the disease or condition, i.e., arresting its development;
3. relieving the disease or condition, i.e., causing regression of the disease or condition; or
4. relieving the symptoms resulting from the disease or condition, i.e., relieving pain without addressing the underlying disease or condition. As used herein, the terms "disease" and "condition" can be used interchangeably or can be different in that the particular malady or condition cannot have a known causative agent (so that etiology has not yet been worked out) and it is therefore not yet recognized as a disease but only as an undesirable condition or syndrome, wherein a more or less specific set of symptoms have been identified by clinicians.

The terms "prevent", "preventing", and "prevention" include delaying or precluding the onset of a disease or disorder, precluding a subject from acquiring a disease or disorder, and reducing a subject's risk of acquiring a disease or disorder.

The compounds of the invention, or their pharmaceutically acceptable salts can contain one or more asymmetric centers and can thus give rise to enantiomers, diastereomers, and other stereoisomeric forms that can be defined, in terms of absolute stereochemistry, as (R)- or (S)- or, as (D)- or (L)- for amino acids. The present invention is meant to include all such possible isomers, as well as their racemic and optically pure forms whether or not they are specifically depicted herein. Optically active (+) and (−), (R)- and (S)-, or (D)- and (L)- isomers can be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposable mirror images of one another.

A "tautomer" refers to a proton shift from one atom of a molecule to another atom of the same molecule. The present invention includes tautomers of any said compounds.

The terms "pharmaceutical combination," "therapeutic combination" or "combination" as used herein, refers to a single dosage form comprising at least two therapeutically active agents, or separate dosage forms comprising at least two therapeutically active agents together or separately for use in combination therapy. For example, one therapeutically active agent may be formulated into one dosage form and the other therapeutically active agent may be formulated into a single or different dosage forms. For example, one therapeutically active agent may be formulated into a solid oral dosage form whereas the second therapeutically active agent may be formulated into a solution dosage form for parenteral administration.

The chemical naming protocol and structure diagrams used herein are a modified form of the I.U.P.A.C. nomenclature system, using the ACD/Name Version 9.07 software program, ChemDraw Ultra Version 11.0.1 and/or ChemDraw Ultra Version 14.0 software naming program (CambridgeSoft). For complex chemical names employed herein, a substituent group is named before the group to which it attaches. For example, cyclopropylethyl comprises an ethyl backbone with cyclopropyl substituent. Except as described below, all bonds are identified in the chemical structure diagrams herein, except for some carbon atoms, which are assumed to be bonded to sufficient hydrogen atoms to complete the valency.

II. Compounds of the Present Disclosure

One embodiment of the present disclosure relates to novel aminopyrimidine compounds. In one embodiment, the present disclosure relates to compound of Formula (A) of Formula (B):

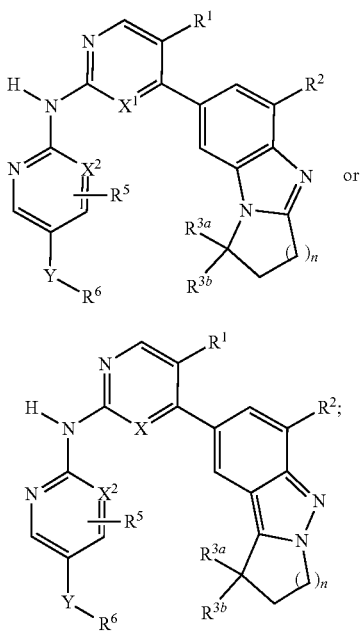

or a pharmaceutically acceptable salt, solvate, ester, or prodrug thereof;
wherein,
$X^1$ and $X^2$ are each independently CH or N;
$R^1$ is selected from hydrogen, fluoro, chloro, bromo, methyl, ethyl, hydroxyl, methoxy, ethoxy, isopropoxy, cyclopropoxy, —$OCF_3$, —$OCH_2CF_3$, —$OCH_2CHF_2$, —$CF_3$, —$CHF_2$, —CHO, —$CH_2OH$, —$CONH_2$, —$CO_2Me$, —CONHMe, —$CONMe_2$, or cyano;
$R^2$ is selected from hydrogen, fluoro, chloro, methyl, hydroxyl, methoxy, ethoxy, isopropoxy, cyclopropoxy, —$OCF_3$, —$CF_3$, —$CHF_2$, —$CH_2OH$, —$CONH_2$, —CONHMe, —$CONMe_2$, or cyano;
$R^{3a}$ and $R^{3b}$ are each independently H, —$C_{1-6}$ alkyl, or —$C_{1-6}$ haloalkyl; or
alternatively, $R^{3a}$ and $R^{3b}$, taken together with the carbon atom to which they are both attached, form a 3-7 membered ring, optionally containing up to two heteroatoms selected from O, $S(O)_x$, or $NR^{11}$, or forms a 7-12 membered heterobicyclic ring which may be fused, bridged or spiro, and includes one to three heteroatoms selected from O, $S(O)_x$, or $NR^{11}$, and wherein the 3-7 membered ring and the 7-12 membered heterobicyclic ring are optionally substituted with up to three substituents selected from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano or halo;
$R^5$ is independently selected from H, —$C_{1-6}$ alkyl, halogen, —CN, —$CD_3$, —$CHF_2$, or —$CF_3$;
Y is -G-, -L-, -G-L-, -L-G-, -L-G-L-, -G-L-G-, -L-G-L-G-, or -G-L-G-L-;
G is a divalent linker that can be connected in a chain in either direction, which is selected from absent, —O—, —$S(O)_x$—, —NR"—, —C(=O)—, —C(=NR")—, —C(=$NOR^o$)—, —C(=O)NR"—, —C(=O)O—, —C(=NR")NR"—, —C(=$NOR^o$)NR"—, —$S(=O)_2$NR"—, —NR"C(=O)NR"—, —OC(=O)NR"—, or —NR"$S(=O)_2$NR"—;

L is a divalent linker that can be connected in a chain in either direction, which is selected from absent, —$(CR^aR^b)_p$—, —$(CR^aR^b)_p$-cycloalkyl-$(CR^aR^b)_p$—, or —$(CR^aR^b)_p$-heterocyclyl-$(CR^aR^b)_p$—, wherein cycloalkyl and heterocyclyl can be optionally further substituted with up to three substituents selected from F, —OH, oxo, —$C_{1-3}$ alkyl, —$C_{1-3}$ haloalkyl, —$CH_2OH$, —$CH_2CH_2OH$, —$CH_2CH_2CH_2OH$, —NR"R", aziridinyl, azetidinyl, pyrrolidinyl, piperidinyl, or morpholinyl;
$R^6$ is H, —$C_{1-6}$ alkyl, —$C_{1-6}$ haloalkyl, —$C_{3-12}$ cycloalkyl, —NR"$R^7$, or a heterocyclyl, wherein —$C_{1-6}$ alkyl, —$C_{1-6}$ haloalkyl, —$C_{3-12}$ cycloalkyl and heterocyclyl are each optionally substituted with up to three substituents independently selected from $C_{1-6}$ alkyl, —$C_{1-6}$ haloalkyl, F, —OH, oxo, —$CH_2OH$, —$CH_2CH_2OH$, —C(=O)$CH_2OH$, —$CH_2CH_2CH_2OH$, —NR"R", aziridinyl, azetidinyl, pyrrolidinyl, piperidinyl, or morpholinyl;
$R^7$ is H, —$C_{1-6}$ alkyl, —$C_{1-6}$ haloalkyl, —$C_{3-12}$ cycloalkyl, heterocyclyl, —$C_6$-$C_{12}$ aryl, $C_6$-$C_{12}$ aryl-$C_1$-$C_6$ alkyl-, 5-12 membered heteroaryl, or 5-12 membered heteroaryl-$C_1$-$C_6$ alkyl-, wherein —$C_{3-12}$ cycloalkyl, heterocyclyl, —$C_6$-$C_{12}$ aryl, $C_6$-$C_{12}$ aryl-$C_1$-$C_6$ alkyl-, 5-12 membered heteroaryl, and 5-12 membered heteroaryl-$C_1$-$C_6$ alkyl- can be optionally further substituted with up to three substituents independently selected from F, —OH, oxo, —$C_{1-3}$ alkyl, —$C_{1-3}$ haloalkyl, —$CH_2OH$, —$CH_2CH_2OH$, —$CH_2CH_2CH_2OH$, —NR"R", aziridinyl, azetidinyl, pyrrolidinyl, piperidinyl, or morpholinyl;
$R^{11}$ is H or —$C_{1-6}$ alkyl;
$R^a$ and $R^b$ are each independently H, F, —$C_{1-6}$ alkyl, or —$C_{1-6}$ haloalkyl;
R" is H, —$C_{1-6}$ alkyl, —$C_{1-6}$ haloalkyl, $C_{1-6}$ alkyl-C(=O)—, or $C_{1-6}$ alkyl-S(=O)$_2$—;
n is 1, 2, or 3;
p is independently 0, 1, or 2; and
x is 0, 1, or 2.
In one embodiment of the compounds of formula (A) or formula (B) excludes the compounds exemplified in WO2017/071516 and WO 2016/173505.
In one embodiment of the compounds of formula (A) or formula (B), Y—$R^6$ does not comprise the following sequence in either direction: —O—$(CR^aR^b)$—O—, —O—$(CR^aR^b)$—NR"—, —O—$(CR^aR^b)$—$S(O)_x$—, —NR"—$(CR^aR^b)$—N, —NR"—$(CR^aR^b)$—$S(O)_x$—, or —$S(O)_x$—$(CR^aR^b)$—$S(O)_x$—.
In one embodiment, in formula (A), Y—$R^6$ is not:

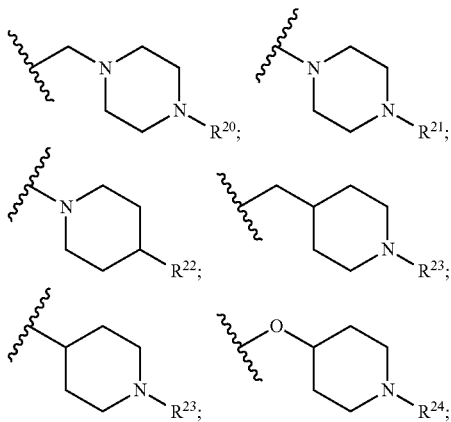

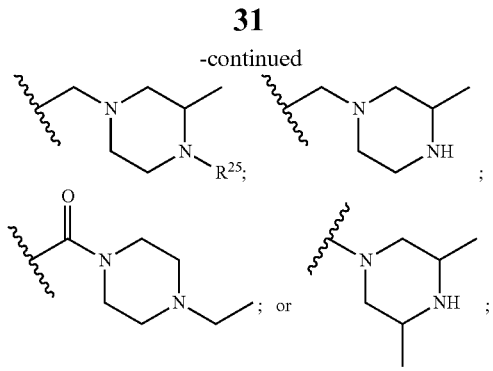

wherein
R²⁰ is H, methyl, ethyl, isopropyl, cyclopropyl, or —CH₂CH₂F;
R²¹ is H, methyl, ethyl, —CH₂CH₂OH or —CH₂CH₂F;
R²² is —NH₂ or —NMe₂;
R²³ is H, methyl, or ethyl;
R²⁴ is H or ethyl; and
R²⁵ is H or methyl.

In one embodiment, in formula (A), Y—R⁶ is not:

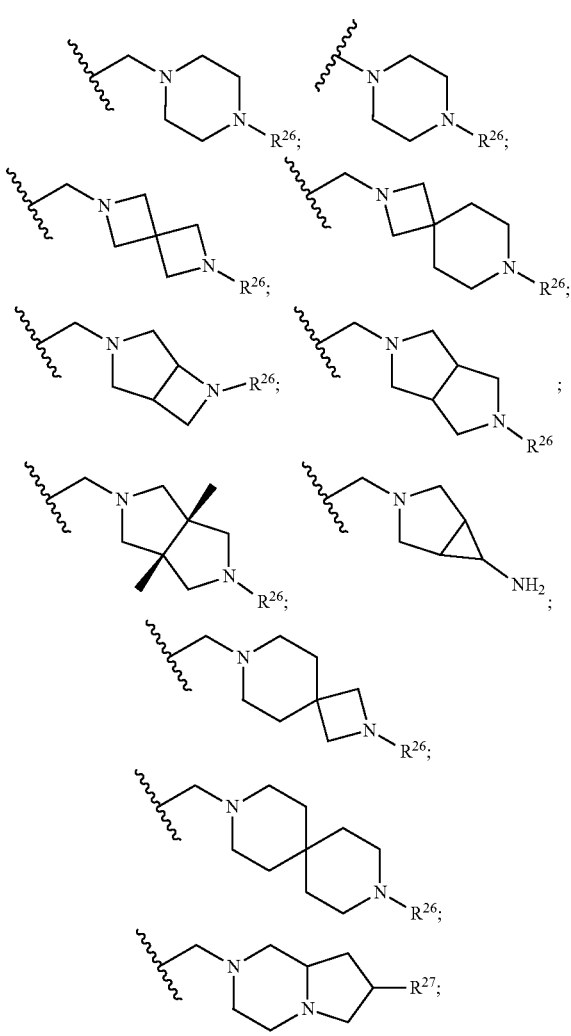

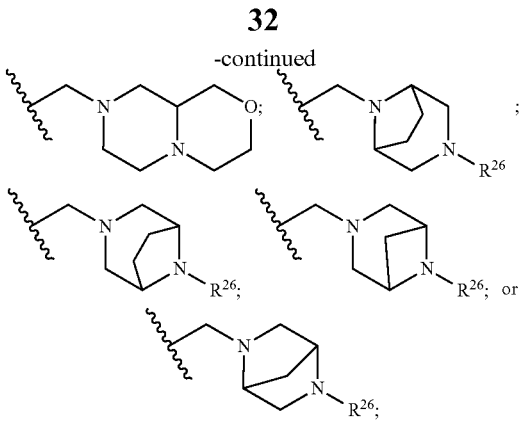

wherein
R²⁶ is H, methyl, or ethyl; and
R²⁷ is H or —OH.

In one embodiment of the compounds of formula (A) or formula (B):
R¹ is selected from hydrogen, fluoro, chloro, methyl, or cyano;
R² is selected from hydrogen, fluoro, or cyano;
R³ᵃ and R³ᵇ are each independently H, —C₁₋₃ alkyl, or —C₁₋₃ haloalkyl; or
alternatively, R³ᵃ and R³ᵇ, taken together with the carbon atom to which they are both attached, form a 3-7 membered cycloalkyl ring, which are optionally substituted with up to three substituents selected from hydroxyl, —C₁₋₆ alkoxy, cyano, oxo, or halo;
R⁵ is independently selected from H, —C₁₋₃ alkyl, F, Cl, —CN, or —CD₃;
G is a divalent linker that can be connected in a chain in either direction; and
G is independently selected from absent, —O—, —S(O)ₓ—, —NR″—, —C(=O)—, —C(=O)NR″—, —C(=O)O—, or —S(=O)₂NR″—;
Rᵃ and Rᵇ are each independently H, F, —C₁₋₃ alkyl, or —C₁₋₃ haloalkyl;
R″ is H, —C₁₋₃ alkyl, —C₁₋₃ haloalkyl, C₁₋₃ alkyl-C(=O)—, or C₁₋₃ alkyl-S(=O)₂—;
R⁶ is a H, —C₁₋₃ alkyl, —C₁₋₃ haloalkyl, —C₃₋₁₂ cycloalkyl, —NR″R⁷, or a heterocyclyl, wherein —C₁₋₃ alkyl, —C₁₋₃ haloalkyl, —C₃₋₁₂ cycloalkyl, and heterocyclyl are each optionally substituted with up to three substituents independently selected from F, —OH, oxo, —CH₂OH, —CH₂CH₂OH, —C(=O)CH₂OH, —CH₂CH₂CH₂OH, —NR″R″, aziridinyl, azetidinyl, pyrrolidinyl, piperidinyl, or morpholinyl; and
R⁷ is H, —C₁₋₃ alkyl, —C₁₋₃ haloalkyl, —C₆-C₁₂ aryl, C₆-C₁₂ aryl-C₁-C₆ alkyl-, 5-12 membered heteroaryl, or 5-12 membered heteroaryl-C₁-C₆ alkyl-, wherein —C₆-C₁₂ aryl, C₆-C₁₂ aryl-C₁-C₆ alkyl-, 5-12 membered heteroaryl, and 5-12 membered heteroaryl-C₁-C₆ alkyl- can be optionally further substituted with up to three substituents selected from F, —OH, —C₁₋₃ alkyl, —C₁₋₃ haloalkyl, —CH₂OH, —CH₂CH₂OH, —CH₂CH₂CH₂OH, —NR″R″, aziridinyl, azetidinyl, pyrrolidinyl, piperidinyl, or morpholinyl.

In one embodiment of the compounds of formula (A) or formula (B), X¹ is N. In another embodiment of the compound of formula (A) or formula (B), X² is CH. In some embodiments, X² is N.

In one embodiment of the compounds of formula (A) or formula (B), X¹ is N and X² is CH or N. In other embodiments, X¹ is N and X² is CH. In one embodiment, X¹ is CH and $X^2$ is CH or N. In another embodiment, $X^1$ is CH and $X^2$ is CH. In some embodiments, $X^1$ is CH and $X^2$ is N. In other embodiments, $X^1$ is CH or N and $X^2$ is N.

In one embodiment of the compounds of formula (A) or formula (B), $R^1$ is hydrogen, fluoro, chloro, bromo, methyl, ethyl, hydroxyl, methoxy, ethoxy, isopropoxy, cyclopropoxy, —OCF$_3$, —OCH$_2$CF$_3$, —OCH$_2$CHF$_2$, —CF$_3$, —CHF$_2$, —CHO, —CH$_2$OH, or cyano. In another embodiment, $R^1$ is hydrogen, fluoro, chloro, bromo, methyl, methoxy, —OCF$_3$, —CF$_3$, —CHF$_2$, or cyano. In some embodiments, $R^1$ is hydrogen, fluoro, chloro, methyl, or cyano. In other embodiments, $R^1$ is hydrogen, fluoro, chloro, or methyl. In one embodiment, $R^1$ is fluoro or chloro.

In one embodiment of the compounds of formula (A) or formula (B), $R^2$ is hydrogen, fluoro, chloro, methyl, hydroxyl, methoxy, ethoxy, isopropoxy, cyclopropoxy, —OCF$_3$, —CF$_3$, —CHF$_2$, —CH$_2$OH, or cyano. In another embodiment, $R^2$ is hydrogen, fluoro, chloro, methyl, methoxy, —OCF$_3$, —CF$_3$, —CHF$_2$, or cyano. In some embodiments, $R^2$ is hydrogen, fluoro, or cyano. In some embodiments, $R^2$ is hydrogen, fluoro, chloro, methyl, or cyano. In other embodiments, $R^1$ is hydrogen, fluoro, chloro, or methyl. In one embodiment, $R^2$ is fluoro or chloro.

In one embodiment of the compounds of formula (A) or formula (B), $R^{3a}$ and $R^{3b}$ are each independently H, —C$_{1-6}$ alkyl, or —C$_{1-6}$ haloalkyl. In another embodiment, $R^{3a}$ and $R^{3b}$ are each independently H, —C$_{1-3}$ alkyl, or —C$_{1-3}$ haloalkyl. In some embodiments, $R^{3a}$ and $R^{3b}$ are each independently H, methyl, ethyl, n-propyl, or isopropyl. In some embodiments, $R^{3a}$ and $R^{3b}$ are each independently H, methyl, or ethyl. In other embodiments, $R^{3a}$ and $R^{3b}$ are each independently H or methyl. In one embodiment, $R^{3a}$ and $R^{3b}$ are each H. In other embodiments, $R^{3a}$ and $R^{3b}$ are each methyl.

In one embodiment of the compounds of formula (A) or formula (B), $R^{3a}$ and $R^{3b}$ together forms a 3-7 membered cycloalkyl ring, optionally substituted with up to three substituents selected from hydroxyl, C$_{1-6}$ alkoxy, cyano, oxo, or halo.

In one embodiment of the compounds of formula (A) or formula (B), Y is absent and $R^6$ selected from H, —C$_{1-3}$ alkyl, —C$_{1-3}$ haloalkyl, —C$_{3-12}$ cycloalkyl, —NR'R$^7$, or a heterocyclyl, wherein —C$_{1-3}$ alkyl, —C$_{1-3}$ haloalkyl, —C$_{3-12}$ cycloalkyl, and heterocyclyl are each optionally substituted with up to three substituents independently selected from F, —OH, oxo, —CH$_2$OH, —CH$_2$CH$_2$OH, —C(=O)CH$_2$OH, —CH$_2$CH$_2$CH$_2$OH, —NR"R", aziridinyl, azetidinyl, pyrrolidinyl, piperidinyl, or morpholinyl.

In one embodiment of the compounds of formula (A) or formula (B), Y is absent and $R^6$ is heterocyclyl optionally substituted with up to three substituents independently selected from —C$_{1-6}$ alkyl, —C$_{1-6}$ haloalkyl, F, —OH, oxo, —CH$_2$OH, —CH$_2$CH$_2$OH, —C(=O)CH$_2$OH, —CH$_2$CH$_2$CH$_2$OH, or —NR"R". In another embodiment, $R^6$ is pyrrolidinyl optionally substituted with up to three substituents independently selected from —C$_{1-6}$ alkyl, —C$_{1-6}$ haloalkyl, F, —OH, oxo, —CH$_2$OH, —CH$_2$CH$_2$OH, —C(=O)CH$_2$OH, —CH$_2$CH$_2$CH$_2$OH, or —NR"R". In a certain embodiment, $R^6$ is

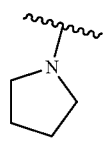

optionally substituted with up to three substituents independently selected from —C$_{1-6}$ alkyl, —C$_{1-6}$ haloalkyl, F, —OH, oxo, —CH$_2$OH, —CH$_2$CH$_2$OH, —C(=O)CH$_2$OH, —CH$_2$CH$_2$CH$_2$OH, or —NR"R". In one embodiment, $R^6$ is

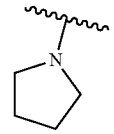 [SMILES: *N1CCCC1]

substituted with —NR"R". In another embodiment, $R^6$ is

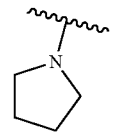 [SMILES: *N1CCCC1]

substituted with —NR"R"; wherein R" is each —C$_{1-6}$ alkyl. In other embodiments, $R^6$ is

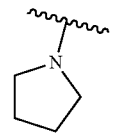

substituted with —NR"R"; wherein R" is each methyl.

In one embodiment of the compounds of formula (A) or formula (B), $R^6$ is cycloalkyl selected from cyclopropyl, cyclobutyl, cyclopentyl, cyclohexyl, bicyclo[3.1.0]hexanyl, octahydropentalenyl, bicycle[1.1.1]pentanyl, or cubanyl, each optionally substituted with up to three substituents selected from F, —OH, oxo, —C$_{1-3}$ alkyl, —CH$_2$OH, —CH$_2$CH$_2$OH, —C(=O)CH$_2$OH, —CH$_2$CH$_2$CH$_2$OH, —NR"R", aziridinyl, azetidinyl, pyrrolidinyl, piperidinyl, or morpholinyl. In another embodiment, $R^6$ is cycloalkyl selected form Table A, wherein the connectivity of each cycloalkyl can be at any one of CH or NH by replacing a hydrogen to form a bond to the heteroaryl containing $X^2$.

TABLE A

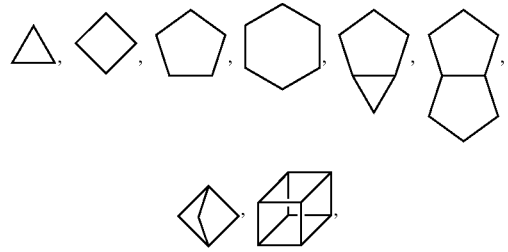

In another embodiment of the compounds of formula (A) or formula (B), $R^6$ is heterocyclyl selected from Table B,
    wherein the connectivity of each heterocyclyl can be at any two CH and/or NH on the heterocyclyl by replacing a hydrogen for a bond; and
    wherein each optionally substituted with up to three substituents selected from F, —OH, oxo, —C$_{1-3}$ alkyl, —CH$_2$OH, —CH$_2$CH$_2$OH, —C(=O)CH$_2$OH, —CH₂CH₂CH₂OH, —NR″R″, aziridinyl, azetidinyl, pyrrolidinyl, piperidinyl, or morpholinyl.
TABLE B
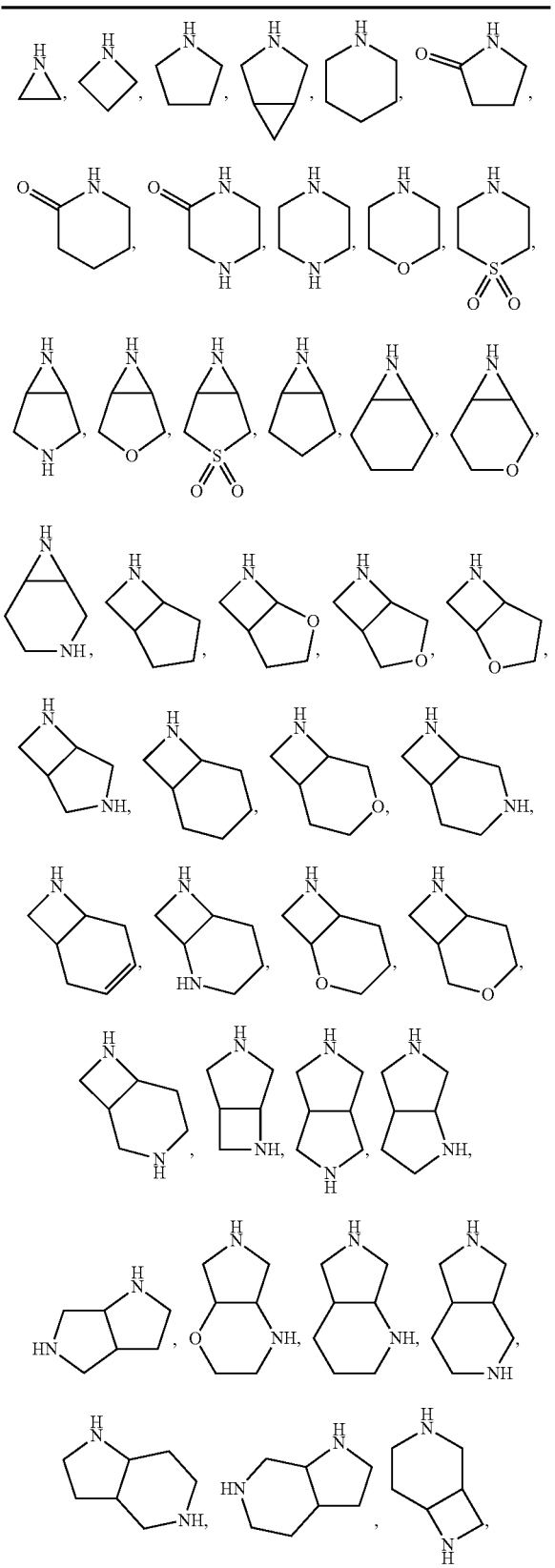
TABLE B-continued
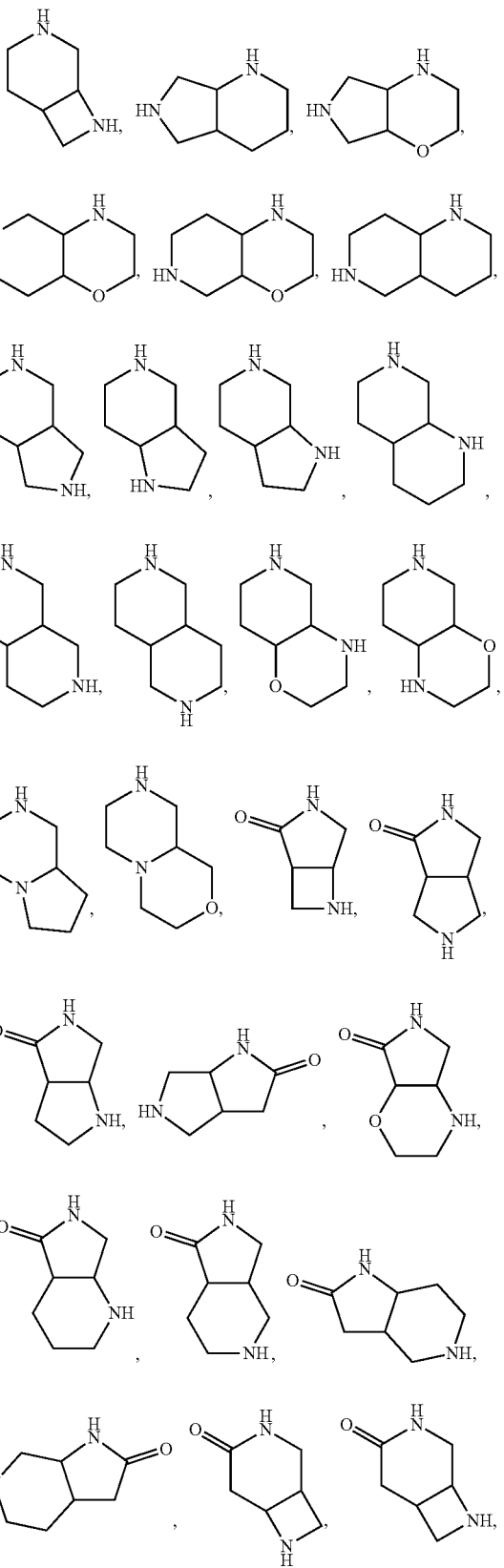

TABLE B-continued
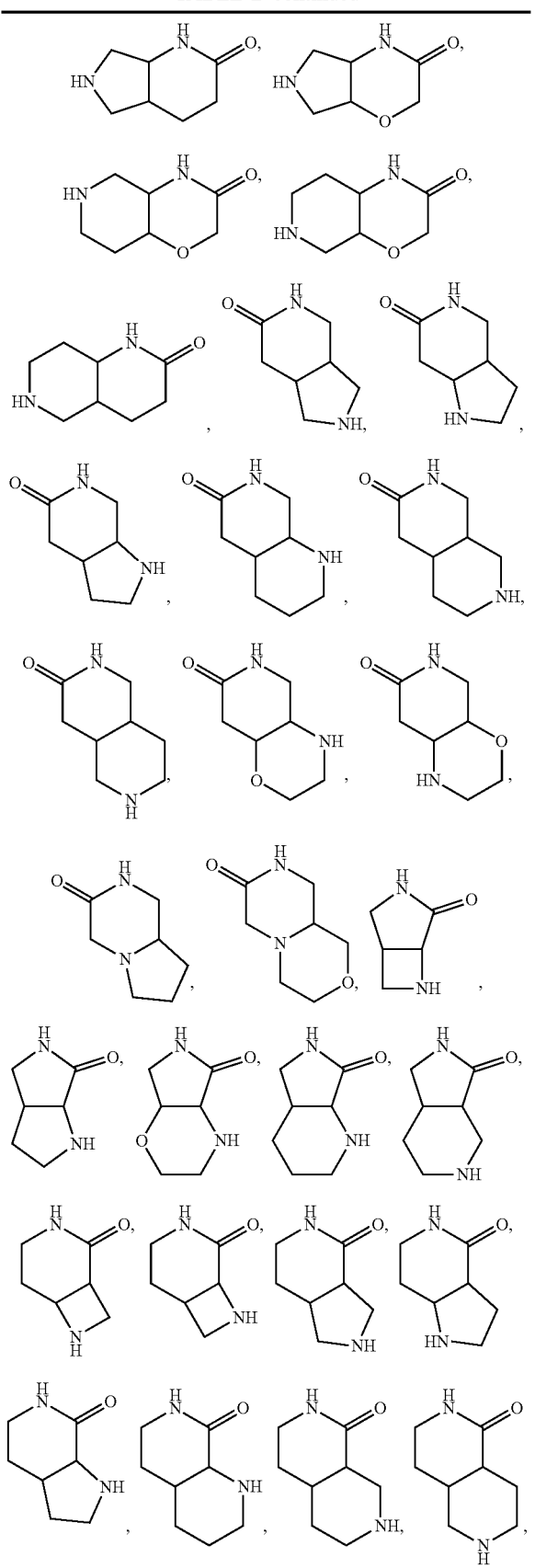
TABLE B-continued
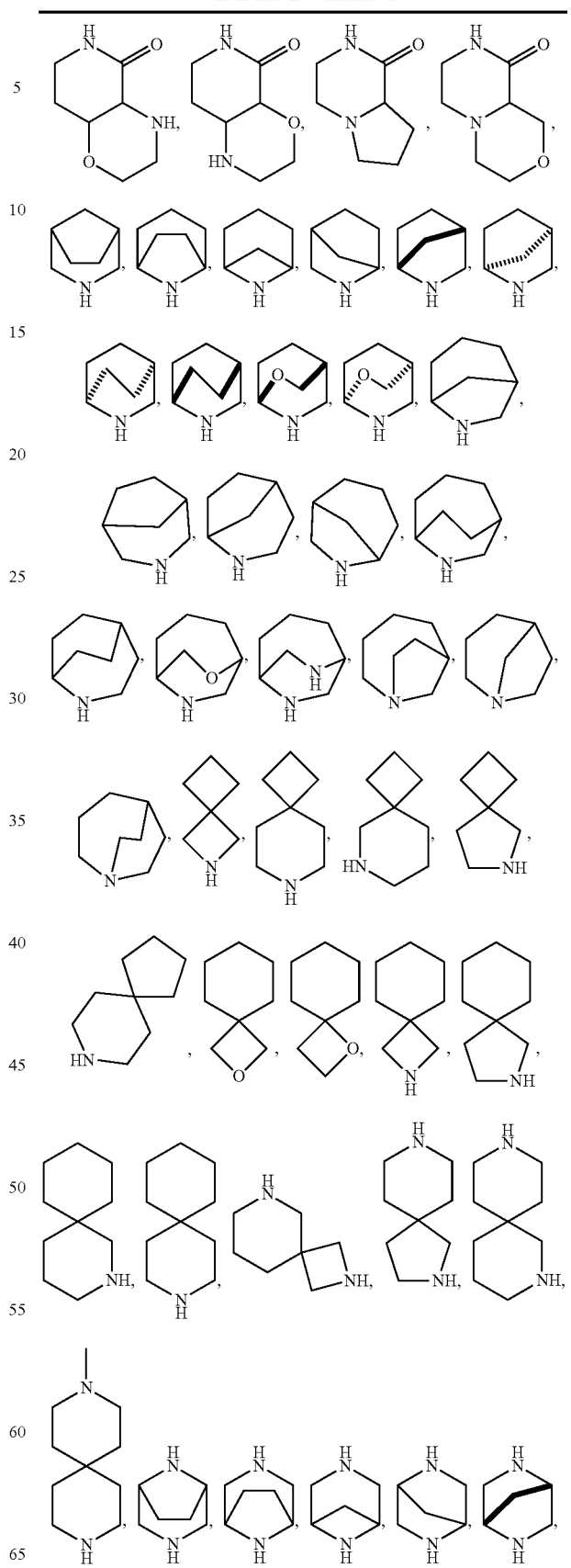

TABLE B-continued

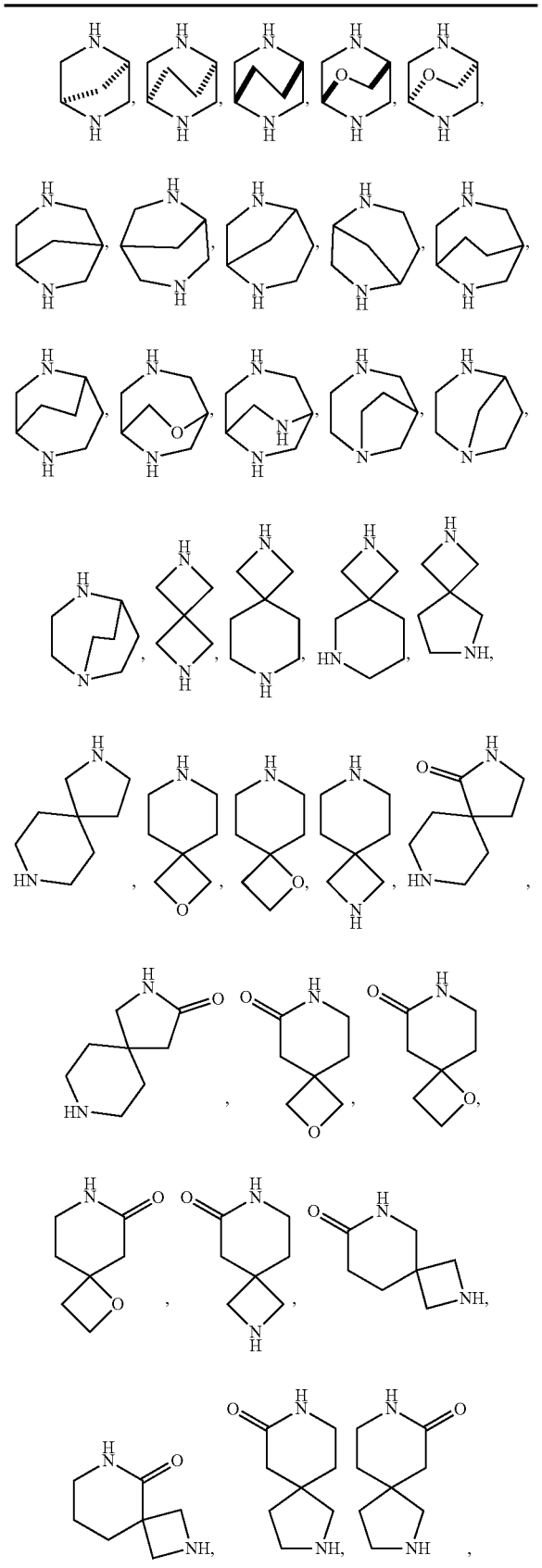

TABLE B-continued

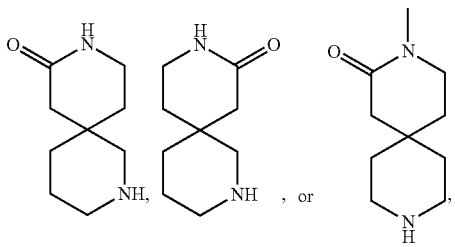

In one embodiment of the compounds of formula (A) or formula (B), Y selected from -G-, -L-, -G-L-, or -L-G-. In another embodiment of the compounds of formula (A) or formula (B), Y is selected from -G-, -L-, -G-L-, or -L-G-, and $R^6$ is heterocyclyl optionally substituted with up to three substituents independently selected from —$C_{1-6}$ alkyl, —$C_{1-6}$ haloalkyl, F, —OH, oxo, —$CH_2OH$, —$CH_2CH_2OH$, —C(=O)$CH_2OH$, —$CH_2CH_2CH_2OH$, or —NR"R". In other embodiment of the compounds of formula (A) or formula (B), Y is selected from -G-, -L-, -G-L-, or -L-G-, and $R^6$ is 5- or 6-membered heterocyclyl, each optionally substituted with up to three substituents independently selected from —$C_{1-6}$ alkyl, —$C_{1-6}$ haloalkyl, F, —OH, oxo, —$CH_2OH$, —$CH_2CH_2OH$, —C(=O)$CH_2OH$, —$CH_2CH_2CH_2OH$, or —NR"R". In other embodiment of the compounds of formula (A) or formula (B), Y is selected from -G-, -L-, -G-L-, or -L-G-, and $R^6$ is pyrrolidinyl, piperidinyl, or piperazinyl, each optionally substituted with up to three substituents independently selected from —$C_{1-6}$ alkyl, —$C_{1-6}$ haloalkyl, F, —OH, oxo, —$CH_2OH$, —$CH_2CH_2OH$, —C(=O)$CH_2OH$, —$CH_2CH_2CH_2OH$, or —NR"R". In some embodiments of the compounds of formula (A) or formula (B), Y is selected from -G-, -L-, -G-L-, or -L-G-, and $R^6$ is pyrrolidinyl, piperidinyl, or piperazinyl, each optionally substituted with —$C_{1-6}$ alkyl, —$CH_2OH$, —$CH_2CH_2OH$, —C(=O)$CH_2OH$, —$CH_2CH_2CH_2OH$, or —NR"R". In a certain embodiment of the compounds of formula (A) or formula (B), Y is selected from -G-, -L-, -G-L-, or -L-G-, and $R^6$ is pyrrolidinyl, piperidinyl, or piperazinyl, each optionally substituted with methyl, ethyl, n-propyl, i-propyl, —$CH_2OH$, —$CH_2CH_2OH$, —C(=O)$CH_2OH$, —$CH_2CH_2CH_2OH$, or —NR"R", wherein R" is each —$C_{1-3}$ alkyl.

In one embodiment where $R^6$ is

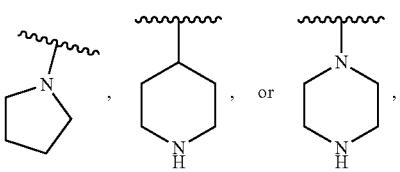 [SMILES: *N1CCCC1 ; *C1CCNCC1 ; *N1CCNCC1]

each optionally substituted with up to three substituents independently selected from —$C_{1-6}$ alkyl, —$C_{1-6}$ haloalkyl, F, —OH, oxo, —$CH_2OH$, —$CH_2CH_2OH$, C(=O)$CH_2OH$, —$CH_2CH_2CH_2OH$, or —NR"R".

In one embodiment of the compounds of formula (A) or formula (B), Y is -G-. In one embodiment of the compounds of formula (A) or formula (B), Y is -G-, wherein G is a divalent linker selected from —O—, —S(O)$_x$—, —NR"—, —C(=O)—, —C(=NR")—, —C(=NOR°)—, —C(=O)NR"—, —C(=O)O—, —C(=NR")NR"—, —C(=NOR°)NR"—, —S(=O)$_2$NR"—, —NR"C(=O)NR"—, —OC (=O)NR″—, or —NR″S(=O)₂NR″—. In another embodiment of the compounds of formula (A) or formula (B), Y is -G-, wherein G is a divalent linker selected from —O— or —C(=O)—. In one embodiment of formula (A), Y is -G-, wherein -G- is

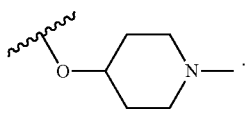 [SMILES: *OC1CCN(C)CC1]

In one embodiment of the compounds of formula (A) or formula (B), Y is -L-. In one embodiment of the compounds of formula (A) or formula (B), Y is -L-, wherein L is a divalent linker selected from —(CR$^a$R$^b$)$_p$—, —(CR$^a$R$^b$)$_p$-cycloalkyl-(CR$^a$R$^b$)$_p$—, or —(CR$^a$R$^b$)$_p$-heterocyclyl-(CR$^a$R$^b$)$_p$—, wherein cycloalkyl and heterocyclyl can be optionally further substituted with up to three substituents selected from F, —OH, oxo, —C$_{1-3}$ alkyl, —C$_{1-3}$ haloalkyl, —CH$_2$OH, —CH$_2$CH$_2$OH, —CH$_2$CH$_2$CH$_2$OH, —NR″R″, aziridinyl, azetidinyl, pyrrolidinyl, piperidinyl, or morpholinyl. In another embodiment of the compounds of formula (A) or formula (B), Y is -L-, wherein L is a divalent linker selected from —(CR$^a$R$^b$)$_p$—, —(CR$^a$R$^b$)$_p$-cycloalkyl-(CR$^a$R$^b$)$_p$—, or —(CR$^a$R$^b$)$_p$-heterocyclyl-(CR$^a$R$^b$)$_p$—. In other embodiments of the compounds of formula (A) or formula (B), Y is -L-, wherein L is a divalent linker —(CR$^a$R$^b$)$_p$—. In other embodiments of formula (A) or formula (B), Y is -L-, wherein L is a divalent linker —CH$_2$—. In one embodiment of formula (A), Y—R$^6$ is

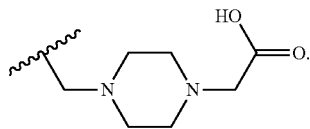 [SMILES: *CN1CCN(CC(=O)O)CC1]

In one embodiment of the compounds of formula (A) or formula (B), Y is -G-L-. In one embodiment of the compounds of formula (A) or formula (B), Y is -G-L-, wherein G and L is not absent. In one embodiment of the compounds of formula (A) or formula (B), Y is -G-L-, wherein G is a divalent linker selected from —O— or —C(=O)—; and L is a divalent linker —(CR$^a$R$^b$)$_p$—. In one embodiment of the compounds of formula (A) or formula (B), Y is -G-L-, wherein -G-L- is —O—CH$_2$—.

In one embodiment of the compounds of formula (A) or formula (B), Y is s -L-G-. In one embodiment of the compounds of formula (A) or formula (B), Y is -L-G-, wherein G and L is not absent. In one embodiment of the compounds of formula (A) or formula (B), Y is -L-G-, wherein G is a divalent linker selected from —O— or —C(=O)—; and L is a divalent linker —(CR$^a$R$^b$)$_p$—. In one embodiment of the compounds of formula (A) or formula (B), Y is -L-G-, wherein -L-G- is —CH$_2$—O—.

In one embodiment of the compounds of formula (A) or formula (B), L is a divalent cycloalkyl selected from cyclopropyl, cyclobutyl, cyclopentyl, cyclohexyl, bicyclo[3.1.0]hexanyl, octahydropentalenyl, bicycle[1.1.1]pentanyl, or cubanyl, each optionally substituted with up to three substituents selected from F, —OH, oxo, —C$_{1-3}$ alkyl, —CH$_2$OH, —CH$_2$CH$_2$OH, —CH$_2$CH$_2$CH$_2$OH, —NR″R″, aziridinyl, azetidinyl, pyrrolidinyl, piperidinyl, or morpholinyl. In another embodiment, L is a divalent cycloalkyl selected form Table A, wherein each cycloalkyl can be attached at any two CH by replacing a hydrogen for a bond.

In another embodiment of the compounds of formula (A) or formula (B), L is divalent heterocyclyl selected from Table B,
wherein the connectivity of each heterocyclyl can be at any two CH and/or NH on the heterocyclyl by replacing a hydrogen for a bond; and
wherein each optionally substituted with up to three substituents selected from F, —OH, oxo, —C$_{1-3}$ alkyl, —CH$_2$OH, —CH$_2$CH$_2$OH, —CH$_2$CH$_2$CH$_2$OH, —NR″R″, aziridinyl, azetidinyl, pyrrolidinyl, piperidinyl, or morpholinyl.

In one embodiment of the compounds of formula (A) or formula (B), R$^a$ is H, —C$_{1-3}$ alkyl, or —C$_{1-3}$ haloalkyl. In another embodiment, R$^a$ is H or —C$_{1-3}$ alkyl. In one embodiment, R$^a$ is H.

In one embodiment of the compounds of formula (A) or formula (B), R$^b$ is H, —C$_{1-3}$ alkyl, or —C$_{1-3}$ haloalkyl. In another embodiment, R$^b$ is H or —C$_{1-3}$ alkyl. In one embodiment, R$^b$ is H.

In one embodiment of the compounds of formula (A) or formula (B), R″ is each H, —C$_{1-6}$ alkyl, or —C$_{1-6}$ haloalkyl. In another embodiment, R″ is each H or —C$_{1-3}$ alkyl. In one embodiment, R″ is each H or methyl. In one embodiment, R″ is each methyl.

In one embodiment of the compounds of formula (A) or formula (B), n is 1. In one embodiment of the compounds of formula (A) or formula (B), n is 2. In one embodiment of the compounds of formula (A) or formula (B), n is 3.

In one embodiment of the compounds of formula (A) or formula (B), p is 1 or 2. In one embodiment of the compounds of formula (A) or formula (B), p is 1.

In one embodiment, the compound of the present disclosure has the structure of formula (A).

In one embodiment of the compounds of formula (A):
Y is —(CR$^a$R$^b$)$_2$—, —(CR$^a$R$^b$)$_p$-cycloalkyl-(CR$^a$R$^b$)$_p$—, —(CR$^a$R$^b$)$_p$-heterocyclyl-(CR$^a$R$^b$)$_p$—, -G-L-, -L-G-, -L-G-L-, -G-L-G-, -L-G-L-G-, or -G-L-G-L-;
R$^a$, R$^b$ and R$^c$ are each independently H, F, —C$_{1-6}$ alkyl, or —C$_{1-6}$ haloalkyl;
R$^{11}$ is H, —C$_{1-6}$ alkyl, —C$_{1-6}$ haloalkyl, C$_{1-6}$ alkyl-C(=O)—, or C$_{1-6}$ alkyl-S(=O)$_2$—;
R$^6$ is H, —C$_{1-6}$ alkyl, —C$_{1-6}$ haloalkyl, —C$_{3-12}$ cycloalkyl, —NR″R$^7$, or a heterocyclyl, wherein —C$_{1-6}$ alkyl, —C$_{1-6}$ haloalkyl, —C$_{3-12}$ cycloalkyl, and heterocyclyl are each optionally substituted with up to three substituents independently selected from F, —OH, oxo, —CH$_2$OH, —CH$_2$CH$_2$OH, —C(=O)CH$_2$OH, —CH$_2$CH$_2$CH$_2$OH, —NR″R″, aziridinyl, azetidinyl, pyrrolidinyl, piperidinyl, or morpholinyl;
G is a divalent linker that can be connected in a chain in either direction, selected from absent, —O—, —S(O)$_x$—, —NR″—, —C(=O)—, —C(=O)NR″—, —C(=O)O—, —S(=O)$_2$NR″—, —NR″C(=O)NR″—, —OC(=O)NR″—, —NR″S(=O)$_2$NR″—;
L is a divalent linker that can be connected in a chain in either direction, selected from absent, —(CR$^a$R$^b$)—, —(CR$^a$R$^b$)$_2$—, —(CR$^a$R$^b$)$_p$-cycloalkyl-(CR$^a$R$^b$)$_p$—, or —(CR$^a$R$^b$)$_p$-heterocyclyl-(CR$^a$R$^b$)$_p$—, wherein cycloalkyl and heterocyclyl can be optionally further substituted with up to three substituents selected from F, —OH, oxo, —C$_{1-3}$ alkyl, —CH$_2$OH, —CH$_2$CH$_2$OH, —CH$_2$CH$_2$CH$_2$OH, —NR″R″, aziridinyl, azetidinyl, pyrrolidinyl, piperidinyl, or morpholinyl; and $R^7$ is H, —$C_{1-6}$ alkyl, —$C_{1-6}$ haloalkyl, —$C_6$-$C_{12}$ aryl, $C_6$-$C_{12}$ aryl-$C_1$-$C_6$ alkyl-, 5-12 membered heteroaryl, or 5-12 membered heteroaryl-$C_1$-$C_6$ alkyl-, wherein —$C_6$-$C_{12}$ aryl, $C_6$-$C_{12}$ aryl-$C_1$-$C_6$ alkyl-, 5-12 membered heteroaryl, and 5-12 membered heteroaryl-$C_1$-$C_6$ alkyl- can be optionally further substituted with up to three substituents selected from F, —OH, —$C_{1-3}$ alkyl, —$C_{1-3}$ haloalkyl, —$CH_2OH$, —$CH_2CH_2OH$, —$CH_2CH_2CH_2OH$, —NR″R″, aziridinyl, azetidinyl, pyrrolidinyl, piperidinyl, or morpholinyl.

In one embodiment of the compounds of formula (A), G is independently selected from —O—, —S(O)$_x$—, —NR″—, —C(=O)—, —C(=O)NR″—, —C(=O)O—, or —S(=O)$_2$NR″—. In another embodiment, G is independently selected from —O—, —S(O)$_x$—, —NR″—, or —C(=O)—.

In one embodiment of the compounds of formula (A), the compound has the structure of formula (C):

(C)

or a stereoisomer or a pharmaceutically acceptable salt, solvate, ester, or prodrug thereof,
wherein,
$R^1$ is selected from hydrogen, fluoro, chloro, methyl, or cyano;
$R^2$ is selected from hydrogen, fluoro, chloro, or cyano;
$R^{3a}$ and $R^{3b}$ are each independently H, —$C_{1-3}$ alkyl, or —$C_{1-3}$ haloalkyl; or
alternatively, $R^{3a}$ and $R^{3b}$, taken together with the carbon atom to which they are both attached, form a 3-7 membered ring, optionally containing up to two heteroatoms selected from O, S(O)$_x$, or NR$^{11}$, and wherein the 3-7 membered ring is optionally substituted with up to three substituents selected from hydroxyl, —$C_{1-3}$ alkoxy, oxo, cyano or F;
Y is —(CR$^a$R$^b$)$_2$—, -cycloalkyl-, -heterocyclyl-, —CR$^a$R$^b$-cycloalkyl-, —CR$^a$R$^b$— heterocyclyl-, -cycloalkyl-CR$^a$R$^b$—, -heterocyclyl-CR$^a$R$^b$—, -G-CR$^a$R$^b$—, -G-cycloalkyl-, -G-heterocyclyl-, —CR$^a$R$^b$-G-, -cycloalkyl-G-, -heterocyclyl-G-, —CR$^a$R$^b$-G-CR$^a$R$^b$—, —CR$^a$R$^b$— cycloalkyl-CR$^a$R$^b$—, —CR$^a$R$^b$-heterocyclyl-CR$^a$R$^b$—, -G-cycloalkyl-G-, -G-heterocyclyl-G-, —CR$^a$R$^b$-G-L-G-, -L-G-CR$^a$R$^b$-G-, -G-CR$^a$R$^b$-G-L-, or -G-L-G-CR$^a$R$^b$—;
$R^a$, $R^b$ and $R^o$ are each independently H, F, —$C_{1-6}$ alkyl, or —$C_{1-6}$ haloalkyl;
$R''$ is H, —$C_{1-6}$ alkyl, —$C_{1-6}$ haloalkyl, $C_{1-6}$ alkyl-C(=O)—, or $C_{1-6}$ alkyl-S(=O)$_2$—;
$R^6$ is H, —$C_{1-6}$ alkyl, —$C_{1-6}$ haloalkyl, —$C_{3-12}$ cycloalkyl, —NR″$R^7$, or a heterocyclyl, wherein —$C_{1-6}$ alkyl, —$C_{1-6}$ haloalkyl, —$C_{3-12}$ cycloalkyl, and heterocyclyl are each optionally substituted with up to three substituents independently selected from F, —OH, oxo, —$CH_2OH$, —$CH_2CH_2OH$, —$CH_2CH_2CH_2OH$, —NR″R″, aziridinyl, azetidinyl, pyrrolidinyl, piperidinyl, or morpholinyl;
G is a divalent linker that can be connected in a chain in either direction, selected from absent, —O—, —S(O)$_x$—, —NR″—, —C(=O)—, —C(=O)NR″—, —C(=O)O—, or —S(=O)$_2$NR″—;
L is a divalent linker that can be connected in a chain in either direction, selected from absent, —(CR$^a$R$^b$)$_p$—, —(CR$^a$R$^b$)$_p$-cycloalkyl-(CR$^a$R$^b$)$_p$—, —(CR$^a$R$^b$)-heterocyclyl-(CR$^a$R$^b$)$_p$—, wherein cycloalkyl and heterocyclyl can be optionally further substituted with up to three substituents selected from F, —OH, oxo, —$C_{1-3}$ alkyl, —$CH_2OH$, —$CH_2CH_2OH$, —$CH_2CH_2CH_2OH$, —NR″R″, aziridinyl, azetidinyl, pyrrolidinyl, piperidinyl, or morpholinyl;
$R^7$ is H, —$C_{1-6}$ alkyl, —$C_{1-6}$ haloalkyl, —$C_6$-$C_{12}$ aryl, $C_6$-$C_{12}$ aryl-$C_1$-$C_6$ alkyl-, 5-12 membered heteroaryl, or 5-12 membered heteroaryl-$C_1$-$C_6$ alkyl-, wherein —$C_6$-$C_{12}$ aryl, $C_6$-$C_{12}$ aryl-$C_1$-$C_6$ alkyl-, 5-12 membered heteroaryl, and 5-12 membered heteroaryl-$C_1$-$C_6$ alkyl- can be optionally further substituted with up to three substituents selected from F, —OH, —$C_{1-3}$ alkyl, —$C_{1-3}$ haloalkyl, —$CH_2OH$, —$CH_2CH_2OH$, —$CH_2CH_2CH_2OH$, —NR″R″, aziridinyl, azetidinyl, pyrrolidinyl, piperidinyl, or morpholinyl;
n is 1, 2, or 3;
p is independently 0, 1, or 2; and
x is 0, 1, or 2.

In one embodiment of the compounds of formula (C), $R^{3a}$ and $R^{3b}$ are each independently H or —$C_{1-3}$ alkyl; and Y is —O—$CH_2$— or —$CH_2$—O—.

In one embodiment, formula (C) is a subgenus of formula (A).

In one embodiment, the compound of the present disclosure has the structure of formula (B).

In one embodiment of the compounds of formula (B):
$X^1$ is N;
$X^2$ is CH;
$R^{3a}$ and $R^{3b}$ are each independently H or —$C_{1-3}$ alkyl;
$R^5$ is H;
Y is selected from —$CH_2$—, —O—$CH_2$—, or —$CH_2$—O—; and
n is 1.

In one embodiment, the compound of the present disclosure relates to a compound having the structure of formula (A-I):

(A-1)

or a pharmaceutically acceptable salt, solvate, ester, or prodrug thereof;

wherein, $X^1$ and $X^2$ are each independently CH or N;

$R^1$ is selected from hydrogen, fluoro, chloro, bromo, methyl, ethyl, hydroxyl, methoxy, ethoxy, isopropoxy, cyclopropoxy, —$OCF_3$, —$OCH_2CF_3$, —$OCH_2CHF_2$, —$CF_3$, —$CHF_2$, —CHO, —$CH_2OH$, —$CONH_2$, —$CO_2Me$, —CONHMe, —$CONMe_2$, or cyano;

$R^2$ is selected from hydrogen, fluoro, chloro, methyl, hydroxyl, methoxy, ethoxy, isopropoxy, cyclopropoxy, —$OCF_3$, —$CF_3$, —$CHF_2$, —$CH_2OH$, —$CONH_2$, —CONHMe, —$CONMe_2$, or cyano;

$R^{3a}$ and $R^{3b}$ are each independently H, —$C_{1-6}$ alkyl, or —$C_{1-6}$haloalkyl; or alternatively, $R^{3a}$ and $R^{3b}$, taken together with the carbon atom to which they are both attached, form a 3-7 membered ring, optionally containing up to two heteroatoms selected from O, $S(O)_x$, or $NR^{11}$, or forms a 7-12 membered heterobicyclic ring which may be fused, bridged or spiro, and includes one to three heteroatoms selected from O, $S(O)_x$, or $NR^{11}$, and wherein the 3-7 membered ring and the 7-12 membered heterobicyclic ring are optionally substituted with up to three substituents selected from hydroxyl, —$C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano or halo;

Y is absent, -G-, -L-, -G-L-, or -L-G-;

$R^5$ is independently selected from H, $C_{1-6}$ alkyl, halogen, —CN, —$CD_3$, —$CHF_2$, or —$CF_3$;

when Y is absent, $R^6$ is —$C_{1-6}$ alkyl, —$C_{1-6}$ haloalkyl, —$C_{3-12}$ cycloalkyl, —$NR''R^7$, or a 5- or 7-membered heterocyclyl, wherein —$C_{1-6}$ alkyl, —$C_{1-6}$ haloalkyl, —$C_{3-12}$ cycloalkyl, and 5- or 7-membered heterocyclyl are each optionally substituted with up to three substituents independently selected from $C_{1-6}$ alkyl, —$C_{1-6}$ haloalkyl, F, —OH, oxo, —$CH_2OH$, —$CH_2CH_2OH$, —$C(=O)CH_2OH$, —$CH_2CH_2CH_2OH$, —$NR''R''$, aziridinyl, azetidinyl, pyrrolidinyl, piperidinyl, or morpholinyl;

when Y is -G-, $R^6$ is —$C_{1-6}$ alkyl, —$C_{1-6}$ haloalkyl, —$C_{3-12}$ cycloalkyl, —$NR''R^7$, a 5- or 7-membered heterocyclyl, or

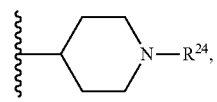

wherein —$C_{1-6}$alkyl, —$C_{1-6}$ haloalkyl, —$C_{3-12}$ cycloalkyl, and 5- or 7-membered heterocyclyl are each optionally substituted with up to three substituents independently selected from $C_{1-6}$ alkyl, —$C_{1-6}$ haloalkyl, F, —OH, oxo, —$CH_2OH$, —$CH_2CH_2OH$, —$C(=O)CH_2OH$, —$CH_2CH_2CH_2OH$, —$NR''R''$, aziridinyl, azetidinyl, pyrrolidinyl, piperidinyl, or morpholinyl;

$R^{24}$ is methyl, —$C_{3-6}$ alkyl, —$C_{1-6}$ haloalkyl, —$CH_2OH$, —$CH_2CH_2OH$, —$C(=O)CH_2OH$, or —$CH_2CH_2CH_2OH$;

when Y is -L-, $R^6$ is —$C_{1-6}$ alkyl, —$C_{1-6}$ haloalkyl, —$C_{3-12}$ cycloalkyl, —$NR''R^7$, a 5- or 7-membered monocyclic heterocyclyl, or

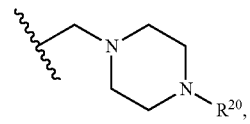

wherein —$C_{1-6}$ alkyl, —$C_{1-6}$ haloalkyl, —$C_{3-12}$ cycloalkyl, and 5- or 7-membered heterocyclyl are each optionally substituted with up to three substituents independently selected from $C_{1-6}$ alkyl, —$C_{1-6}$ haloalkyl, F, —OH, oxo, —$CH_2OH$, —$CH_2CH_2H$, —$C(=O)CH_2OH$, —$CH_2CH_2CH_2OH$, —$NR''R''$, aziridinyl, azetidinyl, pyrrolidinyl, piperidinyl, or morpholinyl;

$R^{20}$ is —$C_{4-6}$ alkyl, —$CF_3$, —$CHF_2$, —$C_{3-6}$ haloalkyl, —$CH_2OH$, —$CH_2CH_2OH$, —$C(=O)CH_2OH$, or —$CH_2CH_2CH_2OH$;

when Y is -L-G- or -G-L-, $R^6$ is —$C_{1-6}$ alkyl, —$C_{1-6}$ haloalkyl, —$C_{3-12}$ cycloalkyl, —$NR''R^7$, or heterocyclyl, wherein —$C_{1-6}$ alkyl, —$C_{1-6}$ haloalkyl, —$C_{3-12}$ cycloalkyl, and heterocyclyl are each optionally substituted with up to three substituents independently selected from $C_{1-6}$ alkyl, —$C_{1-6}$ haloalkyl, F, —OH, oxo, —$CH_2OH$, —$CH_2CH_2OH$, —$C(=O)CH_2OH$, —$CH_2CH_2CH_2OH$, —$NR''R''$, aziridinyl, azetidinyl, pyrrolidinyl, piperidinyl, or morpholinyl;

G is a divalent linker that can be connected in a chain in either direction, which is selected from absent, —O—, —$S(O)_x$—, —NR''—, —C(=O)—, —C(=NR'')—, —C(=NOR$^o$)—, —C(=O)NR''—, —C(=O)O—, —C(=NR'')NR''—, —C(=NOR$^o$)NR''—, —S(=O)$_2$NR''—, —NR''C(=O)NR''—, —OC(=O)NR''—, or —NR''S(=O)$_2$NR''—;

L is a divalent linker that can be connected in a chain in either direction, which is selected from absent, —$(CR^aR^b)_p$—, —$(CR^aR^b)_p$-cycloalkyl-$(CR^aR^b)_p$—, or —$(CR^aR^b)_p$-heterocyclyl-$(CR^aR^b)_p$—, wherein cycloalkyl and heterocyclyl can be optionally further substituted with up to three substituents selected from F, —OH, oxo, $C_{1-3}$ alkyl, —$C_{1-3}$ haloalkyl, —$CH_2OH$, —$CH_2CH_2OH$, —$CH_2CH_2CH_2OH$, —$NR''R''$, aziridinyl, azetidinyl, pyrrolidinyl, piperidinyl, or morpholinyl;

$R^7$ is H, —$C_{1-6}$ alkyl, —$C_{1-6}$ haloalkyl, —$C_{3-12}$ cycloalkyl, heterocyclyl, —$C_6$-$C_{12}$ aryl, $C_6$-$C_{12}$ aryl-$C_1$-$C_6$ alkyl-, 5-12 membered heteroaryl, or 5-12 membered heteroaryl-$C_1$-$C_6$ alkyl-, wherein —$C_{3-12}$ cycloalkyl, heterocyclyl, —$C_6$-$C_{12}$ aryl, $C_6$-$C_{12}$ aryl-$C_1$-$C_6$ alkyl-, 5-12 membered heteroaryl, and 5-12 membered heteroaryl-$C_1$-$C_6$ alkyl- can be optionally further substituted with up to three substituents selected from F, —OH, oxo, —$C_{1-3}$ alkyl, —$C_{1-3}$ haloalkyl, —$CH_2OH$, —$CH_2CH_2OH$, —$CH_2CH_2CH_2OH$, —$NR''R''$, aziridinyl, azetidinyl, pyrrolidinyl, piperidinyl, or morpholinyl;

$R^{11}$ is H or $C_{1-6}$ alkyl;

$R^a$, $R^b$ and $R^o$ are each independently H, F, —$C_{1-6}$ alkyl, or —$C_{1-6}$ haloalkyl;

R'' is H, —$C_{1-6}$ alkyl, —$C_{1-6}$ haloalkyl, $C_{1-6}$ alkyl-C(=O)—, or $C_{1-6}$ alkyl-S(=O)$_2$—;

n is 1, 2, or 3;

p is independently 0, 1, or 2; and x is 0, 1, or 2.

In one embodiment of a compound of formula (A-I), Y is absent and $R^6$ is a 5-membered heterocyclyl, optionally substituted with —NR''R''.

In one embodiment of a compound of formula (A-I), Y is -G- and R⁶ is

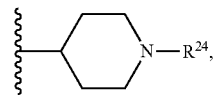

wherein R²⁴ is methyl, —C₃₋₆ alkyl, —C₁₋₆ haloalkyl, —CH₂OH, —CH₂CH₂OH, —C(=O)CH₂OH, or —CH₂CH₂CH₂OH. In one embodiment of a compound of formula (A-I), Y is -G- and R⁶ is 5-membered heterocyclyl, optionally substituted with —NR″R″.

In one embodiment of a compound of formula (A-I), Y is -L- and R⁶ is

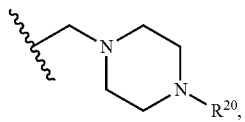

wherein R²⁰ is —C₄₋₆ alkyl, —CF₃, —CHF₂, —C₃₋₆ haloalkyl, —CH₂OH, —CH₂CH₂OH, —C(=O)CH₂OH, or —CH₂CH₂CH₂OH. In one embodiment of a compound of formula (A-I), Y is -L- and R⁶ is

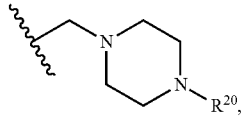

wherein R²⁰ is —CH₂OH, —CH₂CH₂OH, —C(=O)CH₂OH, or —CH₂CH₂CH₂OH.

In one embodiment of a compound of formula (A-I), Y is -L-G- or -G-L-, and R⁶ is heterocyclyl optionally substituted with up to three substituents independently selected from —C₁₋₆ alkyl, —C₁₋₆ haloalkyl, F, —OH, oxo, —CH₂OH, —CH₂CH₂OH, —C(=O)CH₂OH, —CH₂CH₂CH₂OH, —NR″R, aziridinyl, azetidinyl, pyrrolidinyl, piperidinyl, or morpholinyl. In another embodiment, Y is -L-G- or -G-L-, and R⁶ is heterocyclyl optionally substituted with —C₁₋₆ alkyl, —C₁₋₆ haloalkyl, F, —OH, oxo, —CH₂OH, —CH₂CH₂OH, —C(=O)CH₂OH, —CH₂CH₂CH₂OH, or —NR″R″.

In one embodiment of a compound of formula (A-I), R³ᵃ and R³ᵇ are each independently H or —C₁₋₃ alkyl.

In one embodiment, formula (A-I) is a subgenus of formula (A). Any embodiments discussed for the compounds of formula (A) can be applied for compounds of formula (A-I).

In one embodiment of the compounds of formula (A-I), Y is —O—CH₂— or —CH₂—O—.

In one embodiment of the compounds of formula (A), (A-I), (B), (C), (I), or (II), R¹ is hydrogen, fluoro, chloro, methyl, or cyano. In some embodiments, R¹ is fluoro.

In one embodiment of the compounds of formula (A), (A-I), (B), (C), (I), or (II), R² is hydrogen, fluoro, chloro, or cyano. In some embodiments, R² is fluoro.

In one embodiment of the compounds of formula (A), (A-I), (B), (C), (I), or (II), R³ᵃ and R³ᵇ are each independently H or —C₁₋₃ alkyl. In one embodiment, R³ᵃ and R³ᵇ are each independently H or methyl. In some embodiments, R³ᵃ and R³ᵇ are each H. In other embodiments, R³ᵃ and R³ᵇ are each methyl.

In one embodiment of the compounds of formula (A), (A-I), (B), (C), (I), or (II), Y is absent, —C(=O)—, —CH₂—, —O—CH₂—, or —CH₂—O—. In some embodiments, Y is —O—CH₂— or —CH₂—O—. In one embodiment, Y is —O—CH₂—.

In one embodiment of the compounds of formula (A), (A-I), (B), (C), (I), or (II), R⁶ is a heterocyclyl optionally substituted with up to three substituents independently selected from C₁₋₃ alkyl, —C₁₋₃ haloalkyl, F, —OH, oxo, CH₂OH, CH₂CH₂OH, C(=O)CH₂OH, CH₂CH₂CH₂OH, —NH₂, or —N(C₁₋₃ alkyl)₂. In some embodiments, R⁶ is 5 or 6 membered heterocyclyl optionally substituted with up to two substituents independently selected from C₁₋₃ alkyl, —C₁₋₃ haloalkyl, F, —OH, oxo, CH₂OH, CH₂CH₂OH, C(=O)CH₂OH, CH₂CH₂CH₂OH, —NH₂, or —N(C₁₋₃ alkyl)₂. In some embodiments, R⁶ is pyrrolidinyl, piperidinyl, or piperazinyl each optionally substituted with up to two substituents independently selected from C₁₋₃ alkyl, —C₁₋₃ haloalkyl, F, —OH, oxo, CH₂OH, CH₂CH₂OH, C(=O)CH₂OH, CH₂CH₂CH₂OH, —NH₂, or —N(C₁₋₃ alkyl)₂. In some embodiments, R⁶ is;

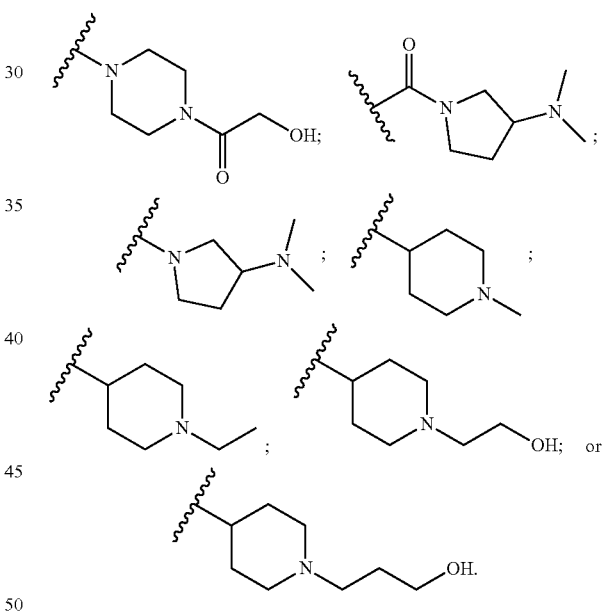

In one embodiment of the compounds of formula (A), (A-I), (B), (C), (I), or (II), —Y—R⁶ is

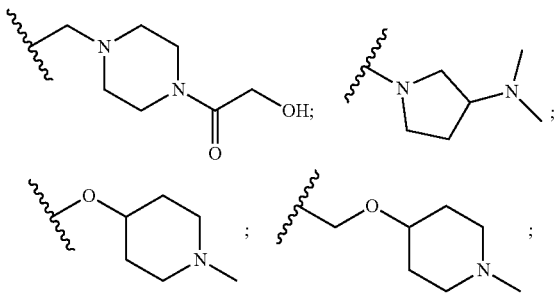

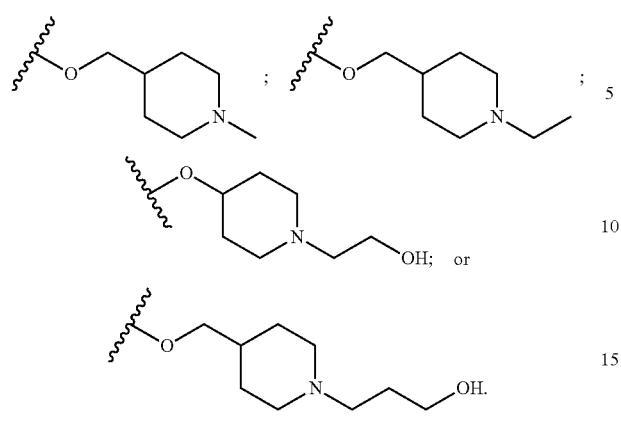
In one embodiment, the compound of the present disclosure is selected from:
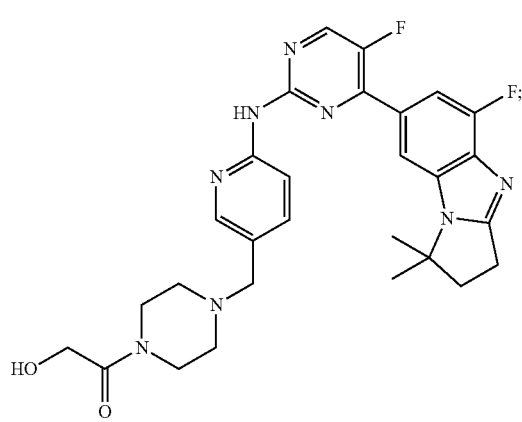
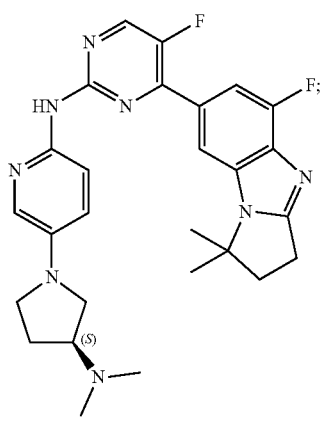
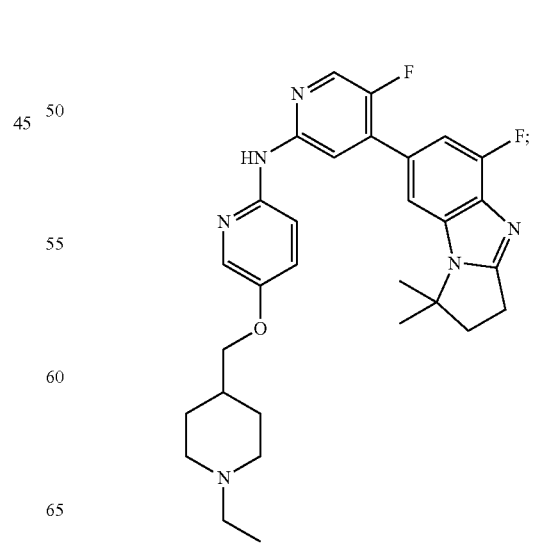

65
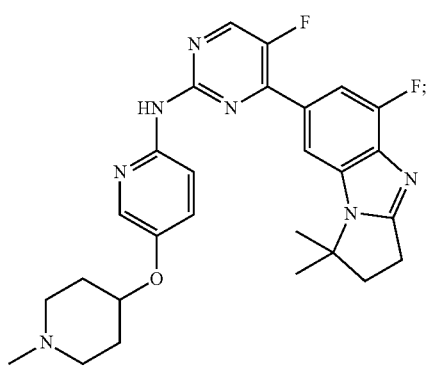
72
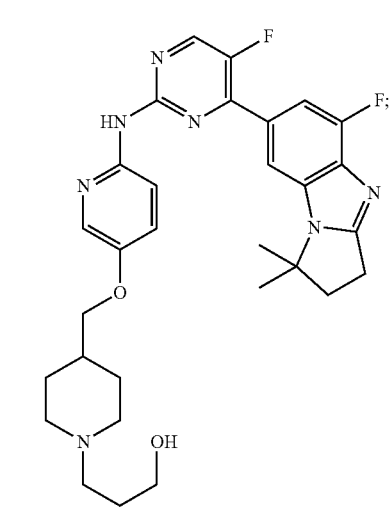
76
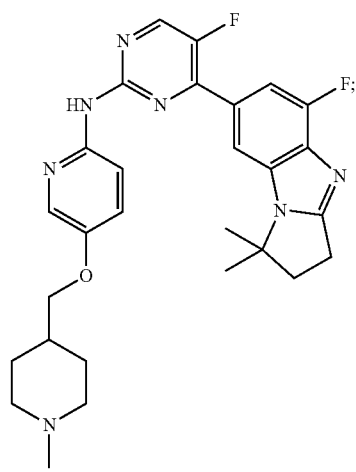
81
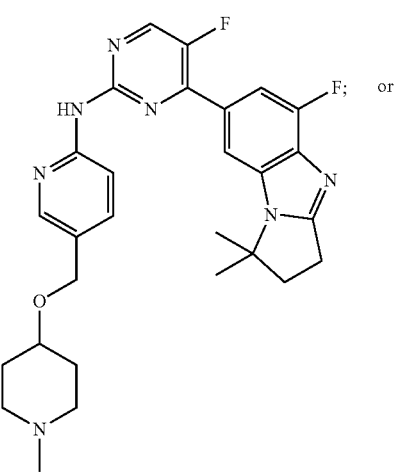
87
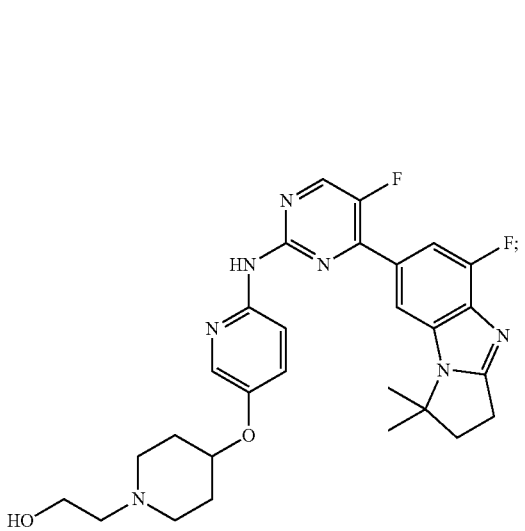
or a pharmaceutically acceptable salt, solvate, ester, or prodrug thereof.
In one embodiment, the compound of the present disclosure is selected from:
105
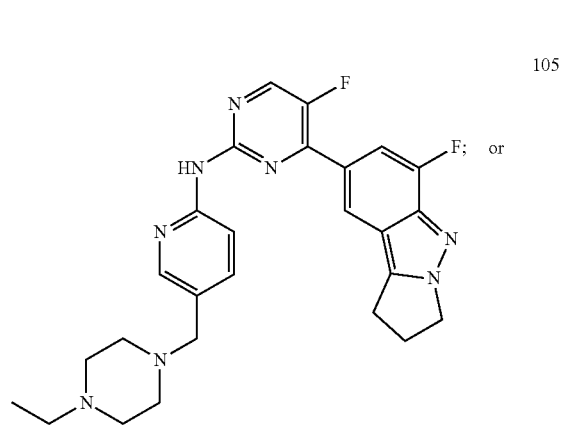

106

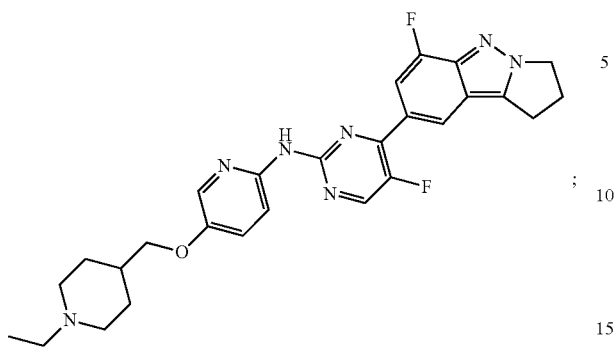

35

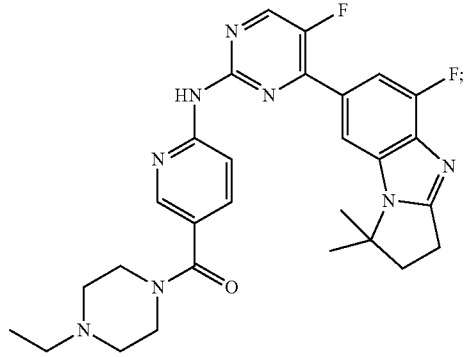

or a pharmaceutically acceptable salt, solvate, ester, or prodrug thereof.

In one embodiment the compound of the present disclosure excludes

15

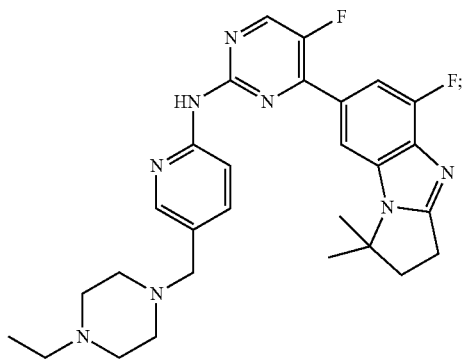

43

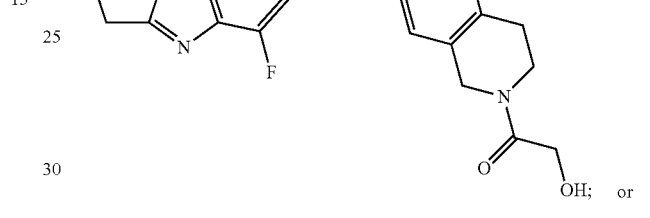

29

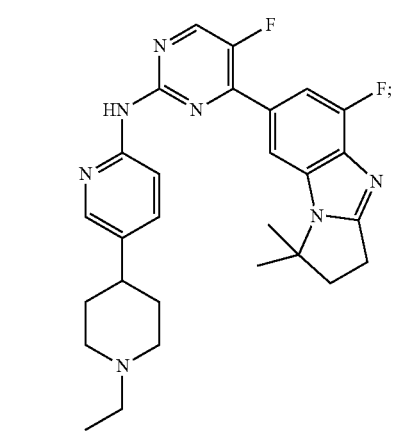

92

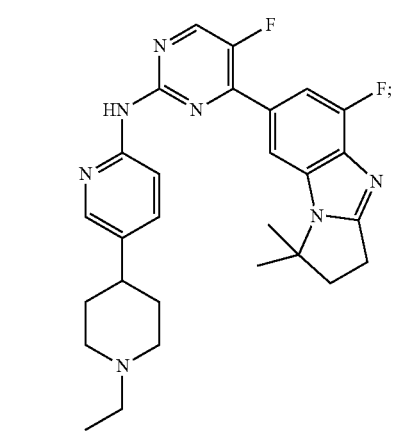

or a pharmaceutically acceptable salt, solvate, ester, or prodrug thereof;

In one embodiment, the compound of the present disclosure excludes compounds in Table X:

TABLE X (S)-(5-fluoro-7-(5-fluoro-2-((5-(piperazin-1-ylmethyl)pyridin-2-yl)amino)pyrimidin-4-yl)-2,3-dihydro-1H-benzo[d]pyrrolo[1,2-a]imidazol-1-yl)methanol,
(S)-(5-fluoro-7-(5-fluoro-2-((5-((4-methylpiperazin-1-yl)methyl)pyridin-2-yl)amino)pyrimidin-4-yl)-2,3-dihydro-1H-benzo[d]pyrrolo[1,2-a]imidazol-1-yl)methanol,
(S)-(7-(2-((5-((4-ethylpiperazin-1-yl)methyl)pyridin-2-yl)amino)-5-fluoropyrimidin-4-yl)-5-fluoro-2,3-dihydro-1H-benzo[d]pyrrolo[1,2-a]imidazol-1-yl)methanol,
(S)-5-fluoro-4-(5-fluoro-1-(fluoromethyl)-2,3-dihydro-1H-benzo[d]pyrrolo[1,2-a]imidazol-7-yl)-N-(5-(piperazin-1-ylmethyl)pyridin-2-yl)pyrimidin-2-amine,
(S)-5-fluoro-4-(5-fluoro-1-(fluoromethyl)-2,3-dihydro-1H-benzo[d]pyrrolo[1,2-a]imidazol-7-yl)-N-(5-((4-methylpiperazin-1-yl)methyl)pyridin-2-yl)pyrimidin-2-amine,
(S)-N-(5-((4-ethylpiperazin-1-yl)methyl)pyridin-2-yl)-5-fluoro-4-(5-fluoro-1-

TABLE X-continued (fluoromethyl)-2,3-dihydro-1H-benzo[d]pyrrolo[1,2-a]imidazol-7-yl)pyrimidin-2-amine,
(S)-5-fluoro-4-(5-fluoro-1-(methoxymethyl)-2,3-dihydro-1H-benzo[d]pyrrolo[1,2-a]imidazol-7-yl)-N-(5-(piperazin-1-ylmethyl)pyridin-2-yl)pyrimidin-2-amine,
(S)-5-fluoro-4-(5-fluoro-1-(methoxymethyl)-2,3-dihydro-1H-benzo[d]pyrrolo[1,2-a]imidazol-7-yl)-N-(5-((4-methylpiperazin-1-yl)methyl)pyridin-2-yl)pyrimidin-2-amine,
(S)-N-(5-((4-ethylpiperazin-1-yl)methyl)pyridin-2-yl)-5-fluoro-4-(5-fluoro-1-(methoxymethyl)-2,3-dihydro-1H-benzo[d]pyrrolo[1,2-a]imidazol-7-yl)pyrimidin-2-amine,
(S)-4-(1-(difluoromethyl)-5-fluoro-2,3-dihydro-1H-benzo[d]pyrrolo[1,2-a]imidazol-7-yl)-5-fluoro-N-(5-(piperazin-1-ylmethyl)pyridin-2-yl)pyrimidin-2-amine,
(S)-4-(1-(difluoromethyl)-5-fluoro-2,3-dihydro-1H-benzo[d]pyrrolo[1,2-a]imidazol-7-yl)-5-fluoro-N-(5-((4-methylpiperazin-1-yl)methyl)pyridin-2-yl)pyrimidin-2-amine,
(S)-4-(1-(difluoromethyl)-5-fluoro-2,3-dihydro-1H-benzo[d]pyrrolo[1,2-a]imidazol-7-yl)-N-(5-((4-ethylpiperazin-1-yl)methyl)pyridin-2-yl)-5-fluoropyrimidin-2-amine,
5-fluoro-4-(5-fluoro-2,3-dihydrospiro[benzo[d]pyrrolo[1,2-a]imidazole-1,1'-cyclopropan]-7-yl)-N-(5-(piperazin-1-ylmethyl)pyridin-2-yl)pyrimidin-2-amine,
5-fluoro-4-(5-fluoro-2,3-dihydrospiro[benzo[d]pyrrolo[1,2-a]imidazole-1,1'-cyclopropan]-7-yl)-N-(5-((4-methylpiperazin-1-yl)methyl)pyridin-2-yl)pyrimidin-2-amine,
N-(5-((4-ethylpiperazin-1-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine,
(S)-5-fluoro-4-(5-fluoro-1-(trifluoromethyl)-2,3-dihydro-1H-benzo[d]pyrrolo[1,2-a]imidazol-7-yl)-N-(5-(piperazin-1-ylmethyl)pyridin-2-yl)pyrimidin-2-amine,
(S)-5-fluoro-4-(5-fluoro-1-(trifluoromethyl)-2,3-dihydro-1H-benzo[d]pyrrolo[1,2-a]imidazol-7-yl)-N-(5-((4-methylpiperazin-1-yl)methyl)pyridin-2-yl)pyrimidin-2-amine,
(S)-N-(5-((4-ethylpiperazin-1-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine,
5-fluoro-4-((S)-5-fluoro-1-(fluoromethyl)-2,3-dihydro-1H-benzo[d]pyrrolo[1,2-a]imidazol-7-yl)-N-(5-(((R)-hexahydropyrrolo[1,2-a]pyrazin-2(1H)-yl)methyl)pyridin-2-yl)pyrimidin-2-amine,
(S)-N-(5-((2,7-diazaspiro[3.5]nonan-2-yl)methyl)pyridin-2-yl)-5-fluoro-4-(5-fluoro-1-(fluoromethyl)-2,3-dihydro-1H-benzo[d]pyrrolo[1,2-a]imidazol-7-yl)pyrimidin-2-amine,
(S)-5-fluoro-4-(5-fluoro-1-(fluoromethyl)-2,3-dihydro-1H-benzo[d]pyrrolo[1,2-a]imidazol-7-yl)-N-(5-((7-methyl-2,7-diazaspiro[3.5]nonan-2-yl)methyl)pyridin-2-yl)pyrimidin-2-amine,
(S)-N-(5-((7-ethyl-2,7-diazaspiro[3.5]nonan-2-yl)methyl)pyridin-2-yl)-5-fluoro-4-(5-fluoro-1-(fluoromethyl)-2,3-dihydro-1H-benzo[d]pyrrolo[1,2-a]imidazol-7-yl)pyrimidin-2-amine,
(S)-N-(5-((2,6-diazaspiro[3.3]heptan-2-yl)methyl)pyridin-2-yl)-5-fluoro-4-(5-fluoro-1-(fluoromethyl)-2,3-dihydro-1H-benzo[d]pyrrolo[1,2-a]imidazol-7-yl)pyrimidin-2-amine,
(S)-5-fluoro-4-(5-fluoro-1-(fluoromethyl)-2,3-dihydro-1H-benzo[d]pyrrolo[1,2-a]imidazol-7-yl)-N-(5-((6-methyl-2,6-diazaspiro[3.3]heptan-2-yl)methyl)pyridin-2-yl)pyrimidin-2-amine,
(S)-N-(5-((6-ethyl-2,6-diazaspiro[3.3]heptan-2-yl)methyl)pyridin-2-yl)-5-fluoro-4-(5-fluoro-1-(fluoromethyl)-2,3-dihydro-1H-benzo[d]pyrrolo[1,2-a]imidazol-7-yl)pyrimidin-2-amine,
5-fluoro-4-((S)-5-fluoro-1-(fluoromethyl)-2,3-dihydro-1H-benzo[d]pyrrolo[1,2-a]imidazol-7-yl)-N-(5-((hexahydropyrrolo[3,4-c]pyrrol-2(1H)-yl)methyl)pyridin-2-yl)pyrimidin-2-amine,
5-fluoro-4-((S)-5-fluoro-1-(fluoromethyl)-2,3-dihydro-1H-benzo[d]pyrrolo[1,2-a]imidazol-7-yl)-N-(5-((5-methylhexahydropyrrolo[3,4-c]pyrrol-2(1H)-yl)methyl)pyridin-2-yl)pyrimidin-2-amine,
N-(5-((5-ethylhexahydropyrrolo[3,4-c]pyrrol-2(1H)-yl)methyl)pyridin-2-yl)-5-fluoro-4-((S)-5-fluoro-1-(fluoromethyl)-2,3-dihydro-1H-benzo[d]pyrrolo[1,2-a]imidazol-7-yl)pyrimidin-2-amine,
(S)-N-(5-((3,9-diazaspiro[5.5]undecan-3-yl)methyl)pyridin-2-yl)-5-fluoro-4-(5-fluoro-1-(fluoromethyl)-2,3-dihydro-1H-benzo[d]pyrrolo[1,2-a]imidazol-7-yl)pyrimidin-2-amine,
(S)-5-fluoro-4-(5-fluoro-1-(fluoromethyl)-2,3-dihydro-1H-benzo[d]pyrrolo[1,2-a]imidazol-7-yl)-N-(5-49-methyl-3,9-diazaspiro[5.5]undecan-3-yl)methyl)pyridin-2-yl)pyrimidin-2-amine,
(S)-N-(5-((9-ethyl-3,9-diazaspiro[5.5]undecan-3-yl)methyl)pyridin-2-yl)-5-fluoro-4-(5-fluoro-1-(fluoromethyl)-2,3-dihydro-1H-benzo[d]pyrrolo[1,2-a]imidazol-7-yl)pyrimidin-2-amine,
N-(5-((3,8-diazabicyclo[3.2.1]octan-8-yl)methyl)pyridin-2-yl)-5-fluoro-4-((S)-5-fluoro-1-(fluoromethyl)-2,3-dihydro-1H-benzo[d]pyrrolo[1,2-a]imidazol-7-yl)pyrimidin-2-amine,
5-fluoro-4-((S)-5-fluoro-1-(fluoromethyl)-2,3-dihydro-1H-benzo[d]pyrrolo[1,2-a]imidazol-7-yl)-N-(5-((3-methyl-3,8-diazabicyclo[3.2.1]octan-8-yl)methyl)pyridin-2-yl)pyrimidin-2-amine,
N-(5-((3-ethyl-3,8-diazabicyclo[3.2.1]octan-8-yl)methyl)pyridin-2-yl)-5-fluoro-4-((S)-5-fluoro-1-(fluoromethyl)-2,3-dihydro-1H-benzo[d]pyrrolo[1,2-a]imidazol-7-yl)pyrimidin-2-amine,
N-(5-((3,8-diazabicyclo[3.2.1]octan-3-yl)methyl)pyridin-2-yl)-5-fluoro-4-((S)-5-fluoro-1-(fluoromethyl)-2,3-dihydro-1H-benzo[d]pyrrolo[1,2-a]imidazol-7-yl)pyrimidin-2-amine,
5-fluoro-4-((S)-5-fluoro-1-(fluoromethyl)-2,3-dihydro-1H-benzo[d]pyrrolo[1,2-a]imidazol-7-yl)-N-(5-((8-methyl-3,8-diazabicyclo[3.2.1]octan-3-yl)methyl)pyridin-2-yl)pyrimidin-2-amine,
N-(5-((8-ethyl-3,8-diazabicyclo[3.2.1]octan-3-yl)methyl)pyridin-2-yl)-5-fluoro-4-((S)-5-fluoro-1-(fluoromethyl)-2,3-dihydro-1H-benzo[d]pyrrolo[1,2-a]imidazol-7-yl)pyrimidin-2-amine,
(S)-4-(1-(difluoromethyl)-5-fluoro-2,3-dihydro-1H-benzo[d]pyrrolo[1,2-a]imidazol-7-yl)-5-fluoro-N-(5-(piperazin-1-yl)pyridin-2-yl)pyrimidin-2-amine,
(S)-4-(1-(difluoromethyl)-5-fluoro-2,3-dihydro-1H-benzo[d]pyrrolo[1,2-a]imidazol-7-yl)-

TABLE X-continued 5-fluoro-N-(5-(4-methylpiperazin-1-yl)pyridin-2-yl)pyrimidin-2-amine,
(S)-4-(1-(difluoromethyl)-5-fluoro-2,3-dihydro-1H-benzo[d]pyrrolo[1,2-a]imidazol-7-yl)-N-(5-(4-ethylpiperazin-1-yl)pyridin-2-yl)-5-fluoropyrimidin-2-amine,
4-((S)-1-(difluoromethyl)-5-fluoro-2,3-dihydro-1H-benzo[d]pyrrolo[1,2-a]imidazol-7-yl)-5-fluoro-N-(5-(((R)-hexahydropyrrolo[1,2-a]pyrazin-2(1H)-yl)methyl)pyridin-2-yl)pyrimidin-2-amine,
(S)-N-(5-((2,7-diazaspiro[3.5]nonan-2-yl)methyl)pyridin-2-yl)-4-(difluoromethyl)-5-fluoro-2,3-dihydro-1H-benzo[d]pyrrolo[1,2-a]imidazol-7-yl)-5-fluoropyrimidin-2-amine,
(S)-4-(1-(difluoromethyl)-5-fluoro-2,3-dihydro-1H-benzo[d]pyrrolo[1,2-a]imidazol-7-yl)-5-fluoro-N-(5-((7-methyl-2,7-diazaspiro[3.5]nonan-2-yl)methyl)pyridin-2-yl)pyrimidin-2-amine,
(S)-4-(1-(difluoromethyl)-5-fluoro-2,3-dihydro-1H-benzo[d]pyrrolo[1,2-a]imidazol-7-yl)-N-(5-((7-ethyl-2,7-diazaspiro[3.5]nonan-2-yl)methyl)pyridin-2-yl)-5-fluoropyrimidin-2-amine,
(S)-N-(5-((2,6-diazaspiro[3.3]heptan-2-yl)methyl)pyridin-2-yl)-4-(difluoromethyl)-5-fluoro-2,3-dihydro-1H-benzo[d]pyrrolo[1,2-a]imidazol-7-yl)-5-fluoropyrimidin-2-amine,
(S)-4-(1-(difluoromethyl)-5-fluoro-2,3-dihydro-1H-benzo[d]pyrrolo[1,2-a]imidazol-7-yl)-5-fluoro-N-(5-((6-methyl-2,6-diazaspiro[3.3]heptan-2-yl)methyl)pyridin-2-yl)pyrimidin-2-amine,
(S)-4-(1-(difluoromethyl)-5-fluoro-2,3-dihydro-1H-benzo[d]pyrrolo[1,2-a]imidazol-7-yl)-N-(5-((6-ethyl-2,6-diazaspiro[3.3]heptan-2-yl)methyl)pyridin-2-yl)-5-fluoropyrimidin-2-amine,
4-((S)-1-(difluoromethyl)-5-fluoro-2,3-dihydro-1H-benzo[d]pyrrolo[1,2-a]imidazol-7-yl)-5-fluoro-N-(5-((hexahydropyrrolo[3,4-c]pyrrol-2(1H)-yl)methyl)pyridin-2-yl)pyrimidin-2-amine,
4-((S)-1-(difluoromethyl)-5-fluoro-2,3-dihydro-1H-benzo[d]pyrrolo[1,2-a]imidazol-7-yl)-5-fluoro-N-(5-((5-methylhexahydropyrrolo[3,4-c]pyrrol-2(1H)-yl)methyl)pyridin-2-yl)pyrimidin-2-amine,
4-((S)-1-(difluoromethyl)-5-fluoro-2,3-dihydro-1H-benzo[d]pyrrolo[1,2-a]imidazol-7-yl)-N-(5-((5-ethylhexahydropyrrolo[3,4-c]pyrrol-2(1H)-yl)methyl)pyridin-2-yl)-5-fluoropyrimidin-2-amine,
(S)-N-(5-((3,9-diazaspiro[5.5]undecan-3-yl)methyl)pyridin-2-yl)-4-(difluoromethyl)-5-fluoro-2,3-dihydro-1H-benzo[d]pyrrolo[1,2-a]imidazol-7-yl)-5-fluoropyrimidin-2-amine,
(S)-4-(1-(difluoromethyl)-5-fluoro-2,3-dihydro-1H-benzo[d]pyrrolo[1,2-a]imidazol-7-yl)-5-fluoro-N-(5-((9-methyl-3,9-diazaspiro[5.5]undecan-3-yl)methyl)pyridin-2-yl)pyrimidin-2-amine,
(S)-4-(1-(difluoromethyl)-5-fluoro-2,3-dihydro-1H-benzo[d]pyrrolo[1,2-a]imidazol-7-yl)-N-(5-((9-ethyl-3,9-diazaspiro[5.5]undecan-3-yl)methyl)pyridin-2-yl)-5-fluoropyrimidin-2-amine,
N-(5-((3,8-diazabicyclo[3.2.1]octan-8-yl)methyl)pyridin-2-yl)-4-((S)-1-(difluoromethyl)-5-fluoro-2,3-dihydro-1H-benzo[d]pyrrolo[1,2-a]imidazol-7-yl)-5-fluoropyrimidin-2-amine,
4-((S)-1-(difluoromethyl)-5-fluoro-2,3-dihydro-1H-benzo[d]pyrrolo[1,2-a]imidazol-7-yl)-5-fluoro-N-(5-((3-methyl-3,8-diazabicyclo[3.2.1]octan-8-yl)methyl)pyridin-2-yl)pyrimidin-2-amine,
4-((S)-1-(difluoromethyl)-5-fluoro-2,3-dihydro-1H-benzo[d]pyrrolo[1,2-a]imidazol-7-yl)-N-(5-((3-ethyl-3,8-diazabicyclo[3.2.1]octan-8-yl)methyl)pyridin-2-yl)-5-fluoropyrimidin-2-amine,
N-(5-((3,8-diazabicyclo[3.2.1]octan-3-yl)methyl)pyridin-2-yl)-4-((S)-1-(difluoromethyl)-5-fluoro-2,3-dihydro-1H-benzo[d]pyrrolo[1,2-a]imidazol-7-yl)-5-fluoropyrimidin-2-amine,
4-((S)-1-(difluoromethyl)-5-fluoro-2,3-dihydro-1H-benzo[d]pyrrolo[1,2-a]imidazol-7-yl)-5-fluoro-N-(5-((8-methyl-3,8-diazabicyclo[3.2.1]octan-3-yl)methyl)pyridin-2-yl)pyrimidin-2-amine,
4-((S)-1-(difluoromethyl)-5-fluoro-2,3-dihydro-1H-benzo[d]pyrrolo[1,2-a]imidazol-7-yl)-N-(5-((8-ethyl-3,8-diazabicyclo[3.2.1]octan-3-yl)methyl)pyridin-2-yl)-5-fluoropyrimidin-2-amine,
5-fluoro-4-((S)-5-fluoro-1-(trifluoromethyl)-2,3-dihydro-1H-benzo[d]pyrrolo[1,2-a]imidazol-7-yl)-N-(5-(((R)-hexahydropyrrolo[1,2-a]pyrazin-2(1H)-yl)methyl)pyridin-2-yl)pyrimidin-2-amine,
(S)-N-(5-((2,7-diazaspiro[3.5]nonan-2-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine,
(S)-5-fluoro-4-(5-fluoro-1-(trifluoromethyl)-2,3-dihydro-1H-benzo[d]pyrrolo[1,2-a]imidazol-7-yl)-N-(5-((7-methyl-2,7-diazaspiro[3.5]nonan-2-yl)methyl)pyridin-2-yl)pyrimidin-2-amine,
(S)-N-(5-((7-ethyl-2,7-diazaspiro[3.5]nonan-2-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine,
(S)-N-(5-((2,7-diazaspiro[3.5]nonan-7-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine,
(S)-5-fluoro-4-(5-fluoro-1-(trifluoromethyl)-2,3-dihydro-1H-benzo[d]pyrrolo[1,2-a]imidazol-7-yl)-N-(5-((2-methyl-2,7-diazaspiro[3.5]nonan-7-yl)methyl)pyridin-2-yl)pyrimidin-2-amine,
(S)-N-(5-((2-ethyl-2,7-diazaspiro[3.5]nonan-7-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine,
(S)-N-(5-((2,6-diazaspiro[3.3]heptan-2-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine,
(S)-5-fluoro-4-(5-fluoro-1-(trifluoromethyl)-2,3-dihydro-1H-benzo[d]pyrrolo[1,2-a]imidazol-7-yl)-N-(5-((6-methyl-2,6-diazaspiro[3.3]heptan-2-yl)methyl)pyridin-2-yl)pyrimidin-2-amine,
(S)-N-(5-((6-ethyl-2,6-diazaspiro[3.3]heptan-2-yl)methyl)pyridin-2-yl)-5-fluoro-4-(5-

TABLE X-continued fluoro-1-(trifluoromethyl)-2,3-dihydro-1H-benzo[d]pyrrolo[1,2-a]imidazol-7-yl)pyrimidin-2-amine,
(S)-N-(5-((3,9-diazaspiro[5.5]undecan-3-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine,
(S)-5-fluoro-4-(5-fluoro-1-(trifluoromethyl)-2,3-dihydro-1H-benzo[d]pyrrolo[1,2-a]imidazol-7-yl)-N-(5-((9-methyl-3,9-diazaspiro[5.5]undecan-3-yl)methyl)pyridin-2-yl)pyrimidin-2-amine,
(S)-N-(5-49-ethyl-3,9-diazaspiro[5.5]undecan-3-yl)methyl)pyridin-2-yl)-5-fluoro-4-(5-fluoro-1-(trifluoromethyl)-2,3-dihydro-1H-benzo[d]pyrrolo[1,2-a]imidazol-7-yl)pyrimidin-2-amine,
5-fluoro-4-((S)-5-fluoro-1-(trifluoromethyl)-2,3-dihydro-1H-benzo[d]pyrrolo[1,2-a]imidazol-7-yl)-N-(5-((hexahydropyrrolo[3,4-c]pyrrol-2(1H)-yl)methyl)pyridin-2-yl)pyrimidin-2-amine,
5-fluoro-4-((S)-5-fluoro-1-(trifluoromethyl)-2,3-dihydro-1H-benzo[d]pyrrolo[1,2-a]imidazol-7-yl)-N-(5-((5-methylhexahydropyrrolo[3,4-c]pyrrol-2(1H)-yl)methyl)pyridin-2-yl)pyrimidin-2-amine,
N-(5-((5-ethylhexahydropyrrolo[3,4-c]pyrrol-2(1H)-yl)methyl)pyridin-2-yl)-5-fluoro-4-((S)-5-fluoro-1-(trifluoromethyl)-2,3-dihydro-1H-benzo[d]pyrrolo[1,2-a]imidazol-7-yl)pyrimidin-2-amine,
N-(5-((3,8-diazabicyclo[3.2.1]octan-8-yl)methyl)pyridin-2-yl)-5-fluoro-4-((S)-5-fluoro-1-(trifluoromethyl)-2,3-dihydro-1H-benzo[d]pyrrolo[1,2-a]imidazol-7-yl)pyrimidin-2-amine,
5-fluoro-4-((S)-5-fluoro-1-(trifluoromethyl)-2,3-dihydro-1H-benzo[d]pyrrolo[1,2-a]imidazol-7-yl)-N-(5-((3-methyl-3,8-diazabicyclo[3.2.1]octan-8-yl)methyl)pyridin-2-yl)pyrimidin-2-amine,
N-(5-((3-ethyl-3,8-diazabicyclo[3.2.1]octan-8-yl)methyl)pyridin-2-yl)-5-fluoro-4-((S)-5-fluoro-1-(trifluoromethyl)-2,3-dihydro-1H-benzo[d]pyrrolo[1,2-a]imidazol-7-yl)pyrimidin-2-amine,
N-(5-((3,8-diazabicyclo[3.2.1]octan-3-yl)methyl)pyridin-2-yl)-5-fluoro-4-((S)-5-fluoro-1-(trifluoromethyl)-2,3-dihydro-1H-benzo[d]pyrrolo[1,2-a]imidazol-7-yl)pyrimidin-2-amine,
5-fluoro-4-((S)-5-fluoro-1-(trifluoromethyl)-2,3-dihydro-1H-benzo[d]pyrrolo[1,2-a]imidazol-7-yl)-N-(5-((8-methyl-3,8-diazabicyclo[3.2.1]octan-3-yl)methyl)pyridin-2-yl)pyrimidin-2-amine,
N-(5-((8-ethyl-3,8-diazabicyclo[3.2.1]octan-3-yl)methyl)pyridin-2-yl)-5-fluoro-4-((S)-5-fluoro-1-(trifluoromethyl)-2,3-dihydro-1H-benzo[d]pyrrolo[1,2-a]imidazol-7-yl)pyrimidin-2-amine,
(R)-5-fluoro-4-(5-fluoro-1-methyl-2,3-dihydro-1H-benzo[d]pyrrolo[1,2-a]imidazol-7-yl)-N-(5-(piperazin-1-ylmethyl)pyridin-2-yl)pyrimidin-2-amine,
(R)-5-fluoro-4-(5-fluoro-1-methyl-2,3-dihydro-1H-benzo[d]pyrrolo[1,2-a]imidazol-7-yl)-N-(5-((4-methylpiperazin-1-yl)methyl)pyridin-2-yl)pyrimidin-2-amine,
(R)-N-(5-((4-ethylpiperazin-1-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine,
5-fluoro-4-((R)-5-fluoro-1-methyl-2,3-dihydro-1H-benzo[d]pyrrolo[1,2-a]imidazol-7-yl)-N-(5-(((R)-hexahydropyrrolo[1,2-a]pyrazin-2(1H)-yl)methyl)pyridin-2-yl)pyrimidin-2-amine,
(R)-N-(5-((2,7-diazaspiro[3.5]nonan-7-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine,
(R)-5-fluoro-4-(5-fluoro-1-methyl-2,3-dihydro-1H-benzo[d]pyrrolo[1,2-a]imidazol-7-yl)-N-(5-((2-methyl-2,7-diazaspiro[3.5]nonan-7-yl)methyl)pyridin-2-yl)pyrimidin-2-amine,
(R)-N-(5-((2-ethyl-2,7-diazaspiro[3.5]nonan-7-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine,
(R)-N-(5-((2,7-diazaspiro[3.5]nonan-2-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine,
(R)-5-fluoro-4-(5-fluoro-1-methyl-2,3-dihydro-1H-benzo[d]pyrrolo[1,2-a]imidazol-7-yl)-N-(5-((7-methyl-2,7-diazaspiro[3.5]nonan-2-yl)methyl)pyridin-2-yl)pyrimidin-2-amine,
(R)-N-(5-((7-ethyl-2,7-diazaspiro[3.5]nonan-2-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine,
(R)-N-(5-((3,9-diazaspiro[5.5]undecan-3-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine,
(R)-5-fluoro-4-(5-fluoro-1-methyl-2,3-dihydro-1H-benzo[d]pyrrolo[1,2-a]imidazol-7-yl)-N-(5-((9-methyl-3,9-diazaspiro[5.5]undecan-3-yl)methyl)pyridin-2-yl)pyrimidin-2-amine,
(R)-N-(5-((9-ethyl-3,9-diazaspiro[5.5]undecan-3-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine,
(R)-N-(5-((2,6-diazaspiro[3.3]heptan-2-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine,
(R)-5-fluoro-4-(5-fluoro-1-methyl-2,3-dihydro-1H-benzo[d]pyrrolo[1,2-a]imidazol-7-yl)-N-(5-((6-methyl-2,6-diazaspiro[3.3]heptan-2-yl)methyl)pyridin-2-yl)pyrimidin-2-amine,
(R)-N-(5-((6-ethyl-2,6-diazaspiro[3.3]heptan-2-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine,
5-fluoro-4-((R)-5-fluoro-1-methyl-2,3-dihydro-1H-benzo[d]pyrrolo[1,2-a]imidazol-7-yl)-N-(5-((hexahydropyrrolo[3,4-c]pyrrol-2(1H)-yl)methyl)pyridin-2-yl)pyrimidin-2-amine,
5-fluoro-4-((R)-5-fluoro-1-methyl-2,3-dihydro-1H-benzo[d]pyrrolo[1,2-a]imidazol-7-yl)-N-(5-((5-methylhexahydropyrrolo[3,4-c]pyrrol-2(1H)-yl)methyl)pyridin-2-yl)pyrimidin-2-amine,
N-(5-((5-ethylhexahydropyrrolo[3,4-c]pyrrol-2(1H)-yl)methyl)pyridin-2-yl)-5-fluoro-4-((R)-5-fluoro-1-methyl-2,3-dihydro-1H-benzo[d]pyrrolo[1,2-a]imidazol-7-yl)pyrimidin-2-amine,
N-(5-((3,8-diazabicyclo[3.2.1]octan-8-yl)methyl)pyridin-2-yl)-5-fluoro-4-((R)-5-fluoro-1-methyl-2,3-dihydro-1H-benzo[d]pyrrolo[1,2-a]imidazol-7-yl)pyrimidin-2-amine,
5-fluoro-4-((R)-5-fluoro-1-methyl-2,3-dihydro-1H-benzo[d]pyrrolo[1,2-a]imidazol-7-yl)-N-(5-((3-methyl-3,8-diazabicyclo[3.2.1]octan-8-yl)methyl)pyridin-2-yl)pyrimidin-2-amine, TABLE X-continued N-(5-((3-ethyl-3,8-diazabicyclo[3.2.1]octan-8-yl)methyl)pyridin-2-yl)-5-fluoro-4-((R)-5-fluoro-1-methyl-2,3-dihydro-1H-benzo[d]pyrrolo[1,2-a]imidazol-7-yl)pyrimidin-2-amine,
N-(5-((3,8-diazabicyclo[3.2.1]octan-3-yl)methyl)pyridin-2-yl)-5-fluoro-4-((R)-5-fluoro-1-methyl-2,3-dihydro-1H-benzo[d]pyrrolo[1,2-a]imidazol-7-yl)pyrimidin-2-amine,
5-fluoro-4-((R)-5-fluoro-1-methyl-2,3-dihydro-1H-benzo[d]pyrrolo[1,2-a]imidazol-7-yl)-N-(5-((8-methyl-3,8-diazabicyclo[3.2.1]octan-3-yl)methyl)pyridin-2-yl)pyrimidin-2-amine,
N-(5-((8-ethyl-3,8-diazabicyclo[3.2.1]octan-3-yl)methyl)pyridin-2-yl)-5-fluoro-4-((R)-5-fluoro-1-methyl-2,3-dihydro-1H-benzo[d]pyrrolo[1,2-a]imidazol-7-yl)pyrimidin-2-amine,
5-fluoro-4-(5-fluoro-1,1-dimethyl-2,3-dihydro-1H-benzo[d]pyrrolo[1,2-a]imidazol-7-yl)-N-(5-(piperazin-1-ylmethyl)pyridin-2-yl)pyrimidin-2-amine,
5-fluoro-4-(5-fluoro-1,1-dimethyl-2,3-dihydro-1H-benzo[d]pyrrolo[1,2-a]imidazol-7-yl)-N-(5-((4-methylpiperazin-1-yl)methyl)pyridin-2-yl)pyrimidin-2-amine,
N-(5-((4-ethylpiperazin-1-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine,
(R)-5-fluoro-4-(5-fluoro-1,1-dimethyl-2,3-dihydro-1H-benzo[d]pyrrolo[1,2-a]imidazol-7-yl)-N-(5-((hexahydropyrrolo[1,2-a]pyrazin-2(1H)-yl)methyl)pyridin-2-yl)pyrimidin-2-amine,
N-(5-((2,7-diazaspiro[3.5]nonan-2-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine,
5-fluoro-4-(5-fluoro-1,1-dimethyl-2,3-dihydro-1H-benzo[d]pyrrolo[1,2-a]imidazol-7-yl)-N-(5-((7-methyl-2,7-diazaspiro[3.5]nonan-2-yl)methyl)pyridin-2-yl)pyrimidin-2-amine,
N-(5-((7-ethyl-2,7-diazaspiro[3.5]nonan-2-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine,
N-(5-((2,7-diazaspiro[3.5]nonan-7-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine,
5-fluoro-4-(5-fluoro-1,1-dimethyl-2,3-dihydro-1H-benzo[d]pyrrolo[1,2-a]imidazol-7-yl)-N-(5-((2-methyl-2,7-diazaspiro[3.5]nonan-7-yl)methyl)pyridin-2-yl)pyrimidin-2-amine,
N-(5-((2-ethyl-2,7-diazaspiro[3.5]nonan-7-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine,
N-(5-((2,6-diazaspiro[3.3]heptan-2-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine,
5-fluoro-4-(5-fluoro-1,1-dimethyl-2,3-dihydro-1H-benzo[d]pyrrolo[1,2-a]imidazol-7-yl)-N-(5-((6-methyl-2,6-diazaspiro[3.3]heptan-2-yl)methyl)pyridin-2-yl)pyrimidin-2-amine,
N-(5-((6-ethyl-2,6-diazaspiro[3.3]heptan-2-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine,
N-(5-((3,9-diazaspiro[5.5]undecan-3-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine,
5-fluoro-4-(5-fluoro-1,1-dimethyl-2,3-dihydro-1H-benzo[d]pyrrolo[1,2-a]imidazol-7-yl)-N-(5-((9-methyl-3,9-diazaspiro[5.5]undecan-3-yl)methyl)pyridin-2-yl)pyrimidin-2-amine,
N-(5-((9-ethyl-3,9-diazaspiro[5.5]undecan-3-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine,
5-fluoro-4-(5-fluoro-1,1-dimethyl-2,3-dihydro-1H-benzo[d]pyrrolo[1,2-a]imidazol-7-yl)-N-(5-((hexahydropyrrolo[3,4-c]pyrrol-2(1H)-yl)methyl)pyridin-2-yl)pyrimidin-2-amine,
5-fluoro-4-(5-fluoro-1,1-dimethyl-2,3-dihydro-1H-benzo[d]pyrrolo[1,2-a]imidazol-7-yl)-N-(5-((5-methylhexahydropyrrolo[3,4-c]pyrrol-2(1H)-yl)methyl)pyridin-2-yl)pyrimidin-2-amine,
N-(5-((5-ethylhexahydropyrrolo[3,4-c]pyrrol-2(1H)-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine,
N-(5-((3,8-diazabicyclo[3.2.1]octan-8-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine,
5-fluoro-4-(5-fluoro-1,1-dimethyl-2,3-dihydro-1H-benzo[d]pyrrolo[1,2-a]imidazol-7-yl)-N-(5-((3-methyl-3,8-diazabicyclo[3.2.1]octan-8-yl)methyl)pyridin-2-yl)pyrimidin-2-amine,
N-(5-((3-ethyl-3,8-diazabicyclo[3.2.1]octan-8-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine,
N-(5-((3,8-diazabicyclo[3.2.1]octan-3-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine,
5-fluoro-4-(5-fluoro-1,1-dimethyl-2,3-dihydro-1H-benzo[d]pyrrolo[1,2-a]imidazol-7-yl)-N-(5-((8-methyl-3,8-diazabicyclo[3.2.1]octan-3-yl)methyl)pyridin-2-yl)pyrimidin-2-amine,
N-(5-((8-ethyl-3,8-diazabicyclo[3.2.1]octan-3-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine,
N-(5-((3,6-diazabicyclo[3.1.1]heptan-3-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine,
5-fluoro-4-(5-fluoro-2,3-dihydrospiro[benzo[d]pyrrolo[1,2-a]imidazole-1,1'-cyclopropan]-7-yl)-N-(5-((6-methyl-3,6-diazabicyclo[3.1.1]heptan-3-yl)methyl)pyridin-2-yl)pyrimidin-2-amine,
N-(5-((6-ethyl-3,6-diazabicyclo[3.1.1]heptan-3-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine,
N-(5-(((1S,4S)-2,5-diazabicyclo[2.2.1]heptan-2-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine,
5-fluoro-4-(5-fluoro-2,3-dihydrospiro[benzo[d]pyrrolo[1,2-a]imidazole-1,1'-cyclopropan]-7-yl)-N-(5-(((1S,4S)-5-methyl-2,5-diazabicyclo[2.2.1]heptan-2-yl)methyl)pyridin-2-yl)pyrimidin-2-amine,
N-(5-(((1S,4S)-5-ethyl-2,5-diazabicyclo[2.2.1]heptan-2-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine, TABLE X-continued N-(5-(((3aR,6aS)-3a,6a-dimethylhexahydropyrrolo[3,4-c]pyrrol-2(1H)-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine,
5-fluoro-4-(5-fluoro-2,3-dihydrospiro[benzo[d]pyrrolo[1,2-a]imidazole-1,1'-cyclopropan]-7-yl)-N-(5-((((3aR,6aS)-3a,5,6a-trimethylhexahydropyrrolo[3,4-c]pyrrol-2(1H)-yl)methyl)pyridin-2-yl)pyrimidin-2-amine,
N-(5-(((3aR,6aS)-5-ethyl-3a,6a-dimethylhexahydropyrrolo[3,4-c]pyrrol-2(1H)-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine,
N-(5-((3,6-diazabicyclo[3.2.0]heptan-3-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine,
5-fluoro-4-(5-fluoro-2,3-dihydrospiro[benzo[d]pyrrolo[1,2-a]imidazole-1,1'-cyclopropan]-7-yl)-N-(5-((6-methyl-3,6-diazabicyclo[3.2.0]heptan-3-yl)methyl)pyridin-2-yl)pyrimidin-2-amine,
N-(5-((6-ethyl-3,6-diazabicyclo[3.2.0]heptan-3-yl)methyl)pyridin-2-yl)-5-fluoro-4-(5-fluoro-2,3-dihydrospiro[benzo[d]pyrrolo[1,2-a]imidazole-1,1'-cyclopropan]-7-yl)pyrimidin-2-amine,
(S)-5-fluoro-4-(5-fluoro-2,3-dihydrospiro[benzo[d]pyrrolo[1,2-a]imidazole-1,1'-cyclopropan]-7-yl)-N-(5-((hexahydropyrrolo[1,2-a]pyrazin-2(1H)-yl)methyl)pyridin-2-yl)pyrimidin-2-amine,
(R)-5-fluoro-4-(5-fluoro-2,3-dihydrospiro[benzo[d]pyrrolo[1,2-a]imidazole-1,1'-cyclopropan]-7-yl)-N-(5-((hexahydropyrrolo[1,2-a]pyrazin-2(1H)-yl)methyl)pyridin-2-yl)pyrimidin-2-amine,
(7R,8aS)-2-((6-((5-fluoro-4-(5-fluoro-2,3-dihydrospiro[benzo[d]pyrrolo[1,2-a]imidazole-1,1'-cyclopropan]-7-yl)pyrimidin-2-yl)amino)pyridin-3-yl)methyl)octahydropyrrolo[1,2-a]pyrazin-7-ol,
3-((6-((5-fluoro-4-(5-fluoro-2,3-dihydrospiro[benzo[d]pyrrolo[1,2-a]imidazole-1,1'-cyclopropan]-7-yl)pyrimidin-2-yl)amino)pyridin-3-yl)methyl)-3-azabicyclo[3.1.0]hexan-6-amine,
(R)-5-fluoro-4-(5-fluoro-2,3-dihydrospiro[benzo[d]pyrrolo[1,2-a]imidazole-1,1'-cyclopropan]-7-yl)-N-(5-((hexahydropyrazino[2,1-c][1,4]oxazin-8(1H)-yl)methyl)pyridin-2-yl)pyrimidin-2-amine,
5-fluoro-4-(5-fluoro-2,3-dihydro-1H-benzo[d]pyrrolo[1,2-a]imidazol-7-yl)-N-(5-(piperazin-1-ylmethyl)pyridin-2-yl)pyrimidin-2-amine,
5-fluoro-4-(5-fluoro-2,3-dihydro-1H-benzo[d]pyrrolo[1,2-a]imidazol-7-yl)-N-(5-((4-methylpiperazin-1-yl)methyl)pyridin-2-yl)pyrimidin-2-amine,
N-(5-((4-ethylpiperazin-1-yl)methyl)pyridin-2-yl)-5-fluoro-4-(5-fluoro-2,3-dihydro-1H-benzo[d]pyrrolo[1,2-a]imidazol-7-yl)pyrimidin-2-amine,
(R)-4-(1-(difluoromethyl)-5-fluoro-2,3-dihydro-1H-benzo[d]pyrrolo[1,2-a]imidazol-7-yl)-5-fluoro-N-(5-(piperazin-1-ylmethyl)pyridin-2-yl)pyrimidin-2-amine,
(R)-4-(1-(difluoromethyl)-5-fluoro-2,3-dihydro-1H-benzo[d]pyrrolo[1,2-a]imidazol-7-yl)-5-fluoro-N-(5-((4-methylpiperazin-1-yl)methyl)pyridin-2-yl)pyrimidin-2-amine,
(R)-4-(1-(difluoromethyl)-5-fluoro-2,3-dihydro-1H-benzo[d]pyrrolo[1,2-a]imidazol-7-yl)-N-(5-((4-ethylpiperazin-1-yl)methyl)pyridin-2-yl)-5-fluoropyrimidin-2-amine,
(S)-5-fluoro-4-(5-fluoro-1-methyl-2,3-dihydro-1H-benzo[d]pyrrolo[1,2-a]imidazol-7-yl)-N-(5-(piperazin-1-ylmethyl)pyridin-2-yl)pyrimidin-2-amine,
(S)-5-fluoro-4-(5-fluoro-1-methyl-2,3-dihydro-1H-benzo[d]pyrrolo[1,2-a]imidazol-7-yl)-N-(5-((4-methylpiperazin-1-yl)methyl)pyridin-2-yl)pyrimidin-2-amine,
(S)-N-(5-((4-ethylpiperazin-1-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine,
(R)-5-fluoro-4-(5-fluoro-1-(methoxymethyl)-2,3-dihydro-1H-benzo[d]pyrrolo[1,2-a]imidazol-7-yl)-N-(5-(piperazin-1-ylmethyl)pyridin-2-yl)pyrimidin-2-amine,
(R)-5-fluoro-4-(5-fluoro-1-(methoxymethyl)-2,3-dihydro-1H-benzo[d]pyrrolo[1,2-a]imidazol-7-yl)-N-(5-((4-methylpiperazin-1-yl)methyl)pyridin-2-yl)pyrimidin-2-amine,
(R)-N-(5-((4-ethylpiperazin-1-yl)methyl)pyridin-2-yl)-5-fluoro-4-(5-fluoro-1-(methoxymethyl)-2,3-dihydro-1H-benzo[d]pyrrolo[1,2-a]imidazol-7-yl)pyrimidin-2-amine,
N-(5-((3,8-diazabicyclo[3.2.1]octan-8-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine,
5-fluoro-4-(5-fluoro-1,1-dimethyl-2,3-dihydro-1H-benzo[d]pyrrolo[1,2-a]imidazol-7-yl)-N-(5-((3-methyl-3,8-diazabicyclo[3.2.1]octan-8-yl)methyl)pyridin-2-yl)pyrimidin-2-amine,
N-(5-((3-ethyl-3,8-diazabicyclo[3.2.1]octan-8-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine,
N-(5-fluoro-4-(5-fluoro-1,1-dimethyl-2,3-dihydro-1H-benzo[d]pyrrolo[1,2-a]imidazol-7-yl)pyridin-2-yl)-5-(piperazin-1-ylmethyl)pyrimidin-2-amine,
N-(5-fluoro-4-(5-fluoro-1,1-dimethyl-2,3-dihydro-1H-benzo[d]pyrrolo[1,2-a]imidazol-7-yl)pyridin-2-yl)-5-((4-methylpiperazin-1-yl)methyl)pyrimidin-2-amine,
5-((4-ethylpiperazin-1-yl)methyl)-N-5-fluoro-4-(5-fluoro-1,1-dimethyl-2,3-dihydro-1H-benzo[d]pyrrolo[1,2-a]imidazol-7-yl)pyridin-2-yl)pyrimidin-2-amine,
N-(5-((3,8-diazabicyclo[3.2.1]octan-8-yl)methyl)pyridin-2-yl)-4-(6,6-dimethyl-7,8-dihydro-6H-pyrrolo[1',2':1,2]imidazo[4,5-b]pyridin-3-yl)-5-fluoropyridin-2-amine,
4-(6,6-dimethyl-7,8-dihydro-6H-pyrrolo[1',2',1,2]imidazo[4,5-b]pyridin-3-yl)-5-fluoro-N-(5-((3-methyl-3,8-diazabicyclo[3.2.1]octan-8-yl)methyl)pyridin-2-yl)pyrimidin-2-amine,and
4-(6,6-dimethyl-7,8-dihydro-6H-pyrrolo[1',2',1,2]imidazo[4,5-b]pyridin-3-yl)-N-(5-((3-ethyl-3,8-diazabicyclo[3.2.1]octan-8-yl)methyl)pyridin-2-yl)-5-fluoropyridin-2-amine In one embodiment, the compound of the present disclosure excludes compounds in Table Y:

TABLE Y 7-(2-chloro-5-fluoropyrimidin-4-yl)-5-fluoro-1,1-dimethyl-2,3-dihydro-1H-benzo[d]pyrrolo[1,2-a]imidazole,
7-(2-chloro-5-fluoropyrimidin-4-yl)-5-fluoro-1-methyl-2,3-dihydro-1H-benzo[d]pyrrolo[1,2-a]imidazole,
7-(2-chloro-5-fluoropyrimidin-4-yl)-1-ethyl-5-fluoro-2,3-dihydro-1H-benzo[d]pyrrolo[1,2-a]imidazole,
7-(2-chloro-5-fluoropyrimidin-4-yl)-5-fluoro-2,2-dimethyl-2,3-dihydro-1H-benzo[d]pyrrolo[1,2-a]imidazole,
7-(2-chloro-5-fluoropyrimidin-4-yl)-5-fluoro-2-methyl-2,3-dihydro-1H-benzo[d]pyrrolo[1,2-a]imidazole,
7-(2-chloro-5-fluoropyrimidin-4-yl)-2-ethyl-5-fluoro-2,3-dihydro-1H-benzo[d]pyrrolo[1,2-a]imidazole,
8-(2-chloro-5-fluoropyrimidin-4-yl)-6-fluoro-1,2,3,4-tetrahydrobenzo[4,5]imidazo[1,2-a]pyridine,
2-(2-chloro-5-fluoropyrimidin-4-yl)-4-fluoro-7,8,9,10-tetrahydro-6H-benzo[4,5]imidazo[1,2-a]azepine,
7-(2-chloropyrimidin-4-yl)-5-fluoro-1,1-dimethyl-2,3-dihydro-1H-benzo[d]pyrrolo[1,2-a]imidazole,
7-(2-chloro-5-fluoropyrimidin-4-yl)-1,1-dimethyl-2,3-dihydro-1H-benzo[d]pyrrolo[1,2-a]imidazole,
7-(2-chloro-5-fluoropyrimidin-4-yl)-5-fluoro-2,3-dihydro-1H-benzo[d]pyrrolo[1,2-a]imidazole,
5-fluoro-4-(6-fluoro-1,2,3,4-tetrahydrobenzo[4,5]imidazo[1,2-a]pyridin-8-yl)-N-(5-(piperazin-1-yl)pyridin-2-yl)pyrimidin-2-amine,
N-(5-((4-ethylpiperazin-1-yl)methyl)pyridin-2-yl)-5-fluoro-4-(6-fluoro-1,2,3,4-tetrahydrobenzo[4,5]imidazo[1,2-a]pyridin-8-yl)pyrimidin-2-amine,
1-(2-((5-fluoro-4-(6-fluoro-1,2,3,4-tetrahydrobenzo[4,5]imidazo[1,2-a]pyridin-8-yl)pyrimidin-2-yl)amino)-7,8-dihydro-1,6-naphthyridin-6(5H)-yl)-2-hydroxyethanone,
N-(5-((4-ethylpiperazin-1-yl)methyl)pyridin-2-yl)-5-fluoro-4-(4-fluoro-7,8,9,10-tetrahydro-6H-benzo[4,5]imidazo[1,2-a]azepin-2-yl)pyrimidin-2-amine,
5-fluoro-4-(4-fluoro-7,8,9,10-tetrahydro-6H-benzo[4,5]imidazo[1,2-a]azepin-2-yl)-N-(5-(piperazin-1-yl)pyridin-2-yl)pyrimidin-2-amine,
5-fluoro-4-(5-fluoro-1,1-dimethyl-2,3-dihydro-1H-benzo[d]pyrrolo[1,2-a]imidazol-7-yl)-N-(5-(piperazin-1-yl)pyridin-2-yl)pyrimidin-2-amine,
1-(2-((5-fluoro-4-(5-fluoro-1,1-dimethyl-2,3-dihydro-1H-benzo[d]pyrrolo[1,2-a]imidazol-7-yl)pyrimidin-2-yl)amino)-7,8-dihydro-1,6-naphthyridin-6(5H)-yl)-2-hydroxyethanone,
N-(5-((4-ethylpiperazin-1-yl)methyl)pyridin-2-yl)-4-(5-fluoro-1,1-dimethyl-2,3-dihydro-1H-benzo[d]pyrrolo[1,2-a]imidazol-7-yl)pyrimidin-2-amine,
4-(5-fluoro-1,1-dimethyl-2,3-dihydro-1H-benzo[d]pyrrolo[1,2-a]imidazol-7-yl)-N-(5-(piperazin-1-yl)pyridin-2-yl)pyrimidin-2-amine,
4-(1,1-dimethyl-2,3-dihydro-1H-benzo[d]pyrrolo[1,2-a]imidazol-7-yl)-N-(5-((4-ethylpiperazin-1-yl)methyl)pyridin-2-yl)-5-fluoropyrimidin-2-amine,
4-(1,1-dimethyl-2,3-dihydro-1H-benzo[d]pyrrolo[1,2-a]imidazol-7-yl)-5-fluoro-N-(5-(piperazin-1-yl)pyridin-2-yl)pyrimidin-2-amine,
5-fluoro-4-(5-fluoro-1,1-dimethyl-2,3-dihydro-1H-benzo[d]pyrrolo[1,2-a]imidazol-7-yl)-N-(5-(piperidin-4-yl)pyridin-2-yl)pyrimidin-2-amine,
N-(5-(4-aminopiperidin-1-yl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine,
5-fluoro-4-(5-fluoro-1,1-dimethyl-2,3-dihydro-1H-benzo[d]pyrrolo[1,2-a]imidazol-7-yl)-N-(6-methyl-5-(piperazin-1-ylmethyl)pyridin-2-yl)pyrimidin-2-amine,
5-fluoro-4-(5-fluoro-1,1-dimethyl-2,3-dihydro-1H-benzo[d]pyrrolo[1,2-a]imidazol-7-yl)-N-(6-methyl-5-(piperidin-4-ylmethyl)pyridin-2-yl)pyrimidin-2-amine
5-fluoro-4-(5-fluoro-1,1-dimethyl-2,3-dihydro-1H-benzo[d]pyrrolo[1,2-a]imidazol-7-yl)-N-(6-methyl-5-(piperazin-1-yl)pyridin-2-yl)pyrimidin-2-amine,
(4-ethylpiperazin-1-yl)(6-((5-fluoro-4-(5-fluoro-1,1-dimethyl-2,3-dihydro-1H-benzo[d]pyrrolo[1,2-a]imidazol-7-yl)pyrimidin-2-yl)amino)pyridin-3-yl)methanone,
N-(5-((1-ethylpiperidin-4-yl)oxy)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine,
5-fluoro-4-(5-fluoro-1,1-dimethyl-2,3-dihydro-1H-benzo[d]pyrrolo[1,2-a]imidazol-7-yl)-N-(5-(piperidin-4-yloxy)pyridin-2-yl)pyrimidin-2-amine,
N-(5-(4-ethylpiperazin-1-yl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine,
5-fluoro-4-(5-fluoro-1,1-dimethyl-2,3-dihydro-1H-benzo[d]pyrrolo[1,2-a]imidazol-7-yl)-N-(5-((4-(2-fluoroethyl)piperazin-1-yl)methyl)pyridin-2-yl)pyrimidin-2-amine,
N-(5-((4-ethylpiperazin-1-yl)methyl)-6-methylpyridin-2-yl)-5-fluoro-4-(5-fluoro-1,1-dimethyl-2,3-dihydro-1H-benzo[d]pyrrolo[1,2-a]imidazol-7-yl)pyrimidin-2-amine,
5-fluoro-4-(5-fluoro-1,1-dimethyl-2,3-dihydro-1H-benzo[d]pyrrolo[1,2-a]imidazol-7-yl)-N-(6-methyl-5-((4-methylpiperazin-1-yl)methyl)pyridin-2-yl)pyrimidin-2-amine,
(S)-5-fluoro-4-(5-fluoro-1,1-dimethyl-2,3-dihydro-1H-benzo[d]pyrrolo[1,2-a]imidazol-7-yl)-N-(5-(3-methylpiperazin-1-yl)pyridin-2-yl)pyrimidin-2-amine,
(R)-5-fluoro-4-(5-fluoro-1,1-dimethyl-2,3-dihydro-1H-benzo[d]pyrrolo[1,2-a]imidazol-7-yl)-N-(5-(3-methylpiperazin-1-yl)pyridin-2-yl)pyrimidin-2-amine,
5-fluoro-4-(5-fluoro-1-methyl-2,3-dihydro-1H-benzo[d]pyrrolo[1,2-a]imidazol-7-yl)-N-(6-methyl-5-(4-methylpiperazin-1-yl)pyridin-2-yl)pyrimidin-2-amine,
2-(4-(6-((5-fluoro-4-(5-fluoro-1,1-dimethyl-2,3-dihydro-1H-benzo[d]pyrrolo[1,2-a]imidazol-7-yl)pyrimidin-2-yl)amino)pyridin-3-yl)piperazin-1-yl)ethanol,
5-fluoro-4-(5-fluoro-1,1-dimethyl-2,3-dihydro-1H-benzo[d]pyrrolo[1,2-a]imidazol-7-yl)-N-(5-(4-methylpiperazin-1-yl)pyridin-2-yl)pyrimidin-2-amine,
5-fluoro-4-(5-fluoro-1,1-dimethyl-2,3-dihydro-1H-benzo[d]pyrrolo[1,2-a]imidazol-7-yl)-N-(5-(1-methylpiperidin-4-yl)pyridin-2-yl)pyrimidin-2-amine,
N-(5-(1-ethylpiperidin-4-yl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine,
(S)-5-fluoro-4-(5-fluoro-1,1-dimethyl-2,3-dihydro-1H-benzo[d]pyrrolo[1,2-a]imidazol-7-yl)-N-(5-((3-methylpiperazin-1-yl)methyl)pyridin-2-yl)pyrimidin-2-amine, TABLE Y-continued (S)-N-(5-((3,4-dimethylpiperazin-1-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine,
N-(5-((4-cyclopropylpiperazin-1-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine,
N-(5-((4-ethylpiperazin-1-yl)methyl)pyridin-2-yl)-5-fluoro-4-(5-fluoro-2-methyl-2,3-dihydro-1H-benzo[d]pyrrolo[1,2-a]imidazol-7-yl)pyrimidin-2-amine,
5-fluoro-4-(5-fluoro-2-methyl-2,3-dihydro-1H-benzo[d]pyrrolo[1,2-a]imidazol-7-yl)-N-(5-(piperazin-1-yl)pyridin-2-yl)pyrimidin-2-amine,
4-(2-ethyl-5-fluoro-2,3-dihydro-1H-benzo[d]pyrrolo[1,2-a]imidazol-7-yl)-N-(5-((4-ethylpiperazin-1-yl)methyl)pyridin-2-yl)-5-fluoropyrimidin-2-amine,
4-(2-ethyl-5-fluoro-2,3-dihydro-1H-benzo[d]pyrrolo[1,2-a]imidazol-7-yl)-5-fluoro-N-(5-(piperazin-1-yl)pyridin-2-yl)pyrimidin-2-amine,
5-fluoro-4-(5-fluoro-1-methyl-2,3-dihydro-1H-benzo[d]pyrrolo[1,2-a]imidazol-7-yl)-N-(5-(3-methylpiperazin-1-yl)pyridin-2-yl)pyrimidin-2-amine,
4-(1-ethyl-5-fluoro-2,3-dihydro-1H-benzo[d]pyrrolo[1,2-a]imidazol-7-yl)-5-fluoro-N-(5-(piperazin-1-yl)pyridin-2-yl)pyrimidin-2-amine,
5-fluoro-4-(5-fluoro-2,2-dimethyl-2,3-dihydro-1H-benzo[d]pyrrolo[1,2-a]imidazol-7-yl)-N-(5-(piperazin-1-yl)pyridin-2-yl)pyrimidin-2-amine,
N-(5-((4-ethylpiperazin-1-yl)methyl)pyridin-2-yl)-5-fluoro-4-(5-fluoro-2,2-dimethyl-2,3-dihydro-1H-benzo[d]pyrrolo[1,2-a]imidazol-7-yl)pyrimidin-2-amine,
5-fluoro-4-(5-fluoro-1,1-dimethyl-2,3-dihydro-1H-benzo[d]pyrrolo[1,2-a]imidazol-7-yl)-N-(5-(3-methylpiperazin-1-yl)pyridin-2-yl)pyrimidin-2-amine,
1-(2-((5-fluoro-4-(5-fluoro-1-methyl-2,3-dihydro-1H-benzo[d]pyrrolo[1,2-a]imidazol-7-yl)pyrimidin-2-yl)amino)-7,8-dihydro-1,6-naphthyridin-6(5H)-yl)-2-hydroxyethanone,
5-fluoro-4-(5-fluoro-1-methyl-2,3-dihydro-1H-benzo[d]pyrrolo[1,2-a]imidazol-7-yl)-N-(5-(piperazin-1-yl)pyridin-2-yl)pyrimidin-2-amine,
N-(5-((4-ethylpiperazin-1-yl)methyl)pyridin-2-yl)-5-fluoro-4-(5-fluoro-1-methyl-2,3-dihydro-1H-benzo[d]pyrrolo[1,2-a]imidazol-7-yl)pyrimidin-2-amine,
5-fluoro-4-(5-fluoro-1-methyl-2,3-dihydro-1H-benzo[d]pyrrolo[1,2-a]imidazol-7-yl)-N-(5-(piperidin-4-yl)pyridin-2-yl)pyrimidin-2-amine,
5-fluoro-4-(5-fluoro-1-methyl-2,3-dihydro-1H-benzo[d]pyrrolo[1,2-a]imidazol-7-yl)-N-(6-methyl-5-(piperidin-4-ylmethyl)pyridin-2-yl)pyrimidin-2-amine,
5-fluoro-4-(5-fluoro-1-methyl-2,3-dihydro-1H-benzo[d]pyrrolo[1,2-a]imidazol-7-yl)-N-(5-((4-methylpiperazin-1-yl)methyl)pyridin-2-yl)pyrimidin-2-amine,
N-(5-((4-ethylpiperazin-1-yl)methyl)-6-methylpyridin-2-yl)-5-fluoro-4-(5-fluoro-1-methyl-2,3-dihydro-1H-benzo[d]pyrrolo[1,2-a]imidazol-7-yl)pyrimidin-2-amine,
5-fluoro-4-(5-fluoro-1-methyl-2,3-dihydro-1H-benzo[d]pyrrolo[1,2-a]imidazol-7-yl)-N-(5-((4-isopropylpiperazin-1-yl)methyl)pyridin-2-yl)pyrimidin-2-amine,
5-fluoro-4-(5-fluoro-1-methyl-2,3-dihydro-1H-benzo[d]pyrrolo[1,2-a]imidazol-7-yl)-N-(5-(1methylpiperidin-4-yl)pyridin-2-yl)pyrimidin-2-amine,
4-(1-ethyl-5-fluoro-2,3-dihydro-1H-benzo[d]pyrrolo[1,2-a]imidazol-7-yl)-5-fluoro-N-(5-((4-methylpiperazin-1-yl)methyl)pyridin-2-yl)pyrimidin-2-amine,
4-(1-ethyl-5-fluoro-2,3-dihydro-1H-benzo[d]pyrrolo[1,2-a]imidazol-7-yl)-5-fluoro-N-(5-(1-methylpiperidin-4-yl)pyridin-2-yl)pyrimidin-2-amine,
N-(5-(1-ethylpiperidin-4-yl)pyridin-2-yl)-5-fluoro-4-(5-fluoro-1-methyl-2,3-dihydro-1H-benzo[d]pyrrolo[1,2-a]imidazol-7-yl)pyrimidin-2-amine,
4-(1-ethyl-5-fluoro-2,3-dihydro-1H-benzo[d]pyrrolo[1,2-a]imidazol-7-yl)-N-(5-((4-ethylpiperazin-1-yl)methyl)pyridin-2-yl)-5-fluoropyrimidin-2-amine,
N-(5-(4-(dimethylamino)piperidin-1-yl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine,
4-(5-fluoro-1-methyl-2,3-dihydro-1H-benzo[d]pyrrolo[1,2-a]imidazol-7-yl)-N-(5-(piperazin-1-yl)pyridin-2-yl)pyrimidin-2-amine,
N-(5-((4-ethylpiperazin-1-yl)methyl)pyridin-2-yl)-4-(5-fluoro-1-methyl-2,3-dihydro-1H-benzo[d]pyrrolo[1,2-a]imidazol-7-yl)pyrimidin-2-amine, and
N-(5-(3,5-dimethylpiperazin-1-yl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine.

In one embodiment, the compounds of the present disclosure (e.g., a compound of formula (A), (B), (I), or (II), and any subgenera thereof, or a pharmaceutically acceptable salt, solvate, ester, or prodrug thereof) excludes the compounds exemplified in WO2017/071516 and WO 2016/173505.

One embodiment of the present disclosure relates to novel aminopyrimidine compounds. In one embodiment, the present disclosure relates to compound of Formula (I):

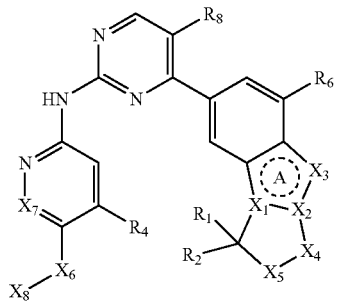

(I)

or a pharmaceutically acceptable salt, a solvate, a stereoisomer, or tautomer thereof, wherein:

$X_1$, $X_2$, and $X_7$ is selected from N, C, or CH; wherein when $X_2$ is C or CH, $X_4$ and $X_5$ is selected from O, NH, $NR_5$ or $CH_2$, provided that $X_4$ and $X_5$ cannot be both O;

when $X_2$ is a N, $X_4$ is selected from NH, $NR_5$ or $CH_2$, and $X_5$ is selected from $CH_2$ or O;

$X_3$ is selected from N or CH;

ring A is an aromatic ring;

$X_6$ is selected from a $CH_2$, C=O or absent;

$X_8$ is selected from:

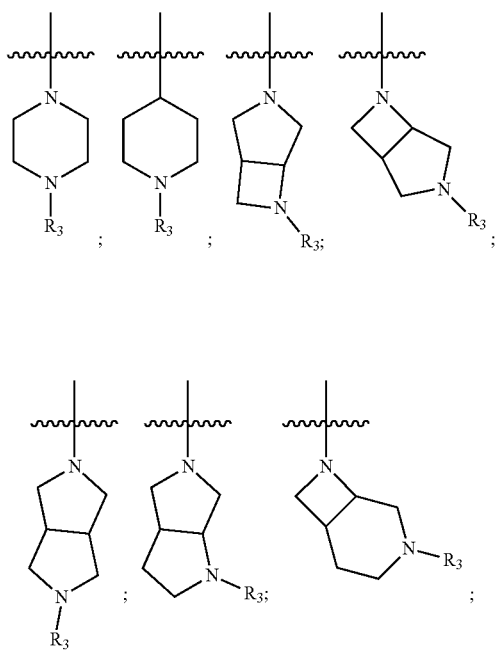

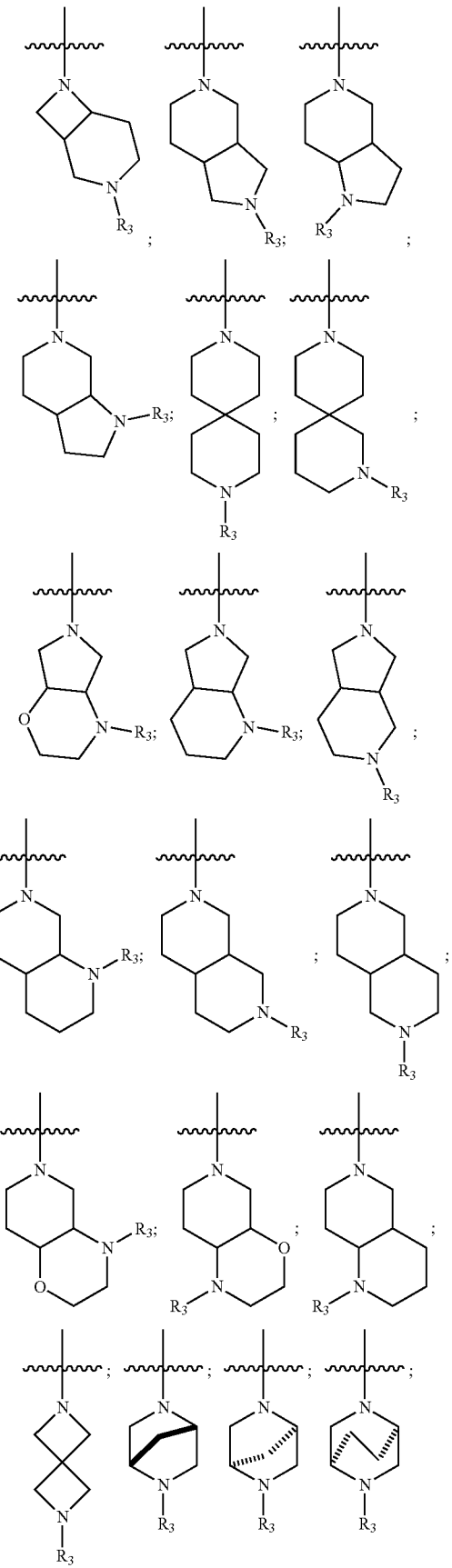

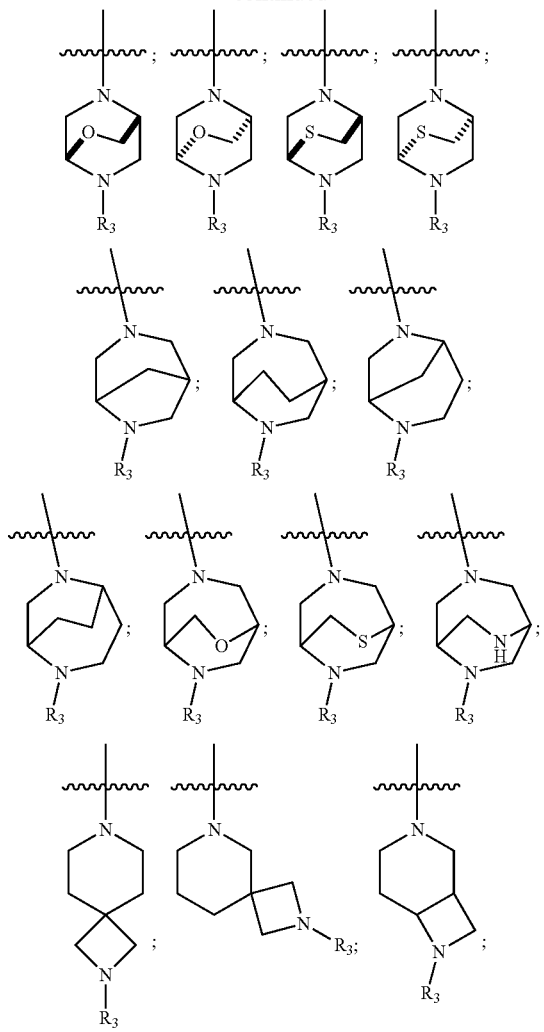

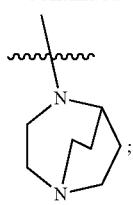

R₃ is selected from acyl or optionally substituted alkyl;

X₈ is optionally substituted with one to four substituents each independently selected from: $C_1$-$C_3$ alkyl optionally substituted with one or two substituents each independently selected from hydroxyl or —S—($C_1$-$C_3$ alkyl); —CD₃; halo; oxo; $C_1$-$C_3$ haloalkyl; hydroxyl; NH₂; dimethylamino; benzyl; or —C(O)—($C_1$-$C_3$ alkyl) optionally substituted with one or two substituents each independently selected from: —SCH₃, —NHC(O)CH₃, —S(O)₂—($C_1$-$C_4$ alkyl), or —C(O)-pyrrolidinyl;

R₁ and R₂ is selected from H, alkyl, substituted alkyl; or R₁ and R₂ together with the carbon atom to which they are attached to can form a 3-8 membered optionally substituted cycloalkyl or a 3-8 membered optionally substituted heterocycloalkyl containing one or more of O, N, S, SO, or SO₂;

R₄ is selected from H, CN, alkyl, substituted alkyl or halogen;

R₅ is selected from H, alkyl, substituted alkyl; and

R₆ and R₈ are each independently selected from H, CN, $C_1$-$C_6$ alkyl, substituted $C_1$-$C_6$ alkyl, Cl, F, or Br.

Ring A refers to the 5-membered ring in formula (I) formed by X₁, X₂, X₃, and the two adjacent carbon atoms. The dotted circle in Ring A demonstrates that the ring is aromatic.

In one embodiment, ring A of formula (I) is a pyrazole ring or an imidazole ring.

In one embodiment, X₁ is C; and X₂ and X₃ are each N in formula (I).

In one embodiment, X₂ is C; and X₁ and X₃ are each N in in formula (I).

In one embodiment, the compound of formula (I) has the structure of formula (Ij) or (Ik):

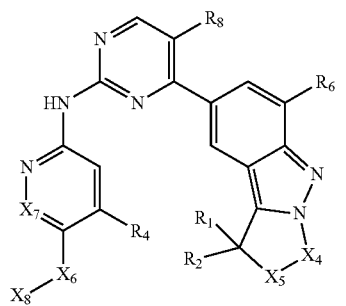

(Ij)

or (Ik)

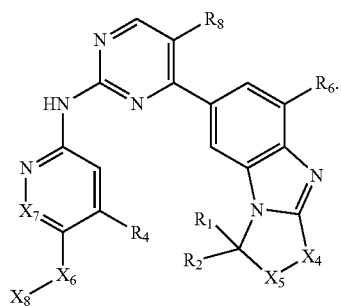

In another embodiment, the compound of formula (I) has the structure of formula (Id), (Ie), (If), (Ig), (Ih), or (Ii):

(Id)

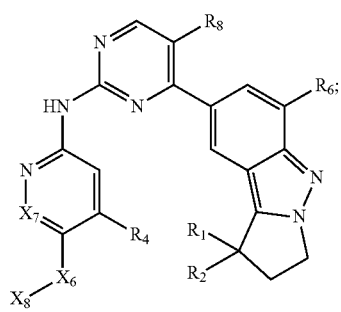

(Ie)

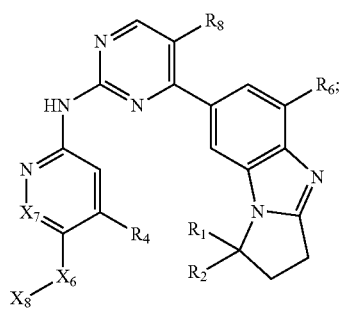

(If)

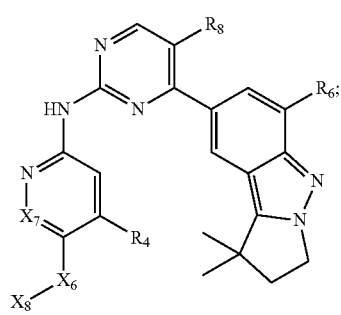

(Ig)

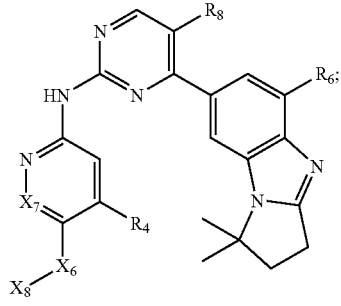

(Ih)

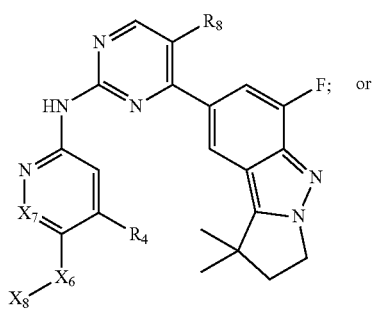

or (Ii)

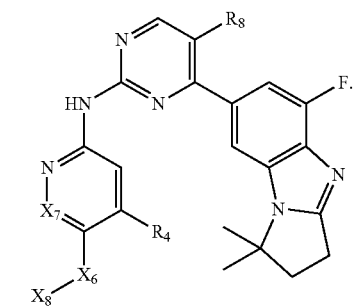

In one embodiment, $X_7$ of formula (I) is N or CH. In one embodiment, $X_7$ is CH.

In one embodiment, $X_6$ of formula (I) is selected from a $CH_2$, C=O or absent. In some embodiments, $X_6$ is $CH_2$. In another embodiment, $X_6$ is C=O. In one embodiment, $X_6$ is absent.

In one embodiment, $X_8$ of formula (I) is

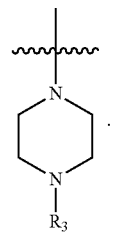

In one embodiment, $X^8$ of formula (I) is

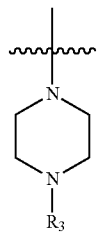

and $R_3$ is selected from methyl, ethyl, propyl, isopropyl, butyl, —C(O)CH$_3$, —C(O)CH$_2$CH$_3$, —C(O)CH$_2$OH, or —C(O)CH$_2$CH$_2$OH. In one embodiment, $X_8$ of formula (Ij) is

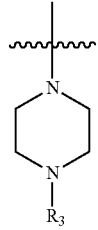

and $R_3$ is —C(O)CH$_2$OH. In one embodiment, $X_8$ of formula (Ik) is

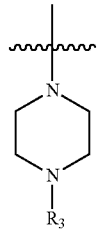

and $R_3$ is methyl, ethyl, propyl, or isopropyl.

In one embodiment, $R_3$ related to formula (I) is selected from —C(O)(C$_1$-C$_3$ alkyl) which is optionally substituted or C$_1$-C$_6$ alkyl which is optionally substituted. In another embodiment, $R_3$ related to formula (I) is —C(O)(C$_1$-C$_3$ alkyl) substituted with a hydroxyl group on the C$_1$-C$_3$ alkyl portion. In one embodiment, $R^3$ is a C$_1$-C$_6$ alkyl. In one embodiment, $R_3$ is a methyl, ethyl, propyl, or isopropyl. In another embodiment, $R_3$ is a C$_1$-C$_6$ alkyl substituted with an acyl group. In another embodiment, $R_3$ is a C$_1$-C$_6$ alkyl substituted with —C(O)CH$_3$ or —C(O)CH$_2$CH$_3$.

In one embodiment, $R_1$ of formula (I) is H or C$_1$-C$_6$ alkyl. In another embodiment, $R_1$ is methyl, ethyl, propyl, or butyl. In another embodiment, $R_1$ is methyl.

In one embodiment, $R_2$ of formula (I) is H or C$_1$-C$_6$ alkyl. In another embodiment, $R_2$ is methyl, ethyl, propyl, or butyl. In another embodiment, $R_2$ is methyl.

In one embodiment, $R_1$ and $R_2$ of formula (I) are each methyl.

In one embodiment, $R_1$ and $R_2$ of formula (I) together with the carbon atom to which they are attached to can form a 3-6 membered optionally substituted cycloalkyl or a 3-6 membered optionally substituted heterocycloalkyl containing one or more of O, N, S, SO, or SO$_2$.

In one embodiment, $R_4$ of formula (I) is H, CN, or halogen. In one embodiment, $R_4$ is H.

In one embodiment, $R_6$ of formula (I) is H, CN, C$_1$-C$_6$ alkyl, Cl, F, or Br. In another embodiment, $R_6$ is H, Cl, F, or Br. In one embodiment, $R_6$ is H, Cl, or F. In some embodiments, $R_6$ is F.

In one embodiment, $R_8$ of formula (I) is H, CN, C$_1$-C$_6$ alkyl, Cl, F, or Br. In another embodiment, $R_8$ is H, Cl, F, or Br. In one embodiment, $R_8$ is H, Cl, or F. In some embodiments, $R_8$ is F.

In one embodiment, $R_6$ and $R_8$ of formula (I) are each F.

In one embodiment, a compound of formula (I) is selected from:

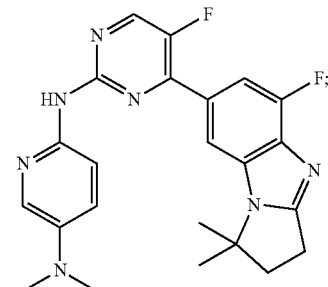

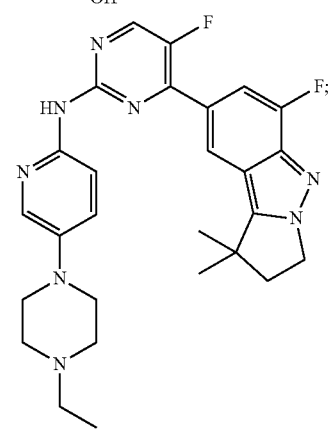

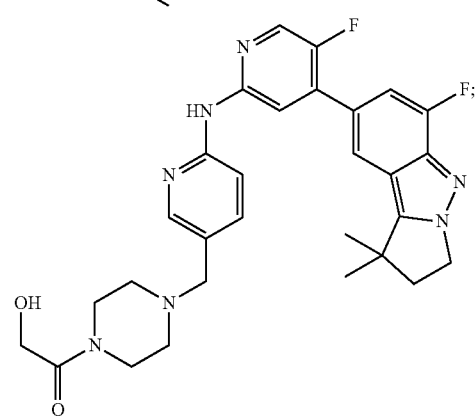

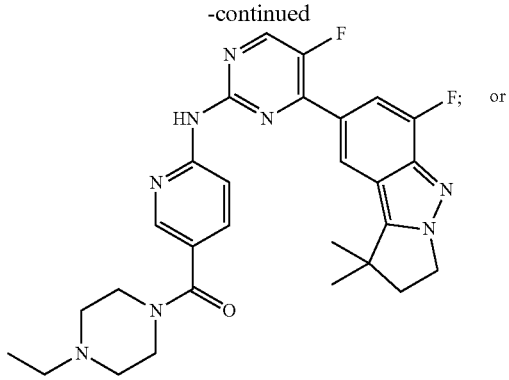

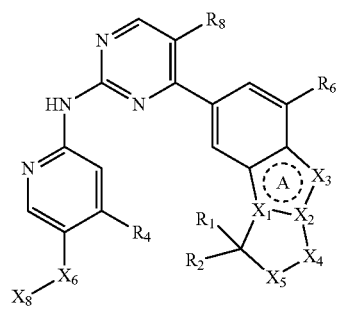

or a pharmaceutically acceptable salt, a solvate, a stereoisomer, or tautomer thereof.

In one embodiment a compound of formula (I) has the structure of formula (Ia):

(Ia)

or a pharmaceutically acceptable salt, a solvate, a stereoisomer, or tautomer thereof, wherein:

$X_1$ and $X_2$ is selected from N, C, or CH; wherein when $X_2$ is C or CH, $X_4$ and $X_5$ is selected from O, NH, $NR_5$ or $CH_2$, provided that $X_4$ and $X_5$ cannot be both O;

when $X_2$ is a N, $X_4$ is selected from NH, $NR_5$ or $CH_2$, and $X_5$ is selected from $CH_2$ or O;

$X_3$ is selected from N or CH;

ring A is an aromatic ring;

$X_6$ is selected from a $CH_2$, C=O or absent;

$X_8$ is selected from:

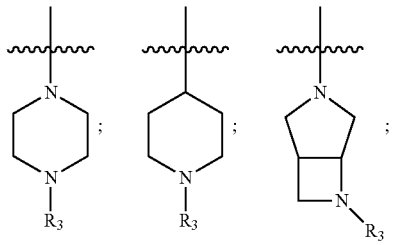

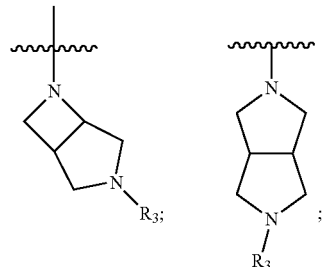

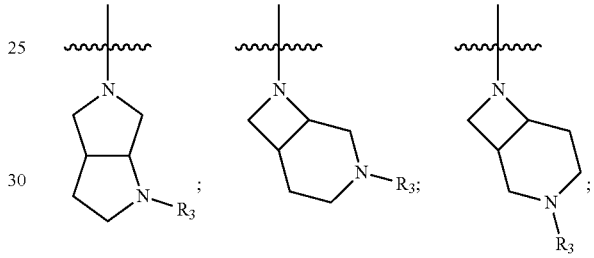

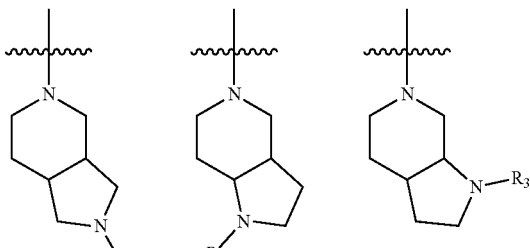

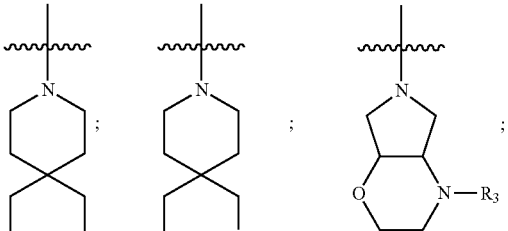

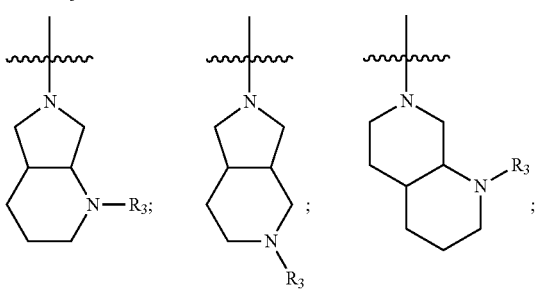

-continued

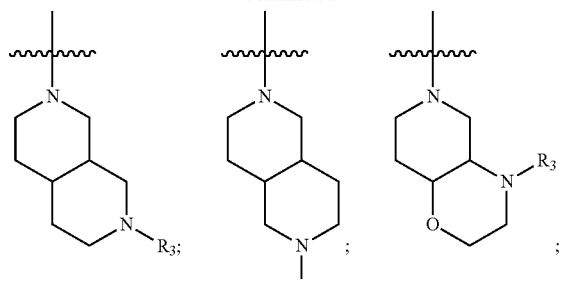
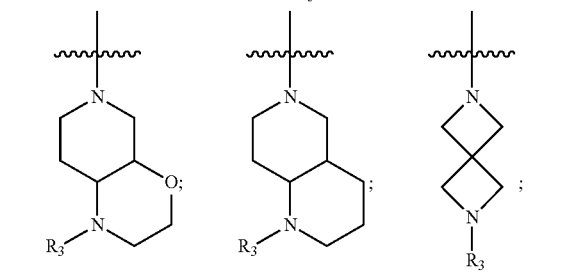
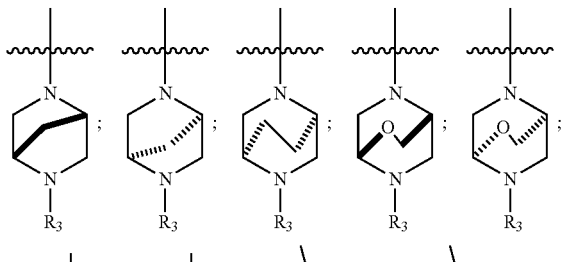
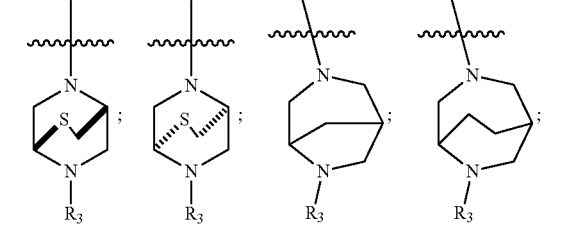
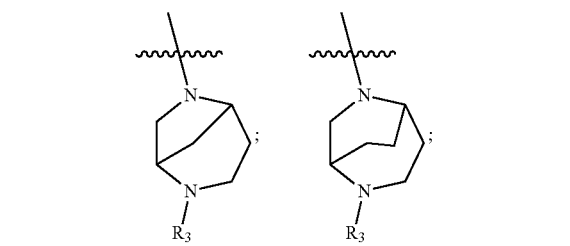
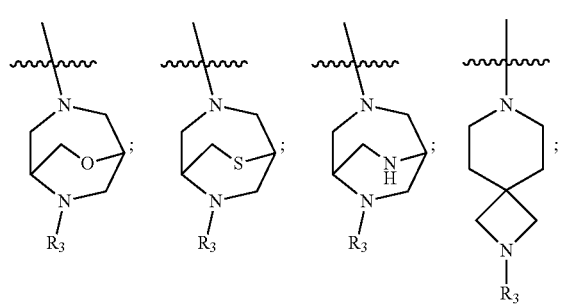

-continued

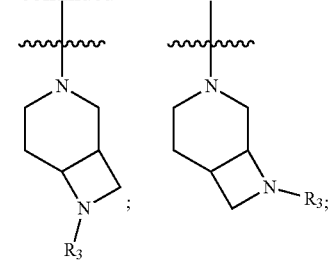
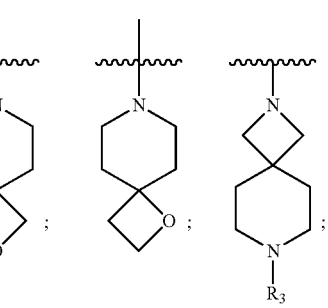
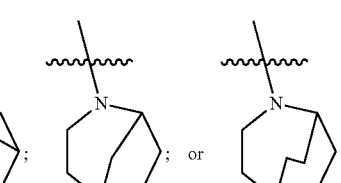

$R_3$ is selected from acyl or optionally substituted alkyl;

$X_8$ is optionally substituted with one to four substituents each independently selected from: $C_1$-$C_3$ alkyl optionally substituted with one or two substituents each independently selected from hydroxyl or —S—($C_1$-$C_3$ alkyl); —$CD_3$; halo; oxo; $C_1$-$C_3$ haloalkyl; hydroxyl; $NH_2$; dimethylamino; benzyl; or —C(O)—($C_1$-$C_3$ alkyl) optionally substituted with one or two substituents each independently selected from: —$SCH_3$, —NHC(O)$CH_3$, —S(O)$_2$—($C_1$-$C_4$ alkyl), or —C(O)-pyrrolidinyl;

$R_1$, $R_2$, and $R_5$ are each selected from H, alkyl, substituted alkyl;

$R_4$ is selected from H, CN, alkyl, substituted alkyl or halogen; and $R_6$ and $R_8$ are each independently selected from H, CN, $C_1$-$C_6$ alkyl, substituted $C_1$-$C_6$ alkyl, Cl, F, or Br.

In one embodiment, various embodiments as described for formula (I) also can be applied to formula (Ia).

In one embodiment, $R_6$ of formula (Ia) is selected from H, CN, Cl, F, or Br. In one embodiment, $R_6$ of formula (Ia) is selected from H, CN, Cl, or F.

In one embodiment, $R_8$ of formula (Ia) is selected from H, CN, Cl, F, or Br. In one embodiment, $R_8$ of formula (Ia) is selected from H, CN, Cl, or F.

In one embodiment a compound of formula (I) has the structure of formula (Ic):

(Ic)
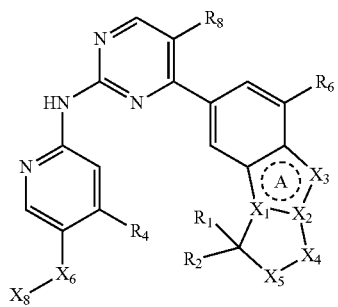
or a pharmaceutically acceptable salt, a solvate, a stereoisomer, or tautomer thereof, wherein:
$X_1$ and $X_2$ is selected from N, C, or CH;
$X_3$ is selected from N;
$X_4$ and $X_5$ are each $CH_2$;
ring A is an aromatic ring;
$X_6$ is selected from a $CH_2$, C=O or absent;
$X_8$ is selected from:
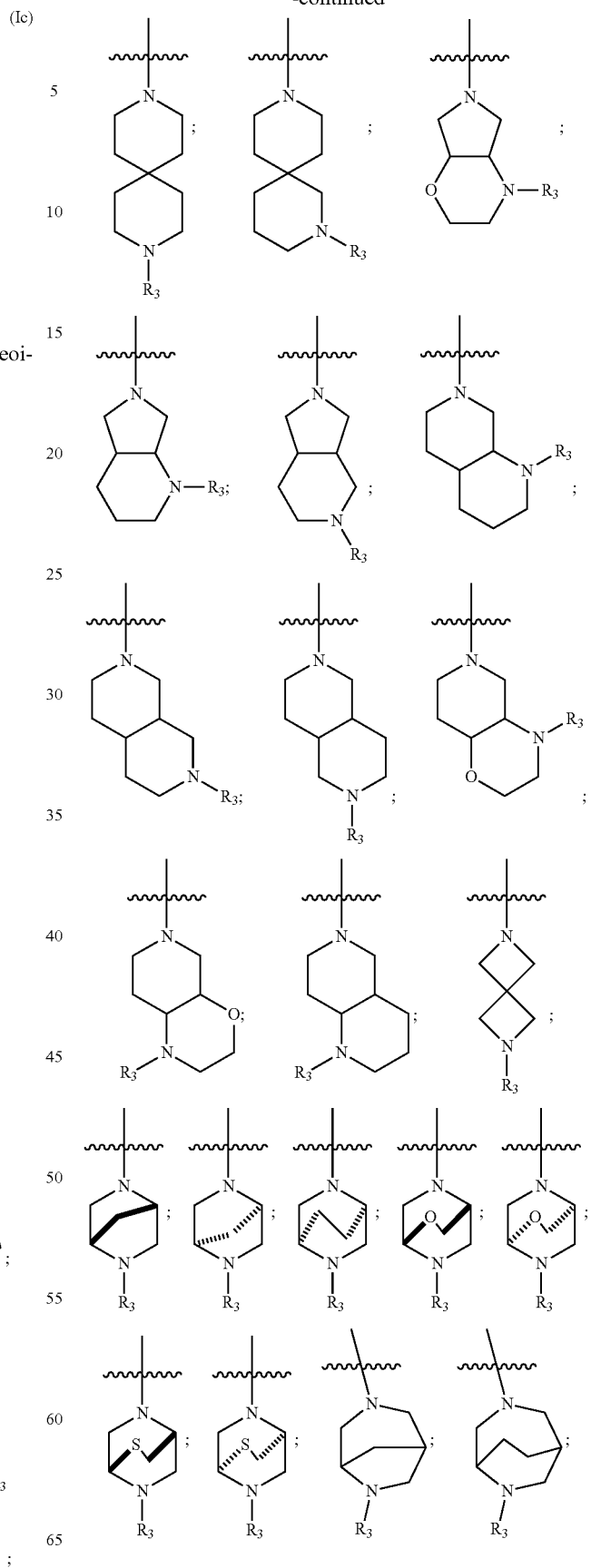

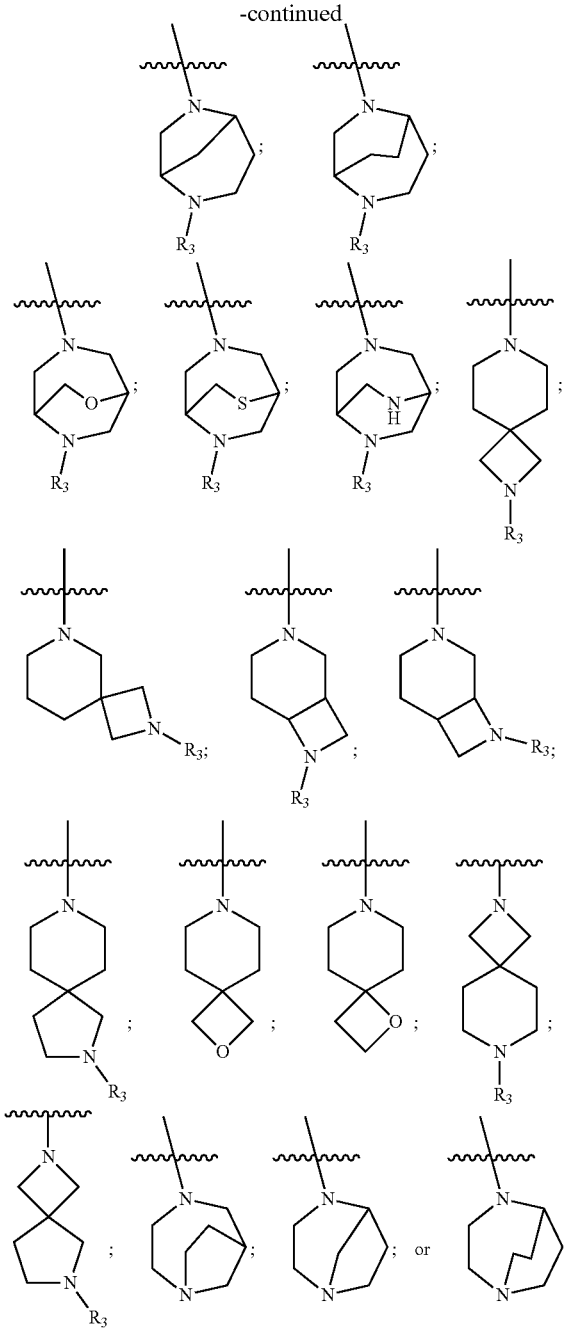

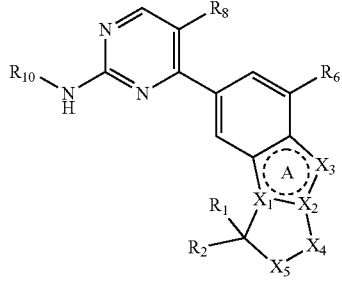

or a pharmaceutically acceptable salt, a solvate, a stereoisomer, or tautomer thereof, wherein:

$X_1$ and $X_2$ are each selected from N, C, or CH; wherein when $X_2$ is C or CH, $X_4$ and $X_5$ is selected from O, NH, $NR_5$ or $CH_2$, provided that $X_4$ and $X_5$ cannot be both O;

when $X_2$ is a N, $X_4$ is selected from NH, NR or $CH_2$, and $X_5$ is selected from $CH_2$ or O;

$X_3$ is selected from N or CH;

ring A is an aromatic ring;

$R_{10}$ is selected from:

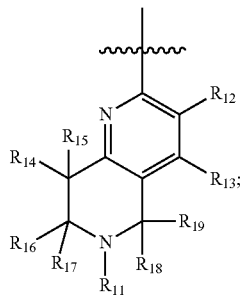

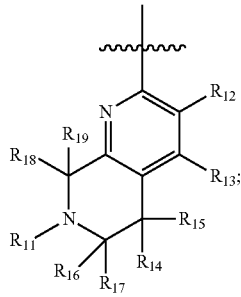

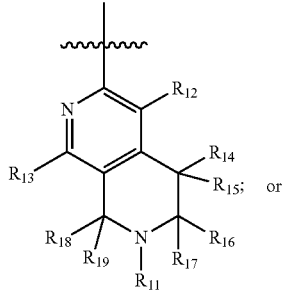

$R_3$ is selected from acyl or optionally substituted alkyl;

$R_1$, $R_2$, and $R_5$ are each selected from H, alkyl, substituted alkyl;

$R_4$ is selected from H, CN, $C_1$-$C_6$ alkyl, or halogen; and $R_6$ and $R_8$ are each independently selected from H, CN, or F.

In one embodiment, various embodiments as described for formula (I) also can be applied to formulae (Ic), (Id), (Ie), (If), (Ig), (Ih), (Ii), (Ij), and (Ik).

One embodiment of the present disclosure relates to novel aminopyrimidine compounds.

In one embodiment the present disclosure relates to compound of Formula (II).

-continued

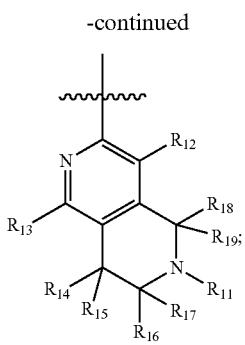
(E)

$R_1$ and $R_2$ is selected from H, alkyl, substituted alkyl; or $R_1$ and $R_2$ together with the carbon atom to which they are attached to can form a 3-8 membered optionally substituted cycloalkyl or a 3-8 membered optionally substituted heterocycloalkyl containing one or more of O, N, S, SO, or $SO_2$;

$R_6$ and $R_8$ are each independently selected from H, CN, $C_1$-$C_6$ alkyl, substituted $C_1$-$C_6$ alkyl, Cl, F, or Br;

$R_{11}$ is selected from —H, —($C_1$-$C_6$ alkyl), —C(=O)—($C_1$-$C_6$ alkyl), —C(=O)—O—($C_1$-$C_6$ alkyl), —C(=O)—C(=O)—OH, —C(=O)—NR'R", —S(=O)$_2$—NR'R", or —S(=O)—NR'R", wherein the alkyl of the —($C_1$-$C_6$ alkyl), —C(=O)—($C_1$-$C_6$ alkyl), and —C(=O)—O—($C_1$-$C_6$ alkyl) groups is optionally substituted with 1-3 substituents independently selected from —OH, F, —S(=O)$_2$—($C_1$-$C_6$ alkyl), —O—($C_1$-$C_6$ alkyl), —NR'R", or —CN;

$R_{12}$ is —H, —$CH_3$, or halo;

when $R_{10}$ is a group of formula B or formula C, $R_{13}$ is —H, optionally substituted —($C_1$-$C_6$ alkyl), halo, —O—($C_1$-$C_6$ alkyl), —$NO_2$, —CN, —NR'R", —$CO_2$H, —C(=O)—O—($C_1$-$C_6$ alkyl), or —C(=O)—NR'R, wherein the optional substituent for —($C_1$-$C_6$ alkyl) is selected from 1-3 substituents from —OH, halo, —O—($C_1$-$C_6$ alkyl), —CN, —NR'R", or —S(=O)$_2$—$CH_3$;

when $R_{10}$ is a group of formula D or formula E, $R_{13}$ is —H, —($C_1$-$C_6$ alkyl), or halo;

$R_{14}$ is selected from —H, —OH, or an optionally substituted —($C_1$-$C_6$ alkyl), wherein the optional substituent for —($C_1$-$C_6$ alkyl) is selected from 1-3 substituents from —OH, halo, or —O—($C_1$-$C_6$ alkyl);

$R_{15}$ is selected from —H, —OH, or an optionally substituted —($C_1$-$C_6$ alkyl), wherein the optional substituent for —($C_1$-$C_6$ alkyl) is selected from 1-3 substituents from —OH, halo, or —O—($C_1$-$C_6$ alkyl);

$R_{16}$ and $R_{17}$ are each independently selected from H, or an optionally substituted —($C_1$-$C_6$ alkyl), wherein the optional substituent for —($C_1$-$C_6$ alkyl) is selected from 1-3 substituents from —OH, halo, or —O—($C_1$-$C_6$ alkyl); or $R_{16}$ and $R_{17}$, when taken together, can represent =O;

$R_{18}$ is —H or an optionally substituted —($C_1$-$C_6$ alkyl), wherein the optional substituent for —($C_1$-$C_6$ alkyl) is selected from 1-3 substituents from —OH, halo, or —O—($C_1$-$C_6$ alkyl);

$R_{19}$ is —H or an optionally substituted —($C_1$-$C_6$ alkyl), wherein the optional substituent for —($C_1$-$C_6$ alkyl) is selected from 1-3 substituents from —OH, halo, or —O—($C_1$-$C_6$ alkyl);

or alternatively, $R_{18}$ and $R_{19}$, when taken together, can represent =O; and R' and R" are each independently selected from —H or optionally substituted —($C_1$-$C_4$ alkyl), wherein the optional substituent for —($C_1$-$C_4$ alkyl) is selected from 1-3 substituents from —OH or —F.

Ring A refers to the 5-membered ring in formula (II) formed by $X_1$, $X_2$, $X_3$, and the two adjacent carbon atoms. The dotted circle in Ring A demonstrates that the ring is aromatic.

In one embodiment, ring A of formula (II) is a pyrazole ring or an imidazole ring.

In one embodiment, $X_1$ is C; and $X_2$ and $X_3$ are each N in formula (II).

In one embodiment, $X_2$ is C; and $X_1$ and $X_3$ are each N in formula (II).

In one embodiment, the compound of formula (II) has the structure of formula (IIj) or (IIk):

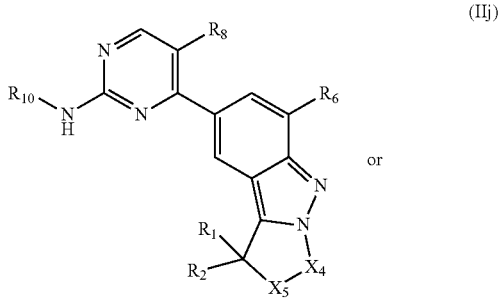
(IIj)

or

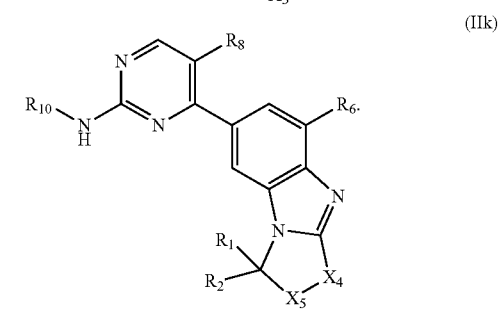
(IIk)

In another embodiment, the compound of formula (II) has the structure of formula (IId), (IIe), (IIf), (IIg), (IIh), or (IIi).

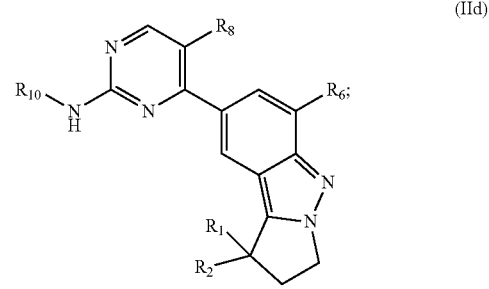
(IId)

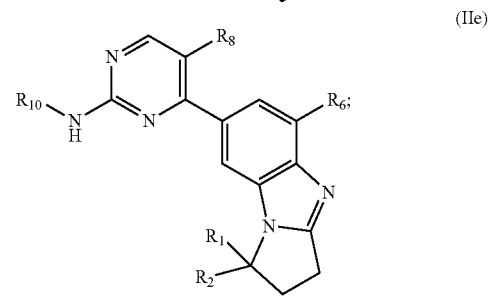
(IIe)

-continued

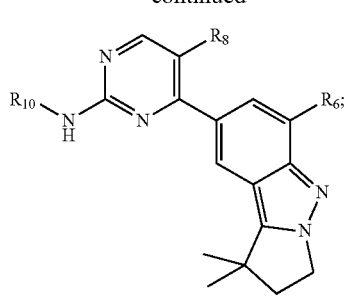

(IIf)

(IIg)

(IIh)

(IIi)

In one embodiment, R$_1$ of formula (II) is H or C$_1$-C$_6$ alkyl. In another embodiment, R$_1$ is methyl, ethyl, propyl, or butyl. In another embodiment, R$_1$ is methyl.

In one embodiment, R$_2$ of formula (II) is H or C$_1$-C$_6$ alkyl. In another embodiment, R$_2$ is methyl, ethyl, propyl, or butyl. In another embodiment, R$^2$ is methyl.

In one embodiment, R$_1$ and R$_2$ of formula (II) are each methyl.

In one embodiment, R$_1$ and R$_2$ of formula (II) together with the carbon atom to which they are attached to can form a 3-6 membered optionally substituted cycloalkyl or a 3-6 membered optionally substituted heterocycloalkyl containing one or more of O, N, S, SO, or SO$_2$.

In one embodiment, R$_6$ of formula (II) is H, CN, C$_1$-C$_6$ alkyl, Cl, F, or Br. In another embodiment, R$_6$ is H, Cl, F, or Br. In one embodiment, R$_6$ is H, CN, Cl, F, or Br. In one embodiment, R$_6$ is H, CN, Cl, or F. In some embodiments, R$_6$ is F.

In one embodiment, R$_8$ of formula (II) is H, CN, C$_1$-C$_6$ alkyl, Cl, F, or Br. In another embodiment, R$_8$ is H, Cl, F, or Br. In one embodiment, R$_8$ is H, CN, Cl, F, or Br. In one embodiment, R$_8$ is H, CN, Cl, or F. In some embodiments, R$_8$ is F.

In one embodiment, R$_6$ and R$_8$ of formula (II) are each F.

In one embodiment, ring R$_{10}$ of formula (II) is formula B:

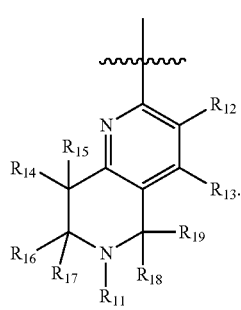

(B)

In one embodiment, R$_{10}$ of formula (II) is formula B where R$_{12}$, R$_{13}$, R$_{14}$, R$_{15}$, R$_{16}$, R$_{17}$, R$_{18}$, and R$_{19}$ are each H. In one embodiment, R$_{10}$ of formula (II) is formula B where R$_{11}$ is —H, —(C$_1$-C$_6$ alkyl), or —C(═O)—(C$_1$-C$_6$ alkyl), wherein the C$_1$-C$_6$ alkyl of the —(C$_1$-C$_6$ alkyl) and —C(═O)—(C$_1$-C$_6$ alkyl) is optionally substituted. In one embodiment, R$_{10}$ of formula (II) is formula B where R$_{11}$ is —(C$_1$-C$_6$ alkyl), or —C(═O)—(C$_1$-C$_6$ alkyl) optionally substituted with —OH. In one embodiment, R$_{10}$ of formula (II) is formula B where R$_{11}$ is methyl, ethyl, propyl, or isopropyl.

In one embodiment, R$_{10}$ of formula (IIe) is formula B where R$_{12}$, R$_{13}$, R$_{14}$, R$_{15}$, R$_{16}$, R$_{17}$, R$_{18}$, and R$_{19}$ are each H and R$_{11}$ is ethyl. In one embodiment, R$_{10}$ of formula (IId) is formula B where R$_{12}$, R$_{13}$, R$_{14}$, R$_{15}$, R$_{16}$, R$_{17}$, R$_{18}$, and R$_{19}$ are each H and R$_{11}$ is ethyl or —C(═O)CH$_2$OH.

In one embodiment, ring R$_{10}$ of formula (II) is formula C:

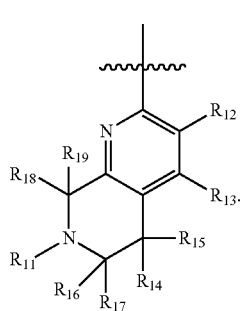

(C)

In one embodiment, R$_{10}$ of formula (II) is formula C where R$_{12}$, R$_{13}$, R$_{14}$, R$_{15}$, R$_{16}$, R$_{17}$, R$_{18}$, and R$_{19}$ are each H. In one embodiment, R$_{10}$ of formula (II) is formula C where R$_{11}$ is —H, —(C$_1$-C$_6$ alkyl), or —C(═O)—(C$_1$-C$_6$ alkyl), wherein the C$_1$-C$_6$ alkyl of the —(C$_1$-C$_6$ alkyl) and —C(═O)—(C$_1$-C$_6$ alkyl) is optionally substituted. In one embodiment, R$_{10}$ of formula (II) is formula C where R$_{11}$ is —(C$_1$-C$_6$ alkyl), or —C(═O)—(C$_1$-C$_6$ alkyl) optionally substituted with —OH. In one embodiment, R$_{10}$ of formula (II) is formula C where R$_{11}$ is methyl, ethyl, propyl, or isopropyl.

In one embodiment, ring $R_{10}$ of formula (II) is formula D:

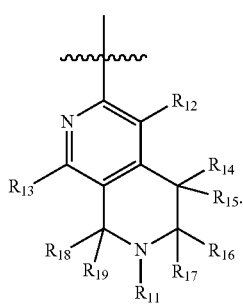

(D)

In one embodiment, $R_{10}$ of formula (II) is formula D where $R_{12}$, $R_{13}$, $R_{14}$, $R_{15}$, $R_{16}$, $R_{17}$, $R_{18}$, and $R_{19}$ are each H. In one embodiment, $R_{10}$ of formula (II) is formula D where $R_{11}$ is —H, —($C_1$-$C_6$ alkyl), or —C(=O)—($C_1$-$C_6$ alkyl), wherein the $C_1$-$C_6$ alkyl of the —($C_1$-$C_6$ alkyl) and —C(=O)—($C_1$-$C_6$ alkyl) is optionally substituted. In one embodiment, $R_{10}$ of formula (II) is formula D where $R_{11}$ is —($C_1$-$C_6$ alkyl), or —C(=O)—($C_1$-$C_6$ alkyl) optionally substituted with —OH. In one embodiment, $R_{10}$ of formula (II) is formula D where $R_{11}$ is methyl, ethyl, propyl, or isopropyl.

In one embodiment, ring $R_{10}$ of formula (II) is formula E:

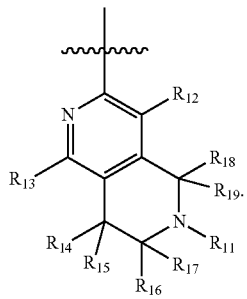

(E)

In one embodiment, $R_{10}$ of formula (II) is formula E where $R_{12}$, $R_{13}$, $R_{14}$, $R_{15}$, $R_{16}$, $R_{17}$, $R_{18}$, and $R_{19}$ are each H. In one embodiment, $R_{10}$ of formula (II) is formula E where $R_{11}$ is —H, —($C_1$-$C_6$ alkyl), or —C(=O)—($C_1$-$C_6$ alkyl), wherein the $C_1$-$C_6$ alkyl of the —($C_1$-$C_6$ alkyl) and —C(=O)—($C_1$-$C_6$ alkyl) is optionally substituted. In one embodiment, $R_{10}$ of formula (II) is formula E where $R_{11}$ is —($C_1$-$C_6$ alkyl), or —C(=O)—($C_1$-$C_6$ alkyl) optionally substituted with —OH. In one embodiment, $R_{10}$ of formula (II) is formula E where $R_{11}$ is methyl, ethyl, propyl, or isopropyl.

In one embodiment, $R_{16}$ and $R_{17}$ relating to formula (II) are each independently selected from H, or an optionally substituted —($C_1$-$C_6$ alkyl), wherein the optional substituent for —($C_1$-$C_6$ alkyl) is selected from 1-3 substituents from —OH, halo, or —O—($C_1$-$C_6$ alkyl).

In one embodiment, $R_{18}$ relating to formula (II) is —H or an optionally substituted —($C_1$-$C_6$ alkyl), wherein the optional substituent for —($C_1$-$C_6$ alkyl) is selected from 1-3 substituents from —OH, halo, or —O—($C_1$-$C_6$ alkyl).

In one embodiment, $R_{19}$ relating to formula (II) is —H or an optionally substituted —($C_1$-$C_6$ alkyl), wherein the optional substituent for —($C_1$-$C_6$ alkyl) is selected from 1-3 substituents from —OH, halo, or —O—($C_1$-$C_6$ alkyl).

In one embodiment, $R_{18}$ and $R_{19}$ relating to formula (II) is each independently selected from —H or an optionally substituted —($C_1$-$C_6$ alkyl), wherein the optional substituent for —($C_1$-$C_6$ alkyl) is selected from 1-3 substituents from —OH, halo, or —O—($C_1$-$C_6$ alkyl).

In one embodiment, a compound of formula (II) is selected from:

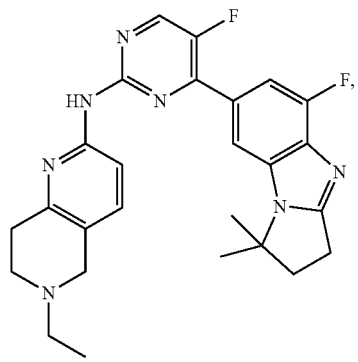

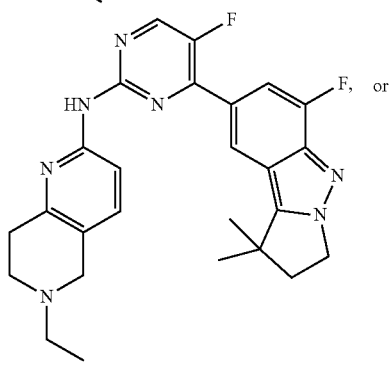

or

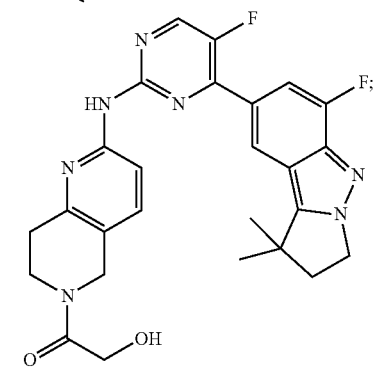

or a pharmaceutically acceptable salt, a solvate, a stereoisomer, or tautomer thereof.

In one embodiment, the compound of formula (II) excludes

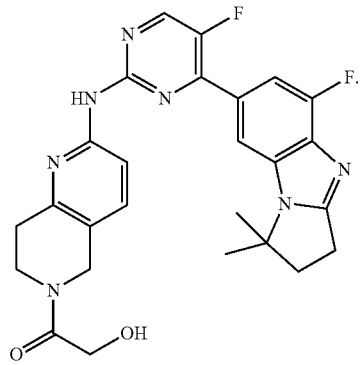 [SMILES: CC1(C)CCc2nc3c(F)cc(-c4nc(Nc5ccc6c(n5)CCN(C(=O)CO)C6)ncc4F)cc3n21]

In one embodiment, various embodiments as described for formula (II) also can be applied to formulae (IId), (IIe), (Id), (Ie), (If), (Ig), (Ih), (Ii), (Ij), and (k).

III. Methods

The present disclosure also includes method of using a compound of formula (A), (B), (I), or (II), and any subgenera thereof, or a pharmaceutically acceptable salt, solvate, ester, or prodrug thereof, and/or a pharmaceutical composition comprising one or more compounds of formula (A), (B), (I), or (II), and any subgenera thereof, or a pharmaceutically acceptable salt, solvate, ester, or prodrug thereof, as described herein. In some embodiments, the present disclosure provides method of modulating cyclin-dependent kinase (CDK) by contacting one or more compounds of formula (A), (B), (I), or (II), and any subgenera thereof, or a pharmaceutically acceptable salt, solvate, ester, or prodrug thereof, with a cell, an organ, or a subject, in need thereof. In one embodiment, a method of modulating CDK comprises administering to a subject, a therapeutically effective amount of one or more compounds of formula (A), (B), (I), or (II), and any subgenera thereof, or a pharmaceutically acceptable salt, solvate, ester, or prodrug thereof. In one embodiment, the subject is a mammal including human.

In one embodiment, the method for modulating CDK as described herein is for inhibiting CDK. In one embodiment, CDK is CDK4. In one embodiment, CDK is CDK6. In one embodiment, CDK is CDK4/6.

In some embodiments, the present disclosure provides a method of treating, ameliorating, or preventing a condition which is responds to modulation of CDK, wherein one or more compounds of formula (A), (B), (I), or (II), and any subgenera thereof, or a pharmaceutically acceptable salt, solvate, ester, or prodrug thereof, is contacted with a cell, an organ, or a subject, in need thereof. In one embodiment, a method of treating, ameliorating, or preventing a condition which is responds to modulation of CDK comprises administering to a subject, a therapeutically effective amount of one or more compounds of formula (A), (B), (I), or (II), and any subgenera thereof, or a pharmaceutically acceptable salt, solvate, ester, or prodrug thereof. In one embodiment, the subject is a mammal including human. In one embodiment, the condition which responds to modulation of CDK is a condition which responds to inhibition of CDK. In one embodiment, CDK is CDK4. In one embodiment, CDK is CDK6. In one embodiment, CDK is CDK4/6. In one embodiment, the condition is cancer.

In one embodiment, a method of treating, ameliorating, or preventing a condition which is responds to modulation of CDK, can be reducing or inhibiting cancer cell growth or tumor growth. In one embodiment, CDK is CDK4. In one embodiment, CDK is CDK6. In one embodiment, CDK is CDK4/6.

In some embodiments, the present disclosure provides a method of treating cell proliferative disorder comprising contacting one or more compounds of formula (A), (B), (I), or (II), and any subgenera thereof, or a pharmaceutically acceptable salt, solvate, ester, or prodrug thereof, with a cell, an organ, or a subject, in need thereof. In one embodiment, a method of treating cell proliferative disorder comprises administering to a subject, one or more compounds of formula (A), (B), (I), or (II), and any subgenera thereof, or a pharmaceutically acceptable salt, solvate, ester, or prodrug thereof. In one embodiment, the subject is a mammal including human. In one embodiment, the cell proliferative disorder is cancer.

In one embodiment, the present disclosure describes a method of treating cancer comprising administration of one or more compounds of formula (A), (B), (I), or (II), and any subgenera thereof, or a pharmaceutically acceptable salt, solvate, ester, or prodrug thereof. Non-limiting examples of cancer applicable by method of treatment as disclosed herein includes: Acute Lymphoblastic Leukemia, Acute Myeloid Leukemia, Adrenocortical Carcinoma, AIDS-Related Cancers, Kaposi Sarcoma, Lymphoma, Anal Cancer, Appendix Cancer, Astrocytomas, Childhood Atypical Teratoid/Rhabdoid Tumor, Basal Cell Carcinoma, Skin Cancer (Nonmelanoma), Childhood Bile Duct Cancer, Extrahepatic Bladder Cancer, Bone Cancer, Ewing Sarcoma Family of Tumors, Osteosarcoma and Malignant Fibrous Histiocytoma, Brain Stem Glioma, Brain Tumors, Embryonal Tumors, Germ Cell Tumors, Craniopharyngioma, Ependymoma, Bronchial Tumors, Burkitt Lymphoma (Non-Hodgkin Lymphoma), Carcinoid Tumor, Gastrointestinal Carcinoma of Unknown Primary, Cardiac (Heart) Tumors, Lymphoma, Primary, Cervical Cancer, Childhood Cancers, Chordoma, Chronic Lymphocytic Leukemia, Chronic Myelogenous Leukemia, Chronic Myeloproliferative Neoplasms Colon Cancer, Colorectal Cancer, Cutaneous T-Cell Lymphoma, Ductal Carcinoma In Situ, Endometrial Cancer, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer, Intraocular Melanoma, Retinoblastoma, Fibrous Histiocytoma of Bone, Malignant, and Osteosarcoma, Gallbladder Cancer, Gastric (Stomach) Cancer, Gastrointestinal Carcinoid Tumor, Gastrointestinal Stromal Tumors, Extragonadal Cancer, Ovarian Cancer, Testicular Cancer, Gestational Trophoblastic Disease, Glioma, Brain Stem Cancer, Hairy Cell Leukemia, Head and Neck Cancer, Heart Cancer, Hepatocellular (Liver) Cancer, Histiocytosis, Langerhans Cell Cancer, Hodgkin Lymphoma, Hypopharyngeal Cancer, Intraocular Melanoma, Islet Cell Tumors, Pancreatic Neuroendocrine Tumors, Kaposi Sarcoma, Kidney Cancer, Renal Cell Cancer, Wilms Tumor and Other Childhood Kidney Tumors, Langerhans Cell Histiocytosis, Laryngeal Cancer, Leukemia, Chronic Lymphocytic Cancer, Chronic Myelogenous Cancer, Hairy Cell Cancer, Lip and Oral Cavity Cancer, Liver Cancer (Primary), Lobular Carcinoma In Situ (LCIS), Lung Cancer, Non-Small Cell Cancer, Small Cell Cancer, Lymphoma, Cutaneous T-Cell (Mycosis Fungoides and Sézary Syndrome), Hodgkin Cancer, Non-Hodgkin Cancer, Macroglobulinemia, Waldenström, Male Breast Cancer, Malignant Fibrous Histiocytoma of Bone and Osteosarcoma, Melanoma, Intraocular (Eye) Cancer, Merkel Cell Carcinoma, Mesothelioma, Malignant, Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia, Chronic, Myeloid Leukemia, Acute, Myeloma Multiple, Chronic Myeloproliferative Neoplasms, Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip and Oropharyngeal Cancer, Osteosarcoma and Malignant Fibrous Histiocytoma of Bone, Epithelial Cancer, Low Malignant Potential Tumor, Pancreatic Cancer, Pancreatic Neuroendocrine Tumors (Islet Cell Tumors), Papillomatosis, Paraganglioma, Parathyroid Cancer, Penile Cancer, Pharyngeal Cancer, Pheochromocytoma, Pituitary Tumor, Plasma Cell Neoplasm/Multiple Myeloma, Pleuropulmonary Blastoma, Primary Central Nervous System Lymphoma, Rectal Cancer, Renal Cell (Kidney) Cancer, Retinoblastoma, Rhabdomyosarcoma, Salivary Gland Cancer, Sarcoma, Ewing Cancer, Kaposi Cancer, Osteosarcoma (Bone Cancer), Soft Tissue Cancer, Uterine Cancer, Sézary Syndrome, Skin Cancer, Childhood Melanoma, Merkel Cell Carcinoma, Nonmelanoma, Small Cell Lung Cancer, Small Intestine Cancer, Soft Tissue Sarcoma, Squamous Cell Carcinoma, Skin Cancer (Nonmelanoma), Childhood Squamous Neck Cancer with Occult Primary, Metastatic Cancer, Stomach (Gastric) Cancer, T-Cell Lymphoma, Cutaneous Cancer, Testicular Cancer, Throat Cancer, Thymoma and Thymic Carcinoma, Thyroid Cancer, Transitional Cell Cancer of the Renal Pelvis and Ureter, Unknown Primary, Carcinoma of Childhood, Unusual Cancers of Childhood, Urethral Cancer, Uterine Cancer, Endometrial Cancer, Uterine Sarcoma, Vaginal Cancer, Vulvar Cancer, Waldenström Macroglobulinemia, Wilms Tumor, and Women's Cancers.

In one embodiment, the present disclosure relates to a method of treating cancer comprising administering one or more compounds of formula (A), (B), (I), or (II), and any subgenera thereof, or a pharmaceutically acceptable salt, solvate, ester, or prodrug thereof, to a subject in need thereof. In another embodiment, cancer is breast cancer, colon cancer, ovarian cancer, lung cancer, or glioblastoma. In some embodiments, the lung cancer is a non-small cell lung cancer. In other embodiments, the glioblastoma is a Rb-positive glioblastoma. In one embodiment, the compound is administered in a therapeutically effective amount.

In one embodiment, the present disclosure relates to a method of protecting a subject from effects of ionizing radiation or chemotherapeutic agent comprising administering one or more compounds of formula (A), (B), (I), or (II), and any subgenera thereof, or a pharmaceutically acceptable salt, solvate, ester, or prodrug thereof, to a subject in need thereof. In one embodiment, the effects of ionizing radiation or chemotherapeutic agents are acute effects and/or chronic toxic effects. In some embodiments, the acute and/or chronic toxic effects are in hematopoietic stem cells and/or progenitor cells (HSPCs). In one embodiment, the hematopoietic stem cells are replication-dependent hematopoietic stem cells. In one embodiment, the method of protecting a subject from effects of ionizing radiation or chemotherapeutic agent further comprises administering another chemotherapeutic agent in combination with the compound of the present disclosure. In some embodiments, the chemotherapeutic agent administered in combination with the compound of the present disclosure is etoposide, carboplatin, topotecan, or a combination thereof. In one embodiment, the administration of the combination of the chemotherapeutic agent administered in combination with the compound of the present disclosure is provided within 24 hours or less. That is, the chemotherapeutic agent can be provided within 24 hours or less after the administration of the compound of the present disclosure. In one embodiment, the compound of the present disclosure and/or the chemotherapeutic agent is administered in a therapeutically effective amount.

In other embodiments, the present disclosure relates to a method of reducing or limiting the effect of DNA-damaging ionizing radiation or chemotherapeutic agent on hematopoietic stem cells and/or progenitor cells (HSPCs), comprising administering one or more compounds of formula (A), (B), (I), or (II), and any subgenera thereof, or a pharmaceutically acceptable salt, solvate, ester, or prodrug thereof, to a subject in need thereof. In one embodiment, the hematopoietic stem cells are replication-dependent hematopoietic stem cells. In one embodiment, the method of reducing or limiting the effect of DNA-damaging ionizing radiation or chemotherapeutic agent on HSPCs further comprises administering another chemotherapeutic agent in combination with the compound of the present disclosure. In some embodiments, the chemotherapeutic agent administered in combination with the compound of the present disclosure is etoposide, carboplatin, topotecan, or a combination thereof. In one embodiment, the administration of the combination of the chemotherapeutic agent administered in combination with the compound of the present disclosure is provided within 24 hours or less. That is, the chemotherapeutic agent can be provided within 24 hours or less after the administration of the compound of the present disclosure. In one embodiment, the compound of the present disclosure and/or the chemotherapeutic agent is administered in a therapeutically effective amount In one embodiment, the present disclosure relates to a method of protecting hematopoietic cell and/or progenitor cell populations in subject, comprising administering one or more compounds of formula (A), (B), (I), or (II), and any subgenera thereof, or a pharmaceutically acceptable salt, solvate, ester, or prodrug thereof, to a subject in need thereof. In one embodiment, the subject is exposed to ionizing radiation or chemotherapeutic agents. In one embodiment, the hematopoietic stem cells are replication-dependent hematopoietic stem cells. In one embodiment, the method of protecting hematopoietic cell and/or progenitor cell populations in a subject further comprises administering another chemotherapeutic agent in combination with the compound of the present disclosure. In some embodiments, the chemotherapeutic agent administered in combination with the compound of the present disclosure is etoposide, carboplatin, topotecan, or a combination thereof. In one embodiment, the administration of the combination of the chemotherapeutic agent administered in combination with the compound of the present disclosure is provided within 24 hours or less. That is, the chemotherapeutic agent can be provided within 24 hours or less after the administration of the compound of the present disclosure. In one embodiment, the compound of the present disclosure and/or the chemotherapeutic agent is administered in a therapeutically effective amount In one embodiment, the present disclosure relates to a method of promoting the recovery of a hematopoietic cell and/or progenitor cell population in subject, comprising administering one or more compounds of formula (A), (B), (I), or (II), and any subgenera thereof, or a pharmaceutically acceptable salt, solvate, ester, or prodrug thereof, to a subject in need thereof. In one embodiment, the subject is exposed to ionizing radiation or chemotherapeutic agents. In one embodiment, the hematopoietic stem cells are replication-dependent hematopoietic stem cells. In one embodiment, the method of promoting the recovery of a hematopoietic cell and/or progenitor cell population in subject further comprises administering another chemotherapeutic agent in combination with the compound of the present disclosure. In some embodiments, the chemotherapeutic agent administered in combination with the compound of the present disclosure is etoposide, carboplatin, topotecan, or a combination thereof. In one embodiment, the administration of the combination of the chemotherapeutic agent administered in combination with the compound of the present disclosure is provided within 24 hours or less. That is, the chemotherapeutic agent can be provided within 24 hours or less after the administration of the compound of the present disclosure. In one embodiment, the compound of the present disclosure and/or the chemotherapeutic agent is administered in a therapeutically effective amount In one embodiment, any one of methods as disclosed herein can comprise additional therapeutically active agents (in addition to the one or more compounds of formula (A), (B), (I), or (II), and any subgenera thereof, or a pharmaceutically acceptable salt, solvate, ester, or prodrug thereof). In one embodiment, the additional therapeutically active agent is an anticancer agent. In one embodiment, the additional therapeutically active agent is administered in a therapeutically effective amount.

IV. Pharmaceutical Compositions and Formulations

The present disclosure also includes pharmaceutical compositions comprising one or more compounds of formula (A), (B), (I), or (II), and any subgenera thereof, or a pharmaceutically acceptable salt, solvate, ester, or prodrug thereof. In some embodiments, one or more compounds of formula (A), (B), (I), or (II), and any subgenera thereof, or a pharmaceutically acceptable salt, solvate, ester, or prodrug thereof, in a pharmaceutical composition as described herein modulates cyclin-dependent kinase (CDK) such as CDK4/6. In other embodiments, one or more compounds of formula (A), (B), (I), or (II), and any subgenera thereof, or a pharmaceutically acceptable salt, solvate, ester, or prodrug thereof, in a pharmaceutical composition as described herein can be useful in a method to treat, ameliorate or prevent a condition, which responds to inhibition of CDK (e.g., CDK4/6) or in a method of treating cell proliferative disorder.

In one embodiment, a pharmaceutical composition, as described herein, comprising one or more compounds of formula (A), (B), (I), or (II), and any subgenera thereof, or a pharmaceutically acceptable salt, solvate, ester, or prodrug thereof, further comprises one or more additional therapeutically active agents. In one embodiment, one or more additional therapeutically active agents are selected from anticancer agents.

Anticancer Agents

Anticancer agents used in combination with the compounds of the present application may include agents selected from any of the classes known to those of ordinary skill in the art, including, for example, alkylating agents, anti-metabolites, plant alkaloids and terpenoids (e.g., taxanes), topoisomerase inhibitors, anti-tumor antibiotics, kinase inhibitors, hormonal therapies, molecular targeted agents, and the like. Generally such an anticancer agent is an alkylating agent, an anti-metabolite, a vinca alkaloid, a taxane, a topoisomerase inhibitor, an anti-tumor antibiotic, a tyrosine kinase inhibitor, an immunosuppressive macrolide, an Akt inhibitor, an HDAC inhibitor an Hsp90 inhibitor, an mTOR inhibitor, a PI3K/mTOR inhibitor, a PI3K inhibitor, CHK (checkpoint kinase) inhibitor, PARP (poly(DP-ribose) polymerase) inhibitors, and the like.

Alkylating agents include (a) alkylating-like platinum-based chemotherapeutic agents such as cisplatin, carboplatin, nedaplatin, oxaliplatin, satraplatin, and (SP-4-3)-(cis)-amminedichloro-[2-methylpyridine] platinum (II); (b) alkyl sulfonates such as busulfan; (c) ethyleneimine and methylmelamine derivatives such as altretamine and thiotepa; (d) nitrogen mustards such as chlorambucil, cyclophosphamide, estramustine, ifosfamide, mechlorethamine, trofosamide, prednimustine, melphalan, and uramustine; (e) nitrosoureas such as carmustine, lomustine, fotemustine, nimustine, ranimustine and streptozocin; (f) triazenes and imidazotetrazines such as dacarbazine, procarbazine, temozolamide, and temozolomide.

Anti-metabolites include (a) purine analogs such as fludarabine, cladribine, chlorodeoxyadenosine, clofarabine, mercaptopurine, pentostatin, and thioguanine; (b) pyrimidine analogs such as fluorouracil, gemcitabine, capecitabine, cytarabine, azacitidine, edatrexate, floxuridine, and troxacitabine; (c) antifolates, such as methotrexate, pemetrexed, raltitrexed, and trimetrexate. Anti-metabolites also include thymidylate synthase inhibitors, such as fluorouracil, raltitrexed, capecitabine, floxuridine and pemetrexed; and ribonucleotide reductase inhibitors such as claribine, clofarabine and fludarabine.

Plant alkaloid and terpenoid derived agents include mitotic inhibitors such as the vinca alkaloids vinblastine, vincristine, vindesine, and vinorelbine; and microtubule polymer stabilizers such as the taxanes, including, but not limited to paclitaxel, docetaxel, larotaxel, ortataxel, and tesetaxel.

Topoisomerase inhibitors include topoisomerase I inhibitors such as camptothecin, topotecan, irinotecan, rubitecan, and belotecan; and topoisomerase II inhibitors such as etoposide, teniposide, and amsacrine.

Anti-tumor antibiotics include (a) anthracyclines such as daunorubicin (including liposomal daunorubicin), doxorubicin (including liposomal doxorubicin), epirubicin, idarubicin, and valrubicin; (b) streptomyces-related agents such as bleomycin, actinomycin, mithramycin, mitomycin, porfiromycin; and (c) anthracenediones, such as mitoxantrone and pixantrone. Anthracyclines have three mechanisms of action: intercalating between base pairs of the DNA/RNA strand; inhibiting topoiosomerase II enzyme; and creating iron-mediated free oxygen radicals that damage the DNA and cell membranes. Anthracyclines are generally characterized as topoisomerase II inhibitors.

Hormonal therapies include (a) androgens such as fluoxymesterone and testolactone; (b) antiandrogens such as bicalutamide, cyproterone, flutamide, and nilutamide; (c) aromatase inhibitors such as aminoglutethimide, anastrozole, exemestane, formestane, and letrozole; (d) corticosteroids such as dexamethasone and prednisone; (e) estrogens such as diethylstilbestrol; (f) antiestrogens such as fulvestrant, raloxifene, tamoxifen, and toremifine; (g) LHRH agonists and antagonists such as buserelin, goserelin, leuprolide, and triptorelin; (h) progestins such as medroxyprogesterone acetate and megestrol acetate; and (i) thyroid hormones such as levothyroxine and liothyronine.

Molecular targeted agents include (a) receptor tyrosine kinase ('RTK') inhibitors, such as inhibitors of EGFR, including erlotinib, gefitinib, and neratinib; inhibitors of VEGFR including vandetanib, semaxinib, and cediranib; and inhibitors of PDGFR; further included are RTK inhibitors that act at multiple receptor sites such as lapatinib, which inhibits both EGFR and HER2, as well as those inhibitors that act at of each of C-kit, PDGFR and VEGFR, including but not limited to axitinib, sunitinib, sorafenib and toceranib; also included are inhibitors of BCR-ABL, c-kit and PDGFR, such as imatinib; (b) FKBP binding agents, such as an immunosuppressive macrolide antibiotic, including bafilomycin, rapamycin (sirolimus) and everolimus; (c) gene therapy agents, antisense therapy agents, and gene expression modulators such as the retinoids and rexinoids, e.g. adapalene, bexarotene, trans-retinoic acid, 9 cis retinoic acid, and N (4 hydroxyphenyl)retinamide; (d) phenotype-directed therapy agents, including: monoclonal antibodies such as alemtuzumab, bevacizumab, cetuximab, ibritumomab tiuxetan, rituximab, and trastuzumab; (e) immunotoxins such as gemtuzumab ozogamicin; (f) radioimmunoconjugates such as 131I-tositumomab; and (g) cancer vaccines.

Akt inhibitors include, but are not limited to, 1L6 Hydroxymethyl-chiro-inositol-2-(R)-2-O-methyl-3-O-octadecyl-sn-glycerocarbonate, SH-5 (Calbiochem Cat. No. 124008), SH-6 (Calbiochem Cat. No. Cat. No. 124009), Calbiochem Cat. No. 124011, Triciribine (NSC 154020, Calbiochem Cat. No. 124012), 10-(4'-(N-diethylamino) butyl)-2-chlorophenoxazine, Cu(II)Cl2(3-Formylchromone thiosemicarbazone), 1,3-dihydro-1-(1-((4-(6-phenyl-1H-imidazo[4,5-g]quinoxalin-7-yl)phenyl)methyl)-4-piperidinyl)-2H-benzimidazol-2-one, GSK690693 (4-(2-(4-amino-1,2,5-oxadiazol-3-yl)-1-ethyl-7-{[(3S)-3-piperidinylmethyl]oxy}-1H-imidazo[4,5-c]pyridin-4-yl)-2-methyl-3-butyn-2-ol), SR13668 ((2,10-dicarbethoxy-6-methoxy-5,7-dihydro-indolo[2,3-b] carbazole), GSK2141795, Perifosine, GSK21110183, XL418, XL147, PF-04691502, BEZ-235 [2-Methyl-2-[4-(3-methyl-2-oxo-8-quinolin-3-yl-2,3-dihydro-imidazo[4,5-c]quinolin-1-yl)-phenyl]-propionitrile], PX-866 ((acetic acid (1S,4E, 10R, 11R, 13S,14R)-[4-diallylaminomethylene-6-hydroxy-1-methoxymethyl-10,13-dimethyl-3,7,17-trioxo-1,3,4,7,10, 11,12,13,14,15,16,17-dodecahydro-2-oxa-cyclopenta[a] phenanthren-11-yl ester)), D 106669, CAL-101, GDC0941 (2-(1H-indazol-4-yl)-6-(4-methanesulfonyl-piperazin-1-yl-methyl)-4-morpholin-4-yl-thieno[3,2-d]pyrimidine), SF1126, SF1188, SF2523, TG100-115 [3-[2,4-diamino-6-(3-hydroxyphenyl)pteridin-7-yl]phenol]. A number of these inhibitors, such as, for example, BEZ-235, PX-866, D 106669, CAL 101, GDC0941, SF1126, SF2523 are also identified in the art as PI3K/mTOR inhibitors; additional examples, such as PI-103 [3-[4-(4-morpholinylpyrido[3',2': 4,5]furo[3,2-d]pyrimidin-2-yl]phenolhydrochloride] are well-known to those of skill in the art. Additional well-known PI3K inhibitors include LY294002 [2-(4-morpholinyl)-8-phenyl-4H-1-benzopyran-4-one] and wortmannin. mTOR inhibitors known to those of skill in the art include temsirolimus, deforolimus, sirolimus, everolimus, zotarolimus, and biolimus A9. A representative subset of such inhibitors includes temsirolimus, deforolimus, zotarolimus, and biolimus A9.

HDAC inhibitors include, but are not limited to, (i) hydroxamic acids such as Trichostatin A, vorinostat (suberoylanilide hydroxamic acid (SAHA)), panobinostat (LBH589) and belinostat (PXD101) (ii) cyclic peptides, such as trapoxin B, and depsipeptides, such as romidepsin (NSC 630176), (iii) benzamides, such as MS-275 (3-pyridylmethyl-N-{4-[(2-aminophenyl)-carbamoyl]-benzyl}-carbamate), CI994 (4-acetylamino-N-(2 aminophenyl)-benzamide) and MGCD0103 (N-(2-aminophenyl)-4-((4-(pyridin-3-yl)pyrimidin-2-ylamino)methyl)benzamide), (iv) electrophilic ketones, (v) the aliphatic acid compounds such as phenylbutyrate and valproic acid.

Hsp90 inhibitors include, but are not limited to, benzoquinone ansamycins such as geldanamycin, 17 DMAG (17-Dimethylamino-ethylamino-17-demethoxygeldanamycin), tanespimycin (17 AAG, 17-allylamino-17 demethoxygeldanamycin), EC5, retaspimycin (IPI-504, 18,21 didehydro-17-demethoxy-18,21-dideoxo-18,21-dihydroxy-17-(2 propenylamino)-geldanamycin), and herbimycin; pyrazoles such as CCT 018159 (4-[4-(2,3-dihydro-1,4-benzodioxin-6-yl)-5-methyl-1H-pyrazol-3-yl]-6-ethyl-1,3-benzenediol); macrolides, such as radicocol; as well as BIIB021 (CNF2024), SNX-5422, STA-9090, and AUY922.

CHK inhibitors include, but are not limited to, 5-(3-fluorophenyl)-3-ureidothiophene-N—[(S)-piperidin-3-yl]-2-carboxamide (AZD7762), 7-nitro-1H-indole-2-carboxylic acid {4-[1-(guanidinohydrazone)-ethyl]-phenyl}-amide (PV1019), 5-[(8-chloro-3-isoquinolinyl)amino]-3-[(1R)-2-(dimethylamino)-1-methylethoxy]-2-pyrazinecarbonitrile (SAR-020106), PF-00477736, CCT241533, 6-bromo-3-(1-methyl-1H-pyrazol-4-yl)-5-(3R)-3-piperidinyl-pyrazolo[1, 5-a]pyrimidin-7-amine (SCH900776), 7-hydroxystaurosporine (UCN-01), 4-[((3S)-1-azabicyclo[2.2.2]oct-3-yl) amino]-3-(1H-benzimidazol-2-yl)-6-chloroquinolin-2(1H)-one (CHIR 124), 7-aminodactinomycin (7-AAD), isogranulatimide, debromohymenialdisine, N-[5-Bromo-4-methyl-2-[(2S)-2-morpholinylmethoxy]-phenyl]-N'-(5-methyl-2-pyrazinylurea) (LY2603618), sulforaphane (4-methylsulfinylbutyl isothiocyanate), 9,10,11,12-Tetrahydro-9,12-epoxy-1H-diindolo[1,2,3-fg:3',2',1'-kl]pyrrolo [3,4-i][1,6]benzodiazocine-1,3(2H)-dione (SB-218078), TAT-S216A (synthetic peptide; YGRKKRRQRRRLYRS-PAMPENL), CBP501 ((d-Bpa)sws(d-Phe-F5)(d-Cha) rrrqrr), and the like.

PARP inhibitors include, but are not limited to, 4-(3-(1-(cyclopropanecarbonyl)piperazine-4-carbonyl)-4-fluorobenzyl)phthalazin-1(2H)-one (olaparib, AZD2281, Ku-0059436), 2-[(2R)-2-methylpyrrolidin-2-yl]-1H-benzimidazole-4-carboxamide (Veliparib, ABT-888), (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one (talazoparib, BMN 673), 4-iodo-3-nitrobenzamide (iniparib, BSI-201), 8-fluoro-5-(4-((methylamino)methyl)phenyl)-3, 4-dihydro-2H-azepino[5,4,3-cd]indol-1(6H)-onephosphoric acid (Rucaparib, AG-014699, PF-01367338), 2-[4-[(dimethylamino)methyl]phenyl]-5,6-dihydroimidazo[4,5,1-jk][1,4] benzodiazepin-7(4H)-one (AG14361), 3-aminobenzamide (INO-1001), 2-(2-fluoro-4-((S)-pyrrolidin-2-yl)phenyl)-3H-benzo[d]imidazole-4-carboxamide (A-966492), N-(5,6-dihydro-6-oxo-2-phenanthridinyl)-2-acetamide hydrochloride (PJ34, PJ34 HCl), MK-4827, 3,4-dihydro-4-oxo-3,4-dihydro-4-oxo-N-[(1S)-1-phenylethyl]-2-quinazolinepropanamide (ME0328), 5-(2-oxo-2-phenylethoxy)-1(2H)-isoquinolinone (UPF-1069), 4-[[4-fluoro-3-[(4-methoxy-1-piperidinyl)carbonyl]phenyl]methyl]-1(2H)-phthalazinone (AZD 2461), and the like.

Miscellaneous agents include altretamine, arsenic trioxide, gallium nitrate, hydroxyurea, levamisole, mitotane, octreotide, procarbazine, suramin, thalidomide, photodynamic compounds such as methoxsalen and sodium porfimer, and proteasome inhibitors such as bortezomib.

Biologic therapy agents include: interferons such as interferon-α2a and interferon-α2b, and interleukins such as aldesleukin, denileukin diftitox, and oprelvekin.

In addition to anticancer agents intended to act against cancer cells, combination therapies including the use of protective or adjunctive agents, including: cytoprotective agents such as armifostine, dexrazonxane, and mesna, phosphonates such as parmidronate and zoledronic acid, and stimulating factors such as epoetin, darbeopetin, filgrastim, PEG-filgrastim, and sargramostim, are also envisioned.

In one embodiment, one or more additional therapeutically active agents can include immunotherapy, anti-angiogenics, and radiotherapy.

In a further embodiment of the present disclosure, a pharmaceutical composition comprising one or more compounds of formula (A), (B), (I), or (II), and any subgenera thereof, or a pharmaceutically acceptable salt, solvate, ester, or prodrug thereof, and a pharmaceutically acceptable excipient or adjuvant is provided. The pharmaceutically acceptable excipients and adjuvants are added to the composition or formulation for a variety of purposes. In another embodiment, a pharmaceutical composition comprising one or more compounds of formula (A), (B), (I), or (II), and any subgenera thereof, or a pharmaceutically acceptable salt, solvate, ester, or prodrug thereof, further comprises a pharmaceutically acceptable carrier. In one embodiment, a pharmaceutically acceptable carrier includes a pharmaceutically acceptable excipient, binder, and/or diluent. In one embodiment, suitable pharmaceutically acceptable excipients include, but are not limited to, water, salt solutions, alcohol, polyethylene glycols, gelatin, lactose, amylase, magnesium stearate, talc, silicic acid, viscous paraffin, hydroxymethylcellulose and polyvinylpyrrolidone.

In one embodiment, excipients can be used to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

In certain embodiments, the pharmaceutical compositions of the present disclosure may additionally contain other adjunct components conventionally found in pharmaceutical compositions, at their art-established usage levels. Thus, for example, the pharmaceutical compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

For the purposes of this disclosure, the compounds of the present disclosure can be formulated for administration by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters.

The compounds disclosed herein can be formulated in accordance with the routine procedures adapted for desired administration route. Accordingly, the compounds disclosed herein can take such forms as suspensions, solutions or emulsions in oily or aqueous vehicles, and can contain formulatory agents such as suspending, stabilizing and/or dispersing agents. The compounds disclosed herein can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). Alternatively, the active ingredient can be in powder form for constitution with a suitable vehicle, e.g., sterile pyrogen-free water, before use. Suitable formulations for each of these methods of administration can be found, for example, in Remington: The Science and Practice of Pharmacy, A. Gennaro, ed., 20th edition, Lippincott, Williams & Wilkins, Philadelphia, Pa., the entire disclosure of which is incorporated by reference herein for all purposes.

In certain embodiments, a pharmaceutical composition of the present disclosure is prepared using known techniques, including, but not limited to mixing, dissolving, granulating, dragee-making, levigating, emulsifying, encapsulating, entrapping or tableting processes.

In one embodiment, the present disclosure provides a pharmaceutical composition comprising a compound of formula (A), (B), (I), or (II), and any subgenera thereof, or a pharmaceutically acceptable salt, solvate, ester, or prodrug thereof, as disclosed herein, combined with a pharmaceutically acceptable carrier. In one embodiment, suitable pharmaceutically acceptable carriers include, but are not limited to, inert solid fillers or diluents and sterile aqueous or organic solutions. Pharmaceutically acceptable carriers are well known to those skilled in the art and include, but are not limited to, from about 0.01 to about 0.1 M and preferably 0.05M phosphate buffer or 0.8% saline. Such pharmaceutically acceptable carriers can be aqueous or non-aqueous solutions, suspensions and emulsions. Examples of non-aqueous solvents suitable for use in the present application include, but are not limited to, propylene glycol, polyethylene glycol, vegetable oils such as olive oil, and injectable organic esters such as ethyl oleate.

Aqueous carriers suitable for use in the present application include, but are not limited to, water, ethanol, alcoholic/aqueous solutions, glycerol, emulsions or suspensions, including saline and buffered media. Oral carriers can be elixirs, syrups, capsules, tablets and the like.

Liquid carriers suitable for use in the present application can be used in preparing solutions, suspensions, emulsions, syrups, elixirs and pressurized compounds. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators.

Liquid carriers suitable for use in the present application include, but are not limited to, water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and *arachis* oil). For parenteral administration, the carrier can also include an oily ester such as ethyl oleate and isopropyl myristate. Sterile liquid carriers are useful in sterile liquid form comprising compounds for parenteral administration. The liquid carrier for pressurized compounds disclosed herein can be halogenated hydrocarbon or other pharmaceutically acceptable propellant.

Solid carriers suitable for use in the present application include, but are not limited to, inert substances such as lactose, starch, glucose, methyl-cellulose, magnesium stearate, dicalcium phosphate, mannitol and the like. A solid carrier can further include one or more substances acting as flavoring agents, lubricants, solubilizers, suspending agents, fillers, glidants, compression aids, binders or tablet-disintegrating agents; it can also be an encapsulating material. In powders, the carrier can be a finely divided solid which is in admixture with the finely divided active compound. In tablets, the active compound is mixed with a carrier having the necessary compression properties in suitable proportions and compacted in the shape and size desired. The powders and tablets preferably contain up to 99% of the active compound. Suitable solid carriers include, for example, calcium phosphate, magnesium stearate, talc, sugars, lactose, dextrin, starch, gelatin, cellulose, polyvinylpyrrolidine, low melting waxes and ion exchange resins. A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach.

Parenteral carriers suitable for use in the present application include, but are not limited to, sodium chloride solution, Ringer's dextrose, dextrose and sodium chloride, lactated Ringer's and fixed oils. Intravenous carriers include fluid and nutrient replenishers, electrolyte replenishers such as those based on Ringer's dextrose and the like. Preservatives and other additives can also be present, such as, for example, antimicrobials, antioxidants, chelating agents, inert gases and the like.

Carriers suitable for use in the present application can be mixed as needed with disintegrants, diluents, granulating agents, lubricants, binders and the like using conventional techniques known in the art. The carriers can also be sterilized using methods that do not deleteriously react with the compounds, as is generally known in the art.

Diluents may be added to the formulations of the present invention. Diluents increase the bulk of a solid pharmaceutical composition and/or combination, and may make a pharmaceutical dosage form containing the composition and/or combination easier for the patient and care giver to handle. Diluents for solid compositions and/or combinations include, for example, microcrystalline cellulose (e.g., AVI-CEL), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol, and talc.

Additional embodiments relate to the pharmaceutical formulations wherein the formulation is selected from the group consisting of a solid, powder, liquid and a gel. In certain embodiments, a pharmaceutical composition of the present invention is a solid (e.g., a powder, tablet, a capsule, granulates, and/or aggregates). In certain of such embodiments, a solid pharmaceutical composition comprising one or more ingredients known in the art, including, but not limited to, starches, sugars, diluents, granulating agents, lubricants, binders, and disintegrating agents.

Solid pharmaceutical compositions that are compacted into a dosage form, such as a tablet, may include excipients whose functions include helping to bind the active ingredient and other excipients together after compression. Binders for solid pharmaceutical compositions and/or combinations include acacia, alginic acid, carbomer (e.g., carbopol), carboxymethylcellulose sodium, dextrin, ethyl cellulose, gelatin, guar gum, gum tragacanth, hydrogenated vegetable oil, hydroxyethyl cellulose, hydroxypropyl cellulose (e.g., KLUCEL), hydroxypropyl methyl cellulose (e.g., METHOCEL), liquid glucose, magnesium aluminum silicate, maltodextrin, methylcellulose, polymethacrylates, povidone (e.g., KOLLIDON, PLASDONE), pregelatinized starch, sodium alginate, and starch.

The dissolution rate of a compacted solid pharmaceutical composition in the patient's stomach may be increased by the addition of a disintegrant to the composition and/or combination. Disintegrants include alginic acid, carboxymethylcellulose calcium, carboxymethylcellulose sodium (e.g., AC-DI-SOL and PRIMELLOSE), colloidal silicon dioxide, croscarmellose sodium, crospovidone (e.g., KOLLIDON and POLYPLASDONE), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB), potato starch, and starch.

Glidants can be added to improve the flowability of anon-compacted solid composition and/or combination and to improve the accuracy of dosing. Excipients that may function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition and/or combination to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that may be included in the composition and/or combination of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In certain embodiments, a pharmaceutical composition of the present invention is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

Liquid pharmaceutical compositions can be prepared using compounds of formula (A), (B), (I), or (II), and any subgenera thereof, or a pharmaceutically acceptable salt, solvate, ester, or prodrug thereof, and any other solid excipients where the components are dissolved or suspended in a liquid carrier such as water, vegetable oil, alcohol, polyethylene glycol, propylene glycol, or glycerin.

For example, formulations for parenteral administration can contain as common excipients sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers can be useful excipients to control the release of active compounds. Other potentially useful parenteral delivery systems include ethylene-vinyl acetate copolymer particles, osmotic pumps, implantable infusion systems, and liposomes. Formulations for inhalation administration contain as excipients, for example, lactose, or can be aqueous solutions containing, for example, polyoxyethylene-9-auryl ether, glycocholate and deoxycholate, or oily solutions for administration in the form of nasal drops, or as a gel to be applied intranasally. Formulations for parenteral administration can also include glycocholate for buccal administration, methoxysalicylate for rectal administration, or citric acid for vaginal administration.

Liquid pharmaceutical compositions can contain emulsifying agents to disperse uniformly throughout the composition and/or combination an active ingredient or other excipient that is not soluble in the liquid carrier. Emulsifying agents that may be useful in liquid compositions and/or combinations of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as aspartame, lactose, sorbitol, saccharin, sodium saccharin, sucrose, aspartame, fructose, mannitol, and invert sugar may be added to improve the taste.

Preservatives and chelating agents such as alcohol, sodium benzoate, butylated hydroxyl toluene, butylated hydroxyanisole, and ethylenediamine tetraacetic acid may be added at levels safe for ingestion to improve storage stability.

A liquid composition can also contain a buffer such as guconic acid, lactic acid, citric acid or acetic acid, sodium guconate, sodium lactate, sodium citrate, or sodium acetate. Selection of excipients and the amounts used may be readily determined by the formulation scientist based upon experience and consideration of standard procedures and reference works in the field.

In one embodiment, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Formulations for intravenous administration can comprise solutions in sterile isotonic aqueous buffer. Where necessary, the formulations can also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where the compound is to be administered by infusion, it can be dispensed in a formulation with an infusion bottle containing sterile pharmaceutical grade water, saline or dextrose/water. Where the compound is administered by injection, an ampule of sterile water for injection or saline can be provided so that the ingredients can be mixed prior to administration.

Suitable formulations further include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

In certain embodiments, a pharmaceutical composition of the present invention is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition of the present invention comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition of the present invention comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80 and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition of the present invention comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

Appropriate pharmaceutical compositions of the present disclosure can be determined according to any clinically-acceptable route of administration of the composition to the subject. The manner in which the composition is administered is dependent, in part, upon the cause and/or location. One skilled in the art will recognize the advantages of certain routes of administration. The method includes administering an effective amount of the agent or compound (or composition comprising the agent or compound) to achieve a desired biological response, e.g., an amount effective to alleviate, ameliorate, or prevent, in whole or in part, a symptom of a condition to be treated, e.g., oncology and neurology disorders. In various aspects, the route of administration is systemic, e.g., oral or by injection. The agents or compounds, or pharmaceutically acceptable salts or derivatives thereof, are administered orally, nasally, transdermally, pulmonary, inhalationally, buccally, sublingually, intraperitoneally, subcutaneously, intramuscularly, intravenously, rectally, intrapleurally, intrathecally, intraportally, and parenterally. Alternatively or in addition, the route of administration is local, e.g., topical, intra-tumor and peri-tumor. In some embodiments, the compound is administered orally.

In certain embodiments, a pharmaceutical composition of the present disclosure is prepared for oral administration. In certain of such embodiments, a pharmaceutical composition is formulated by combining one or more agents and pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a pharmaceutical agent of the invention and a suitable powder base such as lactose or starch.

In other embodiments the compound of the present disclosure are administered by the intravenous route. In further embodiments, the parenteral administration may be provided in a bolus or by infusion.

In certain embodiments, a pharmaceutical composition is prepared for rectal administration, such as a suppository or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, and lanolin and water in oil emulsions. Exemplary suitable cream bases include, but are not limited to, cold cream and hydrophilic ointment.

In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more compounds of formula (A), (B), (I), or (II), and any subgenera thereof, or a pharmaceutically acceptable salt, solvate, ester, or prodrug thereof are formulated as a prodrug. In certain embodiments, upon in vivo administration, a prodrug is chemically converted to the biologically, pharmaceutically or therapeutically more active form. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

In various aspects, the amount of the compounds of formula (A), (B), (I), or (II), and any subgenera thereof, or a pharmaceutically acceptable salt, solvate, ester, or prodrug thereof, can be administered at about 0.001 mg/kg to about 100 mg/kg body weight (e.g., about 0.01 mg/kg to about 10 mg/kg or about 0.1 mg/kg to about 5 mg/kg).

The concentration of a disclosed compound in a pharmaceutically acceptable mixture will vary depending on several factors, including the dosage of the compound to be administered, the pharmacokinetic characteristics of the compound(s) employed, and the route of administration. The agent may be administered in a single dose or in repeat doses. The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. Treatments may be administered daily or more frequently depending upon a number of factors, including the overall health of a patient, and the formulation and route of administration of the selected compound(s). An ordinarily skilled physician or veterinarian can readily determine and prescribe the effective amount of the drug required to prevent, counter or arrest the progress of the condition.

The compounds or pharmaceutical compositions of the present disclosure may be manufactured and/or administered in single or multiple unit dose forms, for example as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form, such unit dosage form can contain from about 1 mg/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, transdermally, or any other methods as disclosed herein.

The compounds or pharmaceutical compositions of the present disclosure may be co-administered with one or more therapeutically active agent, such as chemotherapeutic agents and immunotherapeutic agents. The term "co-administration" or "coadministration" refers to administration of (a) compound of formula (A), (B), (I), or (II), and any subgenera thereof, or a pharmaceutically acceptable salt, solvate, ester, or prodrug thereof, and (b) at least one additional therapeutically active agent, together in a coordinated fashion. For example, the co-administration can be simultaneous administration, sequential administration, overlapping administration, interval administration, continuous administration, or a combination thereof. In one embodiment, the compound of the present disclosure and at least one additional therapeutically active agent are formulated into a single dosage form. In another embodiment, the compound of the present disclosure and at least one additional therapeutically active agent are provided in a separate dosage forms.

In one embodiment, the co-administration is carried out for one or more treatment cycles. By "treatment cycle", it is meant a pre-determined period of time for co-administering the compound of the present disclosure (e.g., a compound of formula (A), (B), (I), or (II), and any subgenera thereof, or a pharmaceutically acceptable salt, solvate, ester, or prodrug thereof) and at least one therapeutically active agent. Typically, the patient is examined at the end of each treatment cycle to evaluate the effect of the present combination therapy. In one embodiment, the co-administration is carried out for 1 to 48 treatment cycles. In another embodiment, the co-administration is carried out for 1 to 36 treatment cycles. In another embodiment, the co-administration is carried out for 1 to 24 treatment cycles.

In one embodiment, each of the treatment cycle has about 3 or more days. In another embodiment, each of the treatment cycle has from about 3 days to about 60 days. In another embodiment, each of the treatment cycle has from about 5 days to about 50 days. In another embodiment, each of the treatment cycle has from about 7 days to about 28 days. In another embodiment, each of the treatment cycle has 28 days. In one embodiment, the treatment cycle has about 29 days. In another embodiment, the treatment cycle has about 30 days. In another embodiment, the treatment cycle has about a month-long treatment cycle. In another embodiment, the treatment cycle has from about 4 to about 6 weeks.

Depending on the patient's condition and the intended therapeutic effect, the dosing frequency for each of the compound of the present disclosure (e.g., a compound of formula (A), (B), (I), or (II), and any subgenera thereof, or a pharmaceutically acceptable salt, solvate, ester, or prodrug thereof) and at least one therapeutically active agent may vary from once per day to six times per day. That is, the dosing frequency may be once per day, twice per day, three times per day, four times per day, five times per day, or six times per day. In some embodiments, dosing frequency may be one to six times per week or one to four times per month. In one embodiment, dosing frequency may be once a week, once every two weeks, once every three weeks, once every four weeks, or once a month.

There may be one or more void days in a treatment cycle. By "void day", it is meant a day when neither the compound of the present disclosure (e.g., a compound of formula (A), (B), (I), or (II), and any subgenera thereof, or a pharmaceutically acceptable salt, solvate, ester, or prodrug thereof) or at least one therapeutically active agent is administered. In other words, none of the compound of the present disclosure and at least one therapeutically active agent is administered on a void day. Any treatment cycle must have at least one non-void day. By "non-void day", it is meant a day when at least one of the compound of the present disclosure and at least one therapeutically active agent is administered.

By "simultaneous administration", it is meant that the compound of the present disclosure e.g., a compound of formula (A), (B), (I), or (II), and any subgenera thereof, or a pharmaceutically acceptable salt, solvate, ester, or prodrug thereof) and at least one therapeutically active agent are administered on the same day. For the simultaneous administration, the compound of the present disclosure and at least one therapeutically active agent can be administered at the same time or one at a time. The administration of the compound of the present disclosure and at least one therapeutically active agent (such as chemotherapeutic agent) occurs within 24 hours or less.

In one embodiment of the simultaneous administration, the compound of the present disclosure (e.g., a compound of formula (A), (B), (I), or (II), and any subgenera thereof, or a pharmaceutically acceptable salt, solvate, ester, or prodrug thereof), is administered from 1 to 4 times per day, 1 to 4 times per week, once every two weeks, once every three weeks, once every four weeks or 1 to 4 times per month; and the at least one additional therapeutically active agent is administered 1 to 4 times per day, 1 to 4 times per week, once every two weeks, once every three weeks, once every four weeks or 1 to 4 times per month. In another embodiment of the simultaneous administration, the compound of the present disclosure, is administered once a week, once every two weeks, once every three weeks, once every four weeks, or once a month; and the at least one additional therapeutically active agent is administered 1 to 4 times per day, 1 to 4 times per week, once every two weeks, once every three weeks, once every four weeks or 1 to 4 times per month.

By "sequential administration", it is meant that during a period of two or more days of continuous co-administration without any void day, only one of the compound of the present disclosure (e.g., a compound of formula (A), (B), (I), or (II), and any subgenera thereof, or a pharmaceutically acceptable salt, solvate, ester, or prodrug thereof) and at least one therapeutically active agent is administered on any given day.

In one embodiment of the sequential administration, the compound of the present disclosure (e.g., a compound of formula (A), (B), (I), or (II), and any subgenera thereof, or a pharmaceutically acceptable salt, solvate, ester, or prodrug thereof), is administered from 1 to 4 times per day, 1 to 4 times per week, once every two weeks, once every three weeks, once every four weeks or 1 to 4 times per month; and at least one additional therapeutically active agent is administered 1 to 4 times per day, 1 to 4 times per week, once every two weeks, once every three weeks, once every four weeks or 1 to 4 times per month. In another embodiment of the sequential administration, the compound of the present disclosure, is administered from once a week, once every two weeks, once every three weeks, once every four weeks, or once a month; and at least one additional therapeutically active agent is administered 1 to 4 times per day, 1 to 4 times per week, once every two weeks, once every three weeks, once every four weeks or 1 to 4 times per month.

By "overlapping administration", it is meant that during a period of two or more days of continuous co-administration without any void day, there is at least one day of simultaneous administration and at least one day when only one of the compound of the present disclosure (e.g., a compound of formula (A), (B), (I), or (II), and any subgenera thereof, or a pharmaceutically acceptable salt, solvate, ester, or prodrug thereof) and at least one therapeutically active agent is administered.

By "interval administration", it is meant a period of co-administration with at least one void day. By "continuous administration", it is meant a period of co-administration without any void day. The continuous administration may be simultaneous, sequential, or overlapping, as described above.

In the present method, the co-administration comprises oral administration, parenteral administration, or a combination thereof. Examples of the parenteral administration include, but are not limited to intravenous (IV) administration, intraarterial administration, intramuscular administration, subcutaneous administration, intraosseous administration, intrathecal administration, or a combination thereof. The compound of the present disclosure (e.g., a compound of formula (A), (B), (I), or (II), and any subgenera thereof, or a pharmaceutically acceptable salt, solvate, ester, or prodrug thereof) and at least one therapeutically active agent can be independently administered orally or parenterally. In one embodiment, the compound of the present disclosure and at least one therapeutically active agent is administered parenterally. The parenteral administration may be conducted via injection or infusion.

When administered for the treatment a particular disease state or disorder, such as cancer, it is understood that an effective dosage can a 'depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

Having now generally described the invention, the same will be more readily understood through reference to the following examples, which are provided by way of illustration and are not intended to be limiting of the present invention.

EXAMPLES

The following schemes provide exemplary synthetic routes for preparing compounds of the present disclosure. These general schemes together with the specific Examples below provide guidance for the synthesis.

Compounds of formula (A) and (B) may be prepared according to the methods outlined in Schemes 1-11.

Scheme 1
Preparation of compounds of formula (A) from coupling of intermediate (IA) and (IE).

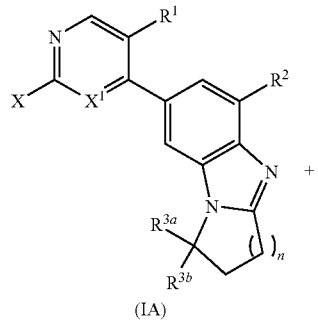

(IA)

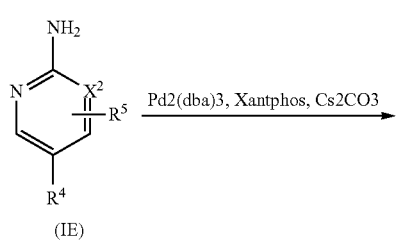

(IE)

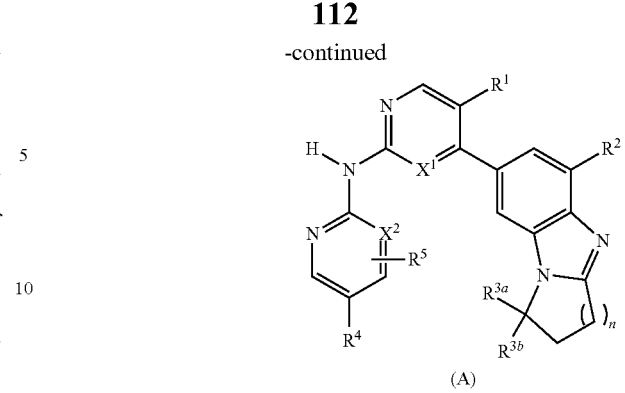

(A)

Scheme 2
Preparation of compounds of formula (B) from coupling of intermediate (IB) and (IE).

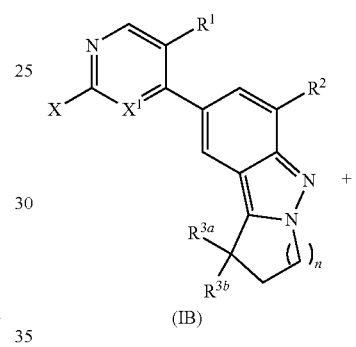

(IB)

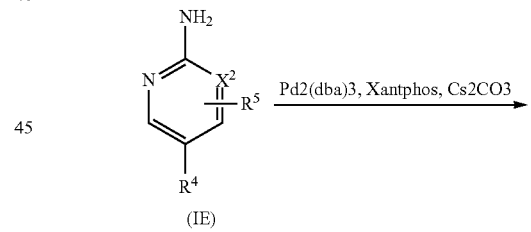

(IE)

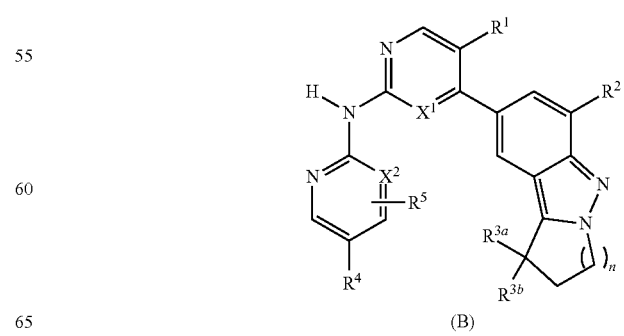

(B)

Scheme 3
Preparation of intermediate (IA) beginning with a nitrobenzene compound to amine (IA-002).
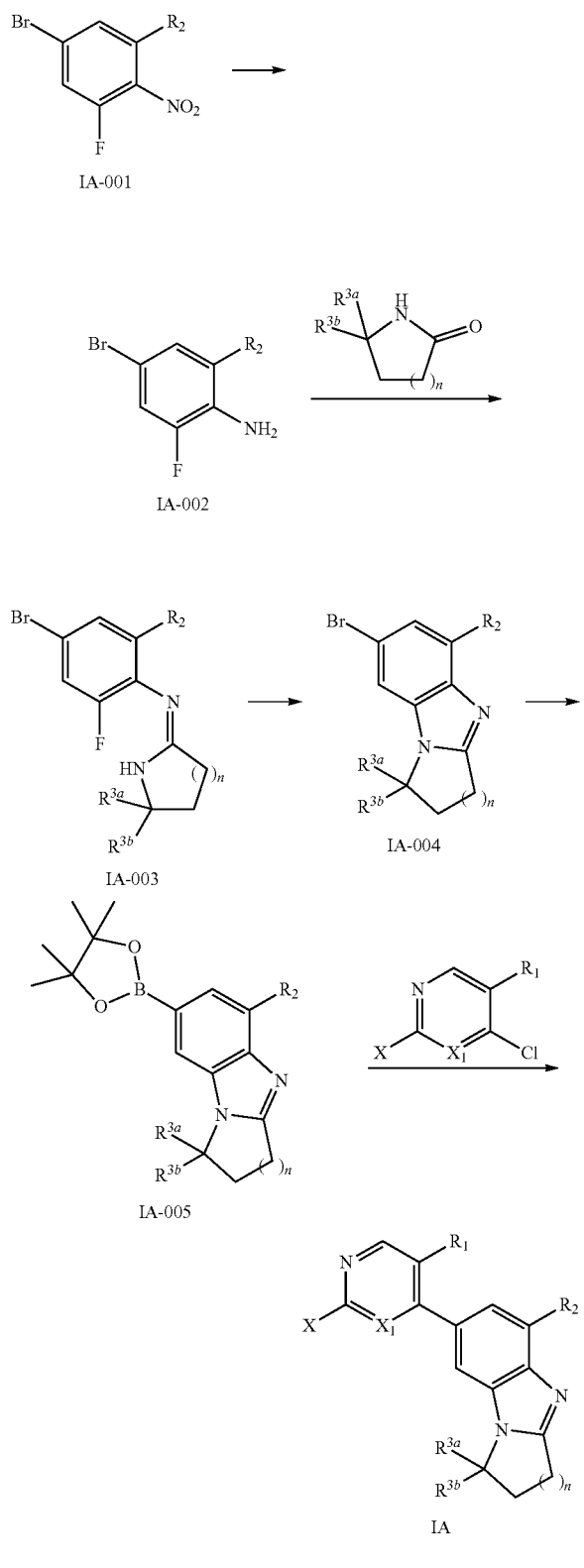
Scheme 4
Preparation of intermediate (IB) with intermediates (IB-003) and (IB-007), prepared from starting materials (IB-001) and (IB-004), respectively.
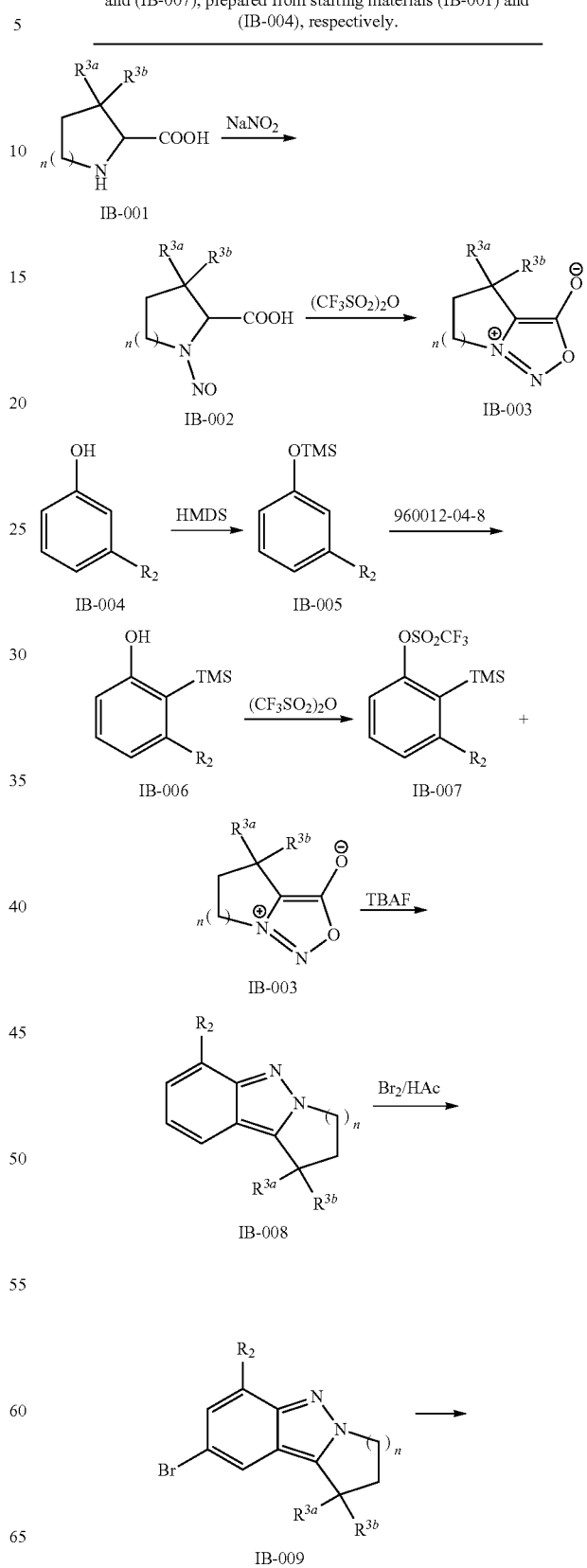

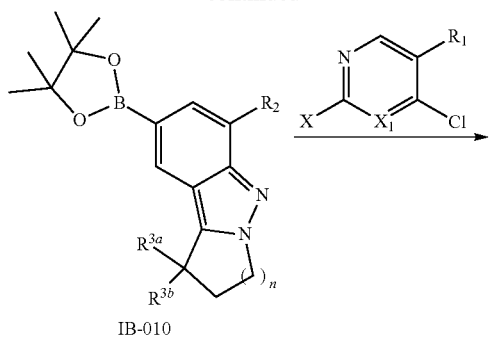

IB-010

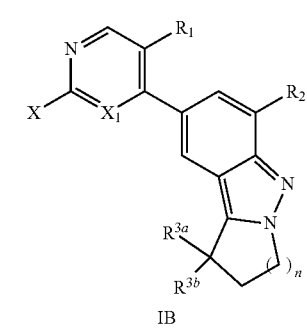

IB

Scheme 5
Preparation of intermediate (IE-I) by reductive amination of aldehyde starting material, followed by amination.

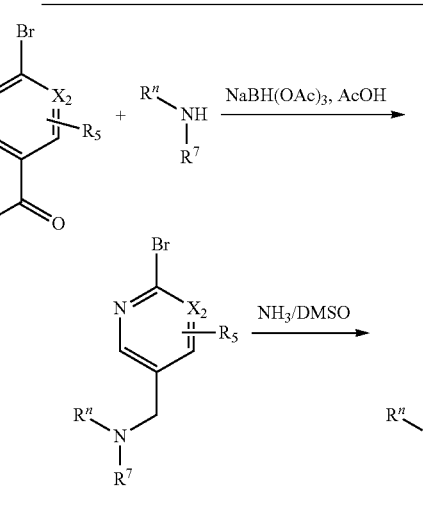

IE-I

Scheme 6
Preparation of intermediate (IE-II) by coupling amine with heteroaryl bromide followed by hydrogenation.

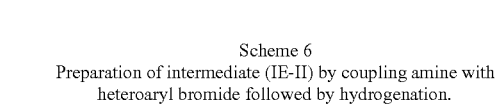

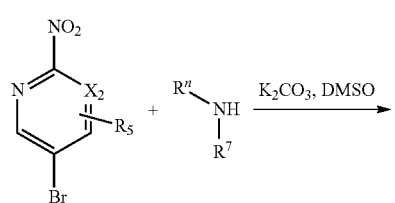

IE-II

Scheme 7
Preparation of intermediate (IE-III) by Suzuki coupling reaction followed by hydrogenation.

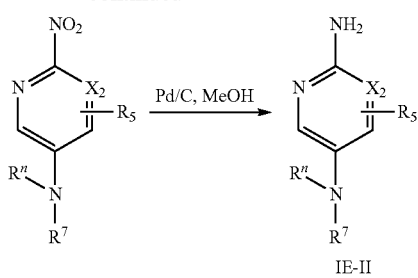

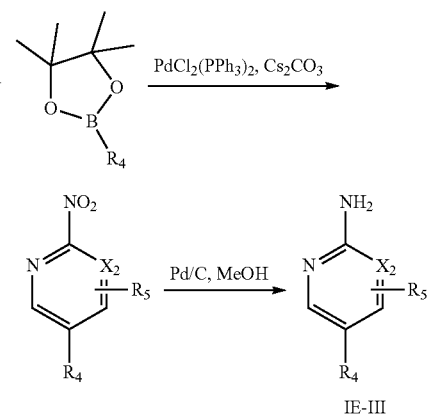

IE-III

Scheme 8
Preparation of intermediate (IE-IV) by coupling of hydroxyl group on the heteroaryl starting material followed by amination.

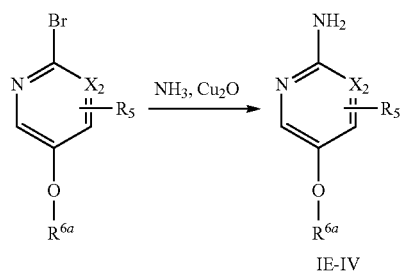

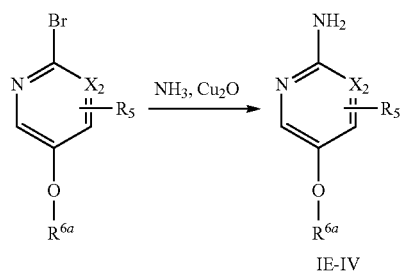

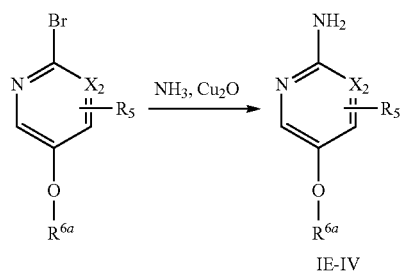

IE-IV

Scheme 9
Preparation of intermediate (IE-V) by coupling of heteroaryl fluoride followed by hydrogenation.

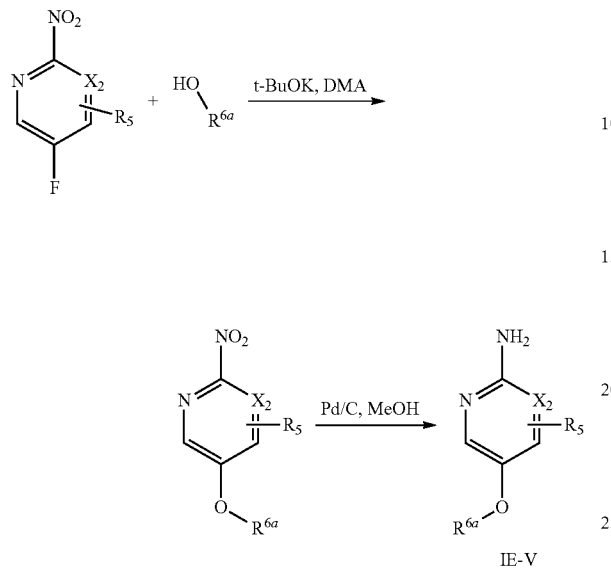

Scheme 10
Preparation of intermediate (IE-VI) by reduction of aldehyde starting material to alcohol, conversion of hydroxyl group to a chloride, coupling of the chloride intermediate, followed by amination.

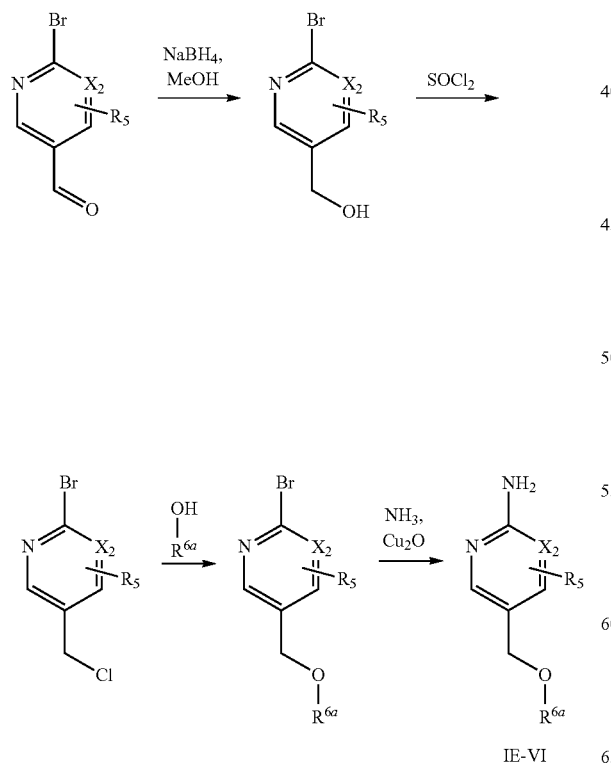

Scheme 11
Preparation of intermediate (IE-VII) by coupling carboxylic acid starting material with an amine, followed by hydrogenation.

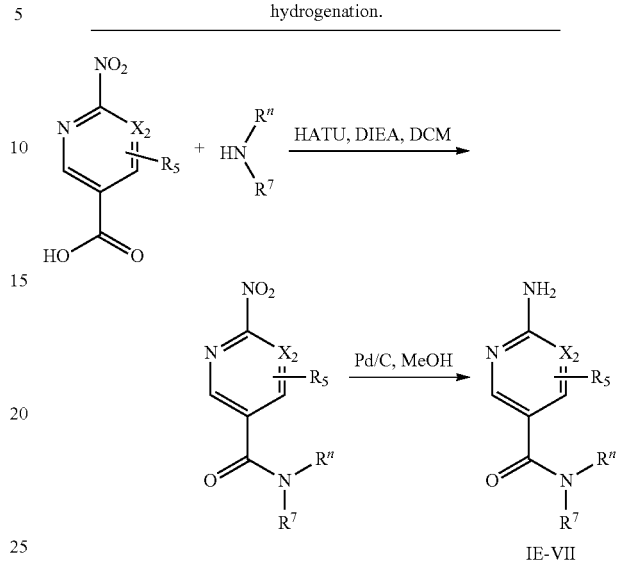

Additional examples for preparation of useful intermediates and compound of the present disclosure are as shown in Schemes 12-18.

Scheme 12
Preparation of Intermediate: Boronic Ester of 5-fluoro-1,1-dimethyl-2,23-dihydro-1H-benzo[d]pyrrolo[1,2-a]imidazole (Compound A1)

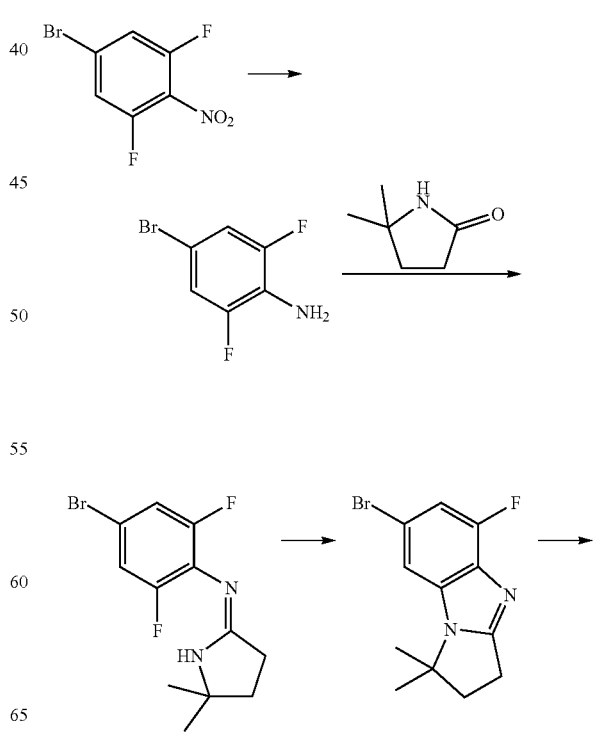

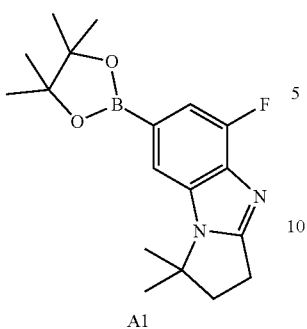
A1
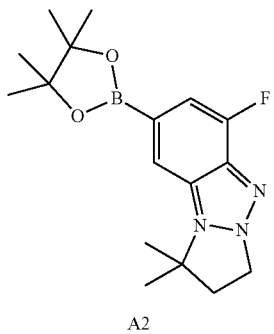
A2
Scheme 13
Preparation of Intermediate: Boronic Ester of 6-fluoro-
1,1-dimethyl-2,3-dihydro-1H-pyrrolo[1,2-b]indazole (Compound A2)
Scheme 14
Preparation of Pyrimidine Coupling Partner (Compound A3)
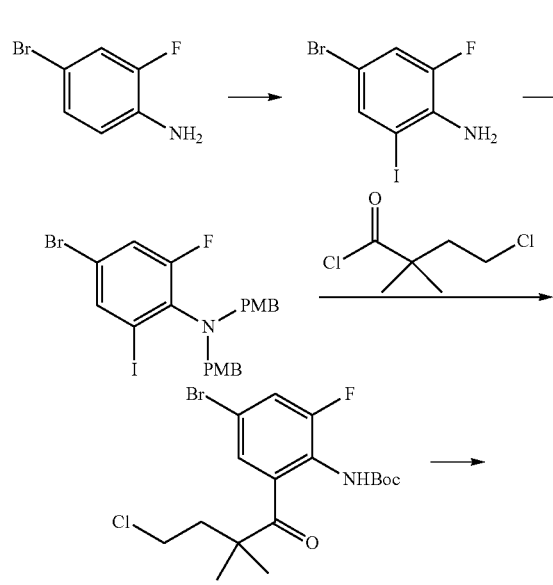
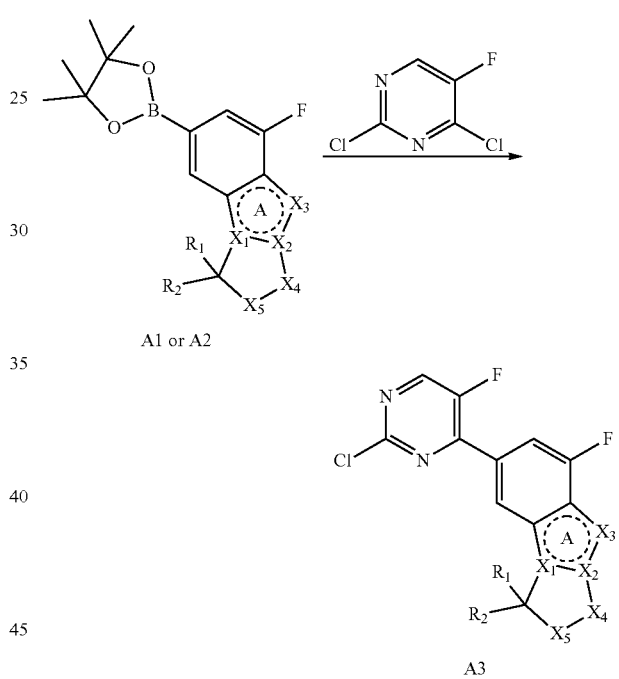
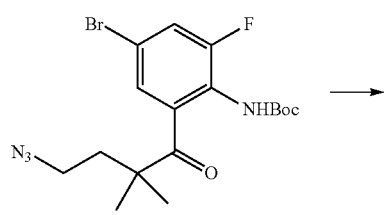
Scheme 15
Preparation of Intermediates: 5-((4-alkylpiperazin-1-yl)methyl)
pyridin-2-amine (Compound B1)
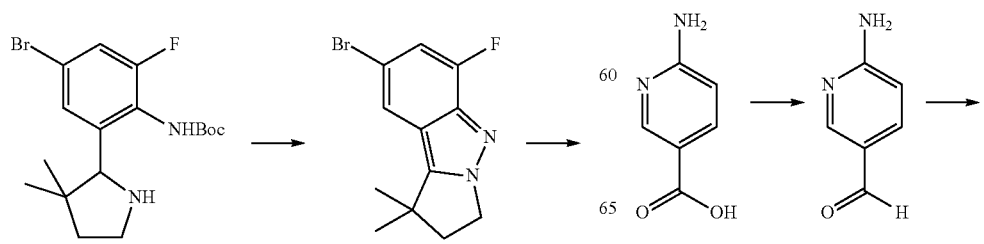

121
-continued

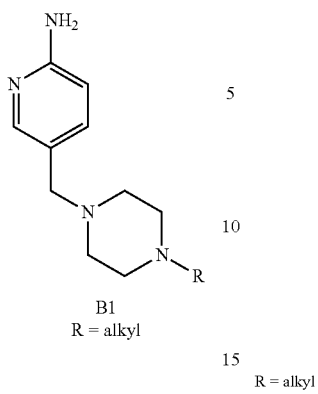

B1
R = alkyl

122
-continued

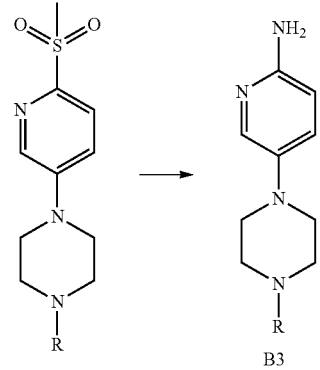

R = alkyl

Scheme 16
Preparation of Intermediates: (6-aminopyridin-3-yl)
(4-alkylpiperazin-1-yl)methanone (Compound B2)

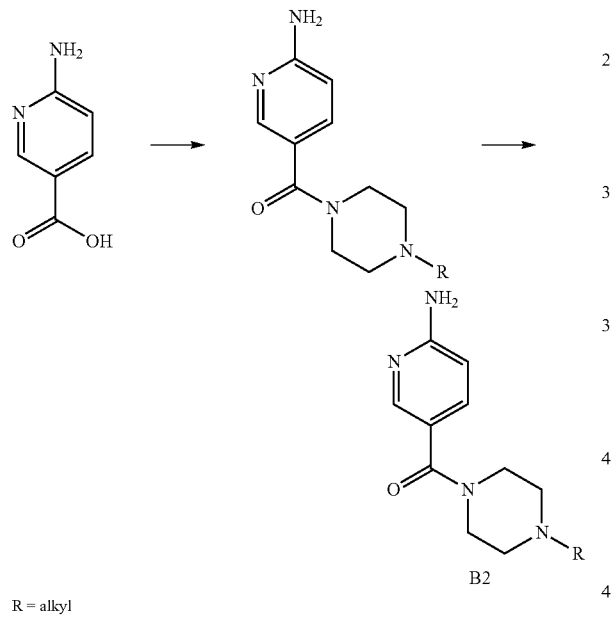

B2
R = alkyl

Scheme 17
Preparation of Intermediates: 5-(4-alkylpiperazin-1-yl)pyridin-2-amine (Compound B3)

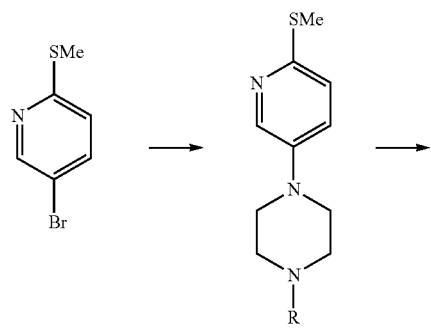

Scheme 18
Preparation of Compounds of formula (I): Coupling of chloropyrimidine (A3) with halogenated pyridines (B1-B3)

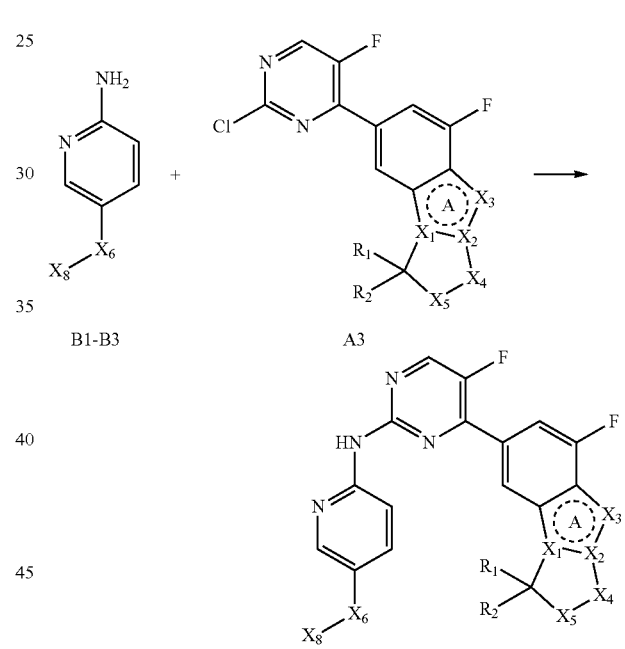

Example 1: Synthesis of N-(5-((4-ethylpiperazin-1-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine (Compound 15; Comparative Example)

Step 1: Synthesis of methyl 4-methyl-4-nitropentanoate (Compound 3)

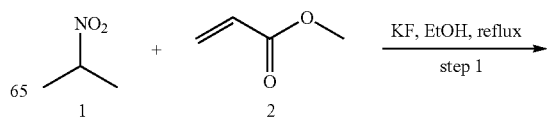

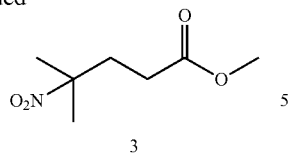

3

To a solution of compound 1 (87.5 g, 0.98 mol, 1 eq) in anhydrous EtOH (490 mL) were added compound 2 (93 g, 1.08 mol, 1.1 eq) and KF (5.71 g, 0.098 mol). The mixture was then refluxed for 4 h. After completion, the mixture was cooled to room temperature (rt) and concentrated. The residue was dissolved in ethyl acetate (800 mL) and washed with water (500 mL). The organic layer was dried over sodium sulfate, concentrated to give the desired product (150 g, crude) which was used in next step directly. $^1$H NMR (300 MHz, CDCl$_3$) δ 3.67 (s, 3H), 2.36-2.03 (m, 4H), 1.58 (s, 6H).

Step 2: Synthesis of 5,5-dimethylpyrrolidin-2-one (Compound 4)

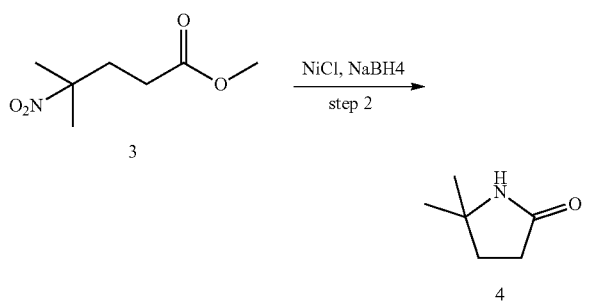

To a suspension of NiCl$_2$.6H$_2$O (35 g, 0.15 mol, 0.5 eq) in MeOH (1 L) was added NaBH$_4$ (17.1 g, 0.45 mmol, 1.5 eq) portion wise under nitrogen, after stirring at rt for 30 minutes, a solution of compound 3 (50 g, 0.31 mol, 1 eq) in MeOH (500 mL) was added drop wise. After addition of compound 3, NaBH$_4$ (35 g, 0.93 mol, 3 eq) was added portion wise. The reaction was stirred at rt and monitored by LCMS. After completion, the reaction was filtered through Celite. The filtrate was concentrated and the residue was re-dissolved in DCM (500 mL), washed with NaHCO$_3$(500 mL×2), dried over sodium sulfate, and concentrated to give the desired product (20 g, 54% over 2 steps) which was used in next step directly. $^1$H NMR (300 MHz, CDCl$_3$) δ 6.40 (br, 1H), 2.45-2.39 (m, 2H), 1.96-1.90 (m, 2H), 1.29 (s, 6H). LCMS: (M+H)$^+$: 114.0.

Step 3: Synthesis of 1-((6-bromopyridin-3-yl) methyl)-4-ethylpiperazine (Compound 7)

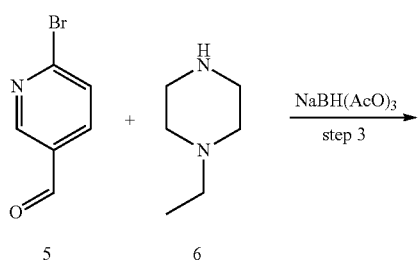

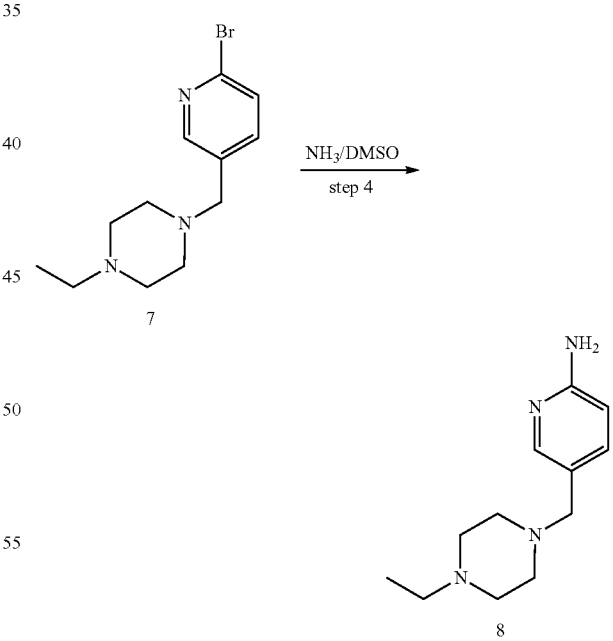

To a solution of compound 5 (10 g, 54 mmol, 1 eq) in DCM (170 mL) was added compound 6 (7.4 g, 65 mmol, 1.2 eq). The mixture was stirred at rt for 30 minutes, then NaBH(OAc)$_3$ (17.1 g, 81 mmol, 1.5 eq) was added portion wise. The mixture was stirred at rt for 12 h. After completion, the mixture was diluted with DCM (300 mL) and 2N NaOH (100 mL). The organic layer was separated and the aqueous layer was extracted with DCM (100 mL). The combined organic layers were dried over sodium sulfate, concentrated and purified by silica column chromatography to give the desired product (7 g, 46%). $^1$H NMR (300 MHz, CDCl$_3$) δ 8.30 (s, 1H), 7.55 (d, J=8.1 Hz, 1H), 7.44 (d, J=8.1 Hz, 1H), 3.49 (s, 2H), 2.55-2.48 (m, 10H), 1.12 (t, J=7.2 Hz, 3H). LCMS: (M+H)+: 283.9.

Step 4: Synthesis of 5-((4-ethylpiperazin-1-yl) methyl)pyridin-2-amine (Compound 8)

A 100 mL sealed tube charged with compound 7 (2 g, 7 mmol), Cu$_2$O (20 mg) and DMSO (20 mL), was then bubbled in NH$_3$ for 10 minutes. The mixture was stirred at 65-75° C. overnight. After completion and cooling down to rt, the mixture was adjusted to PH=12-14 with 2 N NaOH and extracted with DCM (30 mL×3). The combined organic layers were washed with brine (30 mL×3). dried over sodium sulfate, concentrated and the residue was washed with PE to give the product (1.1 g, 71%). ¹H NMR (300 MHz, DMSO-d₆) δ 7.75 (s, 1H), 7.26 (d, J=7.2 Hz, 1H), 6.39 (d, J=7.5 Hz, 1H), 3.23 (s, 2H), 2.54-2.50 (m, 2H), 2.31-2.26 (m, 8H), 0.96 (t, J=7.2 Hz, 3H). LCMS: (M+H)+: 221.0.

Step 5: Synthesis of (E)-4-bromo-N-(5,5-dimethylpyrrolidin-2-ylidene)-2,6-difluoroaniline (Compound 10)

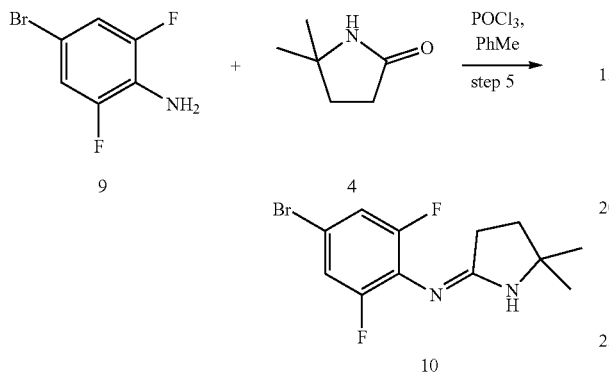

To a solution of compound 9 (4 g, 19.2 mmol, 1 eq), compound 4 (4.4 g, 38.5 mmol, 2 eq) and triethylamine (TEA; 2.9 g, 28.6 mmol, 1.5 eq) in toluene (80 mL) was added POCl₃ (2.95 g, 19.2 mmol, 1 eq) dropwise. After addition, the mixture was refluxed overnight. The mixture was concentrated and the residue was re-dissolved in DCM (100 mL), washed with aq NaHCO₃ (50 mL×2), dried over sodium sulfate and concentrated to give the desired product (6 g, crude) which was used in next step directly without further purification. ¹H NMR (300 MHz, CDCl₃) δ 8.54 (br, 1H), 8.09 (s, 1H), 7.87-7.83 (m, 1H), 3.21-3.16 (m, 2H), 2.64-2.59 (m, 2H), 1.75 (s, 6H). LCMS: (M+H)⁺: 302.8.

Step 6: Synthesis of 7-bromo-5-fluoro-1,1-dimethyl-2,3-dihydro-1H-benzo[d]pyrrolo[1,2-a]imidazole (Compound 11)

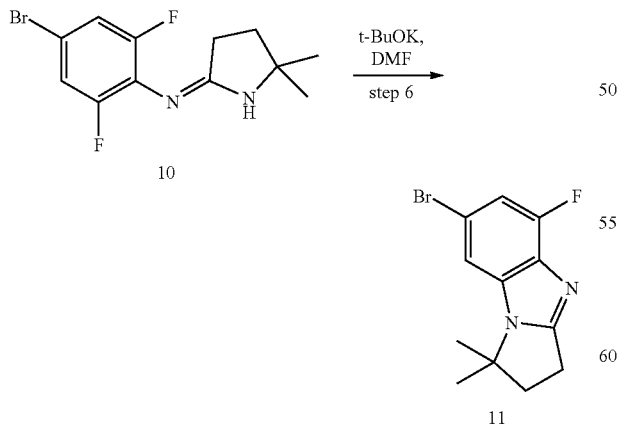

To a solution of compound 10 (6 g, 20 mmol, 1 eq) in DMF (42 mL) was added t-BuOK (2.7 g, 24 mmol, 1.2 eq). The mixture was warmed to 100° C. overnight. After completion, the mixture was diluted with brine (150 mL) and extracted with DCM (100 mL×3). The combined organic layers were washed with brine (100 mL×3), dried over sodium sulfate, concentrated and purified by column chromatography on silica to give the desired product (2.6 g, 47% over 2 steps). ¹H NMR (300 MHz, CDCl₃) δ 7.08-7.06 (m, 2H), 2.50-2.40 (m, 2H), 1.97-1.87 (m, 2H), 1.29 (s, 6H). LCMS: (M+H)⁺: 282.8.

Step 7: Synthesis of 5-fluoro-1,1-dimethyl-7-(4,4,5,5-tetramethyl-1,3,2-dioxaborolan-2-yl)-2,3-dihydro-1H-benzo[d]pyrrolo[1,2-a]imidazole (Compound 12)

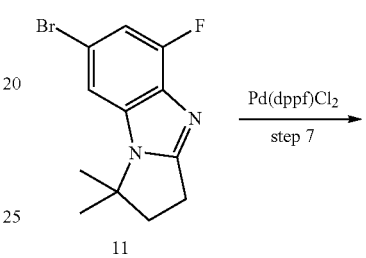

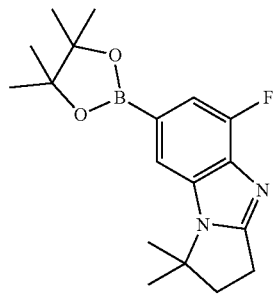

To a solution of compound 11 (2.6 g, 9.2 mmol, 1 eq) in dioxane (52 mL) were added KOAc (2.7 g, 27.6 mmol, 3 eq), Bis(pinacolato)diboron (3.5 g, 13.9 mmol, 1.5 eq) and Pd(dppf)₂Cl₂ (0.68 g, 0.92 mmol, 0.1 eq). The mixture was stirred under nitrogen at 90° C. overnight. After cooling down to rt, the mixture was filtered and washed with ethyl acetate (100 mL). The filtrate was washed with brine (50 mL×2), dried over sodium sulfate, concentrated and purified by column chromatography to give the desired product (1.8 g, 60%). ¹H NMR (300 MHz, CDCl₃) δ 7.65 (s, 1H), 7.39 (d, J=10.8 Hz, 1H), 3.15-3.13 (m, 2H), 2.57-2.55 (m, 2H), 1.71 (s, 6H), 1.38 (s, 12H). LCMS: (M+H)⁺: 331.0

Step 8: Synthesis of 7-(2-chloro-5-fluoropyrimidin-4-yl)-5-fluoro-1,1-dimethyl-2,3-dihydro-1H-benzo[d]pyrrolo[1,2-a]imidazole (Compound 14)

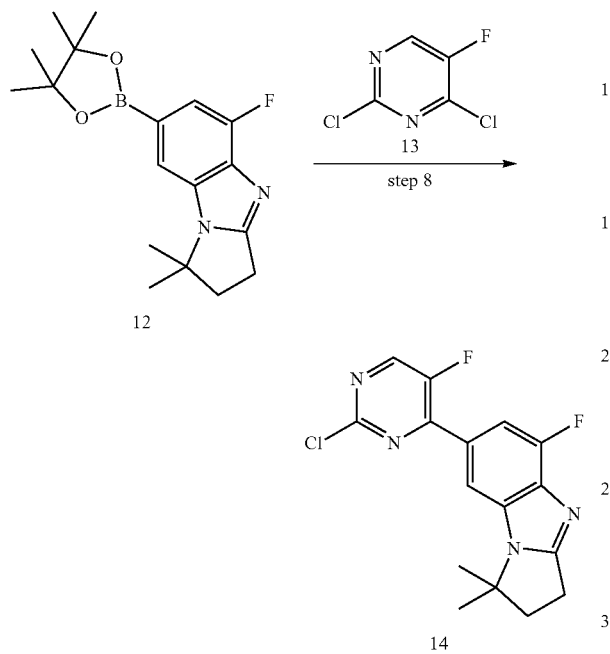

Nitrogen was bubbled into a solution of compound 13 (1 g, 6 mmol, 1.1 eq), Pd(dppf)$_2$C$_2$ (0.38 g, 0.05 mmol, 0.1 eq) and 2 N Na$_2$CO$_3$ (8.4 mL, 16.8 mmol, 3 eq) in DME (17 mL) for 5 minutes. The mixture was warmed to 80° C. and a solution of compound 12 (1.8 g, 5.4 mmol, 1 eq) in DME (18 mL) was added dropwise. After addition, the mixture was stirred at 84° C. for 1 h. After cooling down to rt, the mixture was diluted with ethyl acetate (100 mL) and washed with brine (50 mL×2), dried over sodium sulfate, concentrated and purified by column chromatography to give the desired product (1.8 g, 60%). LCMS: (M+H)$^+$: 334.8.

Step 9: Synthesis of N-(5-((4-ethylpiperazin-1-yl)methyl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine (Compound 15)

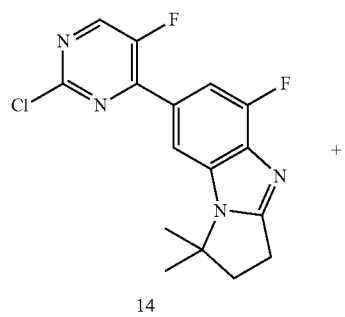

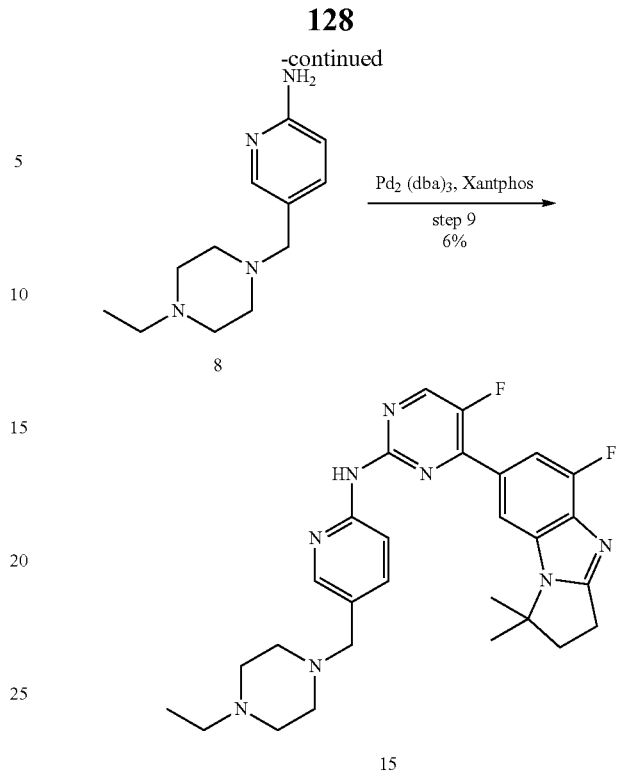

Nitrogen was bubbled into a solution of compound 14 (140 mg, 0.42 mmol, 1 eq), compound 8 (97 mg, 0.44 mmol, 1.05 eq), Pd$_2$(dba)$_3$ (37 mg, 0.04 mmol, 0.1 eq), Xantphos (49 mg, 0.084 mmol, 0.2 eq) and Cs$_2$CO$_3$ (189 mg, 0.84 mmol, 2 eq) in dioxane (28 mL) for 5 minutes. The mixture was stirred at 110° C. for 2 h. After completion, the mixture was cooled down to rt, the mixture was diluted with DCM (50 mL) and filtered through Celite, washed with DCM (20 mL), dried over sodium sulfate, concentrated and purified by pre-HPLC to give the desired product (54 mg, 25%). $^1$H NMR (300 MHz, CDCl$_3$) δ 8.47-8.39 (m, 3H), 8.28 (s, 1H), 8.10 (s, 1H), 7.83 (d, J=11.7 Hz, 1H), 7.70 (d, J=7.8 Hz, 1H), 3.53 (s, 2H), 3.19-3.15 (m, 2H), 2.64-2.50 (m, 12H), 1.74 (s, 6H), 1.14 (t, J=7.5 Hz, 3H). LCMS: (M+H)$^+$: 518.9.

Example 2: Synthesis of 1-(4-((6-(5-fluoro-4-(5-fluoro-1,1-dimethyl-2,3-dihydro-1H-benzo[d]pyrrolo[1,2-a]imidazol-7-yl)pyrimidin-2-ylamino)pyridin-3-yl)methyl)piperazin-1-yl)-2-hydroxyethanone (Compound 22)

Step 1. Synthesis of Compound 18

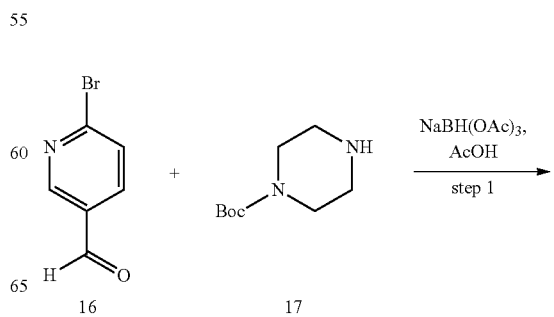

-continued

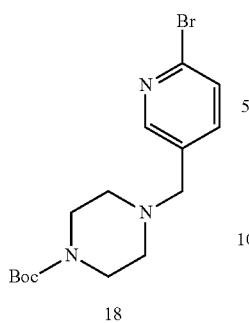

18

To a solution of compound 17 (3 g, 16.1 mmol, 1.5 eq) in DCE (40 mL) under nitrogen was added compound 16 (2 g, 10.7 mmol, 1 eq) and HOAc (2.6 g, 27.8 mmol, 4 eq) successively and stirred for 30 min, cooled to 0° C., sodium triacetyxborohydride (9.1 g, 27.8 mmol, 4 eq) was added in portions. The mixture was stirred at room temperature overnight. The reaction mixture was adjusted with 1N NaOH to pH=8, extracted with DCM (3×25 mL), the combined organic layers were dried, concentrated and purified by silica column to give the desired product (2.6 g, 68%) as a white solid. LCMS: (M+H)$^+$: 357.8. $^1$H NMR (300 MHz, CDCl$_3$): δ 8.3 (s 1H), 7.6 (br, 1H), 7.46 (d, J=7.8 Hz, 1H), 3.30-3.36 (m, 6H), 2.20-2.61 (m, 4H), 1.46 (s, 9H).

Step 2. Synthesis of Compound 19

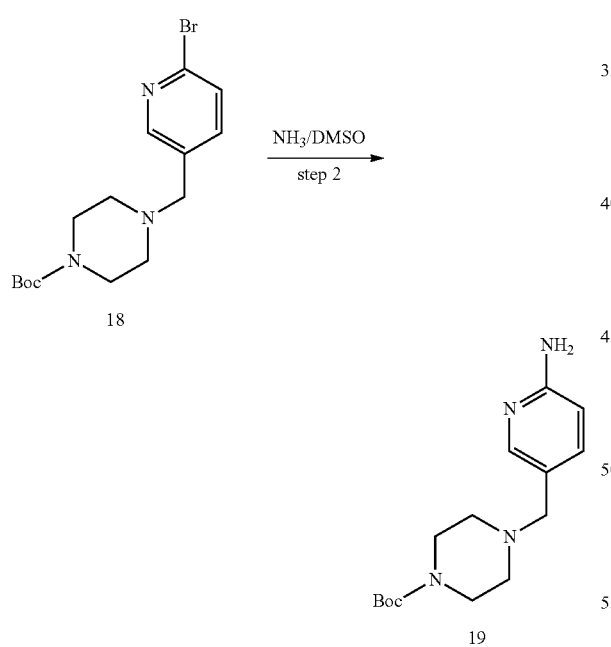

To a solution of compound 18 (4 g, 11.2 mmol, 1 eq) and CuO (0.16 g, 1.12 mmol, 0.1 eq) in DMSO was purged with NH$_3$ (gas) in a sealed tube for 10 min. The mixture was stirred at 100° C. overnight. After completion, the mixture was adjusted with 2N NaOH to pH=12-14, extracted with DCM (25 mL×5), the combined organic layers were dried, concentrated and rinsed with hexane (20 mL) to give the product as a white solid (2.5 g, 81.2%). LCMS: (M+H)$^+$: 237.0. $^1$H NMR (300 MHz, CDCl$_3$): δ 7.94 (d, J=3.3 Hz 1H), 7.41 (d, J=8.4 Hz, 1H), 6.48 (s, 1H), 4.54 (br, 2H), 3.35-3.46 (m, 6H), 2.35 (d, J=3.3 Hz, 4H), 1.42 (s, 9H).

Step 3. Synthesis of Compound 20

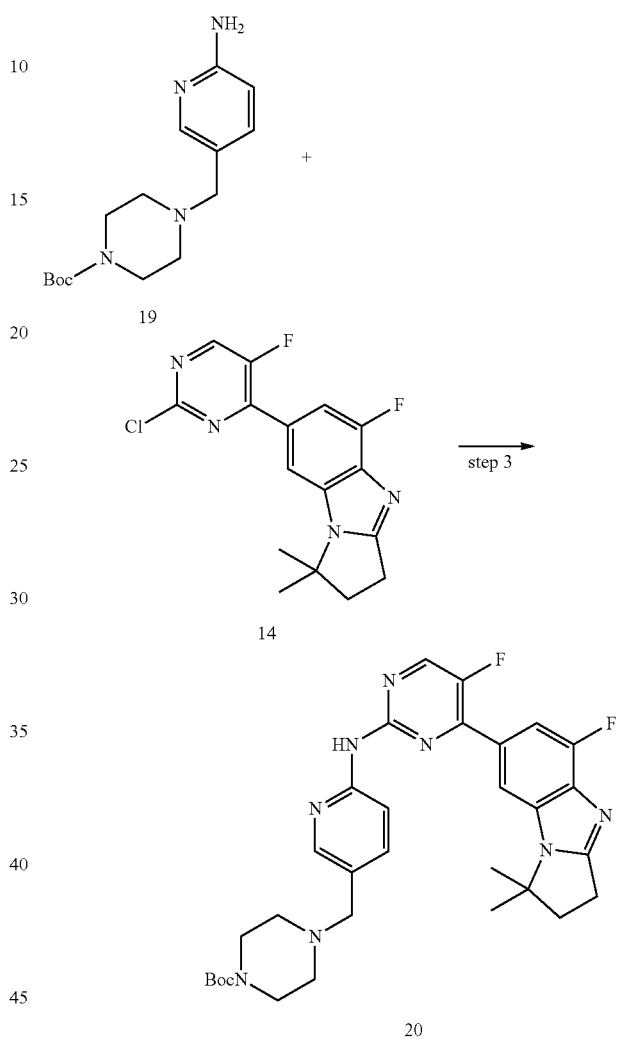

To a mixture of compound 19 (183 mg, 0.63 mmol, 1.05 eq) and compound 14 (200 mg, 0.60 mmol, 1.0 eq) in dioxane (8 mL) were added Pd$_2$(dba)$_3$ (55 mg, 0.06 mmol, 0.1 eq), Xantphos (73 mg, 0.12 mmol, 0.2 eq) and Cs$_2$CO$_3$ (389 mg, 1.20 mmol, 2 eq) under nitrogen. The reaction was purged with nitrogen three times, then stirred at 110° C. overnight. TLC and LCMS indicated completion, and the mixture was cooled to rt, diluted with DCM (20 mL), filtered by Celite, washed with DCM (25 mL×2). The filtrate was concentrated in vacuo to dryness, and the crude was suspended in acetonitrile (10 mL), filtered and dried to give the desired product as a gray solid (200 mg) which was used to the next step without further purification. LCMS: (M+H)$^+$: 590.8. $^1$H NMR (300 MHz, CDCl$_3$): δ 8.45 (s, 2H), 8.26 (s, 2H), 8.10 (s, 1H), 7.85 (s, J=12.6 Hz, 1H), 3.33-3.53 (m, 6H), 3.20 (d, J=7.2 Hz, 2H), 2.64 (t, J=8.1 Hz, 2H), 2.64 (t, J=3.3 Hz, 2H), 2.49 (t, J=3.3 Hz, 4H), 1.74 (s, 6H), 1.47 (s, 9H).

Step 4. Synthesis of Compound 21

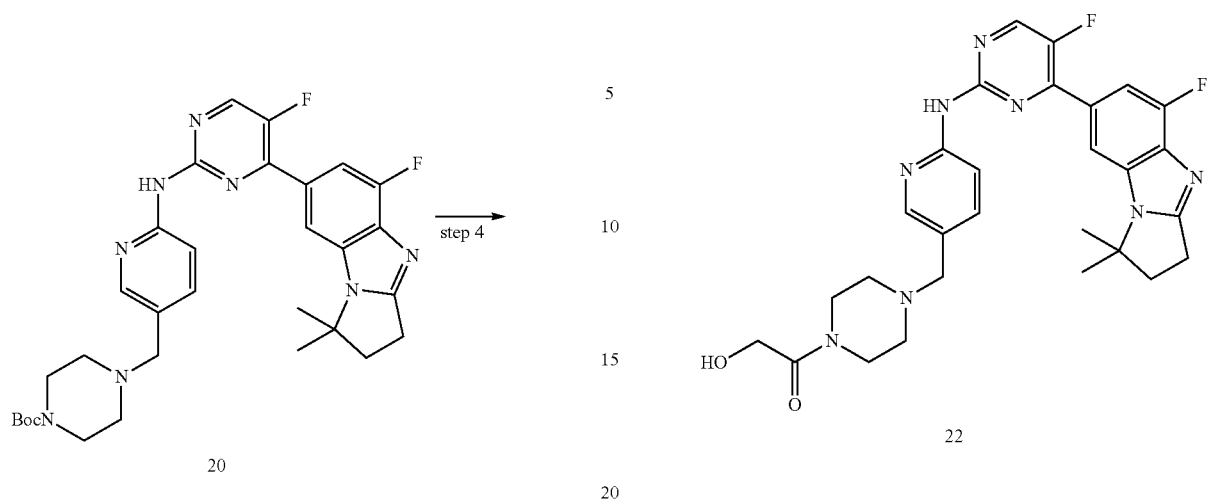

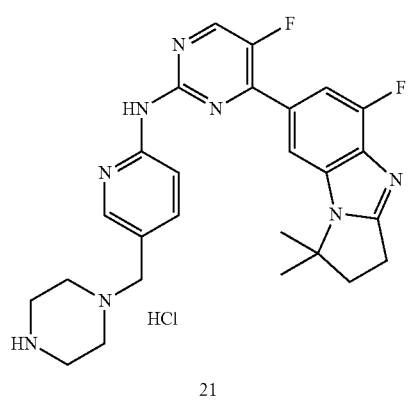

A mixture of compound 20 (200 mg, crude) in 4N HCl in dioxane (4 mL) was stirred for 1 h at room temperature. TLC and LCMS showed completion, concentrated to give a white solid (180 mg) which was used to the next step without further purification. LCMS: (M+H)$^+$: 491.9.

Step 5. Synthesis of Compound 22

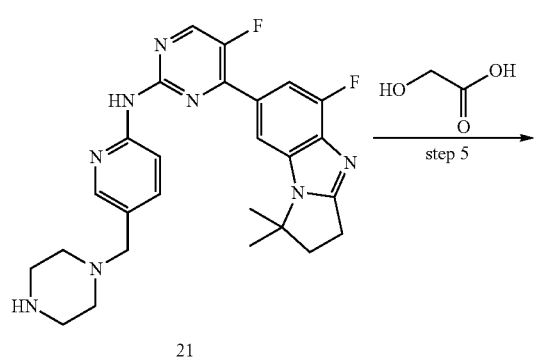

To a mixture of compound 21 (200 mg, 0.38 mmol, 1 eq) and HATU (174 mg, 0.45 mmol, 1.2 eq) in DCM (20 mL) at 0° C. was added glycolic acid (36 mg, 0.45 mmol, 1.2 eq), the reaction mixture was stirred at 0° C. for 30 min, then DIEA (147 mg, 1.14 mmol, 3 eq) was added. The reaction was stirred overnight at 25° C. TLC and LCMS indicated completion; the mixture was cooled to rt and added DCM (20 mL), washed with H$_2$O (15 mL×3), concentrated and purified by pre-HPLC to afford the desired product as a white solid (20 mg). LCMS: (M+H)$^+$: 582.8. $^1$H NMR (300 MHz, DMSO+MeOD): δ 8.71 (s, 1H), 8.38 (d, 1H), 8.34 (s, 2H), 7.85 (t, 3H), 4.20 (s, 2H), 4.14 (s, 2H), 3.32-3.72 (m, 4H), 3.20-3.31 (m, 2H), 3.10-3.25 (m 2H), 2.54 (m, 4H), 1.82 (s, 6H).

Example 3: Synthesis of N-(5-(1-ethylpiperidin-4-yl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine (Compound 29; Comparative Example)

Step 1. Synthesis of Compound 25

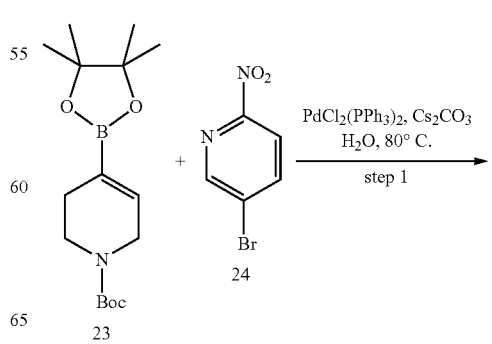

-continued

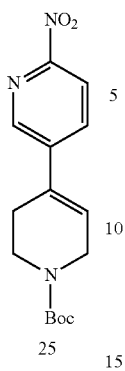

To a mixture of compound 23 (20 g, 98.5 mmol, 1 eq) and 24 (32 g, 103 mmol, 1.05 eq) in dioxane (480 mL) was added $Cs_2CO_3$ (64 g, 196.4 mmol, 2 eq), $H_2O$ (20 mL) under nitrogen. The reaction mixture was evacuated and purged with nitrogen three times, then $PdCl_2(PPh_3)_2$ (7 g, 9.85 mmol, 0.1 eq) was added and purged with nitrogen again. The reaction mixture was stirred at 80° C. overnight. After TLC and LCMS indicated completion; the mixture was cooled to room temperature, $H_2O$ (480 ml) was added and extracted with EA (300 mL×3), the organic layer was washed with NaCl (salt)(200 mL×3), dried over $Na_2SO_4$, concentrated and purified by silica column to give the desired product as a yellow solid (15 g, 76%). LCMS: $(M+H)^+$: 305.9.

$^1$H NMR (300 MHz, $CDCl_3$): δ 8.60 (s, 1H), 8.27 (d, J=8.4 Hz, 1H), 7.98 (d, J=8.7 Hz, 1H), 6.34 (s, 1H), 4.18 (s, 2H), 3.71 (t, J=3.3 Hz, 2H), 2.58 (s, 1H), 1.51 (s, 1H).

Step 2. Synthesis of Compound 26

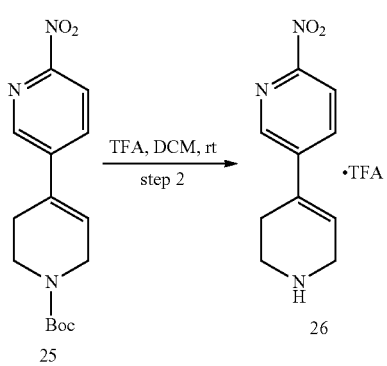 [SMILES: CC(C)(C)OC(=O)N1CC=C(c2ccc([N+](=O)[O-])nc2)CC1 ; O=[N+]([O-])c1ccc(C2=CCNCC2)cn1]

To a solution of compound 25 (2.5 g, 5.17 mmol, 1 eq) in DCM (100 mL) was added $CF_3COOH$ (50 mL). The mixture was stirred at RT for 1 h. After TLC and LCMS indicated completion, the mixture was concentrated and $Et_2O$ (100 mL) was added, the solid was filtered and rinsed with $Et_2O$ (50 mL×3) to give compound 26 as a gray solid (12 g, 57%). LCMS: $(M+H)^+$: 205.9. $^1$H NMR (300 MHz, $CDCl_3$): δ 8.67 (s, 1H), 8.26 (d, J=8.4 Hz, 1H), 7.98 (t, J=1.8 Hz, 1H), 6.42 (s, 1H), 5.31 (s, 2H), 3.94 (m, 2H), 2.69 (s, 2H).

Step 3. Synthesis of Compound 27

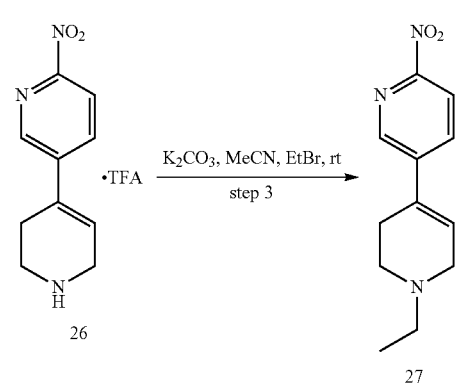 [SMILES: O=[N+]([O-])c1ccc(C2=CCNCC2)cn1 ; CCN1CC=C(c2ccc([N+](=O)[O-])nc2)CC1]

A mixture of compound 26 (20 g, 62.6 mmol, 1 eq) and $K_2CO_3$ (26 g, 188 mmol, 3 eq) in MeCN (200 mL) was stirred at room temperature for 30 min, then bromoethane (10.4 g, 95.4 mmol, 1.5 eq) was added drop wise and the mixture was stirred at rt overnight. TLC and LCMS indicated completion. The mixture was filtered, the filter cake was rinsed with EA (100 mL×2), the filtrate was concentrated to give a crude residue, which was purified by silica gel column to give compound 27 (4 g, 27%). LCMS: $(M+H)^+$: 233.9. $^1$H NMR (300 MHz, $CDCl_3$): δ 8.67 (s, 1H), 8.26 (d, J=8.7 Hz, 1H), 7.99 (d, J=8.7 Hz, 1H), 6.36 (s, 1H), 3.39 (s, 2H), 2.96 (d, J=10.5 Hz, 2H), 2.75 (s, 3H), 1.28 (t, J=6.6 Hz 3H).

Step 4. Synthesis of Compound 28

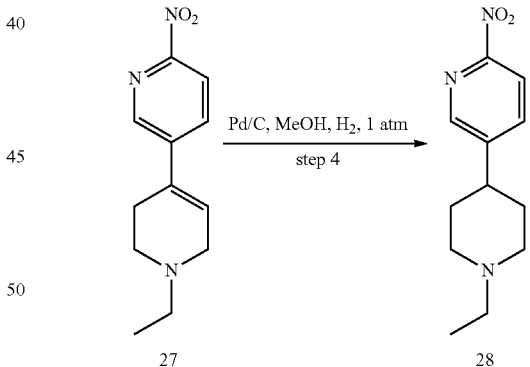

To a solution of 27 (2 g, 9.8 mmol, 1 eq) in MeOH (16 mL) was added 10% palladium on carbon (1.0 g). The mixture was stirred at room temperature with a hydrogen pressure of 0.4 MPa overnight. TLC and LCMS indicated completion. The mixture was filtered, and the filter cake was rinsed with MeOH (10 mL×3), the filtrate was concentrated to give crude compound 28 (1.5 g) which was used directly in the next step without further purification. LCMS: $(M+H)^+$: 206.0. $^1$H NMR (300 MHz, $CDCl_3$): δ 7.95 (s, 1H), 7.36 (d, J=6.3 Hz, 1H), 6.49 (d, J=8.4 Hz, 1H), 4.32 (s, 2H), 3.50 (s, 1H), 3.15 (d, J=11.4 Hz, 2H), 2.30-2.61 (m, 3H), 1.90-2.10 (m, 3H), 1.16 (t, J=6.9 Hz 3H).

Step 5. Synthesis of Compound 29

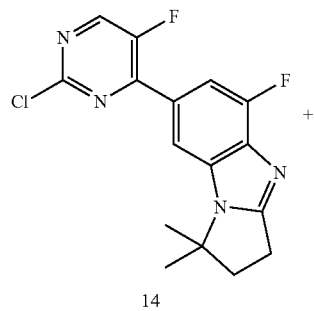

14

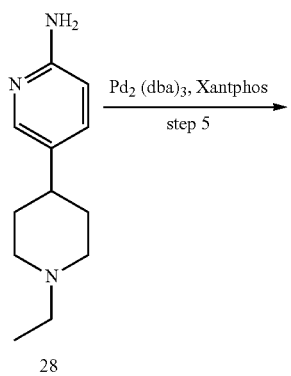

28

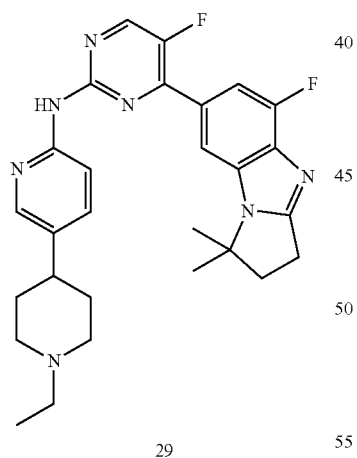

29

To a mixture of compound 28 (65 mg, 0.3 mmol, 1.05 eq) and compound 14 (100 mg, 0.3 mmol, 1 eq) in dioxane (4 mL) were added Pd$_2$(dba)$_3$ (28 mg, 0.03 mmol, 0.1 eq), Xantphos (37 mg, 0.063 mmol, 0.21 eq) and Cs$_2$CO$_3$ (195 mg, 0.6 mmol, 2 eq) under nitrogen. The reaction was purged with nitrogen three times, then stirred at 110° C. for 2 hours. After TLC and LCMS indicated completion; the mixture was cooled to rt and diluted with DCM (10 mL), filtered and the rinsed with DCM (5 mL×3). The filtrate was concentrated in vacuo to give the crude product, which was further purified by pre-HPLC to afford the desired product (14 mg, 9.3%) as an off-white solid. LCMS: (M+H)$^+$: 503.9. $^1$H NMR (300 MHz, CDCl$_3$): δ 8.37-8.33 (m, 3H), 8.18 (s, 1H), 8.04 (s, 1H), 7.75 (d, J=11.7 Hz, 1H), 7.56 (d, J=8.7 Hz, 1H), 3.09 (t, J=6.9 Hz, 4H), 2.56-2.49 (m, 5H), 2.08-1.93 (m, 2H), 1.92-1.84 (m, 4H), 1.66 (s, 6H), 1.18-1.05 (m, 3H).

Example 4: Synthesis of N-(5-(1-ethylpiperidin-4-yl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine (Compound 35; Comparative Example)

Step 1. Synthesis of Compound 31

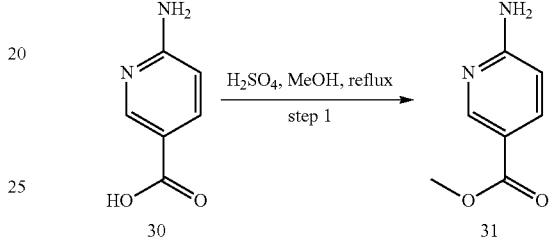

To a solution of compound 30 (10 g, 72.3 mmol) in MeOH (200 mL) was added sulfuric acid (5 mL). The mixture was heated to reflux and stirred overnight. TLC and LC-MS indicated the starting material was disappeared. After cooled to room temperature, solvent was removed in vacuo to give a crude residue, which was neutralized by adding sat.NaHCO$_3$ to pH=7. The precipitates were filtered, rinsed with 1-120 and dried to give a white solid (7 g, 64%) which was used directly in the next step without further purification. LCMS: (M+H)$^+$: 153.0. $^1$H NMR (300 MHz. CDCl$_3$): δ 8.69 (br, 1H), 8.03 (d J:=9.0 Hz, 1H), 6.53 (d, J=9.0 Hz, 1H), 5.20 (br, 2H) 387 (s, 3H).

Step 2. Synthesis of Compound 32

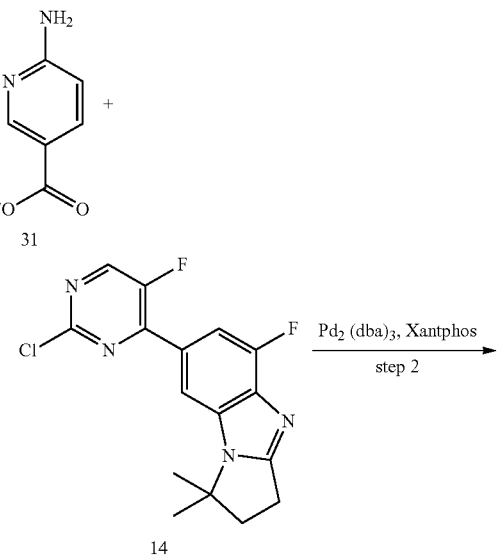

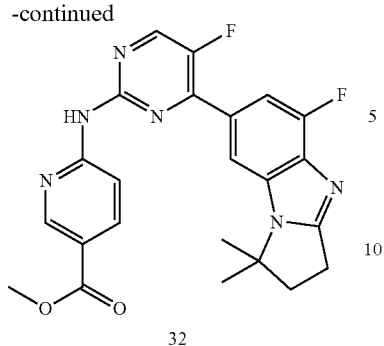

32

Nitrogen was bubbled into a solution of compound 31 (96 mg, 0.63 mmol, 1.05 eq), compound 14 (200 mg, 0.6 mmol, 1 eq; see Example 1), Pd₂(dba)₃ (55 mg, 0.06 mmol, 0.1 eq), Xantphos (73 mg, 0.013 mmol, 0.21 eq) and Cs₂CO₃ (389 mg, 1.2 mmol, 2 eq) in dioxane (8 mL) for 5 min. The mixture was stirred at 110° C. for 2 h. After completion, the mixture was cooled down to rt, the mixture was diluted with DCM (10 mL) and filtered through Celite, rinsed with DCM (10 mL×3). The combined organic layers were dried over sodium sulfate, concentrated and rinsed with CH₃CN (2 mL×2) to give a white solid (70 mg, 26%). LCMS: (M+H)⁺: 450.8. ¹H NMR (300 MHz, CDCl₃): δ 8.99 (s, 1H), 8.89 (s, 1H), 8.57-8.52 (m, 2H), 8.34 (d, J=8.1 Hz, 1H), 8.12 (s, 1H), 7.83 (s, J=11.4 Hz, 1H), 3.94 (s, 3H), 3.19 (t, J=7.5 Hz, 2H), 2.63 (t, J=7.5 Hz, 2H) 1.79 (s, 6H).

Step 3. Synthesis of Compound 33

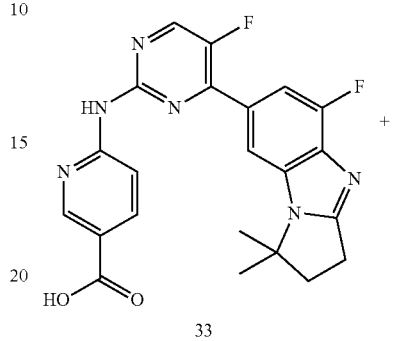

To a solution of compound 32 (200 mg, 0.45 mmol, 1 eq) in MeOH (2 mL) and H₂O (2 mL) was added KOH (50 mg, 0.9 mmol, 2 eq). The mixture was stirred at RT for 1 h. After TLC and LCMS indicated completion, MeOH was removed under reduced pressure. The residue was adjusted to pH=1-2 with 1 N. HCl, the resulting solid was filtered, rinsed with H₂O, and dried to give a white solid (150 mg, 77%), which was used directly in next step without further purification. LCMS: (M+H)⁺: 436.9.

Step 4. Synthesis of Compound 35

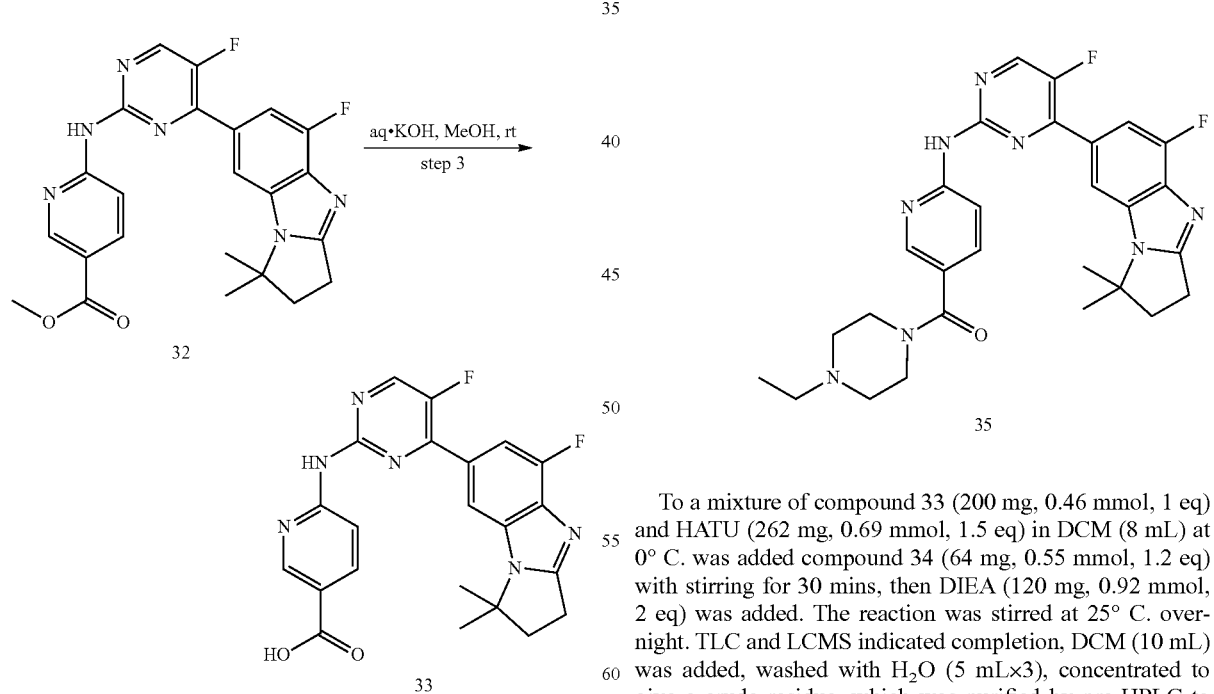

To a mixture of compound 33 (200 mg, 0.46 mmol, 1 eq) and HATU (262 mg, 0.69 mmol, 1.5 eq) in DCM (8 mL) at 0° C. was added compound 34 (64 mg, 0.55 mmol, 1.2 eq) with stirring for 30 mins, then DIEA (120 mg, 0.92 mmol, 2 eq) was added. The reaction was stirred at 25° C. overnight. TLC and LCMS indicated completion, DCM (10 mL) was added, washed with H₂O (5 mL×3), concentrated to give a crude residue, which was purified by pre-HPLC to afford the desired product as a white solid (27 mg, 11%). LCMS: (M+H)⁺:530.8. ¹H NMR (300 MHz, CDCl₃): δ 8.54-8.48 (m, 4H), 8.10 (s, 1H), 7.84-7.80 (m, 2H), 3.97-3.92 (m, 4H), 3.18 (t, J=7.2 Hz, 2H), 3.02 (d, J=4.5 Hz, 1H), 2.77-2.70 (m, 3H), 2.62 (q, J=8.4 Hz, 2H), 1.75 (s, 6H), 1.67-1.65 (m, 2H), 1.27 (t, J=8.4 Hz, 3H).

Example 5: Synthesis of 1-(2-(5-fluoro-4-(5-fluoro-1,1-dimethyl-2,3-dihydro-1H-benzo[d]pyrrolo[1,2-a]imidazol-7-yl)pyrimidin-2-ylamino)-7,8-dihydro-1,6-naphthyridin-6 (5H)-yl)-2-hydroxyethanone (Compound 43; Comparative Example)

Step 1. Synthesis of Compound 37

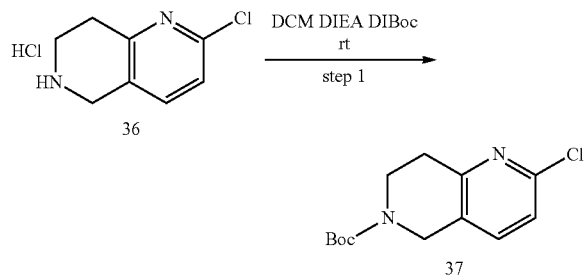

To a solution of compound 36 (5 g, 24.4 mmol, 1 eq) in DCM (40 mL) was added DIEA (9.45 g, 73.1 mmol, 3 eq) and stirred for 20 mins, Boc$_2$O (6.5 g, 29.3 mmol, 1.2 eq) in DCM (30 mL) was added drop wise and then stirred for 1 h. After LCMS and TLC indicated completion, the mixture was concentrated and the residue was dissolved in EA (200 mL), washed with water (100 mL×3) and brine (100 mL), dried over sodium sulfate, concentrated and purified by silica column to give the desired product as white solid (6 g, 92%). $^1$H NMR (300 MHz, CDCl$_3$-d$_6$): δ 7.39 (d, J=8.1 Hz, 1H), 7.18 (d, J=8.1 Hz, 1H), 4.57 (s, 2H), 3.74 (t, J=6.0 Hz, 2H), 2.98 (t, J=5.4 Hz 2H), 1.53 (s, 9H). LCMS: (M+H)$^+$: 268.9.

Step 2. Synthesis of Compound 39

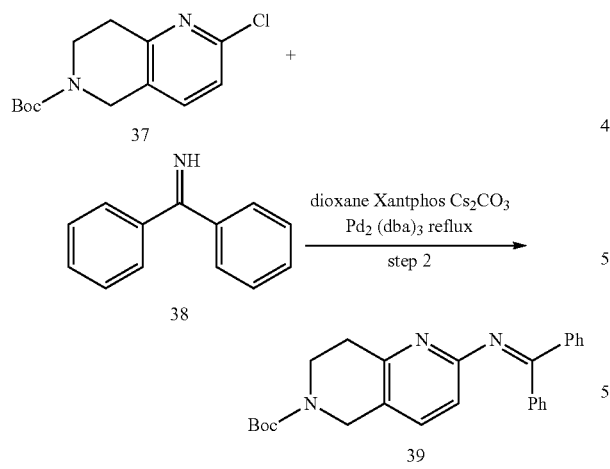

Nitrogen was bubbled into a solution of compound 37 (1.0 g, 3.7 mmol, 1.0 eq), compound 38 (742 mg, 4.1 mmol, 1.1 eq), Pd$_2$(dba)$_3$ (340 mg, 0.37 mmol, 0.1 eq), Xantphos (454 mg, 0.78 mmol, 0.21 eq) and Cs$_2$CO$_3$ (2.4 g, 7.4 mmol, 2 eq) in dioxane (20 mL) for 5 mins. The mixture was stirred at 110° C. for 3 h. After completion, the mixture was cooled down to RT, diluted with DCM (50 mL) and filtered through a pad of Celite, rinsed with DCM (20 mL). The filtrate was dried over sodium sulfate, concentrated and purified by silica column to give the desired product as a yellow solid (0.5 g, 33%). $^1$H NMR (300 MHz, CDCl$_3$): δ 7.36-7.25 (m, 10H), 7.17 (d, J=8.1 Hz, 1H), 6.35 (d, J=8.4 Hz, 1H), 4.48 (s, 2H), 3.70 (t, J=6.0 Hz, 2H), 2.92 (s, J=6.0 Hz, 2H), 1.50 (s, 9H). LCMS: (M+H)$^+$:413.9.

Step 3. Synthesis of Compound 40

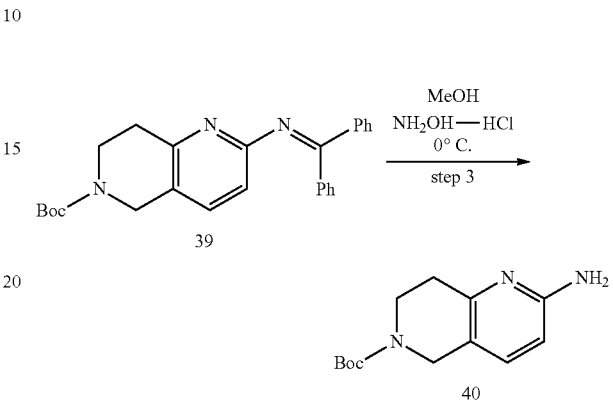

To a solution of compound 39 (1.2 g, 2.9 mmol, 1.0 eq) in MeOH (30 mL) at 0° C. was added Hydroxylamine hydrochloride (0.41 g, 5.8 mmol, 2.0 eq) portion wise. After addition, the mixture was stirred at 0° C. for 30 min. After TLC and LC-MS indicated no starting material, the mixture was concentrated, the resulting residue was diluted with DCM (50 mL) and water (25 mL), separated and extracted with DCM (20 mL×3), dried over sodium sulfate, concentrated and purified by silica column to give the desired product as a yellow solid (0.25 g, 35%). $^1$H NMR (300 MHz, CDCl$_3$): δ 8.25 (d, J=8.1 Hz, 1H), 7.56 (d, J=8.1 Hz, 1H), 4.66 (s, 2H), 3.80 (t, J=5.4 Hz, 1H), 3.12 (t, J=5.4 Hz, 2H), 1.52 (s, 9H). LCMS: (M+H)$^+$: 250.1

Step 4. Synthesis of Compound 41

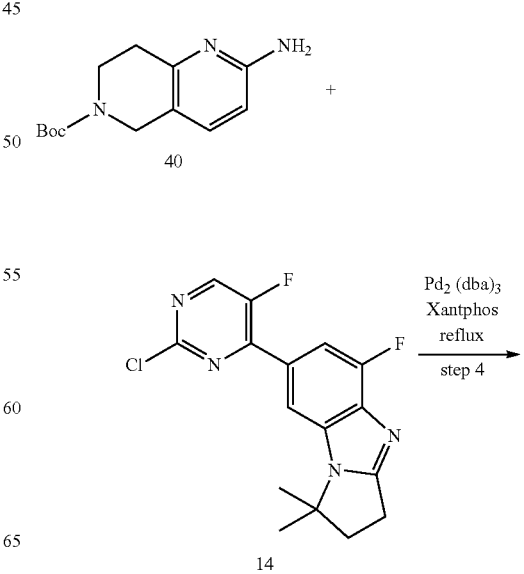

-continued

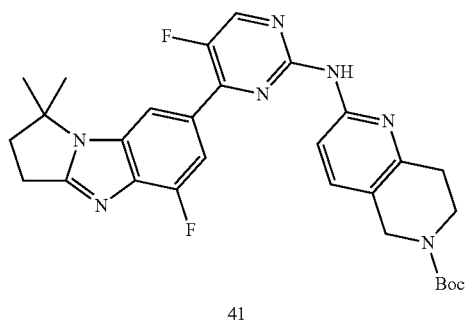

41

To a mixture of compound 40 (150 mg, 0.60 mmol, 1.0 eq) and compound 14 (201 mg, 0.60 mmol, 1.0 eq; see Example 1) in dioxane (7.5 mL) were added Pd$_2$(dba)$_3$ (57 mg, 0.06 mmol, 0.1 eq), Xantphos (75 mg, 0.12 mmol, 0.021 eq) and Cs$_2$CO$_3$ (393 mg, 1.20 mmol, 2.0 eq) under nitrogen. The reaction was purged with nitrogen three times, then stirred at 110° C. for 12 hours. After TLC and LCMS indicated completion, the mixture was cooled to rt and diluted with DCM (20 mL), filtered and the solid was rinsed with DCM (10 mL×3). The filtrate was concentrated and the crude was washed with acetonitrile (2.5 mL×2) and dried to get a gray solid (150 mg, 46%) which was used in the next step without purification. LCMS: (M+H)+: 548.2.

Step 5. Synthesis of Compound 42

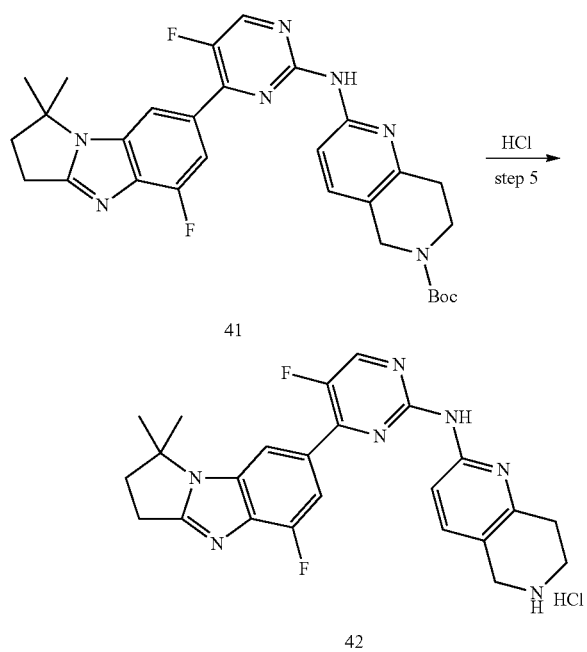

A solution of compound 41 (150 mg, 0.27 mmol, 1.0 eq) in 4 N HCl/dioxane (3 mL) was stirred at room temperature for 1 h. TLC and LCMS indicated completion, the mixture was concentrated to get the crude compound 42 as an yellow solid (120 mg, crude), which was used directly in the next step without purification. LCMS: (M+H)+: 448.2.

Step 6. Synthesis of Compound 43

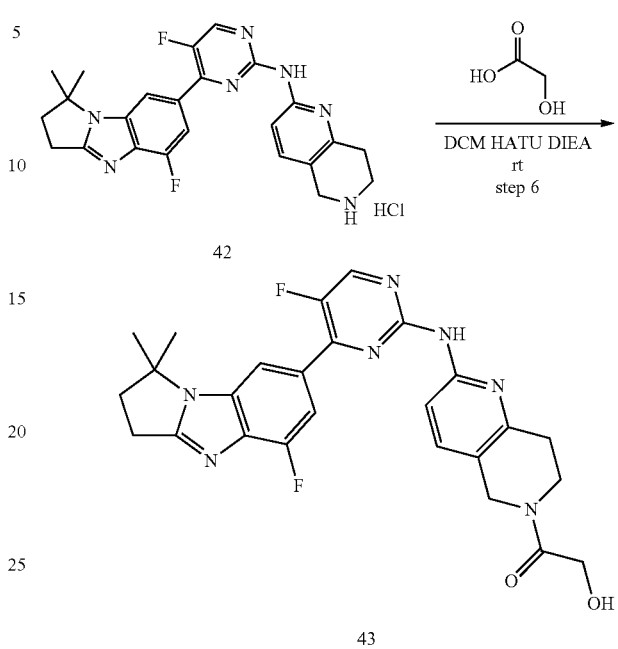

To a mixture of compound 42 (120 mg, 0.25 mmol, 1 eq) in DCM (12 mL) at 0° C. was added HATU (113 mg, 0.30 mmol, 1.2 eq) and glycolic acid (23 mg, 0.30 mmol, 1.2 eq), stirred at 0° C. for 30 mins, then DIEA (96 mg, 0.75 mmol, 3.0 eq) was added. The reaction mixture was warmed to room temperature and stirred overnight. After TLC and LCMS indicated completion, DCM (20 mL) was added, washed with H$_2$O (15 mL×3), concentrated to give a crude residue and purified by pre-HPLC affording desired product (20 mg, 16%). $^1$H NMR (300 MHz, DMSO): δ 10.07 (s, 1H), 8.69 (s, 1H), 8.23 (s, 1H), 8.14-8.13 (m, 1H), 7.72 (d, J=11.4 Hz, 1H), 7.60-7.58 (m, 1H), 4.70-4.56 (m, 3H), 4.22-4.20 (m, 2H), 3.83-3.69 (m, 2H), 3.11-3.09 (m, 2H), 2.89-2.81 (m, 2H), 2.64-2.55 (m, 2H), 1.68 (s, 6H). LCMS: (M+H)$^+$: 507.1.

Example 6: Synthesis of (S)-(3-(dimethylamino)pyrrolidin-1-yl)(6-(5-fluoro-4-(5-fluoro-1,1-dimethyl-2,3-dihydro-1H-benzo[d]pyrrolo[1,2-a]imidazol-7-yl)pyrimidin-2-ylamino)pyridin-3-yl)methanone (Compound 45)

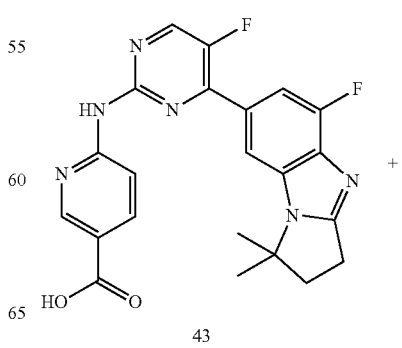

-continued

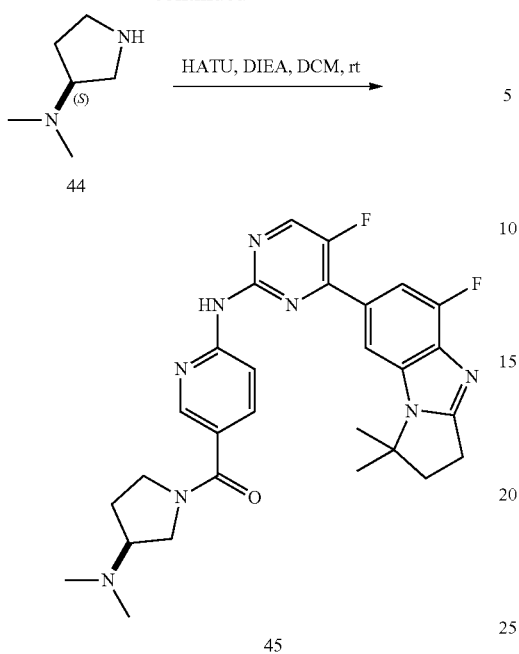

To a mixture of compound 43 (200 mg, 0.46 mmol, 1 eq) and HATU (262 mg, 0.69 mmol, 1.5 eq) in DCM (8 mL) at 0° C. was added compound 44 (64 mg, 0.55 mmol, 1.2 eq) with stirring for 30 min, then DIEA (120 mg, 0.92 mmol, 2 eq) was added. The reaction was stirred overnight at 25° C. TLC and LCMS indicated completion; the mixture was cooled to RT and diluted with DCM (10 mL), washed with H$_2$O (5 mL×3), concentrated and purified by pre-HPLC to afford the desired product as a white solid (17 mg, 7%). LCMS: (M+H)$^+$: 533.8. $^1$H NMR (300 MHz, CDCl$_3$): δ 9.06 (d, J=16.2 Hz 1H), 8.66 (s, 1H), 8.54-8.51 (m, 2H), 8.10 (s, 1H), 7.95 (d, J=8.7 Hz 1H), 7.80 (d, J=12.0 Hz, 1H), 3.94-3.71 (m, 3H), 3.64 (m, 2H), 3.17 (t, J=7.2 Hz 2H), 2.98 (m, 1H), 2.61 (t, J=7.5 Hz, 2H), 2.34 (s, 3H), 2.25 (s, 3H), 1.84-1.73 (m, 1H), 1.26 (s, 6H).

Example 7: Synthesis of (S)—N-(5-(3-(dimethylamino)pyrrolidin-1-yl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine (Compound 49)

Step 1. Synthesis of Compound 47

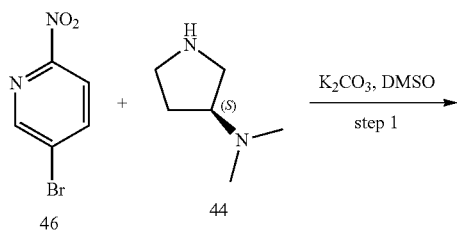

-continued

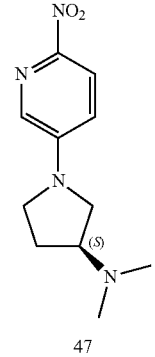

To a solution of compound 46 (1 g, 5.0 mmol, 1 eq) in DMSO (5 mL) was added K$_2$CO$_3$ (1.35 g, 10.0 mmol, 2 eq), (S)—N,N-dimethylpyrrolidin-3-amine (0.85 g, 7.5 mmol, 1.5 eq) and TBAI (0.018 g, 0.05 mmol, 0.01 eq) successively. The mixture was stirred at 120° C. for 2 h. After cooling down to RT, the mixture was diluted with water (30 mL) and filtered, the solid was rinsed with water (5 mL×3), dried to afford the desired product (0.9 g, 78%), which was used to the next step directly. $^1$H NMR (300 MHz, DMSO-d$_6$): δ 8.16 (d, J=9.0 Hz, 1H), 7.88 (s, 1H), 7.07 (dd, J=12.0 Hz, 3.0 Hz, 1H), 3.69-3.57 (m, 2H), 3.22-3.16 (m, 1H), 2.85-2.80 (m, 1H), 2.21 (s, 6H), 1.87-1.81 (m, 1H).

Step 2. Synthesis of Compound 48

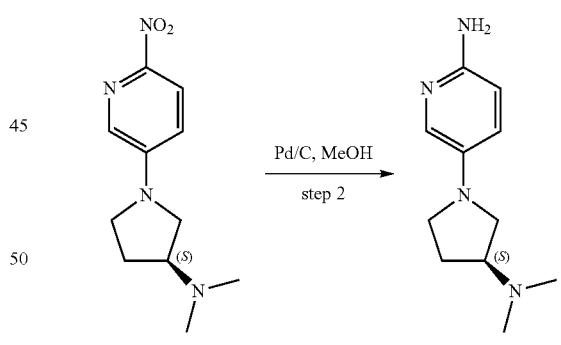

To a solution of compound 47 (0.9 g, 3.8 mmol) in MeOH (10 mL) was added Pd/C (0.5 g). The mixture was stirred under H$_2$ atmosphere overnight. After LCMS indicated completion, the mixture was filtered, rinsed with MeOH. The filtrate was concentrated to afford the crude product (0.4 g, crude) which was used in next step directly. LCMS: (M+H)$^+$: 207.0.

$^1$H NMR (300 MHz, CDCl$_3$): δ 7.49 (s, 1H), 6.87-6.84 (m, 1H), 6.52 (d, J=8.4 Hz, 1H), 4.06 (br, 2H), 3.44-3.29 (m, 3H), 3.26-3.09 (m, 1H), 2.94-2.84 (m, 1H), 2.33 (s, 6H), 2.25-2.20 (m, 2H).

Step 3. Synthesis of Compound 49

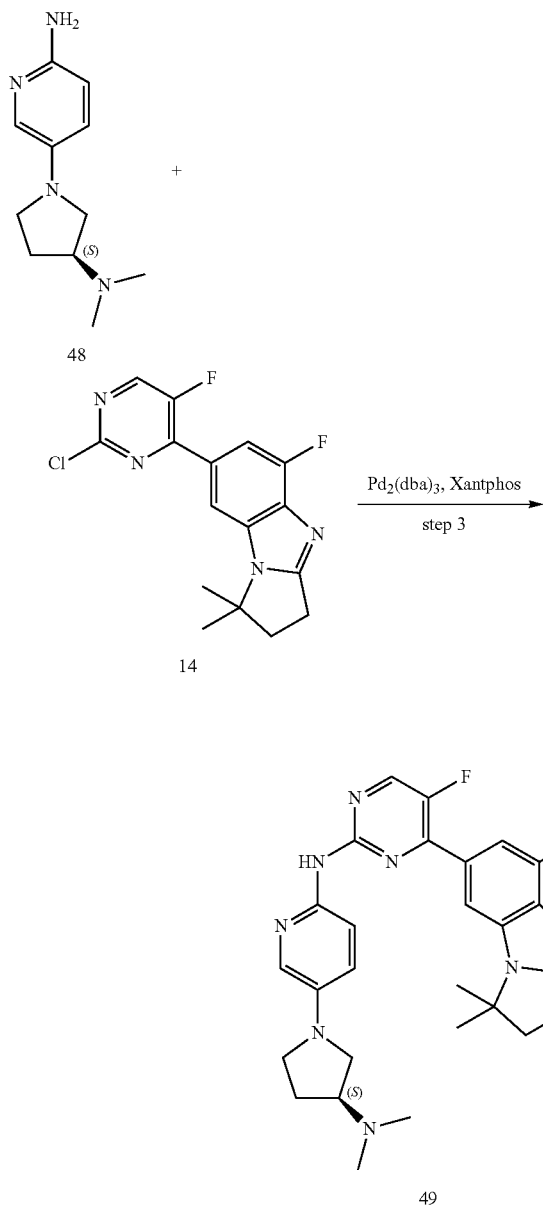

Nitrogen was bubbled into a solution of compound 48 (65 mg, 0.31 mmol, 1.05 eq), compound 14 (100 mg, 0.3 mmol, 1 eq), Pd$_2$(dba)$_3$ (27 mg, 0.03 mmol, 0.1 eq), Xantphos (36.3 mg, 0.063 mmol, 0.21 eq) and Cs$_2$CO$_3$ (195 mg, 0.6 mmol, 2 eq) in dioxane (4 mL) for 5 min. The mixture was stirred at 110° C. for 2 h. After completion, the mixture was cooled down to rt, diluted with DCM (10 mL) and filtered through a pad of Celite, rinsed with DCM (10 mL). The filtrate was dried over sodium sulfate, concentrated and purified by silica gel chromatography to give the desired product (46 mg, 31%). $^1$H NMR (300 MHz, CDCl$_3$): δ 8.37 (d, J=3.6 Hz, 1H), 8.21 (d, J=9.3 Hz, 1H), 8.09 (s, 1H), 7.85-7.82 (m, 2H), 7.72 (s, 1H), 6.99 (d, J=6.0 Hz, 1H), 3.72-3.32 (m, 3H), 3.24-3.14 (m, 3H), 2.95-2.93 (m, 1H), 2.63-2.58 (t, J=7.5 Hz, 2H), 2.37 (s, 6H), 2.35-2.26 (m, 1H), 2.03-1.97 (m, 1H), 1.74 (s, 6H). LCMS: (M+H)$^+$=504.9. HPLC: 97.4%.

Example 8: Synthesis of N-(5-((1-ethylpiperidin-4-yl)methoxy)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine (Compound 57)

Step 1. Synthesis of Compound 51

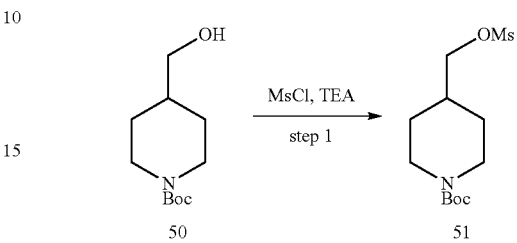

To a solution of compound 50 (20 g, 93 mmol, 1 eq) and TEA (18.8 g, 186 mmol, 2 eq) in THF (320 mL) were added MsCl (12.8 g, 111 mmol, 1.2 eq) drop wise. The mixture was stirred for 30 min after addition. After TLC indicated completion, the reaction was diluted with water (320 mL), extracted with EtOAc (200 mL×3), the combined organic layers were washed with brine, dried over sodium sulfate, concentrated to get the desired (24 g, 89%), which was used in next step directly. $^1$H NMR (300 MHz, CDCl$_3$): δ 4.14-4.12 (m, 2H), 4.08 (d, J=6.3 Hz, 2H), 3.03 (s, 3H), 2.72 (t, J=12.6 Hz, 2H), 1.98-1.90 (m, 1H), 1.78-1.74 (m, 2H), 1.47 (s, 9H), 1.29-1.20 (m, 2H).

Step 2. Synthesis of Compound 53

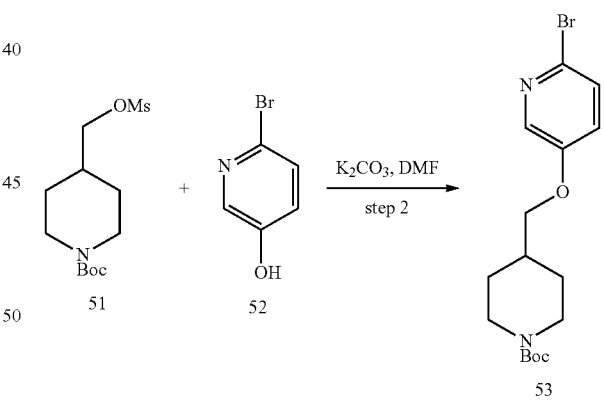

To a solution of compound 52 (12 g, 69 mmol, 1 eq) in DMF (200 mL) was added K$_2$CO$_3$ (19.2 g, 138 mmol, 2 eq) and compound 51 (24 g, 83 mmol, 1.2 eq). The mixture was stirred at 65° C. overnight. After TLC showed completion, cooling down to RT, diluted with water (600 mL) and filtered. The solid was washed with water (100 mL×3), dried to afford the desired product (12 g, 47%) which was used in next step directly. H NMR (300 MHz, CDCl$_3$): δ 8.05 (d, J=2.7 Hz, 1H), 7.39 (d, J=8.7 Hz, 1H), 7.11 (m, 1H), 4.17 (br, 2H), 3.84 (d, J=6.3 Hz, 1H), 2.79 (t, J=12.6 Hz, 2H), 1.98-1.90 (m, 1H), 1.84-1.80 (m, 2H), 1.47 (s, 9H), 1.25-1.35 (m, 2H). LCMS: (M+H)$^+$=314.8.

Step 3. Synthesis of Compound 54

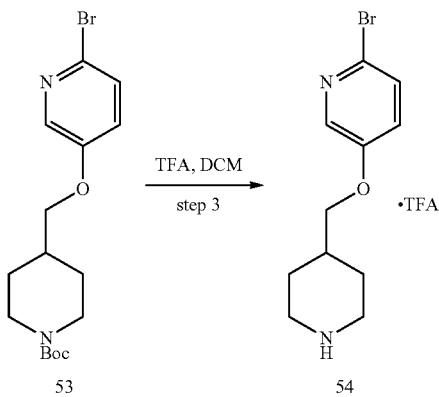 [SMILES: CC(C)(C)OC(=O)N1CCC(COc2ccc(Br)nc2)CC1 ; Brc1ccc(OCC2CCNCC2)cn1]

To a solution of compound 53 (12 g, 3.2 mmol) in DCM (60 mL) was added TFA (30 mL). The mixture was stirred at rt for 1 h. After TLC and LCMS indicated completion, the mixture was concentrated to dryness, and then Et$_2$O (50 mL) was added. The precipitate was filtered and rinsed with Et$_2$O (25 mL×3) to give a gray solid (10 g, 80%). LCMS: (M+H)$^+$=272.8.

Step 4. Synthesis of Compound 55

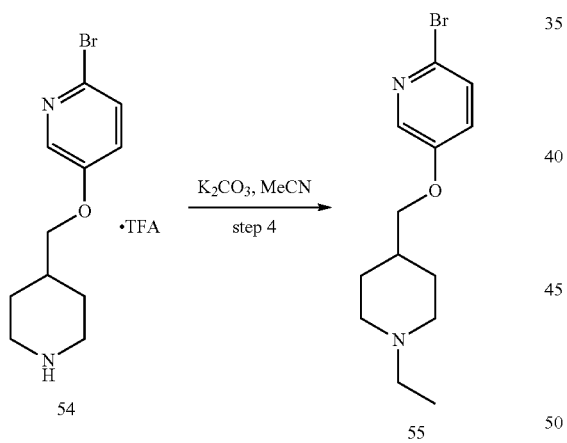

To a solution of 54 (5 g, 13 mmol, 1 eq) in MeCN (50 mL) were added K$_2$CO$_3$ (5.5 g, 39 mmol, 3 eq). The mixture was stirred at rt for 30 min, and then bromoethane (2.15 g, 19 mmol, 1.5 eq) was added drop wise and stirred overnight at rt. After TLC and LCMS indicated completion, the mixture was filtered, and the filter cake was rinsed with EtOAc (50 mL×2). The filtrate was concentrated to dryness, diluted with PE (50 mL×3) and filtered. The filtrate was concentrated to give a yellow solid (2.5 g, 64%). $^1$H NMR (300 MHz, CDCl$_3$): δ 8.05 (d, J=2.7 Hz, 1H), 7.38 (d, J=8.7 Hz, 1H), 7.10 (q, J=3.0 Hz, 8.7 Hz, 1H), 3.85 (d, J=5.7 Hz, 2H), 3.10 (d, J=12 Hz, 2H), 2.46-2.54 (m, 2H), 2.07 (t, J=11.7 Hz, 2H), 1.85-1.99 (m, 3H), 1.45-1.629 (m, 2H), 1.15 (t, J=7.2 Hz, 3H). LCMS: (M+H)$^+$=300.8.

Step 5. Synthesis of Compound 56

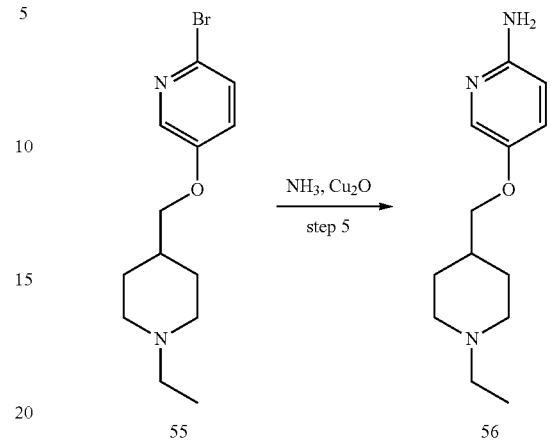

To a solution compound 55 (5 g, 16.7 mmol, 1 eq) and Cu$_2$O (240 mg, 1.67 mmol, 0.1 eq) in DMSO (50 mL) was purged with NH$_3$ (gas) for 10 min. The mixture was stirred in a sealed tube at 80° C. overnight. After completion, the mixture was adjusted with 2 N. NaOH to pH=12, extracted with DCM (100 mL×5). The combined organic layers were dried, concentrated to give a crude residue, which was rinsed with hexane (20 mL) to give a white solid (2.5 g, 64%). LCMS: (M+H)$^+$=236.0.

Step 6. Synthesis of Compound 57

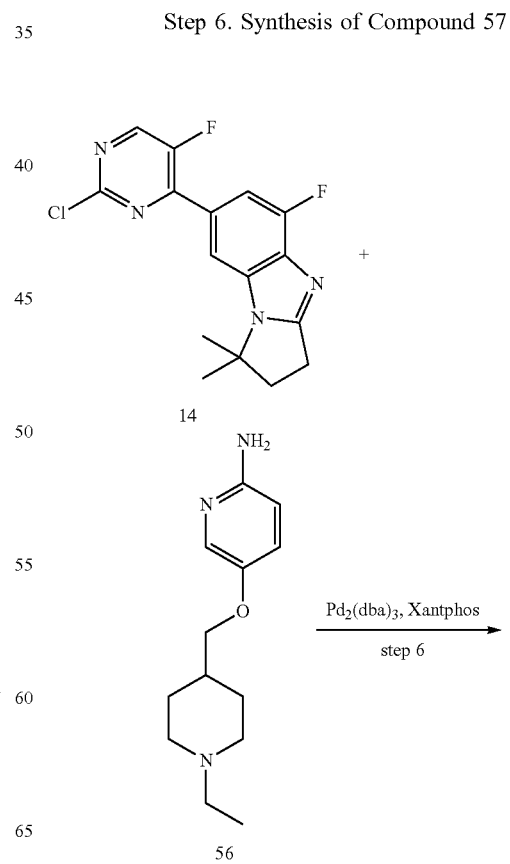

-continued

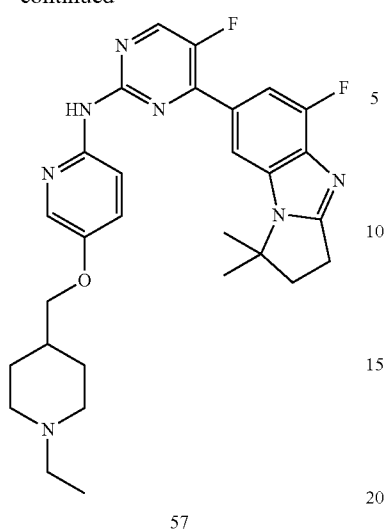

57

A mixture of compound 56 (74 mg, 0.315 mmol, 1.05 eq), compound 14 (100 mg, 0.3 mmol, 1 eq; see Example 1) and Cs$_2$CO$_3$ (195 mg, 0.6 mmol, 2 eq) in dioxane (4 mL) was bubbled with nitrogen for 5 min. Pd$_2$(dba)$_3$ (28 mg, 0.03 mmol, 0.1 eq), Xantphos (37 mg, 0.063 mmol, 0.21 eq) were then added and the mixture was bubbled with nitrogen for 5 min again. The mixture was stirred at 110° C. under nitrogen atmosphere for 2 h. After TLC and LCMS indicated completion, the mixture was cooled to RT and diluted with DCM (20 mL). Filtered and the solid was rinsed with DCM (10 mL×3). The filtrate was concentrated and purified by pre-HPLC to give the desired product as a white solid (17 mg, 10.6%). $^1$H NMR (300 MHz, CDCl$_3$): δ 8.42 (d, J=3.3 Hz, 1H), 8.35 (d, J=8.4 Hz, 1H), 8.21 (s, 1H), 8.09 (s, 1H), 8.05 (s, 1H), 7.83 (d, J=11.4 Hz, 1H), 7.27 (s, 1H), 3.87 (d, J=5.1 Hz, 2H), 3.19 (q, J=7.8 Hz, 4H), 2.63-2.51 (m, 4H), 2.06-2.03 (m, 2H), 1.93-1.89 (m, 3H), 1.73 (s, 6H), 1.58-1.54 (m, 2H), 1.18 (t, J=7.2 Hz, 3H). LCMS: (M+H)$^+$=533.8.

Example 9: Synthesis of N-(5-((1-ethylpiperidin-4-yl)methoxy)pyridin-2-yl)-5-fluoro-4-(5-fluoro-1,1-dimethyl-2,3-dihydro-1H-benzo[d]pyrrolo[1,2-a]imidazol-7-yl)pyridin-2-amine (Compound 60)

Step 1. Synthesis of Compound 59

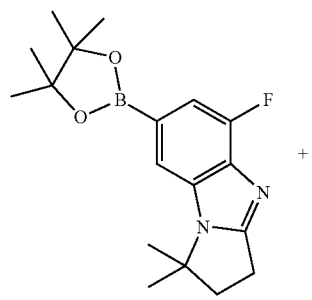

12

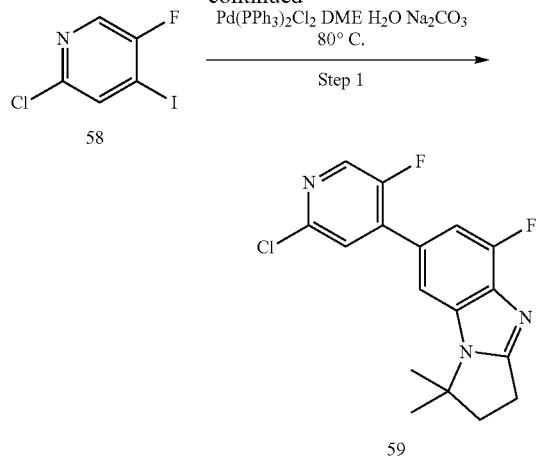

Pd(PPh$_3$)$_2$C$_2$ (430 mg, 0.6 mmol, 0.1 eq) was added to a degassed mixture of compound 12 (2 g, 6.1 mmol, 1.0 eq; see Example 1), compound 58 (1.72 g, 6.7 mmol, 1.1 eq) and Na$_2$CO$_3$ (2.12 g, 20 mmol) in DME (20 mL) and water (10 mL) under nitrogen protection. The mixture was stirred at 80° C. for 1 h. After completion, the mixture was cooled down to rt, diluted with EtOAc (50 mL) and filtered through a pad of Celite, rinsed with EtOAc (20 mL). The filtrate was dried over sodium sulfate, concentrated and purified by silica column to give the desired product as a yellow solid (1.5 g, 75%). $^1$H NMR (300 MHz, CDCl$_3$): δ 8.54 (d, J=3.3 Hz, 1H), 8.10 (s, 1H), 7.88 (s, d, J=12.6 Hz 1H), 7.10-7.20 (m, 1H), 3.25 (t, J=7.2 Hz, 2H), 2.63 (d, J=6.6 Hz, 2H), 1.75 (s, 6H). LCMS: (M+H)$^+$=333.8.

Step 2. Synthesis of Compound 60

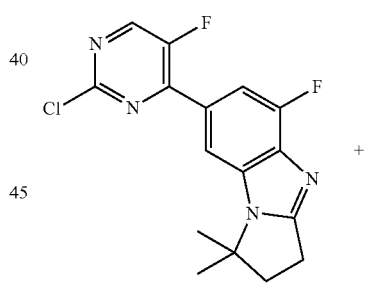

59

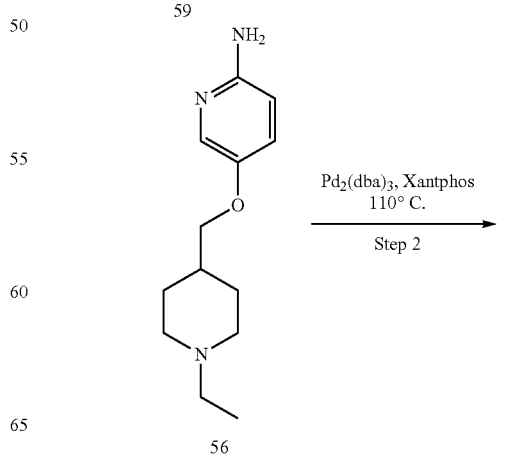

56

-continued

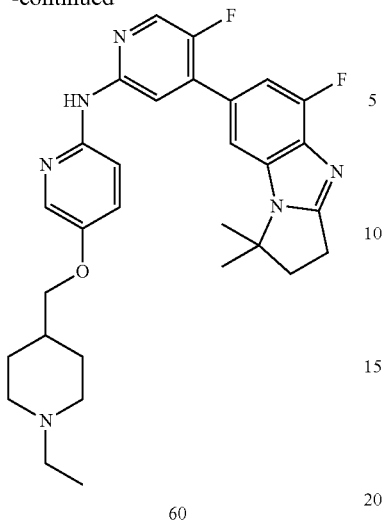

60

To a mixture of compound 59 (500 mg, 1.5 mmol, 1 eq) and compound 56 (370 mg, 1.57 mmol, 1.05 eq) in dioxane (20 mL) was added Pd$_2$(dba)$_3$ (140 mg, 0.15 mmol, 0.1 eq), Xantphos (185 mg, 0.3 mmol, 0.21 eq) and Cs$_2$CO$_3$ (975 mg, 3.0 mmol, 2 eq) under nitrogen. The reaction was stirred at 110° C. under nitrogen atmosphere for 2 hours. After TLC and LCMS indicated completion, the mixture was cooled to RT and diluted with DCM (20 mL), filtered and the solid rinsed with DCM (10 mL×3). The filtrate was concentrated and purified by pre-HPLC to give desired product as a white solid (50 mg, 6.3%). $^1$H NMR (300 MHz, CDCl$_3$): δ 8.17 (s, 1H), 7.95 (s, 1H), 7.70 (s, d, J=5.7 Hz, 1H), 7.49 (s, 1H), 7.41 (s, 1H), 7.39-7.37 (m, 1H), 7.24-7.20 (m, 3H), 3.86-3.84 (m, 2H), 3.18-3.13 (m, 4H), 2.63-2.61 (m, 4H), 2.17-2.14 (m, 2H), 1.95-1.91 (m, 4H), 1.70 (s, 6H), 1.63-1.62 (m, 1H), 1.24 (t, J=6.6 Hz, 3H). LCMS: (M+H)$^+$=532.8.

Example 10: Synthesis of 5-fluoro-4-(5-fluoro-1,1-dimethyl-2,3-dihydro-1H-benzo[d]pyrrolo[1,2-a]imidazol-7-yl)-N-(5-(1-methylpiperidin-4-yloxy)pyridin-2-yl)pyrimidin-2-amine (Compound 65)

Step 1. Synthesis of Compound 63

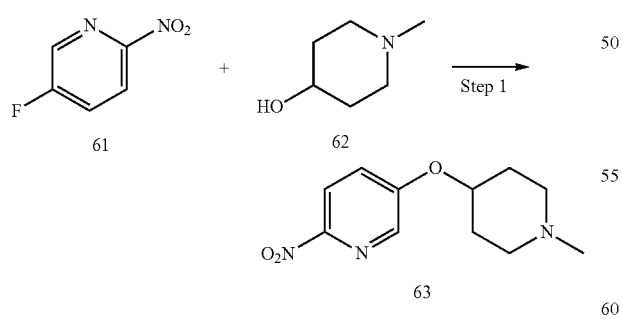

To a solution of compound 62 (486 mg, 4.2 mmol, 1.2 eq) in dimethylacetamide (5 mL) at 0° C. under nitrogen was added potassium tert-butoxide (513 mg, 4.6 mmol, 1.3 eq) portion wise, and then the mixture was stirred at 0° C. for 1 h. A solution of compound 61 (500 mg, 3.5 mmol, 1.0 eq) in DMA (2 mL) was added drop wise. After addition, the mixture was stirred at RT overnight. The reaction was quenched by water (15 mL) and extracted with EA (5 mL×3), dried over Na$_2$SO$_4$, filtered and concentrated to give a crude residue (700 mg), which was used onto next step without further purification. $^1$H NMR (300 MHz, CDCl$_3$, contains DMA): δ 8.28-8.22 (m, 2H), 7.41-7.37 (m, 1H), 4.55-4.51 (m, 1H), 2.72-2.70 (m, 2H), 2.41-2.38 (m, 2H), 2.35 (s, 3H), 2.13-2.09 (m, 2H), 1.98-1.92 (m, 2H). LCMS: (M+H)$^+$=238.1.

Step 2. Synthesis of Compound 64

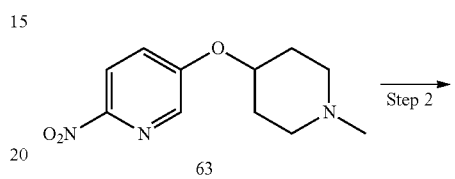

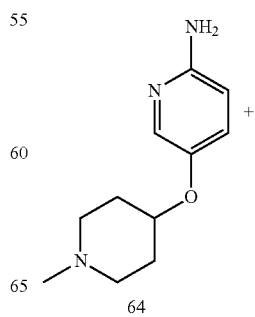

To a solution of compound 63 (700 mg, 2.95 mmol) in MeOH (7 mL) was added Pd/C (200 mg). The mixture was stirred under H$_2$ atmosphere overnight. After LCMS indicated completion, the mixture was filtered, rinsed with MeOH. The filtrate was concentrated to afford the crude product (600 mg, crude) which was used in next step directly. $^1$H NMR (300 MHz, CDCl$_3$, contains DMA): δ 7.80 (d, J=2.7 Hz, 1H), 7.11 (dd, J=3.0 Hz, 9.0 Hz, 1H), 6.48 (d, J=8.7 Hz 1H), 4.22-4.15 (br, 2H), 4.13-4.11 (m, 1H), 2.76-2.71 (m, 2H), 2.37 (s, 3H), 2.36-2.34 (m, 2H), 2.01-1.98 (m, 2H), 1.87-1.82 (m, 2H). LCMS: (M+H)$^+$=208.2.

Step 3. Synthesis of Compound 65

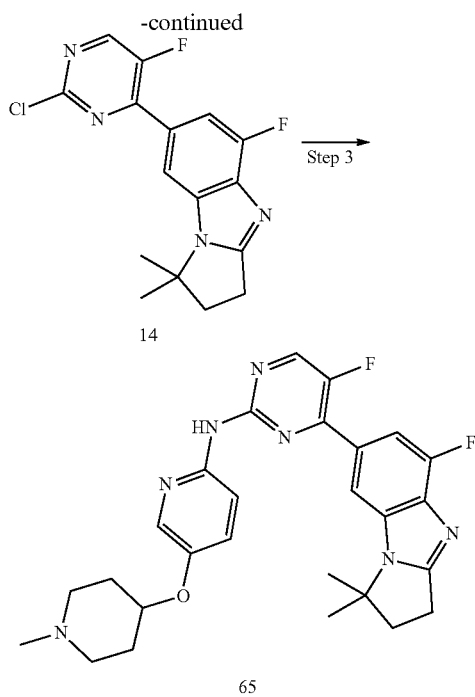

Nitrogen was bubbled into a solution of compound 64 (73 mg, 0.3 mmol, 1 eq), compound 14 (100 mg, 0.3 mmol, 1 eq; see Example 1), Pd$_2$(dba)$_3$ (28 mg, 0.03 mmol, 0.1 eq), Xantphos (36 mg, 0.063 mmol, 0.21 eq) and Cs$_2$CO$_3$ (195 mg, 0.6 mmol, 2 eq) in dioxane (4 mL) for 5 mins. The mixture was stirred at 110° C. for 2 h. After completion, the mixture was cooled down to RT, the mixture was diluted with DCM (10 mL) and filtered through a pad of Celite, rinsed with DCM (10 mL). The filtrate was dried over sodium sulfate, concentrated and purified by pre-HPLC to give the desired product (34 mg) as a gray solid. $^1$H NMR (300 MHz, CDCl$_3$): δ 8.42 (s, 1H), 8.41-8.34 (m, 1H), 8.08-8.05 (m, 3H), 7.82 (d, J=12.0 Hz 1H), 7.36-7.32 (m, 1H), 4.40-4.38 (m, 1H), 3.17 (t, J=7.2 Hz, 2H), 2.98-2.90 (m, 2H), 2.61 (t, J=7.2 Hz, 2H), 2.50 (s, 3H), 2.26-2.22 (m, 2H), 2.06-2.00 (m, 2H), 1.74-1.65 (m, 8H). LCMS: (M+H)$^+$=506.2. HPLC: 98.4%.

Example 11: Synthesis of 3-(4-((6-(5-fluoro-4-(5-fluoro-1,1-dimethyl-2,3-dihydro-1H-benzo[d]pyrrolo[1,2-a]imidazol-7-yl)pyrimidin-2-ylamino)pyridin-3-yloxy)methyl)piperidin-1-yl)propan-1-ol (Compound 72)

Step 1. Synthesis of Compound 67

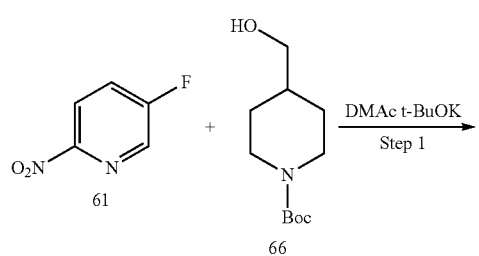

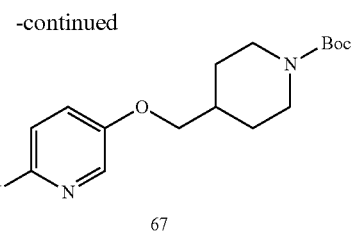

To a solution of compound 66 (564 mg, 4.2 mmol, 1.2 eq) in dimethylacetamide (5 mL) at 0° C. under nitrogen was added potassium tert-butoxide (910 mg, 4.6 mmol, 1.3 eq), the mixture was stirred at 0° C. for 1 h and then a solution compound 61 (500 mg, 3.5 mmol, 1.0 eq) in DMA (2 mL) was added drop wise. After addition, the reaction mixture was stirred at RT overnight. Water (15 mL) was added and the mixture was extracted with EA (10 mL×3). The combined organic layers was dried over Na$_2$SO$_4$, filtered and concentrated to give a crude product (800 mg crude), which was used into next step without further purification. $^1$H NMR (300 MHz, DMSO): δ 8.34-8.31 (m, 2H), 7.74-7.70 (m, 1H), 4.09 (d, J=6.3 Hz 2H), 3.99-3.96 (m, 2H), 2.78-2.74 (m, 2H), 2.00-1.96 (d, J=10.2 Hz, 2H), 1.78-1.73 (m, 2H), 1.40 (s, 9H), 1.21-1.11 (m, 2H). LCMS: (M-56+H)$^+$=282.1.

Step 2. Synthesis of Compound 68

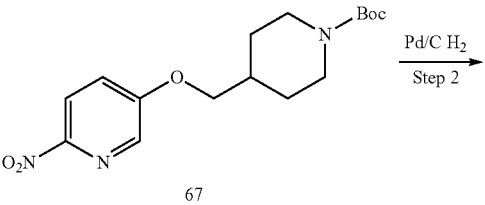

To a solution of compound 67 (800 mg, 2.95 mmol) in MeOH (8 mL) was added Pd/C (160 mg). The mixture was stirred under H$_2$ atmosphere overnight. After LCMS indicated completion, the mixture was filtered, rinsed with MeOH. The filtrate was concentrated to afford the crude product (700 mg, crude), which was used in next step directly. $^1$H NMR (300 MHz, CDCl$_3$): δ 7.71 (d, J=2.7 Hz, 1H), 7.10-7.07 (m, 1H), 6.49 (d, J=9.0 Hz, 1H), 4.15-4.12 (m, 2H), 3.74 (d, J=6.3 Hz, 2H), 2.73 (t, J=12.3 Hz, 2H), 1.91-1.90 (m, 1H), 1.81-1.77 (m, 1H), 1.45 (s, 9H), 1.31-1.17 (m, 2H). LCMS: 308.2.

Step 3. Synthesis of Compound 69

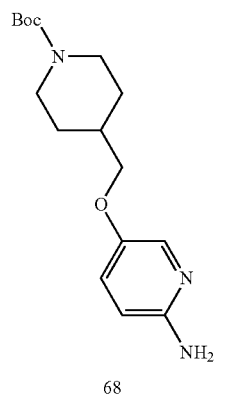

68

+

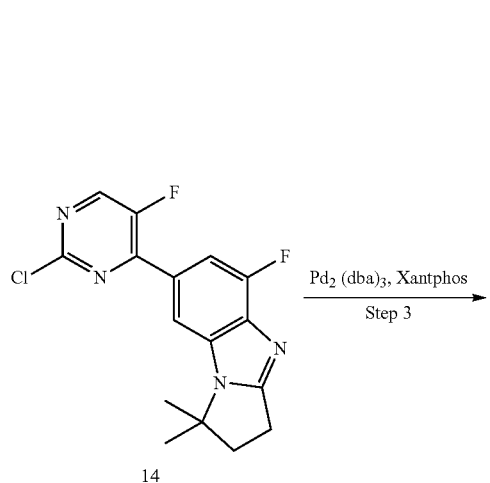

14

69

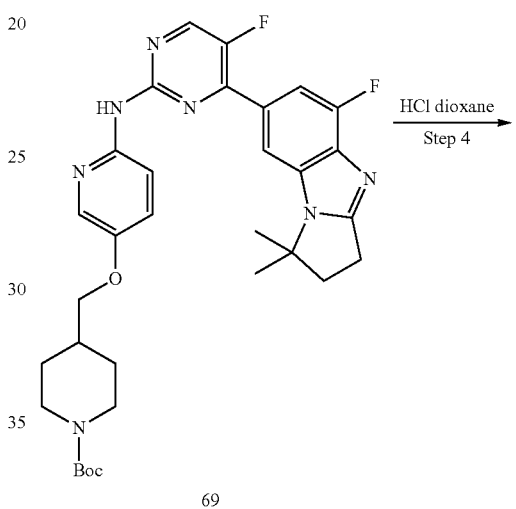

Nitrogen was bubbled into a solution of compound 68 (101 mg, 0.3 mmol, 1 eq), compound 14 (100 mg, 0.3 mmol, 1 eq; see Example 1), Pd₂(dba)₃ (28 mg, 0.03 mmol, 0.1 eq), Xantphos (36 mg, 0.063 mmol, 0.21 eq) and Cs₂CO₃ (195 mg, 0.6 mmol, 2 eq) in dioxane (4 mL) for 5 mins. The mixture was stirred at 110° C. for 2 h. The mixture was cooled down to RT, diluted with DCM (10 mL) and filtered through a pad of Celite, rinsed with DCM (10 mL), concentrated and then acetonitrile (2 mL) was added, filtered and rinsed with acetonitrile (1 mL×2) to give compound 5 as a white solid (50 mg, 27%). $^1$H NMR (300 MHz, CDCl₃): δ 8.40 (d, J=3.9 Hz, 1H), 8.33 (d, J=9.6 Hz, 1H), 8.09 (s, 1H), 8.03 (d, J=2.7 Hz, 1H), 7.96 (s, 1H), 7.82 (d, J=11.7 Hz, 1H), 7.32 (d, J=3.0 Hz, 1H) 4.21-4.20 (m, 2H), 3.86 (d, J=6.3 Hz 2H), 3.17 (t, J=7.5 Hz, 2H), 2.77 (t, J=12.6 Hz, 2H), 2.61 (t, J=7.8 Hz, 1H), 1.88-1.83 (m, 2H), 1.74 (s, 6H), 1.49 (s, 9H), 1.32-1.28 (m, 4H).

Step 4. Synthesis of Compound 70

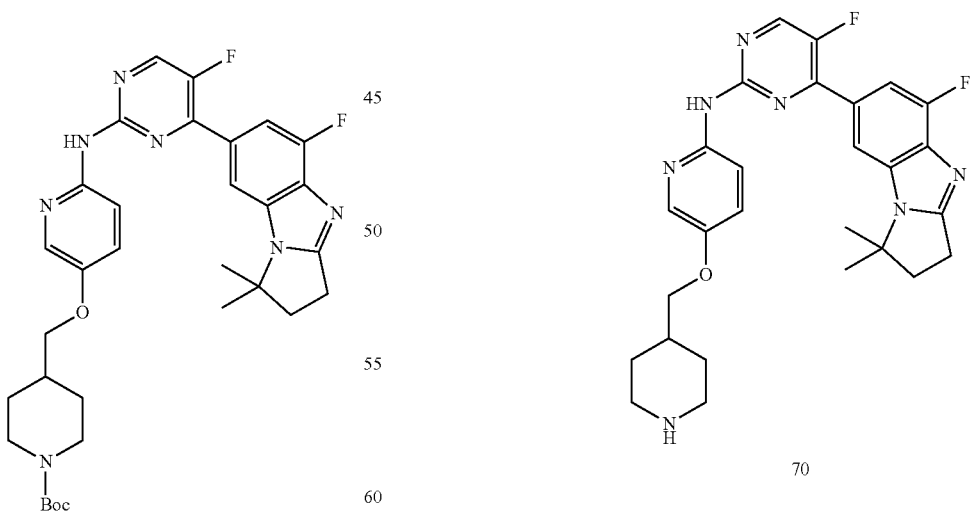

To a stirred solution of compound 69 (450 mg, crude) in dioxane (2 mL) was added 4 N HCl in dioxane (5 mL), the mixture was stirred for 1 h at room temperature. After completion, the mixture was concentrated to give a white solid (300 mg, crude), which was used into next step without purification. LCMS: (M+H)$^+$=506.2.

Step 5. Synthesis of Compound 72

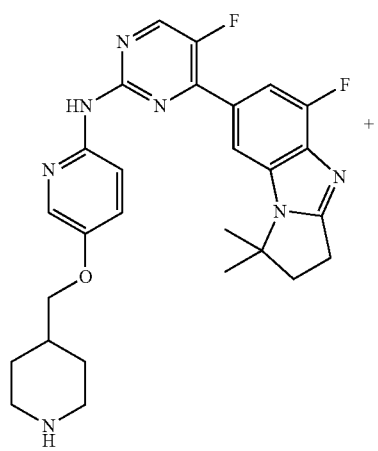

70

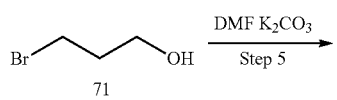

71

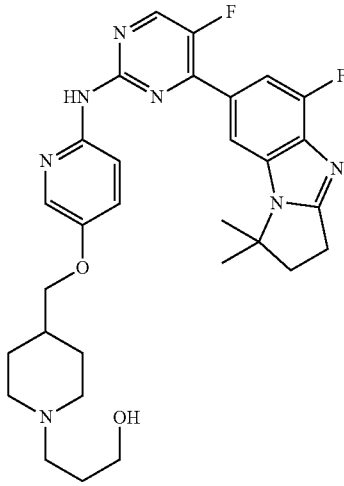

72

To a solution of compound 70 (180 mg, 0.41 mmol, 1 eq) in DMF (6 mL) was added K2CO$_3$ (117 mg, 0.82 mmol, 2 eq) and stirred for 30 mins at room temperature. And then 3-bromopropan-1-ol (54 mg, 0.49 mmol, 1.2 eq) was added and the mixture was heated to 50° C. for overnight. After cooling to room temperature, water (18 mL) was added and extracted with Ethyl acetate (5 mL×5). The combined organic layers was dried with Na$_2$SO$_4$, filtered and concentrated to give a crude residue (800 mg crude), which was purified by silica gel column to give the desired product as a yellow solid (80 mg, yield, 43%). $^1$H NMR (300 MHz, DMSO): δ 9.85 (s, 1H), 8.63 (s, 1H), 8.16-8.03 (m, 3H), 7.68 (d, J=12.9 Hz, 1H), 7.40 (d, J=8.1 Hz, 1H), 4.45 (br, 1H), 3.86 (d, J=6.3 Hz 2H), 3.43-3.33 (m, 2H), 3.08 (t, J=6.6 Hz, 2H), 2.89 (d, J=9.6 Hz 2H), 2.52-2.50 (m, 4H), 2.32 (t, J=6.6 Hz, 2H), 1.90 (t, J=11.4 Hz, 2H), 1.72-1.30 (m, 9H), 1.261-20 (m, 2H). LCMS: (M+H)$^+$=564.3. HPLC: 93.37%.

Example 12: Synthesis of 5-fluoro-4-(5-fluoro-1,1-dimethyl-2,3-dihydro-1H-benzo[d]pyrrolo[1,2-a]imidazol-7-yl)-N-(5-((1-methylpiperidin-4-yl)methoxy)pyridin-2-yl)pyrimidin-2-amine (Compound 76)

Step 1. Synthesis of Compound 74

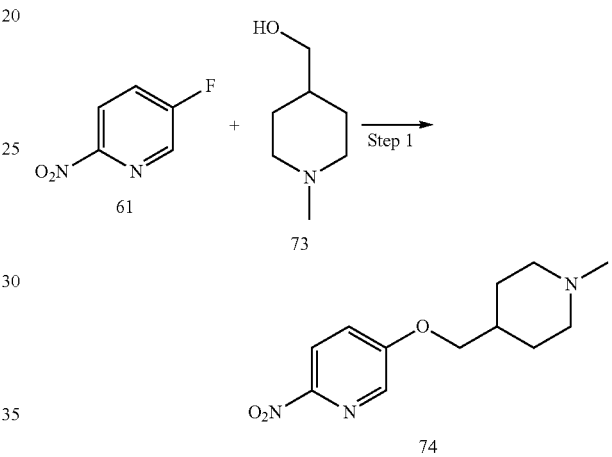

To a solution of compound 73 (564 mg, 4.2 mmol, 1.2 eq) in dimethylacetamide (5 mL) at 0° C. under nitrogen was added potassium tert-butoxide (513 mg, 4.6 mmol, 1.3 eq) portion wise. The mixture was stirred at 0° C. for 1 h, and then a solution of compound 61 (500 mg, 3.5 mmol, 1.0 eq) in DMA (2 mL) was added portion wise. After addition, the reaction mixture was stirred at RT overnight. The reaction was quenched by water (15 mL) and extracted with EA (3×5 mL), dried over Na$_2$SO$_4$, filtered and concentrated to give a crude residue (700 mg crude), which was used into next step without further purification. $^1$H NMR (300 MHz, CDCl$_3$): δ 8.34-8.31 (m, 2H), 7.72 (dd, J=3.0 Hz, 9.0 Hz, 1H), 4.07 (d, J=6.0 Hz 2H), 2.80-2.76 (m, 2H), 2.15 (s, 3H), 1.89-1.81 (m, 2H), 1.75-1.71 (m, 2H), 1.37-1.23 (m, 3H). LCMS: (M+H)$^+$=252.2.

Step 2. Synthesis of Compound 75

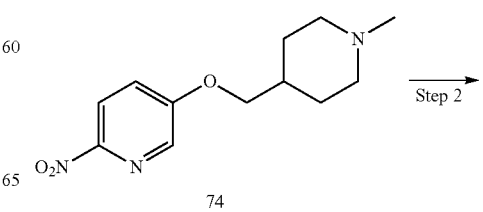

74

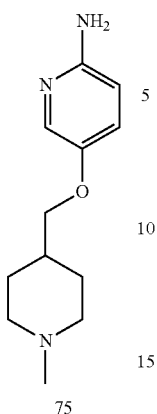

75

To a solution of compound 74 (700 mg, 2.95 mmol) in MeOH (7 mL) was added Pd/C (200 mg). The mixture was stirred under H₂ atmosphere overnight. After LCMS indicated completion, the mixture was filtered, rinsed with MeOH, and then the filtrate was concentrated to afford the crude product (600 mg, crude) which was used for the next step without further purification. ¹H NMR (300 MHz, CDCl₃): δ 7.74 (d, J=2.7 Hz 1H), 7.08 (dd, J=2.7 Hz 1H), 6.48 (d, J=3.0, 9.0 Hz, 1H), 6.47 (d, J=9.0 Hz), 4.63-4.61 (m 1H), 4.22-4.20 (br, 2H), 3.78-3.73 (m, 2H), 2.91-2.88 (m, 2H), 2.28 (s, 3H), 1.97-1.92 (m, 2H), 1.84-1.75 (m, 3H), 1.47-1.35 (m, 2H). LCMS: (M+H)⁺=222.1.

Step 3. Synthesis of Compound 76

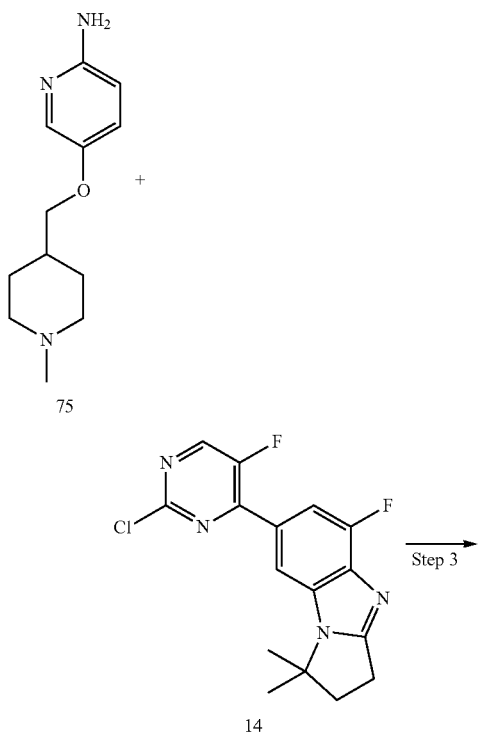

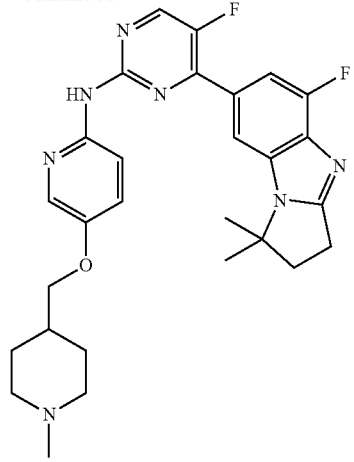

76

Nitrogen was bubbled into a solution of compound 75 (73 mg, 0.3 mmol, 1 eq), compound 14 (100 mg, 0.3 mmol, 1 eq; see Example 1), Pd₂(dba)₃ (28 mg, 0.03 mmol, 0.1 eq), Xantphos (36 mg, 0.063 mmol, 0.21 eq) and Cs₂CO₃ (195 mg, 0.6 mmol, 2 eq) in dioxane (4 mL) for 5 mins. The mixture was stirred at 110° C. for 2 h. After cooling down to RT, the mixture was diluted with DCM (10 mL) and filtered through a pad of Celite, rinsed with DCM (10 mL). The filtrate was dried over sodium sulfate, concentrated and purified by pre-HPLC to give the desired product (17 mg) as a gray solid. ¹H NMR (300 MHz, CDCl₃): δ 8.41 (d, J=3.6 Hz 1H), 8.31-8.34 (d, J=9.3 Hz, 1H), 8.09 (s, 1H), 8.03-8.01 (m, 2H), 7.82 (d, J=12.3 Hz, 1H), 7.31-7.29 (m, 1H), 3.88 (d, J=5.7 Hz, 2H), 3.17 (t, J=7.2 Hz, 2H), 3.09-3.05 (m, 2H), 2.62 (t, J=7.2 Hz, 2H), 2.43 (s, 3H), 2.22-2.18 (m, 2H), 1.95-1.91 (m, 3H), 1.86 (s, 6H), 1.74-1.64 (m, 2H). LCMS: (M+H)⁺=520.3. HPLC: 97.9%.

Example 13: 5-fluoro-4-(5-fluoro-1,1-dimethyl-2,3-dihydro-1H-benzo[d]pyrrolo[1,2-a]imidazol-7-yl)-N-(5-((1-methylpiperidin-4-yloxy)methyl)pyridin-2-yl)pyrimidin-2-amine (Compound 81)

Step 1. Synthesis of Compound 77

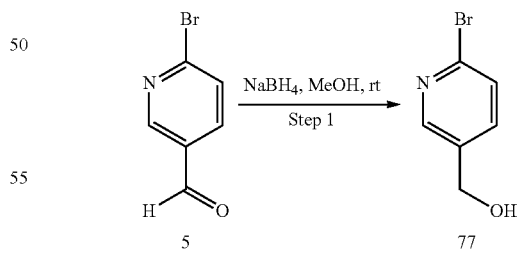

NaBH₄ (0.31 g, 8.1 mmol, 1.5 eq) was added portion wise to a solution of compound 5 (1 g, 5.4 mmol, 1 eq) in MeOH (10 mL) at 0° C. under nitrogen and the mixture was stirred for 1 h at room temperature. After HPLC indicated completion, water (10 mL) was add drop wise at 0° C. The mixture was concentrated and extracted with EA (5 mL×3), dried over Na₂SO₄, filtered and concentrated to give a crude residue (900 mg crude), which was used into next step without further purification. ¹H NMR (300 MHz, CDCl₃): δ 8.30 (s, 1H), 7.58 (s, 1H), 7.48 (s, 1H), 4.70 (s, 2H), 2.93 (s, 1H). LCMS: (M+H)⁺=188.0, 190.0.

Step 2. Synthesis of Compound 78

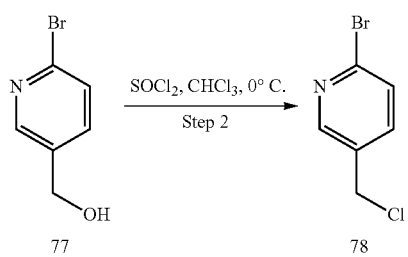 [SMILES: OCc1ccc(Br)nc1 ; ClCc1ccc(Br)nc1]

SOCl₂ (1.26 g, 10.6 mmol, 2 eq) was added drop wise to a stirred solution of compound 77 (1 g, 5.3 mmol, 1 eq) in CHCl₃ (10 mL) at 0° C. The mixture was stirred for 4 h at room temperature. After LC-MS indicated completion, the mixture was poured into ice-water and adjusted pH=7-8 with saturated NaHCO₃, extracted with DCM (10 mL×3). The combined organic layers was washed with brine (5 mL×3) and dried over Na₂SO₄, filtered and concentrated to afford the crude product (870 mg, crude), which was used in next step directly.
¹H NMR (300 MHz, CDCl₃): δ 8.39 (d, J=1.5 Hz, 1H), 7.64-7.60 (m, 1H), 7.52 (d, J=8.1 Hz 1H), 4.56 (s, 1H). LCMS: (M+H)⁺=205.9, 207.9.

Step 3. Synthesis of Compound 79

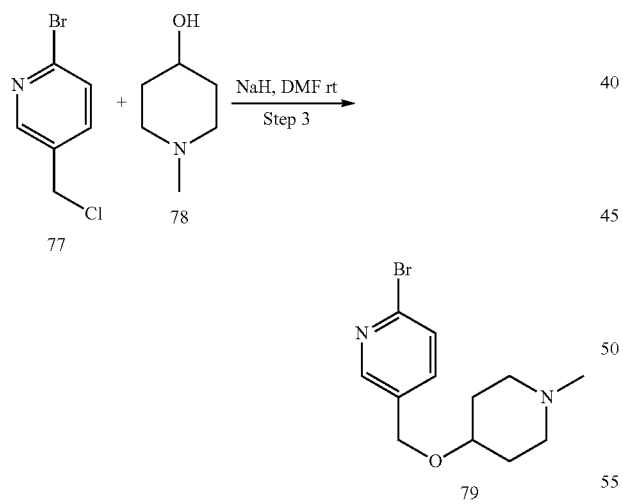

To a stirred solution of compound 78 (250 mg, 2.2 mmol, 1 eq) in DMF (5 mL) at 0° C. was added NaH (60% in oil, 174 mg, 4.4 mmol, 2 eq) portion wise. After the mixture was stirred at room temperature for 30 mins, a solution of compound 77 (493 mg, 2.4 mmol, 1.1 eq) in DMF (2 mL) was added drop wise at 0° C. After the addition, the reaction was allowed to warm to room temperature and stirred overnight. After LC-MS indicated completion, water (21 mL) was added drop wise at 0° C. and the mixture was extracted with EA (6 mL×3). The combined organic layers was washed with brine (5 mL×3) and dried over Na₂SO₄, filtered and concentrated to afford the crude product, which was purified by silica gel column to give the desired product as a yellow solid (0.31 g, 50%). ¹H NMR (300 MHz, CDCl₃): δ 8.32 (s, 1H), 7.56 (d, J=1.5 Hz, 1H), 7.45 (d, J=8.1 Hz, 1H), 4.50 (s, 2H), 3.47-3.45 (m, 1H), 2.74-2.72 (m, 2H), 2.32 (s, 3H), 2.28-2.25 (m, 2H), 1.96-1.90 (m, 2H), 1.79-1.72 (m, 2H). LCMS: (M+H)⁺=285.0, 287.0.

Step 4. Synthesis of Compound 80

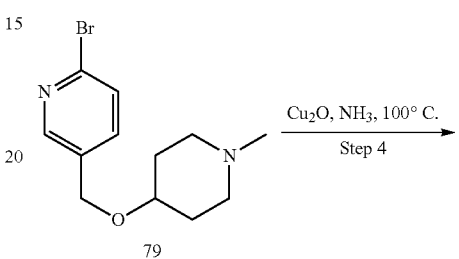

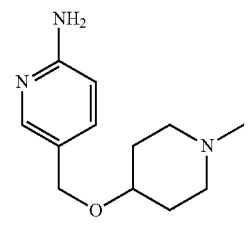

Compound 79 (300 mg, 1.05 mmol, 1 eq), CuO (30 mg, 0.21 mmol, 0.2 eq) and DMSO (6 mL) were added to a sealed tube, then purged with NH₃₍gas₎ for 10 mins. The mixture was stirred at 100° C. overnight. After completion, the mixture was adjusted with 2 N NaOH to pH=12-14, extracted with DCM (25 mL×5). The combined organic layers was dried, concentrated to give crude residue, which was purified by silica gel column to give compound 80 as a yellow solid (200 mg, 86%). ¹H NMR (300 MHz, CDCl₃): δ 8.02 (s, 1H), 7.47-7.43 (m, 1H), 6.50 (d, J=8.1 Hz, 1H), 4.53 (br, 2H), 4.39 (s, 2H), 3.42 (t, J=3.3 Hz, 1H), 2.74 (t, J=4.8 Hz, 2H), 2.30 (s, 3H), 2.20-2.18 (m, 2H), 1.98-1.93 (m, 2H), 1.75-1.68 (m, 2H). LCMS: (M+H)⁺=222.1.

Step 5. Synthesis of Compound 81

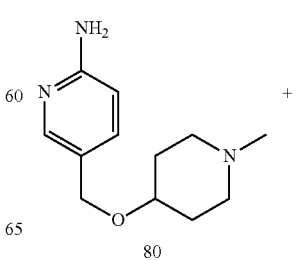

-continued

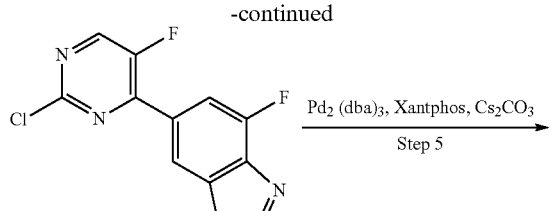

14

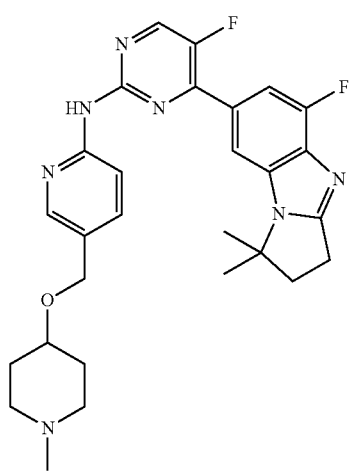

81

Nitrogen was bubbled into a solution of compound 80 (78 mg, 0.3 mmol, 1 eq), compound 14 (100 mg, 0.3 mmol, 1 eq; see Example 1), Pd$_2$(dba)$_3$ (28 mg, 0.03 mmol, 0.1 eq), Xantphos (36 mg, 0.063 mmol, 0.21 eq) and Cs$_2$CO$_3$ (195 mg, 0.6 mmol, 2 eq) in dioxane (4 mL) for 5 mins. The mixture was stirred at 110° C. for 2 h. After cooling down to RT, the mixture was diluted with DCM (10 mL) and filtered through a pad of Celite, rinsed with DCM (10 mL). The filtrate was dried over sodium sulfate, concentrated and purified by pre-HPLC to give the desired product (17 mg) as a gray solid. $^1$H NMR (300 MHz, CDCl$_3$): δ 8.34 (t, J=3.0 Hz, 2H), 8.21 (s, 1H), 8.03 (s, 1H), 7.96 (s, 1H), 7.75 (d, J=9.0 Hz, 1H), 7.65 (d, J=6.3 Hz, 1H), 4.45 (s, 2H), 3.63 (s, 2H), 3.37 (br, 1H), 3.09 (t, J=5.7 Hz, 2H), 2.66-2.64 (m, 2H), 2.53 (t, J=5.7 Hz, 2H), 2.22 (s, 3H), 2.17-2.09 (m, 2H), 1.95-1.93 (m, 2H), 1.66 (s, 6H). LCMS: (M+H)$^+$=520.2. HPLC: 98.5%.

Example 14: 2-(4-(6-(5-fluoro-4-(5-fluoro-1,1-dimethyl-2,3-dihydro-1H-benzo[d]pyrrolo[1,2-a]imidazol-7-yl)pyrimidin-2-ylamino)pyridin-3-yloxy)piperidin-1-yl)ethanol (Compound 87)

Step 1. Synthesis of Compound 83

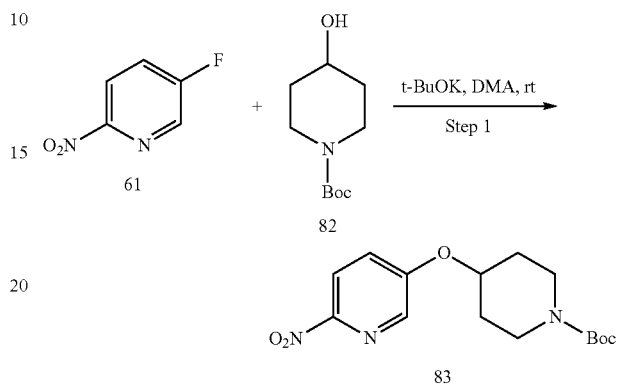

To a solution of compound 82 (564 mg, 4.2 mmol, 1.2 eq) in dimethylacetamide (5 mL) was added potassium tert-butoxide (910 mg, 4.6 mmol, 1.3 eq) at 0° C. under nitrogen and then stirred for 1 h before a solution of compound 61 (500 mg, 3.5 mmol, 1.0 eq) in DMA (2 mL) was added drop wise. After addition, the reaction mixture was stirred at RT overnight. Water (15 mL) was added and the reaction mixture was extracted with EA (5 mL×3). The combined organic layers was dried over Na$_2$SO$_4$, filtered and concentrated to give a crude product (800 mg crude), which was used into next step without further purification. $^1$H NMR (300 MHz, CDCl$_3$): δ 8.30-8.25 (m, 2H), 7.43-7.39 (m, 1H), 4.69-4.66 (m, 1H), 3.77-3.69 (m, 2H), 3.45-3.40 (m, 2H), 2.03-1.97 (m, 2H), 1.85-1.80 (m, 2H), 1.49 (s, 9H). LCMS: (M-56+H)$^+$=268.6.

Step 2. Synthesis of Compound 84

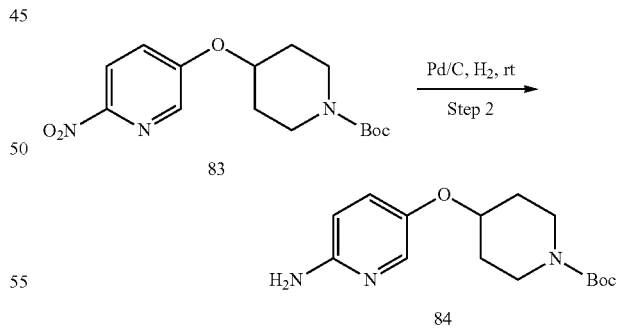

To a solution of compound 83 (1.0 g, crude) in MeOH (10 mL) was added Pd/C (200 mg). The mixture was stirred under H$_2$ atmosphere overnight. After LCMS indicated completion, the mixture was filtered, rinsed with MeOH. The filtrate was concentrated to afford the crude product (800 mg) which was purified by silica gel column to give desired product as a white solid (300 mg). $^1$HNMR (300 MHz, CDCl$_3$): δ 7.81 (d, J=2.7 Hz, 1H), 7.15-7.11 (m, 1H), 6.49 (d, J=8.7 Hz, 1H), 4.27-4.22 (m, 3H), 3.75-3.69 (m, 2H), 3.31-3.23 (m, 2H), 1.93-1.86 (m, 2H), 1.73-1.70 (m, 2H), 1.47 (s, 9H). LCMS: (M+H)+: 294.2.

Step 3. Synthesis of Compound 85

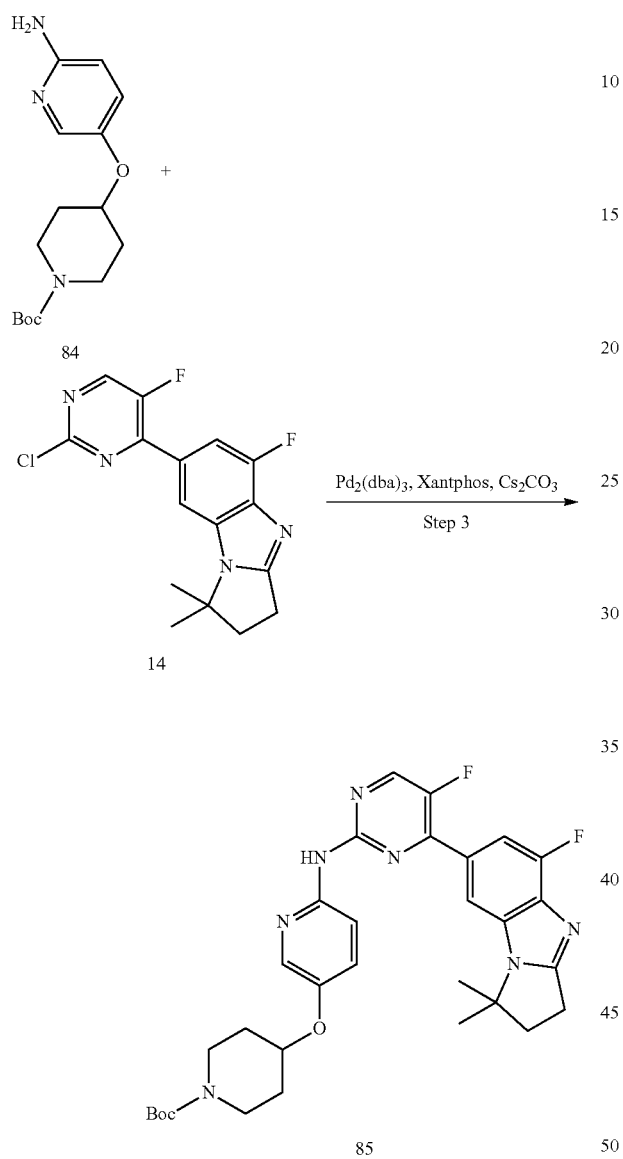

Nitrogen was bubbled into a solution of compound 84 (96 mg, 0.3 mmol, 1 eq), compound 14 (100 mg, 0.3 mmol, 1 eq; see Example 1), Pd$_2$(dba)$_3$ (28 mg, 0.03 mmol, 0.1 eq), Xantphos (36 mg, 0.063 mmol, 0.21 eq) and Cs$_2$CO$_3$ (195 mg, 0.6 mmol, 2 eq) in dioxane (4 mL) for 5 mins. The mixture was stirred at 110° C. for 2 h. After cooling to RT, the mixture was diluted with DCM (10 mL) and filtered through a pad of Celite, rinsed with DCM (10 mL). The filtrate was dried over sodium sulfate, concentrated and then acetonitrile (4 mL) was added and the resulting solid was filtered and rinsed with acetonitrile (1 mL×2) to give a white solid (60 mg, 34%). $^1$H NMR (300 MHz, CDCl$_3$): δ 8.42 (d, J=3.6 Hz, 1H), 8.35 (d, J=9.3 Hz, 1H), 8.11-8.06 (m, 3H), 7.82 (d, J=12.0 Hz, 1H), 7.31-7.35 (m, 1H), 4.44-4.42 (m, 1H), 3.76-3.72 (m, 2H), 3.37-3.29 (m, 2H), 3.17 (t, J=7.5 Hz, 2H), 2.61 (t, J=7.8 Hz, 1H), 1.98-1.93 (m, 2H), 1.80-1.73 (m, 2H), 1.66 (s, 6H), 1.49 (s, 9H). LCMS: (M+H)+=592.3.

Step 4. Synthesis of Compound 86

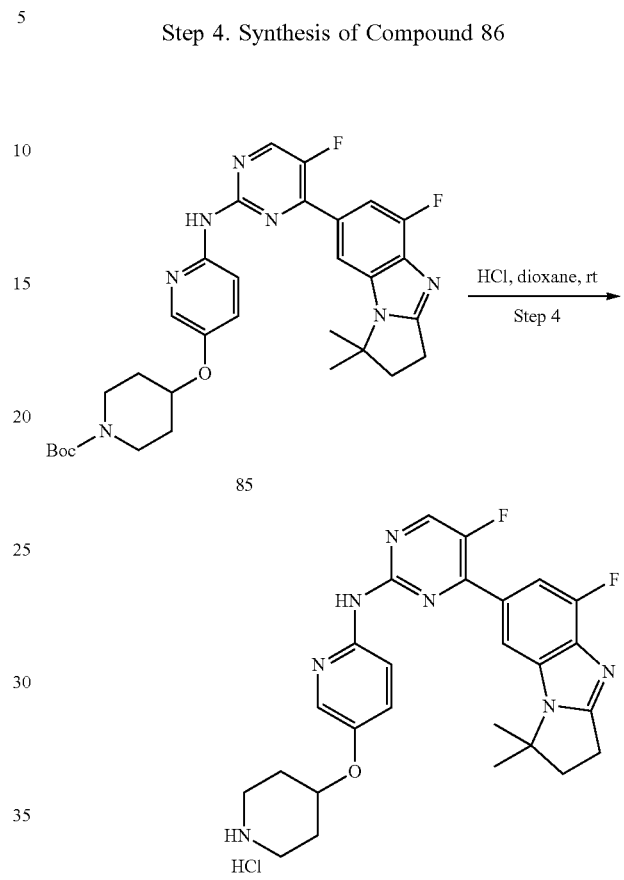

To a solution of compound 85 (450 mg, crude) in dioxane (2 mL) was added 4 N HCl in dioxane (5 mL) and then stirred for 1 h at room temperature. After completion, the mixture was concentrated to give a white solid (300 mg, crude) which was used into next step without further purification. LCMS: (M+H)+: 492.2.

Step 5. Synthesis of Compound 87

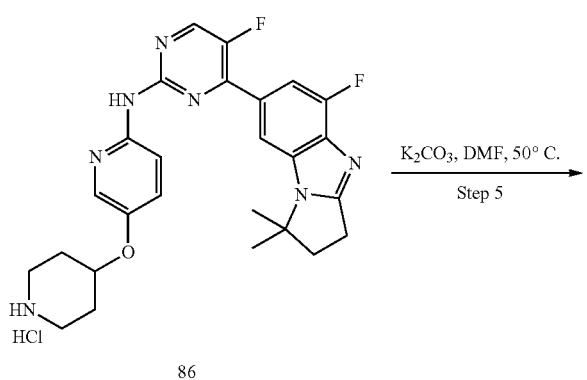

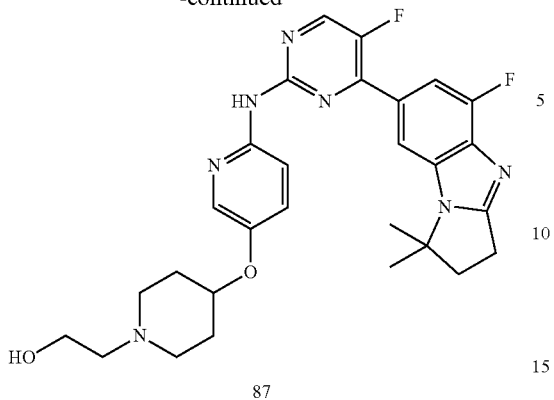

87

To a solution of compound 86 (180 mg, 0.41 mmol, 1 eq) in DMF (6 mL) was added K$_2$CO$_3$ (117 mg, 0.82 mmol, 2 eq) and stirred for 30 mins at room temperature before 2-bromoethanol (54 mg, 0.49 mmol, 1.2 eq) was added. The mixture was stirred at 50° C. overnight. After cooling to room temperature, water (18 mL) was added and the mixture was extracted with Ethyl acetate (5 mL×5). The combined organic layers was dried over Na$_2$SO$_4$, filtered and concentrated to give a crude product (800 mg crude) which was purified by silica gel column to give a yellow solid (60 mg). $^1$H NMR (300 MHz, CDCl$_3$): δ 9.86 (s, 1H), 8.65 (d, J=2.7 Hz, 1H), 8.18 (s, 1H), 8.11 (d, J=6.6 Hz, 1H), 8.04 (d, J=2.1 Hz, 1H), 7.70 (d, J=9.6 Hz, 1H), 7.46-7.44 (m, 1H), 4.38-4.36 (m, 3H), 3.50 (t, J=3.6 Hz, 2H), 3.10 (t, J=4.5 Hz, 2H), 2.75-2.73 (m, 2H), 2.58-2.54 (m, 2H), 2.43-2.40 (m, 2H), 2.25-2.22 (m, 2H), 1.95-1.93 (m, 2H), 1.67 (s, 6H). LCMS: (M+H)$^+$=536.3. HPLC: 93.68%.

Example 15: Synthesis of N-(5-(4-ethylpiperazin-1-yl)pyridin-2-yl)-5-fluoro-4-(5-fluoro-1,1-dimethyl-2,3-dihydro-1H-benzo[d]pyrrolo[1,2-a]imidazol-7-yl)pyrimidin-2-amine (Compound 92; Comparative Example)

Step 1. Synthesis of Compound 90

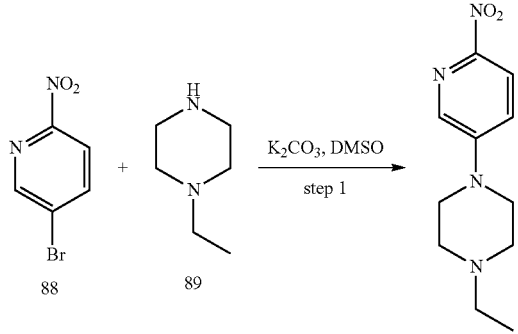

To a solution of compound 88 (2 g, 9.8 mmol, 1 eq) in DMSO (10 mL) was added K$_2$CO$_3$ (2.7 g, 19.7 mmol, 2 eq), 1-ethylpiperazine (compound 89, 1.7 g, 14.7 mmol, 1.5 eq) and TBAI (36 mg, 0.098 mmol, 0.01 eq). The reaction mixture was stirred at 120° C. for 2 h. After cooling down to rt, the mixture was diluted with water (30 mL), thus formed solid was filtered, rinsed with water (5 mL×3), and dried to afford the desired product (1.5 g, 65%) as a yellow solid which was used to the next step directly. $^1$H NMR (300 MHz, CDCl$_3$): δ 8.19-8.14 (m, 2H), 7.23-7.19 (m, 1H), 3.53-3.45 (m, 4H), 2.79-2.65 (m, 4H), 2.57-2.50 (m, 2H), 1.19 (t, J=7.2 Hz, 3H).

Step 2. Synthesis of Compound 91

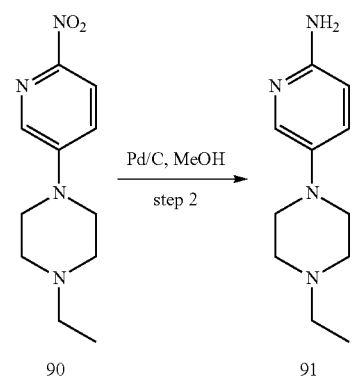 [SMILES: CCN1CCN(c2ccc([N+](=O)[O-])nc2)CC1 ; CCN1CCN(c2ccc(N)nc2)CC1]

To a solution of compound 90 (1.5 g, 6.4 mmol) in MeOH (20 mL) was added Pd/C (0.5 g). The mixture was stirred under H$_2$ atmosphere overnight. After LCMS indicated completion, the mixture was filtered, washed with MeOH, the filtrate was concentrated to afford the crude product (1.3 g, crude) which was used to the next step directly. $^1$H NMR (300 MHz, CDCl$_3$): δ 7.79 (s, 1H), 7.23-7.20 (m, 1H), 6.52-6.49 (m, 1H), 4.25 (br, 2H), 3.16-3.14 (m, 4H), 2.74-2.57 (m, 4H), 2.32-2.28 (m, 2H), 1.21 (t, J=7.2 Hz, 3H).

Step 3. Synthesis of Compound 92

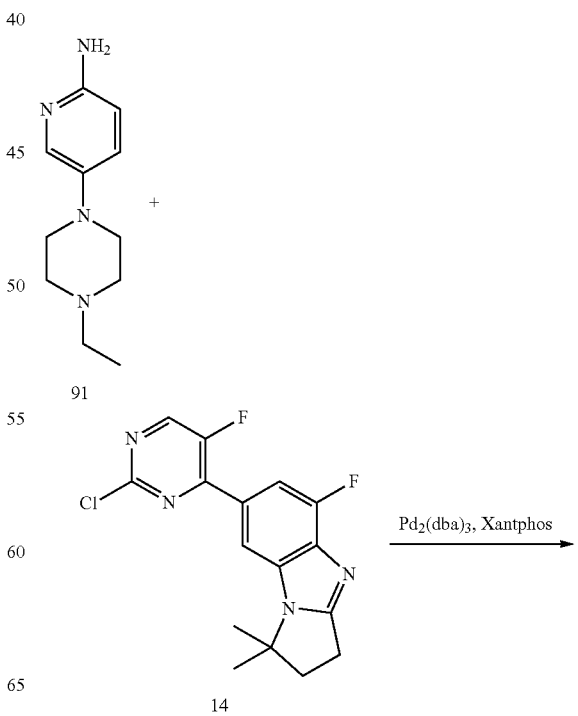

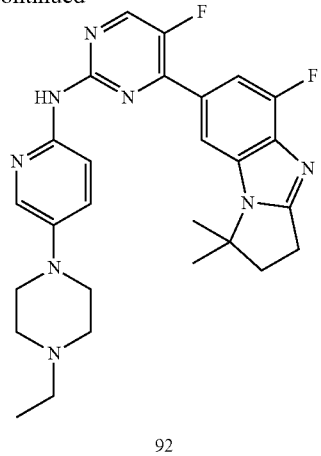

92

Nitrogen was bubbled into a solution of compound 91 (65 mg, 0.3 mmol, 1 eq), Compound 14 (100 mg, 0.3 mmol, 1 eq; see Example 1), Pd$_2$(dba)$_3$ (27 mg, 0.03 mmol, 0.1 eq), Xantphos (36.3 mg, 0.063 mmol, 0.21 eq) and Cs$_2$CO$_3$ (195 mg, 0.6 mmol, 2 eq) in dioxane (28 mL) for 5 min. And then the mixture was stirred at 110° C. for 2 h. After completion, the mixture was cooled down to rt, diluted with DCM (50 mL) and filtered through Celite, rinsed with DCM (20 mL), dried over sodium sulfate, concentrated and purified by pre-HPLC to give the desired product (17 mg, 7%) as a white solid. $^1$H NMR (300 MHz, CDCl$_3$): δ 8.41-8.40 (m, 1H), 8.31 (d, J=9 Hz, 1H), 8.09-8.06 (m, 3H), 7.82 (d, J=11.7 Hz, 1H), 7.38-7.34 (m, 1H), 3.28-3.26 (m, 4H), 3.19-3.14 (m, 2H), 2.76-2.74 (m, 4H), 2.63-2.58 (m, 4H), 1.74 (s, 6H), 1.26-1.20 (m, 3H). LCMS: (M+H)$^+$=504.8. HPLC: 96.3%.

Example 16: N-(5-((4-ethylpiperazin-1-yl)methyl)pyridin-2-yl)-5-fluoro-4-(6-fluoro-2,3-dihydro-1H-pyrrolo[1,2-b]indazol-8-yl)pyrimidin-2-amine (Compound 105)

Step 1. Synthesis of Compound 94

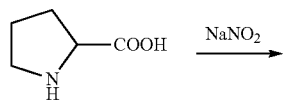

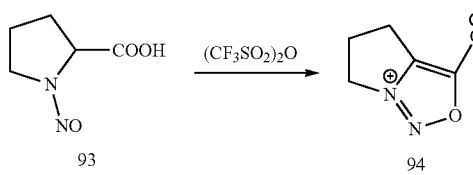

To a solution of L-Proline (1000 mg, 8.69 mmol) and sodium nitrite (845 mg, 12.2 mmol) in water 2.00 mL) cooled to 0° C. was slowly added concentrated hydrochloric acid (1.0 mL, 11.6 mmol). The reaction mixture was allowed to warm to room temp and stirred overnight. The reaction mixture was diluted with water and extracted with MTBE, dried over sodium sulfate and concentrated in vacuo to give a crude residue. The crude residue was then taken up in toluene (4.0 mL) and cooled to 0° C. Trifluoroacetic anhydride (1.81 mL, 13.0 mmol) was then added and the reaction was stirred overnight at room temp. The reaction mixture was concentrated in vacuo, adsorbed onto silica and purified by column chromatography (0-10% MeOH in DCM). The title compound as a brown oil (0.8 g, 74%). $^1$H NMR (400 MHz, CDCl$_3$): δ 4.41 (t, J=7.5 Hz, 2H), 2.96-2.86 (m, 2H), 2.85-2.73 (m, 2H). LC-MS (ESI): (M+H)$^+$=127.2.

Step 2. Synthesis of Compound 96

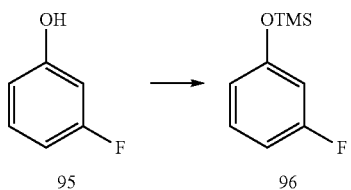

To a solution of compound 95 (11.2 g, 100 mmol) in freshly distilled THF (100 mL) was added 1,1,1,3,3,3-hexamethyldisilazane (HMDS, 31.3 mL, 150 mmol), the mixture was stirred at 50° C. under Ar atmosphere for overnight. TLC and LC-MS indicated starting material disappeared, the reaction mixture was concentrated under reduced pressure to give a crude residue, which was purified by distillation under reduced pressure to give desired product (8.1 g, 44%). $^1$H NMR (400 MHz, CDCl$_3$): δ 7.20-7.17 (m, 1H), 6.72-6.65 (m, 2H), 0.29 (s, 9H).

Step 3. Synthesis of Compound 98

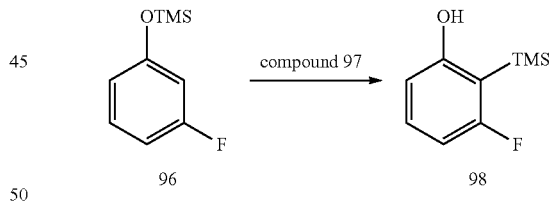

Compound 96 (3.68 g, 20 mmol) in freshly distilled THF (20 mL) was cooled to −78° C., bis(2,2,6,6-tetramethylpiperidin-1-yl) magnesium-bis(lithium chloride) complex (compound 97) (1.2 eq) was added under an Ar atmosphere. After stirring at the same temperature for 1 h, raise the reaction mixture to 0° C. and stirred for 12 hours at the same temperature. The reaction mixture was quenched with a cold 0.5M (+)—diluted with sodium tartrate solution, then extracted with hexane or ethyl acetate. The organic phase was dried over Na$_2$SO$_4$ and concentrated under reduced pressure. The residue was purified by flash silica gel column chromatography to afford the desired product 98 (920 mg, 25%) $^1$H NMR (300 MHz, CDCl$_3$): δ 9.85 (br, 1H), 7.18-7.16 (m, 1H), 6.59-6.57 (m, 1H), 6.52-6.46 (m, 1H), 0.28 (s, 9H). LC-MS (ESI): (M+H)$^+$=183.1.

Step 4. Synthesis of Compound 99

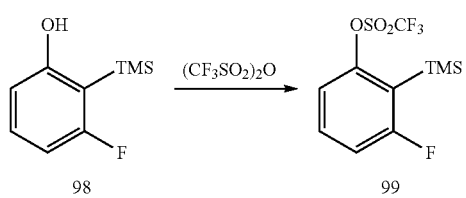

To a solution of compound 98 (920 mg, 5 mmol) in dichloromethane (15 mL) was added N,N'-diisopropylethylamine (839 mg, 6.5 mmol) at room temperature under Ar atmosphere. The solution was cooled to −40° C., trifluoromethanesulfonic anhydride (0.69 g, 6 mmol) was added drop wise. After addition, the mixture was warmed to room temperature and stirred at the same temperature for overnight. The reaction mixture was diluted with ice water, then extracted with dichloromethane. The organic phase was dried over $Na_2SO_4$ and concentrated under reduced pressure. The residue was purified by flash silica gel column chromatography to give the desired compound 99 (1.1 g, 70%). $^1$H NMR (300 MHz, $CDCl_3$): δ 7.47-7.39 (m, 1H), 7.18 (d, J=8.4 Hz, 1H), 7.05 (t, J=8.4 Hz, 1H), 0.44 (s, 9H).

Step 5. Synthesis of Compound 100

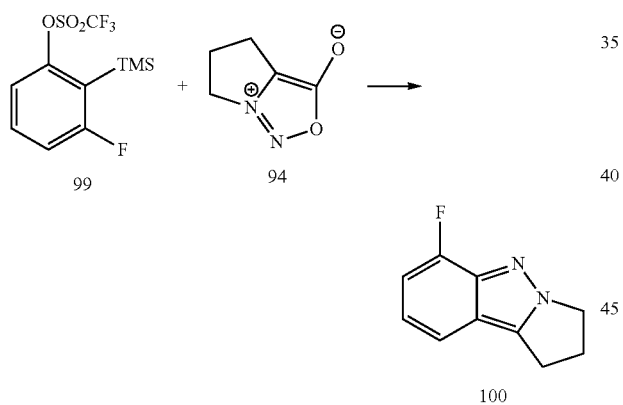

To an oven-dried 10 mL round-bottom flask equipped with a stir bar were added compound 99 (379 mg, 1.2 mmol, 1.2 eq) and compound 94 (126 mg, 1.0 mmol). THF (4 mL) was added and the mixture was stirred until all solid dissolved. To this solution was added TBAF (1.6 mL of 1 M THF solution, 1.6 eq) in one portion. The flask was sealed with a septum and a nitrogen balloon was attached. The reaction mixture was heated to reflux and stirred overnight. Upon completion, the reaction mixture was poured into saturated $NaHCO_3$ and extracted three times with EtOAc. The combined organic layers was washed once with brine, dried over $MgSO_4$, filtered and evaporated, purified via flash column chromatography to afford the desired product 100 (20 mg). $^1$H NMR (300 MHz, $CDCl_3$): δ 7.36 (d, J=8.4 Hz, 1H), 6.97-6.90 (m, 2H), 4.50 (t, J=7.2 Hz, 2H), 3.24 (t, J=7.2 Hz, 2H), 2.86-2.76 (m, 2H). LC-MS (ESI): $(M+H)^+$=177.1.

Step 6. Synthesis of Compound 101

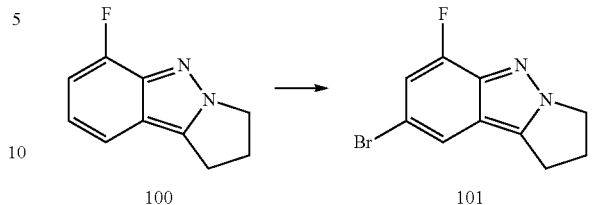

Compound 100 (176 mg, 1.0 mmol) was dissolved in acetic acid (5 mL) and stirred at room temperature under nitrogen. Bromine (240 mg, 1.5 mmol) was added over about 1 min, and the reaction then stirred for a further 16 h. Excess bromine was removed by bubbling nitrogen gas through the solution for 30 min, whereupon a thick solid was produced in the flask. Aqueous $NaHCO_3$ (15 mL) was added, extracted with EA (3×10 mL), the combined organic layers were dried over $MgSO_4$, filtered and concentrated to give a crude residue, which was purified on silica gel chromatography to give the desired product 101 (100 mg, 39%). $^1$H NMR (300 MHz, $CDCl_3$): δ 7.52 (s, 1H), 7.04 (d, J=10.8 Hz, 1H), 4.46 (t, J=7.2 Hz, 2H), 3.18 (t, J=7.2 Hz, 2H), 2.82-2.77 (m, 2H). LC-MS (ESI): $(M+H)^+$=255.0.

Step 7. Synthesis of Compound 102

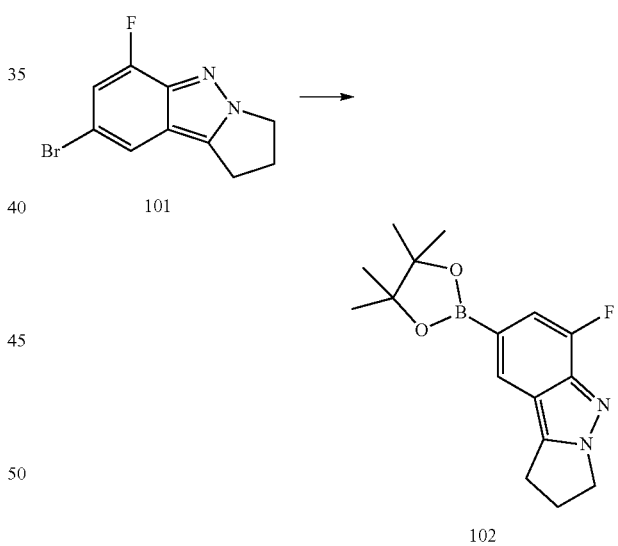

To a solution of compound 101 (100 mg, 0.39 mmol, 1 eq) in dioxane (2 mL) were added KOAc (115.7 mg, 1.18 mmol, 3 eq), Bis(pinacolato)diboron (148.6 mg, 0.59 mmol, 1.5 eq) and $Pd(dppf)_2Cl_2$ (27.7 mg, 0.039 mmol, 0.1 eq). The mixture was stirred under nitrogen at 90° C. overnight. After cooling down to RT, the mixture was filtered and washed with EA (10 mL). The filtrate was washed with brine (10 mL), dried over sodium sulfate, concentrated and purified by column chromatography to give the desired product (70 mg, 59%). $^1$H NMR (300 MHz, $CDCl_3$): δ 7.94 (s, 1H), 7.28 (d, J=12.0 Hz, 1H), 4.49 (t, J=7.2 Hz, 2H), 3.22 (t, J=7.2 Hz, 2H), 2.83-2.78 (m, 2H), 1.38 (s, 12H). LC-MS (ESI): $(M+H)^+$=303.2.

Step 8. Synthesis of Compound 104

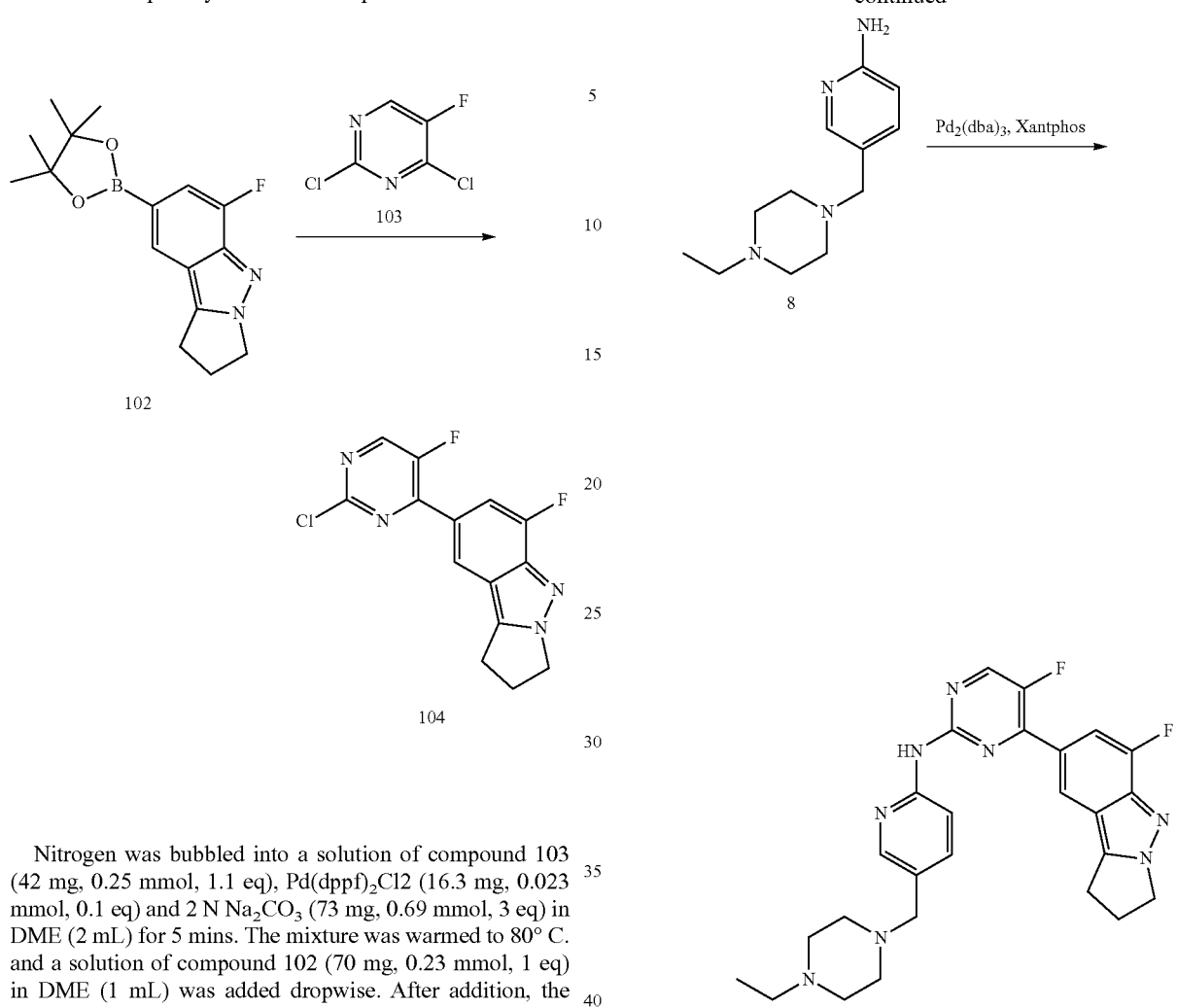

Nitrogen was bubbled into a solution of compound 103 (42 mg, 0.25 mmol, 1.1 eq), Pd(dppf)$_2$Cl2 (16.3 mg, 0.023 mmol, 0.1 eq) and 2 N Na$_2$CO$_3$ (73 mg, 0.69 mmol, 3 eq) in DME (2 mL) for 5 mins. The mixture was warmed to 80° C. and a solution of compound 102 (70 mg, 0.23 mmol, 1 eq) in DME (1 mL) was added dropwise. After addition, the mixture was stirred at 80° C. for 1 h. After cooling down to RT, the mixture was diluted with EA (6 mL) and washed with brine (5 mL), dried over sodium sulfate, concentrated and purified by column chromatography to give the desired product (40 mg, 57%). $^1$H NMR (300 MHz, CDCl$_3$): δ 8.51 (d, J=3.3 Hz, 1H), 8.36 (s, 1H), 7.82 (d, J=13.2 Hz, 1H), 4.54 (t, J=7.2 Hz, 2H), 3.33 (t, J=7.2 Hz, 2H), 2.90-2.85 (m, 2H). LC-MS (ESI): (M+H)$^+$=307.1.

Step 9. Synthesis of Compound 105

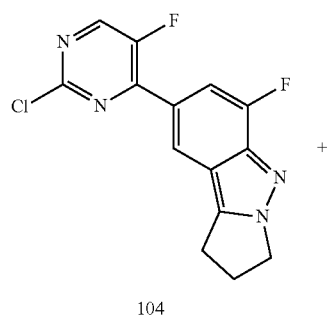

Nitrogen was bubbled into a solution of compound 104 (40 mg, 0.13 mmol, 1.0 eq), compound 8 (30.2 mg, 0.137 mmol, 1.05 eq), Pd$_2$(dba)$_3$ (11.9 mg, 0.013 mmol, 0.1 eq), Xantphos (15 mg, 0.026 mmol, 0.2 eq) and Cs$_2$CO$_3$ (84.7 mg, 0.26 mmol, 2.0 eq) in dioxane (2 mL) for 5 mins. The mixture was stirred at 110° C. for 2 h. After completion, the mixture was cooled down to RT, the mixture was diluted with DCM (5 mL) and filtered through celite, washed with DCM (4 mL), dried over sodium sulfate, concentrated and purified by pre-HPLC to give the desired product (20 mg, 31%). $^1$H NMR (300 MHz, CDCl$_3$): δ 8.40-8.34 (m, 2H), 8.27 (s, 1H), 8.23 (s, 1H), 8.09 (s, 1H), 7.82 (d, J=13.5 Hz, 1H), 7.72 (d, J=7.8 Hz, 1H), 4.53 (t, J=7.2 Hz, 2H), 3.50 (s, 1H), 3.32 (t, J=7.2 Hz, 2H), 2.88-2.83 (m, 2H), 2.61-2.43 (m, 10H), 1.09 (t, J=6.9 Hz, 3H). LC-MS (ESI): (M+H)$^+$=491.3.

Example 17: N-(5-((4-ethylpiperazin-1-yl)methoxy)pyridin-2-yl)-5-fluoro-4-(6-fluoro-2,3-dihydro-1H-pyrrolo[1,2-b]indazol-8-yl)pyrimidin-2-amine (Compound 106)

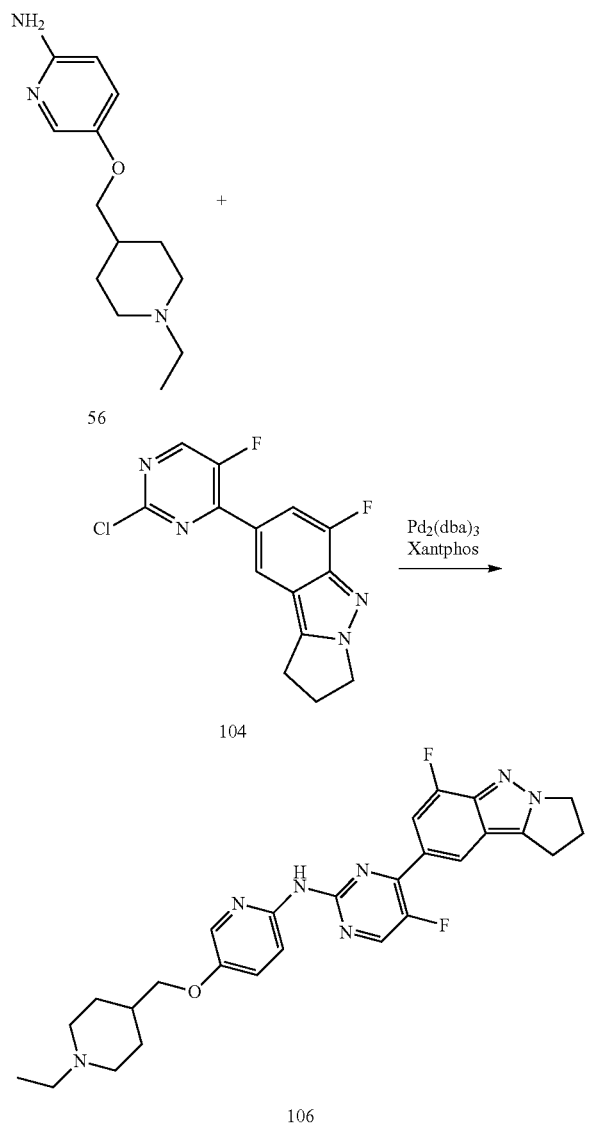

Nitrogen was bubbled into a solution of compound 56 (26 mg, 0.11 mmol), compound 104 (30 mg, 0.1 mmol), Pd$_2$(dba)$_3$ (9 mg, 0.01 mmol), Xantphos (11 mg, 0.02 mmol) and Cs$_2$CO$_3$ (97 mg, 0.3 mmol) in dioxane (3 mL) for 5 mins. The mixture was stirred at 110° C. for 2 h. After completion, the mixture was cooled down to RT, the mixture was diluted with DCM (5 mL) and filtered through celite, washed with DCM (4 mL), dried over sodium sulfate, concentrated and purified by pre-HPLC to give the desired product (13 mg, 25.7%). $^1$H NMR (400 MHz, MeOD): δ 8.56 (s, 1H), 8.30 (s, 1H), 8.12 (d, J=7.6 Hz, 1H), 7.99 (s, 1H), 7.79 (d, J=12.8 Hz, 1H), 7.46 (d, J=7.2 Hz, 1H), 4.65-4.50 (m, 2H), 4.48 (s, 2H), 3.98 (d, J=4.0 Hz, 2H), 2.57-3.60 (m, 2H), 3.17 (d, J=6.8 Hz, 2H), 2.95-3.10 (m, 2H), 2.75-2.90 (m, 2H), 2.10-2.25 (m, 3H), 1.65-1.82 (m, 2H), 1.35 (t, J=6.8 Hz, 3H). Chemical Purity: 96%, measured by HPLC (215 nm).

Example 18: Enzymatic Assay Assessment

CDK4 Inhibition Assay. Test compounds (compound of the present invention, reference compound Abemaciclib, and comparative example compounds) were dissolved in DMSO at 10 mM. 45 µL of compound solution was transfer into a 384-well compound source plate (LABCYTE cat #P-05525) and serially diluted at 1:3 ratio to create a 12-point dilution. The same volume of DMSO was adopted as high control (HC). 20 nL of compound solution in DMSO (diluted) were dispensed into anew 384-well assay plate by Echo 550. CDK4 protein (0.48 nM, CARNA BIOSCIENCE, cat #04-105), florescent labeled substrate FLPeptide34 (2 M, PerkinElmer, cat #760643) was prepared in kinase assay buffer (100 mM HEPES (pH 7.5), 10 mM MgCl$_2$, 0.05% Brij-35, 0.5 mM DTT and 0.1 mg/ml BSA). 15 µL of kinase assay buffer containing CDK4 protein and substrate was transferred to assay plate and incubate at rt for 30 minutes. Kinase assay buffer supplemented with substrate peptides was employed as low control (LC) to monitor the background. 400 M ATP was prepared in kinase assay buffer containing and 15 µL of ATP solution was added to each well to start the reaction. The assay plate was incubated at 25° C. for 90 minutes and the reaction was stopped by adding 40 µL of 0.5 M EDTA.

Phosphorylated fluorescent-tagged peptides were differentiated from non-phosphorylated peptides by separating using Caliper EZ Reader II and the detection was directly converted to conversion ratio (ratio of phosphorylated to non-phosphorylated peptide).

For estimation of IC$_{50}$, the % substrate conversion values are transformed to % relative activity by applying the following equation:

$$\% \text{ relative activity} = \frac{\text{Ratio}_{cpd} - \text{Ratio}_{LC}}{\text{Ratio}_{HC} - \text{Ratio}_{LC}}$$

The IC$_{50}$ was then calculated by fitting in XLFit (IDBS, Guildford, Surrey) to a four parameters logistic curve (Tables 1 and 2).

CDK6 Inhibition Assay. Test compounds (compound of the present invention, reference compound Abemaciclib, and comparative example compounds) were respectively dissolved in DMSO at 10 mM. 45 µL of compound solution was transfer into a 384-well compound source plate (LABCYTE cat #P-05525) and serially diluted at 1:3 ratio to create a 12-point dilution. The same volume of DMSO was adopted as high control (HC). 20 nL compound solution in DMSO (diluted) were dispensed into a new 384-well assay plate by Echo 550. CDK6 protein (8.81 nM, CARNA BIOSCIENCE, cat #04-107), florescent labeled substrate FLPeptide34 (2 µM, PerkinElmer, cat #760643) was prepared in kinase assay buffer (100 mM HEPES (pH 7.5), 10 mM MgCl$_2$, 0.05% Brij-35, 0.5 mM DTT and 0.1 mg/ml BSA). 15 µL of kinase assay buffer containing CDK6 protein and substrate was transferred to assay plate and incubate at rt for 30 minutes. Kinase assay buffer supplemented with substrate peptides was employed as low control (LC) to monitor the background. 400 M ATP was prepared in kinase assay buffer containing and 15 µL of ATP solution was added to each well to start the reaction. The assay plate was incubated at 25° C. for 90 minutes and the reaction was stopped by adding 40 µL of 0.5 M EDTA.

The result was analyzed in the same manner of CDK4 (Tables 1 and 2).

CDK2 Inhibition Assay. Test compounds (compound of the present invention, reference compound Abemaciclib, and comparative example compounds) were dissolved in DMSO at 10 mM. 45 μL of the test compound solution was transferred into a 384-well compound source plate (LABCYTE cat #P-05525) and serially diluted at 1:3 ratio to create a 12-point dilutions. The same volume of DMSO was adopted as high control. 20 nL of the test compound solution in DMSO were dispensed into a new 384-well assay plate by Echo 550. CDK2 protein (2.19 nM, CARNA BIOSCIENCE, cat #04-103), florescent labeled substrate FLPeptide18 (2 μM, PerkinElmer, cat #760362) was prepared in kinase assay buffer (100 mM HEPES (pH 7.5), 10 mM $MgCl_2$, 0.05% Brij-35, 0.5 mM DTT and 0.1 mg/ml BSA). 15 μL of kinase assay buffer containing CDK2 protein and substrate was transferred to assay plate and incubate at RT for 30 minutes. Kinase assay buffer supplemented with substrate peptides was employed as low control to monitor the background. 400 M ATP was prepared in kinase assay buffer containing and 5 μL of ATP solution was added to each well to start the reaction. The assay plate was incubated at 25° C. for 90 minutes and the reaction was stopped by adding 40 μL of 0.5 M EDTA.

Phosphorylated fluorescent-tagged peptides were differentiated from non-phosphorylated peptides by separating using Caliper EZ Reader II and the detection was directly converted to conversion ratio.

The result was analyzed in the same manner of CDK4 (Tables 1 and 2).

CDK5 Inhibition Assay. Test compounds (compound of the present invention, reference compound Abemaciclib, and comparative example compounds) were dissolved in DMSO at 10 mM. 45 μL of the test compound solution was transferred into a 384-well compound source plate (LABCYTE cat #P-05525) and serially diluted at 1:3 ratio to create a 12-point dilutions. The same volume of DMSO was adopted as high control. 20 nL of the test compound solution in DMSO were dispensed into a new 384-well assay plate by Echo 550. CDK5 protein (0.08 nM, CARNA BIOSCIENCE, cat #04-106), florescent labeled substrate FLPeptide29 (2 μM, PerkinElmer, cat #760429) was prepared in kinase assay buffer (100 mM HEPES (pH 7.5), 10 mM $MgCl_2$, 0.05% Brij-35, 0.5 mM DTT and 0.1 mg/ml BSA). 15 μL of kinase assay buffer containing CDK5 protein and substrate was transferred to assay plate and incubate at RT for 30 minutes. Kinase assay buffer supplemented with substrate peptides was employed as low control to monitor the background. 40 M ATP was prepared in kinase assay buffer containing and 5 μL of ATP solution was added to each well to start the reaction. The assay plate was incubated at 25° C. for 90 minutes and the reaction was stopped by adding 40 μL of 0.5 M EDTA.

The result was analyzed in the same manner of CDK4 (Tables 1 and 2).

TABLE 1

| | CDK $IC_{50}$ (nM) | | | |
|---|---|---|---|---|
| Example # | CDK4 $IC_{50}$ (nM) | CDK6 $IC_{50}$ (nM) | CDK2 $IC_{50}$ (nM) | CDK5 $IC_{50}$ (nM) |
| Abemaciclib | 0.26 (run 1) | 3.41 (run 1) | 305.89 (run 1) | 192 |
| | 0.40 (run 2) | 6.82 (run 2) | 57.86 (run 2) | — |
| | 0.39 (run 3) | 4.50 (run 3) | — | — |
| Example 2 | 0.73 (run 3) | 8.84 (run 3) | 79.92 (run 2) | 132.36 |
| Example 6 | 0.20 (run 1) | 1.19 (run 1) | 20.41 (run 1) | 19.07 |
| | — | — | 5.62 (run 2) | — |
| Example 7 | 0.18 (run 1) | 3.96 (run 1) | 65.52 (run 1) | 50.60 |
| | — | — | 16.11 (run 2) | — |
| Example 8 | 0.16 (run 1) | 4.72 (run 1) | 368.27 (run 1) | 705.33 |
| | — | — | 284.99 (run 2) | — |
| Example 9 | 0.10 (run 1) | 2.90 (run 1) | 24.66 (run 1) | 11.31 |
| | — | — | 14.75 (run 2) | — |
| Example 10 | 0.26 | 2.46 | 64.11 | 136.41 |
| Example 11 | 0.11 | 1.02 | 44.88 | 128.34 |
| Example 12 | 0.11 | 1.89 | 55.24 | 158.63 |
| Example 13 | 0.25 | 3.92 | 173.63 | 433.35 |
| Example 14 | 0.25 | 2.72 | 70.34 | 213.09 |
| Example 16 | 9.46 | 93.69 | >10000 | >10000 |

TABLE 2

| | CDK $IC_{50}$ (nM) of Comparative Examples | | | |
|---|---|---|---|---|
| Example # | CDK4 $IC_{50}$ (nM) | CDK6 $IC_{50}$ (nM) | CDK2 $IC_{50}$ (nM) | CDK5 $IC_{50}$ (nM) |
| Abemaciclib | 0.26 (run 1) | 3.41 (run 1) | 305.89 (run 1) | 192 |
| | 0.40 (run 2) | 6.82 (run 2) | 57.86 (run 2) | — |
| | 0.39 (run 3) | 4.50 (run 3) | — | — |
| Example 1 | 0.14 (run 2) | 2.71 (run 2) | 51.12 (run 2) | 132.36 |
| Example 3 | 0.08 (run 1) | 1.93 (run 1) | 113.86 (run 1) | 38.26 |
| | — | — | 90.96 (run 2) | — |
| Example 4 | 0.17 (run 1) | 2.42 (run 1) | 119.92 (run 1) | 124.50 |
| | — | — | 69.96 (run 2) | — |
| Example 5 | 0.12 (run 3) | 1.87 (run 3) | 17.64 (run 2) | 36.75 |
| Example 15 | 0.07 (run 1) | 0.88 (run 1) | 116.74 (run 1) | 46.82 |
| | — | — | 21.61 (run 2) | — |

Examples 19: HS68 G1 Arrest (Cellular G1 and S-Phase) Assay: Cell-Cycle Analysis HS68 cells (human skin fibroblast cell line, ATCC) were treated for 24 hours with compounds of the present invention at 0, 1, 3, 10, 30, 100, 300, or 1,000 nmol/L final concentration. Cells were harvested and fixed in ice-cold 70% ethanol (Sigma-Aldrich). Fixed cells were washed with PBS, stained with 40 μg/mL propidium iodide (Thermofisher Scientific), 10 g RNAseA (Sigma-Aldrich) in PBS-CMF (calcium magnesium free). Samples were processed using flow cytometer (Fisher), and cell-cycle analysis was completed using FlowJo software (Tree Star).

TABLE 3

| | HS68 Assay $EC_{50}$ (nM) | |
|---|---|---|
| Example # | $EC_{50}$ (nM) | G1 % (max) |
| Example 8 | 43 | 79.35 |

Example 20: Metabolic Stability

Metabolic stability of compounds is assessed at 1 M with human, rat, mouse, dog, and monkey liver microsomes (0.5 mg/mL). Compound and protein are equilibrated at 37° C. for 5 min prior to reaction initiation with co-factor NADPH. Time points were taken at 0, 5, 15, 30, and 45 min. After quenching and centrifugation, supernatants were analyzed by LC-MS with methods specific to compounds tested. Intrinsic clearance ($CL_{int}$) and $T_{1/2}$ are calculated as following:

$T_{1/2}$=0.693/K (K is the rate constant from a plot of ln [concentration] vs. incubation time)

$Cl_{int}$=(0.693/$T_{1/2}$)×(1/(microsomal protein concentration (0.5 mg/mL)))×Scaling Factors (see Table 4)

TABLE 4

Scaling Factors for Intrinsic Clearance Prediction in the Mouse, Rat, Dog, Monkey, and Human

| Species | Microsomal protein (per gram of liver) | Liver Weight per Kilogram of Body Weight | Scaling Factor[a] | Hepatic Blood Flow (mL/min/kg) |
|---|---|---|---|---|
| Mouse | 45 | 87.5 | 3937.5 | 90 |
| Rat | 44.8 | 40 | 1792 | 55.2 |
| Dog | 77.9 | 32 | 2492.8 | 30.9 |
| Monkey | 45 | 32.5 | 1462.5 | 44 |
| Human | 48.8 | 25.7 | 1254.2 | 20.7 |

[a]Scaling Factor = (microsomal protein per gram of liver) × (liver weight per kilogram of body weight)

TABLE 5

Stability of Compounds in Liver Microsomes across Species

| Test Compound | Species | $T_{1/2}$ (minutes) | $Cl_{int}$ (mL/min/kg) |
|---|---|---|---|
| Example 8 | human | 80.21 | 21.67 |
| | rat | 77.18 | 32.18 |
| | mouse | 26.99 | 202.23 |
| | dog | 24.10 | 143.37 |
| | monkey | 13.40 | 151.25 |

Examples 21: Pharmacokinetic and Pharmacodynamic Properties of CDK4/6 Inhibitors Compounds of the present invention demonstrate good pharmacokinetic and pharmacodynamic properties. Compound G1T28 and the compound of Example 8 were dosed to mice at 10 mg/kg by oral gavage (p.o.) or 2 mg/kg by intravenous injection (i.v.). Blood samples were taken at 0.083, 0.25, 0.5, 1.0, 3.0, 6.0 and 24 hours post i.v. dosing and at 0.25, 0.5, 1.0, 3.0, 6.0 and 24 hours post p.o. dosing. The plasma concentration of compounds were determined by HPLC. Pharmacokinetic (PK) and pharmacodynamic (PD) properties are shown in Table 6.

TABLE 6

PK/PD properties of CDK4/6 inhibitors

| Mouse PK | Example 8 |
|---|---|
| CL (L/hr/kg) | 0.94 |
| Vss (L/kg) | 3.71 |
| $T_{1/2}$ (hr) i.v. | 3.36 |
| $AUC_{last}$ (hr*ng/mL) i.v. | 2113 |
| $AUC_{last}$ (hr*ng/mL) p.o. | 4823 |
| $C_{max}$ (ng/mL) p.o. | 340 |
| $T_{max}$ (hr) p.o. | 6.00 |
| F (%) | 45.6 |

In Tables 1-6 Example numbers corresponds to compounds prepared in referenced Example numbers. For example, Example 1 corresponds to Compound 15.

All publications and patent applications mentioned in the specification are indicative of the level of those skilled in the art to which this disclosure pertains. All publications and patent applications are herein incorporated by reference for all purposes to the same extent as if each individual publication or patent application was specifically and individually indicated to be incorporated by reference. Nothing herein is to be construed as an admission that the present disclosure is not entitled to antedate such publication by virtue of prior disclosure. All publications and patent applications mentioned in the specification are indicative of the level of those skilled in the art to which this disclosure pertains. All publications and patent applications are herein incorporated by reference for all purposes to the same extent as if each individual publication or patent application was specifically and individually indicated to be incorporated by reference. Nothing herein is to be construed as an admission that the present disclosure is not entitled to antedate such publication by virtue of prior disclosure.

Many modifications and other embodiments of the disclosures set forth herein will come to mind to one skilled in the art to which these disclosures pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. Although specific terms are employed herein, they are used in a generic and descriptive sense only and not for purposes of limitation.

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosure as come within known or customary practice within the art to which the disclosure pertains and as may be applied to the essential features hereinbefore set forth and as follows in the scope of the appended claims.

What is claimed is:

1. A compound of formula (A-1):

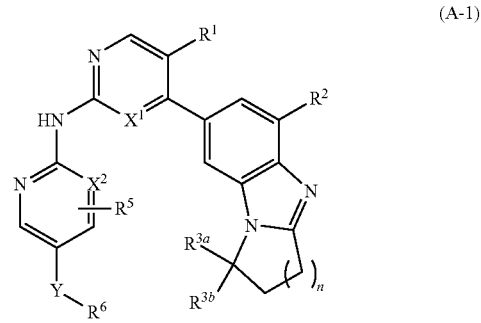

(A-1)

or a pharmaceutically acceptable salt, stereoisomer, or tautomer thereof, wherein:

$R^1$ is H, F, Cl, Br, CN, $CH_3$, $CHF_2$, $CF_3$, $CH_2CH_3$, $CH_2OH$, C(O)H, $C(O)NH_2$, $C(O)NHCH_3$, $C(O)N(CH_3)_2$, $C(O)OCH_3$, OH, $OCH_3$, $OCF_3$, $OCH_2CH_3$, $OCH_2CHF_2$, $OCH_2CF_3$, $OCH(CH_3)_2$, or O(cyclopropyl);

R² is H, F, Cl, CN, CH₃, CHF₂, CF₃, CH₂OH, C(O)NH₂, C(O)NHCH₃, C(O)N(CH₃)₂, OH, OCH₃, OCF₃, OCH₂CH₃, OCH(CH₃)₂, or O(cyclopropyl);

$R^{3a}$ is H or $C_{1-3}$ alkyl;

$R^{3b}$ is H or $C_{1-3}$ alkyl;

each $R^5$ is independently H;

$R^6$ is $C_{1-6}$ alkyl, $C_{1-6}$ haloalkyl, NR″R⁷, $C_{3-12}$ cycloalkyl, or heterocyclyl, wherein the $C_{1-6}$ alkyl, $C_{1-6}$ haloalkyl, $C_{3-12}$ cycloalkyl, or heterocyclyl is optionally substituted with 1, 2, or 3 substituents independently selected from the group consisting of F, $C_{1-6}$ alkyl, $C_{1-6}$ haloalkyl, CH₂OH, CH₂CH₂OH, CH₂CH₂CH₂OH, C(O)CH₂OH, NR″R″, OH, =O, aziridinyl, azetidinyl, pyrrolidinyl, piperidinyl, and morpholinyl;

$R^7$ is H, $C_{1-6}$ alkyl, $C_{1-6}$ haloalkyl, $C_{1-6}$ alkylene-$C_{6-12}$ aryl, $C_{1-6}$ alkylene-5- to 12-membered heteroaryl, $C_{3-12}$ cycloalkyl, heterocyclyl, $C_{6-12}$ aryl, or 5- to 12-membered heteroaryl, wherein the $C_{1-6}$ alkylene-$C_{6-12}$ aryl, $C_{1-6}$ alkylene-5- to 12-membered heteroaryl, $C_{3-12}$ cycloalkyl, heterocyclyl, $C_{6-12}$ aryl, or 5- to 12-membered heteroaryl is optionally substituted with 1, 2, or 3 substituents independently selected from the group consisting of F, CH₂OH, CH₂CH₂OH, CH₂CH₂CH₂OH, $C_{1-3}$ alkyl, $C_{1-3}$ haloalkyl, NR″R″, OH, =O, aziridinyl, azetidinyl, pyrrolidinyl, piperidinyl, and morpholinyl;

each R″ is independently H, $C_{1-6}$ alkyl, $C_{1-6}$ haloalkyl, C(O)$C_{1-6}$ alkyl, or S(O)₂$C_{1-6}$ alkyl;

$X^1$ is N;

$X^2$ is CH;

Y is —CH₂O— or —OCH₂—; and n is 1.

2. The compound of claim 1, or a pharmaceutically acceptable salt, stereoisomer, or tautomer thereof, wherein:
$R^1$ is H, F, Cl, CN, or CH₃; and
$R^2$ is H, F, or CN.

3. The compound of claim 1, or a pharmaceutically acceptable salt, stereoisomer, or tautomer thereof, wherein $R^6$ is 5- or 6-membered heterocyclyl, wherein the 5- or 6-membered heterocyclyl is optionally substituted with 1, 2, or 3 substituents independently selected from the group consisting of F, $C_{1-3}$ alkyl, $C_{1-3}$ haloalkyl, CH₂OH, CH₂CH₂OH, CH₂CH₂CH₂OH, NR″R″, OH, and =O.

4. The compound of claim 1, or a pharmaceutically acceptable salt, stereoisomer, or tautomer thereof, wherein $R^6$ is piperidinyl, wherein the piperidinyl is optionally substituted with 1, 2, or 3 substituents independently selected from the group consisting of F, $C_{1-6}$ alkyl, $C_{1-6}$ haloalkyl, CH₂OH, CH₂CH₂OH, CH₂CH₂CH₂OH, C(O)CH₂OH, NR″R″, OH, =O, aziridinyl, azetidinyl, pyrrolidinyl, piperidinyl, and morpholinyl.

5. The compound of claim 1, or a pharmaceutically acceptable salt, stereoisomer, or tautomer thereof, wherein $R^6$ is piperidinyl, wherein the piperidinyl is optionally substituted with 1, 2, or 3 substituents independently selected from the group consisting of F, $C_{1-3}$ alkyl, $C_{1-3}$ haloalkyl, CH₂OH, CH₂CH₂OH, CH₂CH₂CH₂OH, NR″R″, OH, and =O.

6. The compound of claim 1, or a pharmaceutically acceptable salt, stereoisomer, or tautomer thereof, wherein $R^6$ is piperidinyl, wherein the piperidinyl is substituted with 1 or 2 substituents independently selected from the group consisting of F, $C_{1-3}$ alkyl, and $C_{1-3}$ haloalkyl.

7. The compound of claim 1, or a pharmaceutically acceptable salt, stereoisomer, or tautomer thereof, wherein $R^6$ is:

[structure: piperidinyl with N-$C_{1-3}$alkyl]

8. The compound of claim 1, or a pharmaceutically acceptable salt, stereoisomer, or tautomer thereof, wherein $R^6$ is:

[structure: piperidinyl with N-CH₂CH₃]

9. The compound of claim 1, wherein the compound is selected from the group consisting of:

57

[structure 57]

72

[structure 72]

76

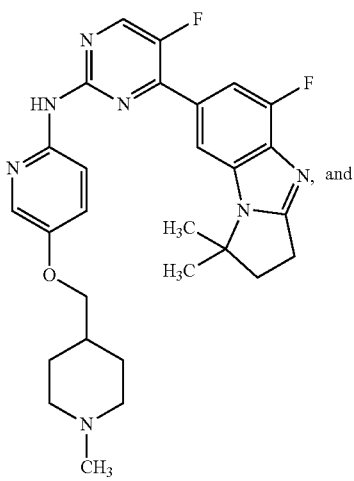

, and

81

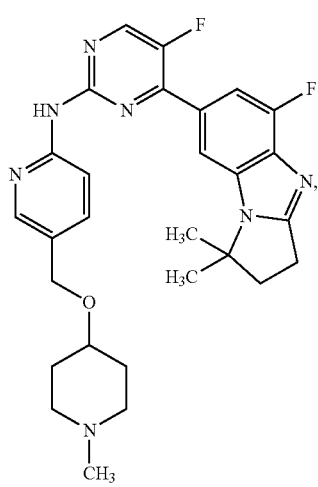

or a pharmaceutically acceptable salt, stereoisomer, or tautomer thereof.

10. A pharmaceutical composition comprising a pharmaceutically acceptable carrier and a compound of claim 1, or a pharmaceutically acceptable salt, stereoisomer, or tautomer thereof.

11. A method for protecting a hematopoietic cell population or a progenitor cell population in a subject from effects of ionizing radiation or chemotherapeutic agents, wherein the method comprises administering to the subject in need thereof a therapeutically effective amount of a compound of claim 1, or a pharmaceutically acceptable salt, stereoisomer, or tautomer thereof.

12. A method for inhibiting cyclin-dependent kinase activity in a subject, wherein the method comprises administering to the subject in need thereof a therapeutically effective amount of a compound of claim 1, or a pharmaceutically acceptable salt, stereoisomer, or tautomer thereof.

13. The method of claim 12, wherein the subject has cancer.

14. A compound of formula (B):

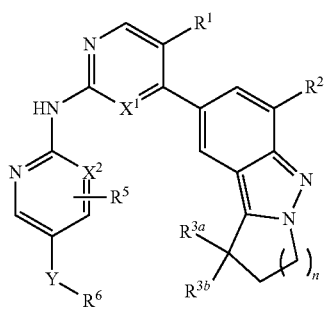

(B)

or a pharmaceutically acceptable salt, stereoisomer, or tautomer thereof,
wherein:
  $R^1$ is H, F, Cl, Br, CN, $CH_3$, $CHF_2$, $CF_3$, $CH_2CH_3$, $CH_2OH$, $C(O)H$, $C(O)NH_2$, $C(O)NHCH_3$, $C(O)N(CH_3)_2$, $C(O)OCH_3$, OH, $OCH_3$, $OCF_3$, $OCH_2CH_3$, $OCH_2CHF_2$, $OCH_2CF_3$, $OCH(CH_3)_2$, or O(cyclopropyl);
  $R^2$ is H, F, Cl, CN, $CH_3$, $CHF_2$, $CF_3$, $CH_2OH$, $C(O)NH_2$, $C(O)NHCH_3$, $C(O)N(CH_3)_2$, OH, $OCH_3$, $OCF_3$, $OCH_2CH_3$, $OCH(CH_3)_2$, or O(cyclopropyl);
  $R^{3a}$ is H or $C_{1-3}$ alkyl;
  $R^{3b}$ is H or $C_{1-3}$ alkyl;
  each $R^5$ is independently H;
  $R^6$ is $C_{1-6}$ alkyl, $C_{1-6}$ haloalkyl, $NR''R^7$, $C_{3-12}$ cycloalkyl, or heterocyclyl, wherein the $C_{1-6}$ alkyl, $C_{1-6}$ haloalkyl, $C_{3-12}$ cycloalkyl, or heterocyclyl is optionally substituted with 1, 2, or 3 substituents independently selected from the group consisting of F, $C_{1-6}$ alkyl, $C_{1-6}$ haloalkyl, $CH_2OH$, $CH_2CH_2OH$, $CH_2CH_2CH_2OH$, $C(O)CH_2OH$, $NR''R''$, OH, =O, aziridinyl, azetidinyl, pyrrolidinyl, piperidinyl, and morpholinyl;
  $R^7$ is H, $C_{1-6}$ alkyl, $C_{1-6}$ haloalkyl, $C_{1-6}$ alkylene-$C_{6-12}$ aryl, $C_{1-6}$ alkylene-5- to 12-membered heteroaryl, $C_{3-12}$ cycloalkyl, heterocyclyl, $C_{6-12}$ aryl, or 5- to 12-membered heteroaryl, wherein the $C_{1-6}$ alkylene-$C_{6-12}$ aryl, $C_{1-6}$ alkylene-5- to 12-membered heteroaryl, $C_{3-12}$ cycloalkyl, heterocyclyl, $C_{6-12}$ aryl, or 5- to 12-membered heteroaryl is optionally substituted with 1, 2, or 3 substituents independently selected from the group consisting of F, $CH_2OH$, $CH_2CH_2OH$, $CH_2CH_2CH_2OH$, $C_{1-3}$ alkyl, $C_{1-3}$ haloalkyl, NR'R'', OH, =O, aziridinyl, azetidinyl, pyrrolidinyl, piperidinyl, and morpholinyl;
  each R'' is independently H, $C_{1-6}$ alkyl, $C_{1-6}$ haloalkyl, $C(O)C_{1-6}$ alkyl, or $S(O)_2C_{1-6}$ alkyl;
  $X^1$ is N;
  $X^2$ is CH;
  Y is $-CH_2O-$ or $-OCH_2-$; and
  n is 1.

15. The compound of claim 14, or a pharmaceutically acceptable salt, stereoisomer, or tautomer thereof, wherein:
  $R^1$ is H, F, Cl, CN, or $CH_3$; and
  $R^2$ is H, F, or CN.

16. The compound of claim 14, or a pharmaceutically acceptable salt, stereoisomer, or tautomer thereof, wherein Y is $-CH_2O-$.

17. The compound of claim 14, or a pharmaceutically acceptable salt, stereoisomer, or tautomer thereof, wherein Y is $-OCH_2-$.

18. The compound of claim 14, wherein the compound is selected from the group consisting of:
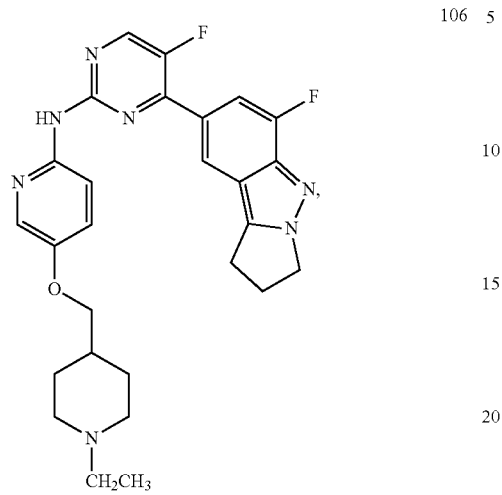
106
or a pharmaceutically acceptable salt, stereoisomer, or tautomer thereof.
* * * * *